US007767398B2

(12) United States Patent
Barden et al.

(10) Patent No.: US 7,767,398 B2
(45) Date of Patent: Aug. 3, 2010

(54) MEANS AND METHODS FOR DIAGNOSING AND TREATING AFFECTIVE DISORDERS

(75) Inventors: Nicholas Barden, Sainte-Foy (CA); Inge Sillaber, Munich (DE); Marcelo Paez-Pereda, Munich (DE)

(73) Assignee: Affectis Pharmaceuticals AG, Munich (DE)

(*) Notice: Subject to any disclaimer, the term of this patent is extended or adjusted under 35 U.S.C. 154(b) by 81 days.

(21) Appl. No.: 11/749,645

(22) Filed: May 16, 2007

(65) Prior Publication Data

US 2008/0057504 A1 Mar. 6, 2008

Related U.S. Application Data

(62) Division of application No. 10/825,593, filed on Apr. 16, 2004.

(60) Provisional application No. 60/474,232, filed on May 30, 2003, provisional application No. 60/501,011, filed on Sep. 9, 2003.

(30) Foreign Application Priority Data

Apr. 17, 2003 (EP) ................... 03008753
Sep. 4, 2003 (EP) ................... 03019626

(51) Int. Cl.
    *G01N 33/53* (2006.01)
(52) U.S. Cl. .......................................... 435/6
(58) Field of Classification Search ................ None
    See application file for complete search history.

(56) References Cited

U.S. PATENT DOCUMENTS

| | | | |
|---|---|---|---|
| 6,214,581 B1 | 4/2001 | Lynch et al. | |
| 6,759,435 B1 | 7/2004 | Chen | |
| 6,943,241 B2 * | 9/2005 | Isogai et al. | 536/23.1 |
| 7,344,860 B2 * | 3/2008 | Franco et al. | 435/69.1 |
| 2003/0170650 A1 | 9/2003 | Karube et al. | |
| 2004/0229262 A1 | 11/2004 | Franco et al. | |

FOREIGN PATENT DOCUMENTS

| | | |
|---|---|---|
| EP | 1 199 372 A2 | 4/2002 |
| EP | 1 310 493 A1 | 5/2003 |
| WO | WO 99/55901 A | 11/1999 |
| WO | WO 01/44213 A | 6/2001 |
| WO | WO 01/62787 A1 | 8/2001 |
| WO | WO 03/042190 A | 5/2003 |
| WO | WO 2004/090097 A1 | 10/2004 |
| WO | WO 2005/093097 | 10/2005 |

OTHER PUBLICATIONS

Brooks, et al. "Subtractive Immunization Yields Monoclonal Antibodies that Specifically Inhibit Metastasis", *The Journal of Cell Biology*, vol. 122, No. 6, 1993, pp. 1351-1359.
Cerchia, et al. "Neutralizing Aptamers from Whole-Cell SELEX Inhibit the RET Receptor Tyrosine Kinase", PLoS Bilogy, Apr. 2005, vol. 3, Issue 4, pp. 697-704.
Pestourie, et al. "Aptamers Against Extracellular Targets for in Vivo Applications", *Biochimie*, 87, 2005, 921-930.
Pollock, et al. "Monoclonal Antibodies: a Powerful Tool for Selecting and Analyzing Mutations in Antigens and Antibodies", *Ann. Rev. Microbiol*, 1984, 38, pp. 389-417.
Sleister, et al. "Subtractive lmmunizatio: A Tool for the Generation of Discriminatory Antibodies to Proteins of Similar Sequence", *Journal of Immunological Methods*, 261, 2002, pp. 213-220.
Williams, et al. "Subtractive Immunization Techniques for the Production of Monoclonal Antibodies to Rare Antigens", *BioTechniques*, vol. 12, No. 6, 1992, pp. 842-847.
Database EMBL, May 14, 1999, XP002284283, Database accession No. AC007546.
Muzny et al., "Homo sapiens 12 BAC RP11-946P6 (Roswell Park Cancer Institute BAC Library) complete sequence", Dec. 2, 2002, XP002284283.
The Notice of Reference Cited in the corresponding U.S. Appl. No. 11/749,629 dated Sep. 17, 2009.
Kato, et al. "SNP (single nucleotide polymorphism) Detection Based on the Formation of Cholic-Acid Binding DNA aptamer", *Nucleic Acids Symposium Series*, 49, 2005, pp. 359-260.

\* cited by examiner

*Primary Examiner*—Michael Pak
(74) *Attorney, Agent, or Firm*—Foley & Lardner LLP

(57) ABSTRACT

Nucleic acid molecules encoding an ATP-gated ion channel P2X7R which contains a mutation or a deletion are disclosed. Polypeptides encoded by the nucleic acid molecules and antibodies that specifically are directed to these polypeptides are disclosed. Aptamers that specifically bind the nucleic acid molecules, and primers for selectively amplifying the nucleic acid molecules are provided, kits, compositions, particularly pharmaceutical and diagnostic compositions comprising the nucleic acid molecules, vectors, polypeptides, aptamers, antibodies and/or primers, are provided. Methods for diagnosing affective disorders associated with a non-functional P2X7R protein, an altered ATP-gating of the P2X7R protein, an over- or underexpression of the P2X7R protein or associated with the presence of any one of the nucleic acid molecules or polypeptides encoded thereby are disclosed. Additionally, the present invention relates to uses and methods for treating affective disorders employing a functional or non-functional ATP-gated ion-channel P2X7R, such as treatment with modulators of P2X7R activity.

4 Claims, 41 Drawing Sheets

Figure 1A:
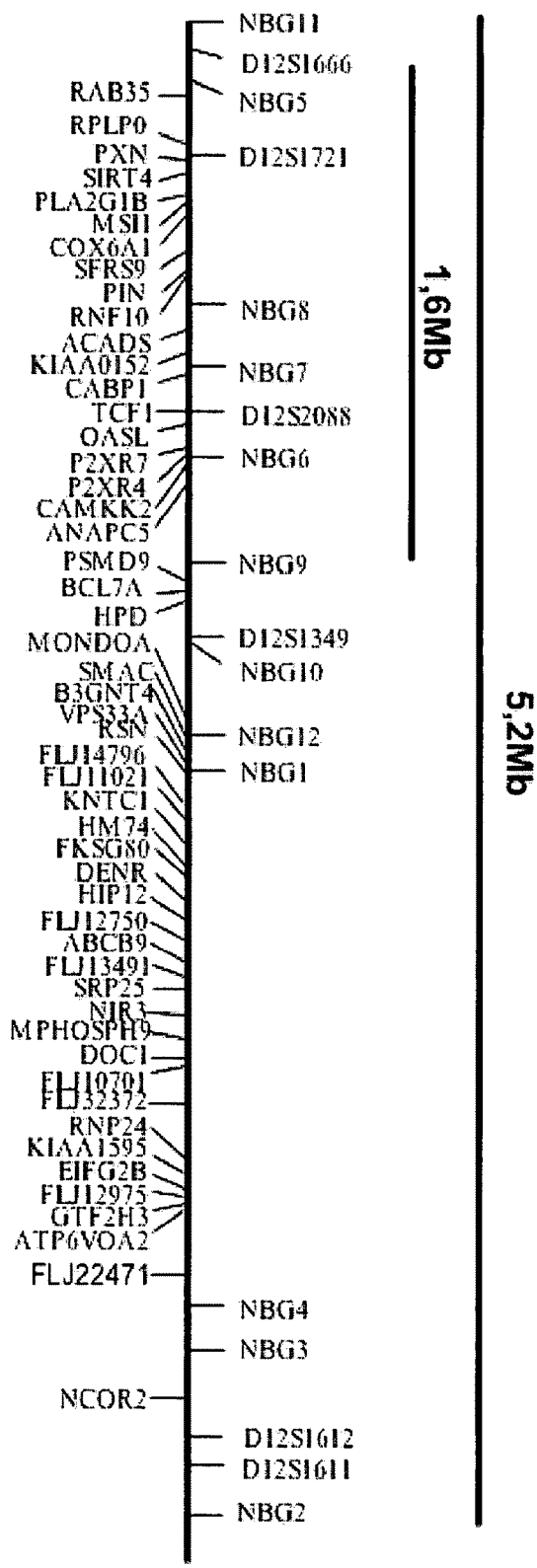

```
P2X7v01  MPACCSCSDVFQYETNKVTRIQSMNYGTIKWFFHVIIFSYVCFALVSDKLYQRKEPVISS
P2X7v04  MPPVD------------------------AFPCLPFS---FALVSDKLYQRKEPVISS
P2X7v02  MPACCSCSDVFQYETNKVTRIQSMNYGTIKWFFHVIIFSYVCFALVSDKLYQRKEPVISS
P2X7v03  MPACCSCSDVFQYETNKVTRIQSMNYGTIKWFFHVIIFSYVCFALVSDKLYQRKEPVISS
         1.......10........20........30........40........50

P2X7v01  VHTKVKGIAEVKEEIVENGVKKLVHSVFDTADYTFPLQGNSFFVMTNFLKTEGQEQRLCP
P2X7v04  VHTKVKGIAEVKEEIVENGVKKLVHSVFDTADYTFPLQGNSFFVMTNFLKTEGQEQRLCP
P2X7v02  VHTKVKGIAEVKEEIVENGVKKLVHSVFDTADYTFPLQGNSFFVMTNFLKTEGQEQRLCP
P2X7v03  VHTKVKGIAEVKEEIVENGVKKLVHSVFDTADYTFPLQGNSFFVMTNFLKTEGQEQRLCP
         61.......70........80........90........100.......110
```

Figure 16a

```
P2X7v01  EYPTRRTLCSSDRGCKKGWMDPQSKGIQTGRCVVHEGNQKTCEVSAWCPIEAVEEAPRPA
P2X7v04  EYPTRRTLCSSDRGCKKGWMDPQSKGIQTGRCVVHEGNQKTCEVSAWCPIEAVEEAPRPA
P2X7v02  EYPTRRTLCSSDRGCKKGWMDPQSKGLLS-------------------------------
P2X7v03  EYPTRRTLCSSDRGCKKGWMDPQSKGIQTGRCVVHEGNQKTCEVSAWCPIEAVEEAPRPA
         121......130.......140.......150.......160.......170

P2X7v01  LLNSAENFTVLIKNNIDFPGHNYTTRNILPGLNITCTFHKTQNPQCPIFRLGDIFRETGD
P2X7v04  LLNSAENFTVLIKNNIDFPGHNYTTRNILPGLNITCTFHKTQNPQCPIFRLGDIFRETGD
P2X7v02  -----------------------------------------------------------
P2X7v03  LLNSAENFTVLIKNNIDFPGHNYTTRNILPGLNITCTFHKTQNPQCPIFRLGDIFRETGD
         181......190.......200.......210.......220.......230
```

Figure 16b

```
P2X7v01  NFSDVAIQGGIMGIEIYWDCNLDRWFHHCHPKYSFRRLDDKTTNVSLYPGYNFRYAKYYK
P2X7v04  NFSDVAIQGGIMGIEIYWDCNLDRWFHHCHPKYSFRRLDDKTTNVSLYPGYNFRYAKYYK
P2X7v02  ------
P2X7v03  NFSDVAIQGGIMGIEIYWDCNLDRWFHHCHPKYSFRRLDDKTTNVSLYPGYNFRYAKYYK
         241......250......260......270......280......290

P2X7v01  ENNVEKRTLIKVFGIRFDILVFGTGGKFDIIQLVVYIGSTLSYFGLAAVFIDFLIDTYSS
P2X7v04  ENNVEKRTLIKVFGIRFDILVFGTGGKFDIIQLVVYIGSTLSYFGLAAVFIDFLIDTYSS
P2X7v02  ------
P2X7v03  ENNVEKRTLIKVFGIRFDILVFGTGGKFDIIQLVVYIGSTLSYFGLVRDSLFHALGKWFG
         301......310......320......330......340......350
```

Figure 16c

```
P2X7v01  NCCRSHIYPWCKCCCQPCVVNEYYYRKKCESIVEPKPTLKYVSFVDESHIRMVNQQLLGRS
P2X7v04  NCCRSHIYPWCKCCCQPCVVNEYYYRKKCESIVEPKPTLKYVSFVDESHIRMVNQQLLGRS
P2X7v02  ------
P2X7v03  EGSD--
         361......370......380......390......400......410

P2X7v01  LQDVKGQEVPRPAMDFTDLSRLPLALHDTPPIPGQPEEIQLLRKEATPRSRDSPVWCQCG
P2X7v04  LQDVKGQEVPRPAMDFTDLSRLPLALHDTPPIPGQPEEIQLLRKEATPRSRDSPVWCQCG
P2X7v02  ------
P2X7v03  ------
         421......430......440......450......460......470
```

Figure 16d

```
P2X7v01  SCLPSQLPESHRCLEELCCRKKPGACITTSELFRKLVLSRHVLQFLLLYQEPLLALDVDS
P2X7v04  SCLPSQLPESHRCLEELCCRKKPGACITTSELFRKLVLSRHVLQFLLLYQEPLLALDVDS
P2X7v02  ------
P2X7v03  ------
         481......490......500......510......520......530

P2X7v01  TNSRLRHCAYRCYATWRFGSQDMADFAILPSCCRWRIRKEFPKSEGQYSGFKSPY
P2X7v04  TNSRLRHCAYRCYATWRFGSQDMADFAILPSCCRWRIRKEFPKSEGQYSGFKSPY
P2X7v02  ------
P2X7v03  ------
         541......550......560......570......580......590
```

Figure 16e

SEQUENCE LISTING

```
<160> NUMBER OF SEQ ID NOS: 111

<210> SEQ ID NO 1
<211> LENGTH: 56580
<212> TYPE: DNA
<213> ORGANISM: Homo sapiens
<220> FEATURE:
<221> NAME/KEY: exon1
<222> LOCATION: (3000)..(3124)
<223> OTHER INFORMATION:
<220> FEATURE:
<221> NAME/KEY: exon2
<222> LOCATION: (24841)..(25009)
<223> OTHER INFORMATION:
<220> FEATURE:
<221> NAME/KEY: exon3
<222> LOCATION: (26134)..(26202)
<223> OTHER INFORMATION:
<220> FEATURE:
<221> NAME/KEY: exon4
<222> LOCATION: (30958)..(31030)
<223> OTHER INFORMATION:
<220> FEATURE:
<221> NAME/KEY: exon5
<222> LOCATION: (32481)..(32577)
<223> OTHER INFORMATION:
```

```
<220> FEATURE:
<221> NAME/KEY: exon6
<222> LOCATION: (35416)..(35496)
<223> OTHER INFORMATION:
<220> FEATURE:
<221> NAME/KEY: exon7
<222> LOCATION: (36113)..(36242)
<223> OTHER INFORMATION:
<220> FEATURE:
<221> NAME/KEY: exon8
<222> LOCATION: (37541)..(37677)
<223> OTHER INFORMATION:
<220> FEATURE:
<221> NAME/KEY: exon9
<222> LOCATION: (45470)..(45560)
<223> OTHER INFORMATION:
<220> FEATURE:
<221> NAME/KEY: exon10
<222> LOCATION: (47229)..(47295)
<223> OTHER INFORMATION:
<220> FEATURE:
<221> NAME/KEY: exon11
<222> LOCATION: (47380)..(47529)
<223> OTHER INFORMATION:
<220> FEATURE:
<221> NAME/KEY: exon12
<222> LOCATION: (50438)..(50539)
<223> OTHER INFORMATION:
<220> FEATURE:
<221> NAME/KEY: exon13
<222> LOCATION: (54392)..(54889)
<223> OTHER INFORMATION:

<400> SEQUENCE: 1
tgtggtccca gctactcagg aggctgtggt aggggggatca ctggagccca gaagtttgaa      60
gctgcagtga gctatgattg cgccactgca ctccagcctg gacgacagag caagacccag     120
tctctaaaat aaattaatta aattaatttt ttaaaaagaa agataagata aagagtcata     180
gaagtacaaa tgagaaacca ggagaacatg ggacccagga aagtcatgga aaccaaggga     240
aaatactggt ccaagatgca gaaagtagcc agtgatgttg aatgcatcca agagatcaag     300
taacataagg aataaaatat atccacccag tctggcaact gagaagtctt tggtaacctc     360
attgagaaca gaatccatgg agtggaggag gtagcagtga tgaaatagcg gacaagggct     420
gaaggagtgg agaggggaga gcatgaggga ccagtgcaag agtgcagcag aaagacaaca     480
aacaggccgg gtgtagtggc tcacgcctgt aatcccaaca ctttggtagg ctaaggcggg     540
cagatcgctt gtgaccagga gttcgagacc aacctagcca acatggtgaa accccatctc     600
tactaaaaac acaaaaatca gctgagcgtg cgcatggctg taattgcaga tactcatgag     660
gctgaggcac aagaatcgct tgaacccagg aggcaggggt tgcagtgacc caaagtcttg     720
ccactgcact acagcctggg caacaggggg agactccatc tcaaaaaaac aaaaaaaaaa     780
aagaaagaaa gaaaagacaa agaaagaaag aaagaaagaa agaaagaaag aaagaaagaa     840
agaaagaaag aaagaaagaa agaaagaaag agaaagaagg aaagaaagac aagaaaatag     900
atgtctttga gtggtagcaa gagcaacact gaagtgattt gcctattctg gacatttcct     960
ataaatggag tcgtaaaaga tgtatccttt tgtgtctggc ctctttcact taagcgtagt    1020
gttttcaagg ttcatccatg ttggagcatg ggtcagtgtt tcattccttt ttatggctga    1080
ataatattcc cttgtatgga ctttcgtgct tttgtgtatc catccatcag ctgatggaca    1140
tttgacttgt ctgcctgttc actgccatat ctactattcc tggtgctctt gggaatgagt    1200
gaatgaatag cataaacaga gctgtccaag gtcacagagc tggtaagatg tgaagccagg    1260
atcggaagcc aggccattag tcccctagag cctatgttct aagcatcagg ctttacctgt    1320
```

```
gaatctcctc tttttacaga tgaagatgac tgtatcactc agattcccgg caggaaagca    1380
atggcatact caagtggggt aactaatgat ggaaccattt acaaaggtgt ggacagagtt    1440
aagaaaaagc aataggagat agtgagcttc ctggggctgg taagagtggg gagcccttac    1500
cactcccagg actaaaggag ggagtggtgc ccagaagccc tgcctatatg caactgagaa    1560
gggcagggcc agggagtcac gtccatcctc actgctctcc agtctcctga actggaagcc    1620
agaaggtgag gggaaccctg atgcagtttg tatgtgtgag aaagtacaat tagtttagac    1680
tgaaaaactg aaaatctacc cggccactta gcaggctgga ataacagaaa tggatcaagc    1740
cagctgtaaa gataacaggg aacaataatt ctctgtagct gtaaagtgat aatacaaccc    1800
tgcatctttg agtgactgct gaaacattgt cctttaaaat cagagacctt cagaaacttc    1860
gctgtttgaa attacatgac taagactgaa atattccaat tttgcctgga agatttaagt    1920
catcttgaca cagagaagca gcctcaattt acaactcagg agcagagctt cagataaaga    1980
ttttctggac acatttgaca tgtatcttag ctatgttgct tcctaggaaa cagggccctg    2040
ggtcctcttt gcaatccaga ctgaagttga ctgctttgta caaacctgtt ttgctttgag    2100
tccatcaaaa catgacttca tttagatttt atctcaactc cactttcctc ggaatcctat    2160
actaaattgc tgttttcctt tgtttggtga tgtgcgtagc tcttctggtg ggtggtgtcc    2220
ctcactgaat aggtcaacaa acctaacttt gttggactgc cactgtgtcc ctggtgatct    2280
ttggctgatt ggtctaggtc atagatcgac ctgccgggt gcagaggagg gtggagagta    2340
actcagaggg tcaagcatga aagatctggc agaaaaataa agcccctcca cccccaccac    2400
ccctacccct gcaaatctga tttcccccac caactgcaga ccagagtatt ataaggggcg    2460
gtggaagaag agggggagat cttcatttac ccagagctcc tatacatcag ggctgaata    2520
aagggttgta gaaatgaatg aatcaatctc tgagtggggc ttcaggcagt ggaaagatct    2580
cagtcctttt ctgaggcata atggaagctc ccagtcttgt gacatttgca aggctgcccc    2640
tttctcccaa gagacatgag accaaaaaag tgaaggaaa ggggggaaaa gggagaattc    2700
tgaaaatgcc catcctctga acaccatctt tgtgtaggca tctggggag gccagctggg    2760
gtgaggtcat ctgccagcca ggcccgtagg acttggcgct tcttgtttat cacagccaca    2820
tgtggggcca ctgccagggc ccgccccaac tctgcagtca ttggaggagc ttgaagttaa    2880
agactcctgc taaaaaccag tacgtttcat tttgcagtta ctgggagggg gcttgctgtg    2940
gccctgtcag gaagagtaga gctctggtcc agctccgcgc agggagggag gctgtcacca    3000
tgccggcctg ctgcagctgc agtgatgttt tccagtatga gacgaacaaa gtcactcgga    3060
tccagagcat gaattatggc accattaagt ggttcttcca cgtgatcatc ttttcctacg    3120
tttggtaagt gggatctggg gaggaccag atctctgcag tggccgacag cacagaaagc    3180
cccagcgggc agcttcaggt gcacattctg aatctcacat ggttttcgaa tctgagacgt    3240
gctctcacag ccagctgggc gggagggagg aagcagcagc aggcaagagg aaacggtgcc    3300
aggctgcagc agagagaagc cacaggacaa gcgggattcc tttctgctct acttcaggcc    3360
cgccagggcg cgcagggcag ggcgtgcctg ggaaggtag gaaagcgcag gcaacaccc    3420
tggatcccca gggaggaggc gaggatctca gggcacgcct ggtgatcatg ctggcatctg    3480
agtcaccatg cttgggagga ataggaccag gcttgaaaat gtgttataac tttaggtcct    3540
caccaacgtc aggaaggccc tgctttttgg ttttgtttc ttctaaaaga aacttactga    3600
gatataattt atacaccata caattgaccc atttaaaggg taccatttaa tgattttcag    3660
attattccca gagttgtgca accatcccca aaatcaattt tagaatattt taatcgactc    3720
```

-continued

```
aaaaggaatc ccacactcct tcaccatcat ttccaacact gttcctcctc cttcccaccc    3780
atcaatttcc tttctgcctc tatggatttg ccgattctgg acatttcata taaatggaat    3840
cacataatat gtggtccttt gtggcactta gcgtgttttc aatgctcatc catgttgtag    3900
catgtgttga tacttcattc aattttttt tttaaagaga cggggtctca ctattttgtc     3960
caggctggtc tcaaactcct ggactcaagt gatctgcctg cctcggcctc ccaaagtgtc    4020
aggattacag gcgtgagcca ttgcacccgg ctgatacttc attcctttt acggctgagt    4080 agtactccat tgcatggata gaccactttt ttctatccat tcatccattg atggacattg    4140
gggttgtttc tcttttttgg ctatcatgaa taatgccaca tgaacatttg tgtacaaggt    4200
tttatgtgga tatatattct cctttctctc gaatatgtac ctaagagtaa aaattgctag    4260
gtcatatgtt aactatgttt caccttgggg ggaatgtgg agctgaattt cacagcagct     4320 gcagttttt acattcctat cagcagagta tgagggatcc aatttctcca catcctcacc     4380
aacgcttgtt atcgtctgtc tttttgggtt ttgttgttgt cattttgttt ttgtctttga    4440
gatgaagtct tgctctgttg cccaggctgg agtgcagtgg cgcaatcttg gctcactgca    4500
acctccacct ccccggttca gcgattctc ctgcctcagc ctcatgagta gctgggatta     4560
caggtgtgcg tcaccactcc tcactaattt ttgtattttt agtagagatg aggtttcgcc    4620
atgtaggcca ggctggtctc aaactcctga cctcaagtga tccgcccacc ttggcctccc    4680
aaagtgctgg gattacaggc atgagccgcc acgcccggct gattgtctgt cttttttatt    4740
atagccatgc tagtgggtgt gaagtggtag ttcattgtgg ttgtgatttg aatttccctg    4800
atggtgagtg cctcttattc tctgtgctga ttgataatga tgatgaaggc aatttgtatc    4860
tatagagtgg cagtgtagtt tactaagagt tagggtaact tatttcatag tactggctat    4920
gtcttctggg ccaagtcatt aacttctctg agcctcagtt tctgcatctg ttcatagggt    4980
tgtggcaatt aaccaaaaaa aaaggcatg aacagcccctt atcatgatga ctgacatagg     5040
ataagagctc cataactagt atctattttt aaaaataatc ttttaagtc tgggagtggt     5100 ggctcacacc tgtaatccca cactttggg aggccgaggc gggtggatca cgaagtcagg     5160
agtttgagac cagcctggcc aatatggtga acccatct ctactaaaaa tacaaaaatt      5220
agtggggagt ggtggtgcac acctgtaatc ccagctacta gggaggctga ggcaggagaa    5280
tcgcttgaac ccggaggcgg aggttgcagt gagccgagat caagccactg cactccagcc    5340
tgggtgacag agcaagactc catctcaaaa taataataat agtaataatt tttttgatta    5400
tataatagta tatatgtata taaaatacat gtatgtattt ttatctatat cctctgctct    5460
gaccctcaaa gtaaccacgt ccaagttcag gatttgaaat ctggaaacgt ggattcaaaa    5520
atccttcacc tctttgagcc ttggtttcat catctgtaaa atggggagaa ttgttgatag    5580
gaatattaaa tgaactaata aatgcaaagc tgtttgagaa atatatggca tatagtaatc    5640
cctgattaag tgttagttct tattattaat aatgctatta ttaggattat tattattcga    5700
ttcatatgtt tactgttcaa caaatattga atgataaaca tatatgctgg gtccggcatg    5760
gtggcccatg cctgtaattc cagcactttg ggaggccaag gcgggcaggt cacttgaggt    5820
caagagtttg agaccagcct ggccaacgtg gtggaaactc cgtctgtgct aaaaatacaa    5880
aaattagccg ggcatggtgg tgggtgcctg taatcccagc tactcgggag gctgagacag    5940
gagaatcact tgaacccagg aggtggaggt tgcagtgagc caagattgca ccactgcact    6000
ccagcctgag ccacagagca agactctgtc tcaaaaaaaa aaaaaaaaa aaaaaaaaa      6060 tatatatata tatatatata tatatatata tagtattttt agtagagatg gggttttgcc    6120
```

```
atctcttata tattttata tatttatatt tttatatat ttatatatat ttatatgtat    6180
tttatatatt tatatatg tgctgaaatc taaaataaga catatcactt aaaccagcta    6240
tcacaggacc aatggtaaag agcataatta gtaaatgccc ccttctgcat taatacgtag   6300
attgtatgtc acaatttcat gtagcaggtg atggggcttc ctgacattct tgggcccagc  6360
atacaatctt tttatttctt ttttagagac agggtctcat tgtgttgccc taggctggag  6420
tgcagtgtca ttatcacagc tcgccacagc ctcaacttct caggctcaag tgatcctccc  6480
gcctcatcct cccaagtagc tgggaccata ggcacacgcc atgatgtctg actaattttt  6540
tattttttt tgtggagatg ggggtctccc tatgttgctc aggctagtct caaactcctg   6600
gactcaagtg atcctcctgc tttggcctcc caaagtgctg ggattatagg catgagccac  6660
tttgtctggc ctacaattcc ttttctttct ttctttcttt ttttttttt ttttgagtt    6720
gagtctcact ctgtcaccta ggctgtagtg cagtggtgtg atctcagctc actgcaacct  6780
ataccctccca ggcccaagca atcctcccac ctcaacctcc cgagtagctg ggaccacagg 6840
tgtacaccac cacgcccagc taattttttg tattttggt agagacaggg tttcaccata   6900
gttgtccagg ctggtcttga actcctgagc tcaagcaatc cacccgcctt ggcctcccaa  6960
agtgctggga ttacaggtgt gggtcaccat gcccagcctt caatttcttc agattattgt  7020
ataataataa aatttctaaa aacagattac tatgagaaca ccttgtaatg ataaatattt  7080
ttcttttcaca tggtgaaatc ataacttaca tgtatttaac tccctcaaat tcagttatac 7140
atgttccatg gggacatgga gagagagaga acaatataaa taatgcaatg attcagcaac  7200
cgggttcgct ggagtaggtg tgagatggga tactggcatc tggtgttccc tccgtcaatc  7260
tctgttccca cgtgcttttt agcgagcatc ttgctgctct acttattaat ctaggtacat  7320
attttcagc cacatgaccc ctaaaataag tcaactcctt caccttcacc tggagcaaaa   7380
ctgtaaaaac agcaacttgt tctagatctg gaggcaaaat tggttccagc agacccactg  7440
ggaagtggga ggtgtttgct atgctttgtg gacaatttaa gtgtttaaaa ggcaattttg  7500
atgagccatg attttcatct taagtgccaa ctttagaaga taaccttcat ataaaagttt  7560
ctctacagtt tgtattttaa aatataaaat ggaagaaaaa actatcacca gctttgcttt  7620
tttcctcttg gttaatggac tatctattaa cgtctcacta aatggccaaa tggagtctca  7680
cagtacacag tttgggaaat gctgccttaa gttgctctgt gaagccttaa gttcgtgtaa  7740
ccatgactta gccatctgtg aaatgggtag acccatgggg cataggaatt ggggaatgta  7800
ttttgcatca agtaggactg gtgtggacca caggtggaaa tccagacagg ctcgagcaat  7860
gttcaggata cagcagcaag tgacaggttc tggccagctg tccctactgg ggctgcaagg  7920
actaagagcc aggataagga gacagggcct cggttattga aaatgggata caaagcaggg  7980
actggttatg gcggaaatta accaagaggc tgttcagctt cttctattct cacaaccaat  8040
tcagatctgg attcaaaggc agggatgcag ctacaagagg agtttgtgtt ggaggtctgt  8100
gtagatagga tgctaagcag gtctgtgtca gccaggatcg tttgggcagt aagtgacaga  8160
aacccaactt acgttaacca caaagcctca aaggggaatt tattggatca tgtaactggc  8220
cagttgaaga gatggtgctg tcctcggacg tggatgaaga taagagttca aactgtgtca  8280
tcaggacgga tccgtctccc tacatcctgg ctccatttgc ttctatttgg cttccttctt  8340
gaacaactct gtatgtacaa gatatcctca cattctcttc ttttaacaac ctcagaggag  8400
caaacaagtc tttcctgata gctctgctaa gaaagtccca ggaaagactc tgattgatca  8460
gatgtgagtt acagatccat ccctgaacca atcactgtgg ccagggccaa ggtgtcatcc  8520
```

```
cattggccag cctgggtcat gtgctggctc ccgtagcagg aagtagggag aagacgaggg   8580
agccgtgtga gccctacgtg aaccacatcc agtggatttt ccttaggaag gaagattctg   8640
tgaccagacc aaatggaaaa ggaagtgggg agggtaggca gacaaaaatc ggtgatctat   8700
tacaaggtct ttccaaaagc cagaaattag ggatttctaa gtgtacctct ctagtcctgg   8760
cttgtctcag ccctgcagct gggctgtgga gactccatca gcaattgctg acccccctatt  8820 cttacctcgg cccccttcctg agtcccacca ggagccctgc tcctcatctg ggacatgctt  8880
cttggcccat ggaggttgcc agctcacctt ggtactttac tactatttgg tttctgtgac   8940
caccaagctg ttgcttaaac caagccgcct atggtggcac cactttggag aattcttttt   9000
tattttttga dacaggttct cactctggtt accgagactg gagtgcagtg gtatgatctt   9060
ggctcactgc agcctcgacc tcccgggttc aggtgatttt cccacctcag cctccccagt   9120
agctgggact attggtgcat gccactacac ccggctcatt tttgtatttt tagtagagac   9180
ggggttttgc catgttggcc gggctggtct tgaactcctg acctcaggtg atctgccccc   9240
ctcggcctgt caaagtgctg aaattacagg cgtgagccac cgcacccggc tggataattc   9300
tttagatttt attccaagtg ggttgagaag ccatgggaag attgtaagca aggaataaa   9360 agttggttgc attctctttg gaggatttcc ctcttccctg gagaccagtc ctcacagaag   9420 ctttttccaat ggccacagaa gactaaggaa gattgagaga ggcacaggaa acaattccac  9480
tcagagctgc tgcttcgcca ctgcccagtc agcctccact ggcgccaaca cgagcctatg   9540
ctgtcattcc tgggcccagg ctggctgtcg ctgtggagat ggtgctgctg tgctagtttg   9600
tggctgttaa aatggagctc ctggctggac acctgtttcc cagtgggtgg ccacaaacct   9660
gtgagtctgg gcctcctcca gctgagtaga agtgagccca gcacagaggc cggggaggcc   9720
ccagacgcca ggaggagcaa atccaaatcc aacccaagca tggcccctct gaccctgacc   9780 atctttttt tttttttttt ttttgagaca gagtctccct ctgtcaccca gactggagtg   9840
cagtggcacg atcttggctc attgcaaccc ccacctcctg ggttcatgcg attctcctgc   9900
ctcagcctcc ctagtaggga ctacaggcat gcaccactac acccagataa tgtctgtatt   9960
tttagtagag atggggttct gctatgttgg ctaggctggt ctcgaactcc tggcctcaag  10020
cgatccatcc gtcttggctt cccaaaatgc tgagattaca ggtgtgagcc actgcgccca  10080
gcctgcccct gactgccttc agaaaagtag aagcaggagg tctgccacat tctcatccca  10140
tccttgacac ctgggtgatg tgctagagct tgaggggaag gtcagaggta acccagttcg  10200
ggaagtgacc ccgtaggagg agaagaatcc agccacgtga cacacagtac gaagagaaca  10260
gtaaatgcaa agacctggaa acgaggaaca gcaaggacag catgtcccag aacctgggga  10320
gagaggaggg agcagccgga gctgagggca gctcagggga agagttgcta tttgattttc  10380
agtgcatggg aagccactga aaagttttat gcagagaagt aaaaccatct cactcatgtt  10440
tctagaagcc ttatgggcca ctgtgcagag catagagtgt ggtgggacaa gaatgacggt  10500
gaggaaccag tgagaaggtt cctggagtca ccagatgcga ggagatagag gcttgggcta  10560
gaatgggctg gcgagctgg agagaggtgg acaaagctga gatgtgtttt ggaggcagaa  10620
atgatagatt tgccaggagg tgaaagatgg ctctagattc ctgaggaacg atgatgcctt  10680
ttaccaacct gaagaagacc aaggagaggc ttgaggacta acacggaact gtgaaggagg  10740
ccaggcaaag gtggagactg ccgtgagctg tgatcacgcc actgcaccct cgcctgggtg  10800
acagactgag accctgtctt aaaatatata tgtaataaaa aataataaat aaagggccag  10860
gcgtggtggc tcaacgcctg taatcccaac actgggaggc tgaagcaggt ggatcacctg  10920
```

```
aggtcagaag ttcaagacca gcctggtcaa catggcgaaa tcccatctat aataaaaata    10980
caaaaattag ccagacatgg tggcacatgc ctgtaatccc agctacttgg gaggctgagg    11040
caggagaatc acttgaacct gggaggcaga ggttgcagtg agcctaaatc acaccactgc    11100
actccagcct gggcaacaga gtgagacccc ataaataaat aaataaatac ataaataaag    11160
gatatcaggc aagcaattaa acacctgcc tactaccatc tatccgcatc cttttttttca   11220
tgtctaacac caaaacacca aaatagctgg aaacatatca tgtcaaaaga taagcatgat    11280
tctttcaaat gaatggctgt ggacttatga aaagctgcct ccgcgtctga ttttcttgtt    11340
tcaagggta atgatggagg tttctctcct gcacctgcag gcctccgggg atgctgcccc     11400
agtgcagcct cccaccctgg gctggagcct cccagccccg ctgcatgggt agcacagtgt    11460
tgggaagagg aaggagcagt ttgtctggct ttttcacagg cccacagctg ccggtacag    11520
tggcagagaa ggcgaggctg aggtggggct ggggaagcca gcaggggcct gatcatggag    11580
cgccttgagc tgcatcccac aggtactgag aaagcatgga gagctgtccc ccagccccca    11640
gcatcttatt agaaaatatt gaaacataac agaaacatg aagggtttta tgttcatatt     11700
ttcattttag agagatcatt ctgcttgaaa tataacacct actgagtact gctgaggact    11760
taccatgtgc cgggttctgt cttagcatg tgacatgtat tggcctattt gattctccta    11820
cataatcctg gaagattggt tgtgggagtg ggtgatcatg acctgaacag cctaaccatg    11880
tttagggaac actctgtgtt atgcgttcca ccacacaatt catgtcacag ctgaatgtcc    11940
cagtttccct tgcagctagg acacaacggg agacccaagc tttccaaaca tatgccccag    12000
gcaacacttt gatacacaag gaataacact ggatgctggg tgtgcacaga attcaaattc    12060
aggaatggag ggaagtactg cccttttgacc catacaatag gggatccct tccttggacc    12120
ccatggctta gagggcccca ctctgtccct ctgcagactg tgagctgccc tatggaatga    12180
ggggtgtctg aggctgtatt aatttctatt tgttacacag cagtggaaac taatacagtc    12240
ccacaggcct aaatcaaggc gtcagcaggc tgagttcctg cctggagact ctggggaaaa    12300
ttcacttcca aactcatttt tgttgttggc aaaattcaat cccttgaggc tgcaggactg    12360
ggctctgctc ctcactggct gtcagcctgg ggccactctc agattctgaa gtcctcccac    12420
attccctgcc acatggtcct ctccatctcc aagcctgcta tgacacaacg cattgttctc    12480
atgcttcaaa tctctgactt ctctcccggg accagaagaa gaatactctc ttcttttaag    12540
gggctcatgt gattgggtca ggtcaactct atcatatcat ggagtctcac cgtcttgccc    12600
aggtgggtct tgaacacctg gctcaagtg atcctcctgc gttggcctcc caaagtgctg    12660
ggattacagg cgggaactgc tgtgcccagc caaggccagc atcttcagac ctctctgccc    12720
tgttttcaca tggtcttctc ctctttgtgt gtgtgtcaaa tctccttctg cctctcttat    12780
aaggacgtgt gtaatagcac tcagggccca cctggatgac acagggtcat ctcgccatct    12840
caaaatcgtt aactttggcc aggtgcagtg gctcatgcct gtaatctcag cactttggga    12900
ggctgagaca ggtggatcac ttgaggtcag gagttcaaga ccagcctggc cagcatggtg    12960
aaaccctgtc tctactaaaa atacaaaagt tagctgggca cgcacctgta gtcccagcta    13020
ctcaggagac tgaggcaaaa gaatctctag aacctgggag gcagagactg cagtgagcca    13080
agattatgcc actgcacttc cagcctgggg gacagagtga gacttcatct caaaaaaaaa    13140
aaaaaaaaga tgactgggca cggtggctca catctgtaat cccagcattt gggaggccca    13200
ggtgggcaga tcacctgggt tcaggagttc attcaagacc agcctggcca acatggtgaa    13260
agtctctctc tactaaaaaa aaaaaaaata caaaaattac ccagatgtgg tggcaggtgc    13320
```

```
ctgtaatccc agctacttgg caggccgagg caggagaatc acttaaacct gggaggcaga    13380
gggtgcagtg agctgagatc actctgctgc actccagcct ggacgacaga gcgaaactcc    13440
atctcagaaa aacaaattaa ccaggcatgg tgctgcgtgc ctgtagtccc agctactggg    13500
aaggctgagg tgggaggatt gcttgatcct gggaggttga ggctgcagtg agctgtgttt    13560
gtgccactgc actccagcct gggcgacaga gtgagaccct atctgaaaaa aaaaaaatcg    13620
gccaggcgcg gtggctcacg tctgtaatcc cagaactctg ggagactgag gtgggtggat    13680
cacctgaggt caggagttcg agaccagcct gaccaacagg gtgaaacccc gtctctacta    13740
aaaatacaaa aattagctgg gcatggtggc aggcacctat ataatcccag ctactcggga    13800
ggctgaggca ggagaatcgc ttgaactcag gaggcagagg ttgcagtgag ccgaggtcat    13860
ggcattgcac tccagcctgg tggcagagtg agactccgtc tcaaaaaaaa gaaagtctct    13920
ttttacaact tttttgaggt ataacttaca tatcagaaaa tcaccggttt taaatataca    13980
tttcaacgac tttagtaaa tttcccaagt tgtgcaacca tcatcacaat ccagtttcag     14040
aacatttcat cagcccagta agagccctca cacccattaa cagtcactcc ccactcccac    14100
ttcctcctgg tggttgctca acccaggtaa ccatgaatct attctctgcc tctggagatt    14160
tgtcttttct ggacaatctt tcttcttaaa ctcagcagag tgagttctgt tgtttagaac    14220
tagaaaccct gcccaataga atactaatat cctcttgttt tgcaagggag ttagagtctc    14280
gctctgtcgc ccaggctgga gtgcagtggt atgatctcgc ctcacttcga cctctacctt    14340
ccggattcaa gcgattctcc tacctcagct tcctgagtag ctgggattac agacgtgcac    14400
caacacacct ggctaatttt tgtacttta gtagagatgg ggtctcacca tgttggccaa     14460
gctggtcttg aactcctgac ttcaaatgag ccacccgcct tggcctccca agttctgggg    14520
attacaggca tgagccactg cacccagccc taatatcctc ttattacaaa agaagaaaca    14580
atgactcaga aagattaagt cacttaccca aggtcatgta gtcagtaagc aatagagctg    14640
agactgaacc tcactccaaa gtctatgctc tcactaaagt attgcagtgt agagagtaga    14700
ggggacaggg tgagactgga ggaagggagg gcatttagga gactattggg atgtccagat    14760
ctgagagctg ttggcgacct ggactgggga ggtgatagag cagaggaga gaagtagatg     14820
aatttgagca tattaggaag tgaaacagta ggatttggca actgaacggg tgagtggaca    14880
agaaggagag gatgagtcaa agagtgcacc atgcttctgg cttgggcaac tgatgggtac    14940
tggaataact tgctgggata ggaaatgcag gagaaacagc caatttgggg tggaagatga    15000
ggtcaggact aaaggcattg agtttgaggt gtctatggaa tgtacaaatg gagatgttga    15060
atggatggtt ggatatacga atctgcagct gagatgtagg tttctatatc accagcatat    15120
agacggcaac cagaaccctg gaagaaggtg caaccgacca gcaagagaag atgtagatga    15180
gaaagcaaaa gggcctagaa cacgccccaa aggagtgcta acctttaagg cgtgggagcg    15240
cagaagtccc caaaagattc tgaggagtag ccacggcgat ccagtgaaag tcaggcacaa    15300
gtggactcct gcaagctaag ggaaggaggc gagggaagtg gggcatggtc acagtcagtg    15360
tcaactgctg ctgagagttc caggaaggtc aggtccatgg tgtatctatt ggatttagtg    15420
acaacgacat tgttgtttac ttggcaagag aggctttaga aagggatgg gggtgggagc     15480
cagactagag tgggtagagg agtgagtgaa tcaagatgcg gaagtggatg tgatgactcg    15540
cccttctttt cttctttctt tcttttttt tttttgaga tgcagtcttc ctctgtcgcc      15600
caggctggag tgcgatggtg tgatctccac tcaccacaac ctctgcctcc tgggttcaag    15660
tgattctcct gcctcagcct tccaagtagc tgggattaca ggcatgtgcc accacacccg    15720
```

```
cctaattttt tgtattttta gtagagacgg ggtttcacca tgttggccag gctggtctca   15780
aactcctgac ctcttgatcc acctgcctca gcctcccaaa gtgctgggat tacaggcgtg   15840
agccaccgta cccggcctgg tgactcactc tttcaaggga ctcagctata agaagagag    15900 gcatggagtg gtggtaggat ggattaagct ggggagggga ggcatttta agatgagaaa    15960 tgatgtttaa atgcagatgg aaatgggaca ggagagaaag ggaagttgat gggataaatg   16020
aaaattatca tcatcatctt cctcaccatc accagcagca accacaagga aagctcgttc   16080
tgctctggga ctgccctgtt agacatttct tccttatact gagccacaat ctatctccct   16140
gtaactttcg cctttggtta gagttctgcc ttgtgtccct cttctactct tcaaatggct   16200
gcacgctgct actatgtctg tcctcttctt caaactcaca gccccatcc tacgggccct    16260 gtgctcccag cctggtgacc cgaccctcta ctgtcccagc caagttcaca tgaccatcct   16320
cttatttgtc aagcctctct tttttttttt tttttttttt ttttgggag gagtcttact    16380 ctgtcccagg ctggagggca tggcacaatc tcagctcact gcaacctctg cctcctggtt   16440
tcaagtgatt ctcctgcctc agcctcctga atgctgggat tacaggcata tcgccatg    16500 cctggttaat ttttgtattt ttagtagaga cggggtttca ccatgttggc caggctggtc   16560
ttgaactcct gacctccagt gatccccctg cctcagcttc ccaaagtgct gggattacag   16620
cgtgagccac tgagccgggc caagcccctc tgaagaggca gtgtgcacac tcttgctttg   16680
ctgatagaag catgaaatgg ttcaagtttt tgtgatttgg gaaaatgaac tcagctataa   16740
aatgtgcaca cccagaagtt gtcctatgga cttaatgtct tagggtgag aagaagcttg    16800 tgcagggatt cctggcaaca tgaatgcggg atggacagac agtgagcaca gtgttgagga   16860
gcacagcctg agtgcatctc cctgagatca ggaacaggac aaggatgccc gctttcaccg   16920
ctgctgttcg acattgtact ggaagttcta gccagagcaa ttaggcaaga aaaagcaata   16980
aaaggcatcc agattgtaaa ggatgaagta aaactatctt tagtcacagg tggcacaatc   17040
ccatataggg agaatcccaa agaattcaca agaaaactgt tagagcaaat aaactaattc   17100
agtcaagttg caaggaacaa gatcaaccac aaaaattaat tgtgtgggtt ttttttacac   17160
cagcaatgaa catttgaaaa ggaaattcga aaagtattc cattcactgt agcatttaag    17220
aaagctgagg ctgtgaagct acatggctgt gtttggagct ggtgctgcta tttaccatgt   17280
gaccttggac aagcttctca cttcattcat gacaccgttt attcagctat taagtggggg   17340
taataatagt accttcctta tagagttggt tttttgtttt tgtttttgtt tttggtgggg   17400
gagagtaagg attgcaagag ttaatatatg ttagcaaaat ggacttagaa gagtggttgg   17460
cacatggtaa ggactatatt agggttacca aaaatgttt ataattggga aaattgaaca    17520
aaggttccag taaatatcca tcccagaggc tggttgacaa attatcacaa tgtacctttt   17580
agcttgaacc atatggaact gcctatattc tatagctatg gcctacaaaa tgcaaaatgg   17640
gcagtttttt ttgttgttgt tgtttgtttg tttgtttgtt tgtcttgaga cagtctcagt   17700
ctgtcaccag gctgaagtgc agtggcacga tcttggctca ctgcaacctc tgcctcccag   17760
gttcaagcga ttctcctgcc tcagcctccc aagtagctgg gattacaggt gtgcaccacc   17820
acgcccagct aattttgta tttttagtag atgggggtt tccaccatgt tggccaggcg     17880
ggtcttgaac tcctggcctc aattaatctg cctgcctcgg cctcccagag ttctgggatt   17940
acatgagtga gccaccgagc ccagccaaaa tgggccgttt catatgttca atttaaacac   18000
taagatactc tttagccact gaaaatgact gtgtatcata gatctatctt tatcacagat   18060
ctatctttac tgtcatagaa agaactaata acatattatt gaacaaaaat aacaagttac   18120
```

```
aaaacagctt gcagccacgt tgtaacatc agtatatcta tttgtgtgtc taggtgtgga    18180
cataaagaga tatctagaag acactcccat tgcctatggg aatgacttgg gctgggatct   18240
ttttattta tttatttatt tatttattta tttatttatt tattttgaga cagagtctca    18300
ctctgtcacc caggctggag tgcaatggca tgatcttggc tcactgcaac ctccgcctcc   18360
caggttcaaa cgattctccc acctcagcct cccaagtagc tggaattata ggcacccatc   18420
accgcaccta gctaattttt gccttttag tagaaatggg gtttcgccat gttgcccagg    18480
ctggtctcaa actcttgatc tcaaattatc cacctgcctc agcctcccaa agtgctggaa   18540
ttacaggcgt gagtcaccgc acccagctgt gatcttaatt tatatttttt cttttaacc    18600
cttgattttt accctgtttg actgacttta ggagtctgac ccccaaaact gcaaagaat    18660
aaattagtgt tgttgaaagc cactaagttt gtggtaattt gttagagcaa caaccagaaa   18720
ctaatacaat cgggattaaa cttgccctgg gggtgctggc tctcccccac tttcttctca   18780
gagcatctct tgggtcctcg ccccttgctg agccccacc atggccgggt ggaccagcga    18840
tggacctgat cggattctcc tcttgggatt ttaaataaga gatgcagagg ctgcacgcca   18900
agcttctctg tgccgcactg caggcacagt cctggcgcta ctgttcttta ggggtccatg   18960
aagatgtttg ttggcctggc ttaggtgtga gctaagagat acaagggata cactttggag   19020
gctcagccct tgatgttac cttttgcgctg gaagcccagg ggctgtaaga cggagaggaa    19080
ctttgctgaa agggaggtcc tccctgcaga gcttgaagag caatctaacc atgctggcat   19140
ggggcccatc ccacctgtga tgccagtgta agtctgtgac agtcactcat attcagagca   19200
tgtggattga gactctgaag aacgactta tggtgggcac cttcatctcc atctggtggg    19260
tccagagcaa gcagcctcag ggtcccatgg gcccaacctc accctccatc cttatttccc   19320
tgccactcca gggctcctcc tcagccagac ttgcctgtga gtgccccttg atggctgtat   19380
tagtctgttc tcacgctgct aataaagaca tacccaagac caggtaattt ataaaggaaa   19440
gaggtttaat gggcccacag ttccacatgg ctgggaaggc ctcacaatca tggcagaggg   19500
cgaaaggcat gtcttacatg gtggcaggca aaaagtgaat gacaaccaag caaaagaaga   19560
aacctcttat aaaaccatca gatcccatga gacttactca ctaccacgag aacagtatgg   19620
gggaaactgc ccccatgatt caattatctc ccaccaggtc cctcccacaa cacatggaaa   19680
ttatgggagc tataattcaa gatgaaattt ggatggggac acagccaaac catatcagtg   19740
gccctggctt ctctcccatt agctctgttc tacttcccaa aatctttcca gctttgttct   19800
tttttagaga ctggagtctc actgtgttgc ccaggcttgt cttgaactcc tgggctcaag   19860
ggatcctcct acctcggtct aacaagtagc tgcgaatata ggtgcacacc accacacccc   19920
cacaacttac ccatcctccc cggctcagtg aaatccctag gtccttcaca ctcccgttag    19980
ctccaggtac cagcggcttt gccttctaca gaatgcataa cattatagcc tcttagagca   20040
aaaaggtcat ggggatgggg aaggctggga gttctctctt cattcaggga ttaaacctac   20100
cacctggagg ggtgacatgg ctcaccttag tcaccaagca aggtcgggag agtatttctg   20160
ggatggtcat tagcactttc tttccaaagg gaggatacta caaactcact ttcatgatca   20220
cagtatcccc cccgacaggt aaagtgtgca aactcgcttt cattcccttt ttgtctttga   20280
cgcagctctg aagcatttta attcttaaaa tttacatgtt catgatgaca cagagacacg   20340
ttttctgttt aggagagggc ctgattccat taaggctgat cgatcatatg ttgcacattc   20400
tgggataaat atgagagatc agaattgagc ttcccaaatg gtgggtcaca tgacccagtg   20460
ttgttccagg agaacgttgc aacatccagc atgagaaagc gctgcatgca ccatgtatgt   20520
```

```
gttgggatgc tgggctgaaa tgtattaatg agcaagtgtt atcatatttg tctatggaat   20580
tctatttaat agctatgtct cgtatgtgct gattgggtct caaatctggg tatcttaccc   20640
caacatcttt cttgaaaatc cttcttttta aataaatgtt ggccgtgtgc actggcttat   20700
gcctgtaatc ccaacacttt gggaggccaa ggcgggtgga tcacctgagg tcaggagttc   20760
aagaccagcc tgaccaacat ggagaaaccc catctctact aaaaatacaa aaattagctg   20820
ggcacgatgg tggatgcctg taatcccagc tacttgggag gctgaggcag gagaatcact   20880
tgaacctggg aggcggaggt tgcagtaagc tgagatcgcg ccattgcact ccagccttgg   20940
caacagagtg agactccgtc tcaaataagt aataaataaa tgttatagaa atactaaagt   21000
gtattgtgca taatataaca cccacgtacc accatccaac ttaagaaata agcattact    21060 aatccagttt tgctccctgc aaactcatcc ttcatcccat tctctttcct tttgctttat   21120
aaacatcctg cagccaggca cagtggctgc acctgcagcc tgagctactt gggaggctga   21180
gatgggagga tcacttgagc ccaggagttt gtggctgtcg tgtgctgatt gcacctgtga   21240
aatagccact gtgttccagc atgggcaaca tagcaagact ccatctctaa atgaaatcct   21300
tttttttttt tttcttttg agacagagtc tcactctatc acccaggctg gagtgcagtg    21360
gcgccatctc ggctcactgc aacctccgtc tccagggttc ctgcctcagc ctccggagta   21420
gctgggacta caggcacatg ccaccacaac tggctaattt ttgtattttt agtagagacg   21480
gggtttggcc aggttggttt cgaacccagg acctcagatg atccacctgc ctcggcctcc   21540
caaagattac aggcatgagc caccatgccc agcctaaaag aaatcctgaa tttgacattt   21600
ttaattccct tgtttgtttt aatatttcta cagcacatat atgtctacat atataaaaaa   21660 tataatttt tattggggtg aaattcacat aacgtaaaat taaccactgt aaacatgaac     21720
aattcagtgg catttaggac attcatagta ctgtgcaacc accacctcta tctagctcca   21780
gaacattttc atcaccccaa aaggacactc catgccccccc aggagtcact ccccatttct    21840
tcccactctg tccctgcaa cgaccaatct actctctgtc tctgtggatt cacctattct     21900
ggatatttca tataaatgga atcatacaat atgtggcctt ttgtgactgg tctctttgac   21960
ttagctgggt gtggtggcac gagctaccca cctacttggg aggctgaggc aggagaatcg   22020
cttgaactcc agccataaat tatattgttt tcaaggttca tcaatattac tcgcccaggc   22080
tggagtgcag taatgtgacc ttggccccct gcaacctcca cctccccggt tcaaaggatt   22140
ctcctgcctc accctcccga gtagttggga ttacaggcgc cccccccccc cacccggcta   22200
attttttgta tttttagtag agagagggtt tcaccatgtt ggtcatgctg gtcctgaact   22260
cctaatctca agtgatccac ccaccttggc ctcccaaaat gctgagatta caggtgtgag   22320
acactatgtc aggcctagtc aattcatttt cactgctgca aagcatctca ttttaaaaaa   22380
ttattttatt attatttttt tgagacaggg tctcactctg ttgcccaggc tggagtacag   22440
gggtgcaatc acagcttact atagccttga cctcccgggc ccaagcaatc ctcccactgt   22500
ggcctccaga gtagctggga ctacaggcat gtgccaccac acacagctaa tttttgttct   22560 ttgtttttg tttgtttg tttgttttt tgagatggag ctttgctctt gttgcccagg     22620
ctggagtgca gtggcgcgat ctcagctcac cacaacctcc atctcccagg ttcaagcgat   22680
tctcctgcct cagcctcccg aataggtggg attacaggct cacgccaccg tacccagtta   22740
atttttattt ttagtagaga tgaggtttca ccatattggc caggatggcc tcaaactcct   22800
gacctcaggt gatccatccg ccttggcatc ccaaagttct gggattacag gcgtgagcca   22860
ctgtgcctgg ctcaaagcat ctcattgtat gaatccaaca atttatttat ccattcgttg   22920
```

```
tttgagtaca tgtaggttat ttcctgcttt ccctcttaca agcaatgctg cagaaacatt   22980
cttgtccata gctcctccgg cacatgtaca agagcttctc tagggcacaa atgtaagagt   23040
tttattgctg ggccatgggg aatgctcttc ttcaaatgta cttgctattg tcaaatctga   23100
gctatctttt caggagccta ctactggttc tcagccctgg ctatgcatta gaatcacttg   23160
ggaactttaa aaaatatgt gggtatctgg ataactcccc cgacccgtgg aatcctagtc   23220
tccagggatg ggactgggga cttgaaagct ccctgggtga ttacacagcc aaggtggaga   23280
acagctggga ctgagtcttg gcccactctg tctcagcttc ccaaggtcag ctcatagagg   23340
gcagccatca tcttagactt gctaatatca ctcagcagct gagcagatag aagggactaa   23400
ataaataaag tctgaatgag taaataaagc atttaaaaca aacccctttag ggctgggtgt   23460 ggtggctcac acctgtaatc ccagcacttt gggaggccaa ggtgggtgga tcccttgagg   23520
ttgggcattc aagaccagcc tgaccaacat ggcgaaacct tgtctctact aaaaatacaa   23580
aaattagcaa agtgtggtgg tacgcgcctg taatcccagc tactcggaag gctgaggcag   23640
gagaatcact tgaacccggc aggcagaagt tgcagtgagc tgagatggag tcactgcact   23700
ccagcccggg ctacagagca agactccatc tcaaaaaaaa cataataaaa caaacccttt   23760
aggctgggtg cggtggcgca tgccggtaat cctggtaact atctcctact gttgtgacga   23820
ttaaaggaga tggtgcatgc agagtacttg gcacatatga agtgctcaat aaagagtaac   23880
tcctgcagcc tggtgtggtg gcccacacct gtaaccacaa catgttggga ggctcaacat   23940
gttggcagga ggattgcttg aggccaaggg tttgagacca gcctgggcaa cataaagaga   24000 ccccccgtctc tataaaaaat aataaaaact agctgagcat ggtgatacat gcctgtagtt   24060
ccagctactc aggaggctga ggtgggagga tcaacttgag ctcgggagtt ggaggctgca   24120
gtgagctacg atcacgccac tgccctccag cctgggcaac agagcaaggc cctttctctg   24180
gaataaaaaa aaaagagagg ctgggcgcag tggctcacac ctgtaatccc agctacttgg   24240
gaggctgagg caggagaatc acttgaacct gggaggtgga agttgcagtg agccaagatc   24300
gcaccattgc actccagtct gggcaacaag agcaaaactc tgtttcaaaa aaaaaaaaag   24360
agagagagag agagtagctg ccattttcaa tgttattgat aaagcaggtg ggtgtttctg   24420
aaaatgcacc agatgcagcc ttagactgga aggtgctgat gtgttactga gcctccagac   24480
aaagctggcg aacccaccgg ggcgagactt tatgacttga gaagctgtcc tatctatgag   24540
ggtccatgtt agggaatatt aaagaatagg attgggggca gtagctttcc tgtagcaagt   24600
gctagctatg tgccagatac tgggcaaagg agtctgcaga cgtctctcat ttcatcctca   24660
caatccatga ggcaggtatg actattcttc ccattatcca gagagggaaa acaagtcaca   24720
cggaagcaag tcacgcagca gagctaggat tggaacagaa gtgcctgcat cctccaacgc   24780
ctgcatccca acccgctgtg ctatgcctcc cgttgatgct ttcccatgtc tgccatttag   24840 cttttgctctg tgagtgaca agctgtacca gcggaaagag cctgtcatca gttctgtgca   24900
caccaaggtg aagggatag cagaggtgaa agaggagatc gtggagaatg gagtgaagaa   24960
gttggtgcac agtgtctttg acaccgcaga ctacaccttc cctttgcagg tgagcacctc   25020
gtagcattct cccaggctcg tcgctggtca ccgtcgccag ggcctagctc ccttcccta   25080 ggatctacag cctcactcca gaaaaaacgc tggtcctatt ttaaaagctc tgtgaacatc   25140
ccaactgaga aaacctaaaa attgcaaaac tgggtgagat ccaggagatg attctttgct   25200
ttatcaagtc ctacagggtt tctcaaaata gcctcatgtc ctggtgcatt gaaaacagga   25260
tttgattcac tcgcgcttga tttacccgca gcttttagaa cgcacagcca ccaagccagc   25320
```

```
aaggtctgcc gagattcaga aggacagaga actttctacc aaagagcacc agcccttcta   25380
gattgtgtag catttcatca acaaaaatga ctccaggaga ccattcttgg gtacattttt   25440
ccacaaagaa aggatgtaaa tgacaaaaag aagaaaggca tcggtcactg agagaaggcg   25500
tgtgacttct agatttgcaa gcagggaaaa tgaaagcaga attgccaaaa aagagaaatt   25560
aaagtagggt tgaggagtcc aaaaaacaga taaggggggcg agagggacaa aggggcacgt   25620
ttgcggcttg gggggctaaa atgctttgca aagacccatg aagcccaagc tgctgtttgt   25680
ttctaacagt gggtcattaa atcctgtga ttgctcaggt ggtgggatgc cctagtgccc   25740
tttcattaaa gtctgggaaa atctgaacag tgttgtgatg aaggctgctc ccctaccctc   25800
gcctccccag gtctcctgag tttcaattta atgagatttt tactgcgtaa aaaaaaaaa   25860
aaacaaaaac aaaaacatga aaaggctgct tttgagactg cattggtaaa tgactcttca   25920
acccattcaa acgctccttc actctccctc agctcagcag ggctgctcgt ccagctttga   25980
tattaagccc ttggcatatt ccaagttgcc cacagatcct gatttctaga agcttagaaa   26040
agtggagagg ttcgcccagc aagctggatt attataatta agtagttctc ttttcaaagg   26100
ccttgcattt tcttagcctc tccttctcca caggggaact cttcttcgt gatgacaaac    26160
tttctcaaaa cagaaggcca agagcagcgg ttgtgtcccg aggtaaggag gggacctgga   26220
gtggtgggtc aggtcttaag agttcctggg ggaggtgcaa gtcggaagaa gcagaaatgc   26280
ggaccctggg gtgtatttga gcccacaaat atctactgag cacctgcctc ttttgtgggg   26340
tagggctggg ctgagtggag gaagggagag aacacatggc agtgtctctc catggccacc   26400
agatctttgt ctgcctgcct cggtctctgg ttctagcact agggacccgt gcagacggca   26460
accctgctct ttctatctct ggctctcttc gcagcttatg acaatggtga ttcttggcat   26520
ttgcacaaca tttcacattt tacttgaggc tcacaatgac tttaggagaa aaatggcatt   26580
ttacaaacca gaacacagat tcagagatgt tgtgacttcc cccagggtca cacagcttgc   26640
tgcaggcaga gccagggtta ggacctgagt gtcctcactc acagcttctc ctaccatggt   26700
tcacagtgaa ctgtctgcag ggctggtctt ggaaaaccct ggcacacagc tctcttgctc   26760
attcatccac ttcttagagt ctcagcctct ccatcacgtg catgtgcccc catgactccc   26820
tgccaccacc ccagacaatc tttcccaact tggctttgct ctctccaaag agccgcctct   26880
ttctggaaga gcttcttccc tatcaaatca tatttgtttt attctgggct aggcacggtg   26940
gctcacacct ataatctcag cactttggga ggccaaggca ggaggatcac tggagcccag   27000
gagttcaaga ccagcctggg caacatagtg agaccttgtc tctaaaaaca aaacaaaaca   27060
aaaactgtat ttgtcctatt ctttacctca ccatcctgct ctctcctctt aaaccagctt   27120
ttcttctaag tttatctata ccagcgtgtt actgctaggc attacctgta actcccaacc   27180
tcccagcctc ccctctcagg taacgtaact gtgctgtacc agggaccatt tccaacactg   27240
accgttgcag cagcgctggt gatacccagc cagatcctcc actgatgagc aggaccagcc   27300
ctgccggtgg agttttgctc acgggcccac tctggcaaca aggtctagct tcctgagtgt   27360
ccaggacctc tgggcaaaag tgctgtcttt gagtacagtc tttgccatca tttgtaccca   27420
aattcagaac caagataaca ttcccttggt gtctatcttg ataacactcc gtctaaaagg   27480
agagcttcct acatttgttt tgtcctcatc accccttaac tgtccctgct gctcagatga   27540
aatctctgac agccaggcca gccaagccct ccttctgtc tcccttccca gcagtgttcc   27600
gtctccaatc cagtttgggg gcctgttttcc cttttgtccc atcctttggt catctctaca   27660
ccacactcta cctccatgta cacataaaga cacttttgga cttattgaga cttggaagaa   27720
```

```
aaagagttag gatagcccag agattaagag cctgggctca gaagctagac cgctaaaggt   27780
tcaaaactta aacttcttaa ctctgtgacc tcaggcaggt gactcttcac ctctctgtgc   27840
caagttgtgt gcatctgtaa aatggggctg agaacaaaac ctagctgttc ggattattga   27900
aacaaatgag tgaatacctg tgacacgctt aaaacaaggc atggtacatt ataagcactc   27960
aatgaatgtc agttgttatg attcaaatga catgttactc ctcagatagg atgtcactca   28020
gagtgactgg aacccaacag gttccatcga agcacttcca gcccagagag cacatgtgac   28080
tctttgggat tttaacttat gctccaggct ggtttgggct ggtctaattg ggcatttgcc   28140
tcctctctgc ccatcaacac ccctctatct cgggttgtct cggtaaatat gaccaagttc   28200
cagttacaca ccaacatgaa tagatatttg ctccatttat ctgtggctgc aaaacaaact   28260
accctgatca tggtgggctt aacacaagca ttttattaac tctcacagtt cagtggttga   28320
ctgagttcag ctggttggtt cttctgctgg tctcactagg gatctctcaa ggagctgcag   28380
tcagatggca gctggggttg gcatcccttg gagcctcaat tggcacccag ggatagctag   28440
acatctcttc ctctctggga acccctaaga gttaccctct cttcaaggtc tgtccgcatt   28500
gtctctccag cagggtagtc aaactttcta atagtggctc aggttcctca aaacaaaaca   28560
aaaaaataga agcttccagg ccttcttaag gcttaggcct ggaactggca acagcattcc   28620
ttctgctgct tctattggct ttgcagtcac agcacaggct cagcttcaga aagtagggga   28680
aacactccac ctctcaatgg agaaagtgac caagaatttg tggccatctt taatccatgc   28740
aacaatcaca aaagagaaga ttaaaacaaa actaatgtgc tgttttttaa aaaaaaaatt   28800
agaattcctt ttggagagca aaataaaact gatttctctt ctttcctgag attcatctcc   28860
agttgataat gaaaatgtaa cttttccatga gccacaatga atgatcacac attcattcct   28920
tccatgacta tcaagaccta ctatttgcca ggcacttggg ctgcaaagat atgaccttgg   28980
ctctgtattc aaagggttca taatctaatc tggggagtca caaggggagg agaccaacgg   29040
catgccatgt gacaaggcag cctgggaaat aaagagatca tgagagagtt tgaaaactac   29100
aagaaacatt cattgagcat gtactatgtg ctaaaccctt tcttttcata actcacttaa   29160
tcttcacaac aaccaggcaa gacaatttgt tggctgggca tgatggctca cgcctataat   29220
cccagcactt tgggaggtcg aggcaggcag atcatgaggt caggagttca agaccagcct   29280
ggccaagatg gggaaacacc gtctctacta aaaatacaaa aattagccag gcatggtggt   29340
gcgtgcctgt aatcccagct actcaggagg ctgaggcagg agaattgcct gaactcagga   29400
ggtggaggtt acagtgagcc aagatcacac cattgcactc tagcctggtc gacagagcaa   29460
gactctgtct ccaaaaaaaa aaaaaaaaa aaaaagaca aatctgttca ccctgctttt   29520
acagatgaac agtgagctgg ccaaggtctc tcagctagaa aatggtgcag ctactgctga   29580
accagatata cctgggtcca agacctaggt ccttgacctg aatcactgta gaagccacaa   29640
attgcacaga tgacaaagag cagaggccat tttcacacct atgtcatgtt ctggcttccc   29700
caagactggc catgaagcct gctccctaga aaacaggaag agaaatatgc ataaaccagg   29760
gcagctcatt tctctcttcc gtgttctgtc cttcagccct gagacccagc tggtctcatt   29820
ttcttgggcc aggcgagtgt cctggccaat gtctctcagt tccatgtgtc ctgctgagtc   29880
tccgcacctg tttgccctgc tcagtccttt cagccacagg gccacttgga ccaagccacc   29940
tgtcccccat cccagccagc atccctgaaa gtgatcccta gcttcccaga cctctgcttt   30000
tcccattttt atttatttgt attgggatat aattcacata ccataaaccc caccatttta   30060
aagtgtacat acggttcagt ggttttttagt ataatcacag agttgtgcaa ccatcaccac   30120
```

```
cgtctaattc cagaatatttt tcttccttct ttctttctttt ttttttcctt tctttctttc    30180 ttttctttc tttcttcctt ccttcctttc tttctttttt taggtggagt tttgctcttg      30240
tcacccaggc tggagtgcag tgacgcaatc tcagctcact gcaacctcca cctcccaggt     30300
tcaagtgatt ctcctgcctc agcccccta gtagctggga ttacaggcgc acaccaccac     30360
atctgataat ttttgtattt ttagtagaga cggggtttca ccatgttgag caggctggtc     30420
tcagactcct gacctcaggt gatctgcccg ccttggcctc ccaaagtgct gggattacag     30480
gcgtgataag ccacggcgcc cagccccag aacattttca tcacctacaa aggaaacccc      30540
aaatccagta gcagtcactc cccattctcc ccttcccctg tccctggcca cagtctactt     30600
tctgtctcta tagatgccta ttctggacat ttcctataaa tagaattgta tatggtgtgg    30660 cctttgtgt ctgtcttctt tcactcagca tcatgttctc caggtccatc catgttgtag      30720
cctgtgtcat tgcttcatcc ttcttatggc taaataagat tctgtgtatg aatgtaccac     30780
attttatttg tccattcatc cgtcagtggc cacttgcatg gtttccactt ttttggcgat     30840
tctgagtagt gctgctataa gcattcgtgt gcacattctg gtggatatcg aatcacttct     30900
ccacatctta gtaacacacg tcacttactc cccactctgt catccttcta tctgcagtat     30960
cccacccgca ggacgctctg ttcctctgac cgaggttgta aaagggatg gatggacccg      31020 cagagcaaag gtaccttctg tttcttttcc cgagaccct ggggtggatg gtctggcatc       31080
ttggtgacat ttgtgatgcc caggtcaggt cttcagcctc tgctctcagc tgccctcttc     31140
caccatcacc aagccatagg cgagtctgcc catgcttcgg ctctgtcccc agcagaccag     31200
ctgctgactg taaacatgac tccagttttc cagtgagaga agaagctcct aaaaacctag     31260
caggttcagg attctaatcg gtagaaaatt cacatggcct atagcatcat ctgagtattc     31320
taaactttcc ccctgaattt cctcaaaggt tgaggaccat gaacttttac ccccagggaa     31380
cctggcagca atacccatat taacctgcag aattttttt gttttttatt ttattttatt       31440
ttttaaacat tttttgcact gttttatttt gattttgatt ttgatttat ttatatctaa       31500 gtgcagtgct attgcgatac ctgcagaatt tctttatctc acattttaac ttaaaaaggc     31560
acagggcagc gagcgcagag gctggtgcct gtaatcccag cactttggga gggtgaggca     31620
gatggatgct tgaggtcagg ggttcgagaa cagcctggaa aacatggtga aaccccgtct     31680
ctactaaaaa tacaaaaatc agccagacat ggtggcacac gcttataatc ccagctactt     31740
gggaggctga gacgtgagaa tcacttgaac ctggaaggca gaggttgcag tgagccaaga     31800
tcatgccact gcactccagc atgggtgaca gagcgagacc cctttaaaaa aaaaaaaaa     31860 aggcacaggg caattttaaa aatactgcaa atagtaaaaa aaaaaaatc agtggttata     31920 atgcaaacac acacaaaaag gcatatgccc attactgcat tctactccat actgtatgtg     31980
tatttgagtt agtataaaag ttattttaac attgctcact atttaattaa ttctcccttg     32040
gaaactgatt aatcatcctg gcactccagg aagatgtgcc atgctgattt catggctttg     32100
cacatcctgg gcaggctgtg taccccttga gggacttgtg cccctttgag aggccatgtt     32160
ctagtccatt tatactaagt gagagcatac acctgttccg ctcccctcat gggcaccttt     32220
tcttataaag aaacaaaaga gccagcagaa tccacagtct ttctgtgttc tctctgatct     32280
ttattatgtt ttgcttgttt gccttgcctt gtgttcgttg tggttaggat gggcttgatg     32340
gaagctgaag ctgcgtgggt tggaaagcct ggtcaaagcc tagtctctcg cccgggttga     32400
gttaatgatg tccctcctgg agaacgtcct ctctgcagtt ctttcacatc tgtgttcta     32460 cgatgctttg acccctatag gaattcagac cggaaggtgt gtagtgcatg aagggaacca     32520
```

-continued

```
gaagacctgt gaagtctctg cctggtgccc catcgaggca gtggaagagg ccccccggtg  32580
agtcgcatgg ggagacagac acagtggccc tcagcggcga ccagatgagg ccttgccgag  32640
gctgcttggg ccttcccctc tcagcacagc cctgcaaagt cctgggtcct accggcttgg  32700
ggacccctgc gctctggatg cactgcttgg cacaaactag tatctctggg agggccatgg  32760
tggttggtaa actgttgtaa caatcctgta ccaactggta aatagctact accctgagca  32820
tccttgggtg tccctggccc cttccttccc ccagatcttc cagggtaccc ccagaccccc  32880
tcctgtagtg ccacagcagg atcccttctg acttgtcagt gtccatactg agtgatcaag  32940
gatagaaagg aaggagggag atggaaggga aggacgaagc gaggaaagag aaggggaagg  33000
ggaggaaaaa gcaaaagggg tgagggtaaa aggggggga aaggaagttt tctcagatta  33060
aatgcttaca atgacataca gatttggtgg tcccttgtat tgatgcttcg cttcaataca  33120
caaagtcaca atgttaaatc tcagaagcca caagggctga tgtatttcag cagagaatag  33180
ttagaaagac ctggattcaa ttcctaactc taacaccatt ttgctgtgtg tccttgggaa  33240
aatggcttaa cctctctgag tttcagtgtc ctcacctgta aaagcagaat aataatttca  33300
ccaacttcat agggctgttg taaggattaa atgagatgat acttgtacag ttattgtaag  33360
gtaagcccca tgcatgcctg gcttacacac acacacacac acacacacac acacgcacac  33420
acgcacacac acacacacac acacaatcta cccctagaag tgtggtggtt ctagaccagc  33480
actgtccaat tgaacttgat gcagtgatgg aaatttctgt atctgtgctg tccaataggg  33540
cagctactag gtacatgtgg ctattgagta catgaaatgc gactactgaa tttttgaaag  33600
agatgataga tgatagatag aaagatagat agatagataa atagataata gatagataga  33660
caggtagata gatagataga tagatagata gatagataga tagatagata gatagagttt  33720
tgctatgttg cccaggctgg ttttgaactc ctgggctcaa gcgatcctcc tgccttggcc  33780
tcccaaagtg ctggggttac aggtttgagc cattgctccc agcctgaatt tttaattaaa  33840
tttaaattta aatagccaca catgtctagt ggctaccata ttggacagcg cagttctaga  33900
ccgatgtgat tcaggatcat tccctcagca tcgtggggca aagagaaaac tgccccaagc  33960
tggcctgtag aaggctcagg cgaaggtttc ccaatgccgg gatgggggt gcgctcagca  34020
gcatcacccc ttatgattct caatcgctaa tagctccact caggttcatt tctcggtcag  34080
gggcatttct ttgggaatca cccagctctg ggagatacag cagcctccac tcaggtagtc  34140
cttgttcaag acaagcggcc cttgactgac tgcagtttca gttccagctc tgctatcaac  34200
tcactcatta aataaactgc atctccagtg tgcctgcctc tgggctggat tttgacgtga  34260
cctgggcaag caactccctg aacttcagtt tctcatatat tatatgaatt agctaagatg  34320
gttcgtttaa tcattcattc aacacatcca tcaccacgta gtaggtgtta gatatttatt  34380
tcatacgtaa ctacgcataa gagactttgc taagttttag gtaaaataca agtcccagat  34440
acggagcaag tctcaaccac tgtacatacc tgaatgtgta attacatcac tgtaagaggt  34500
gccacagtaa atgccactgg gtcttgtgtt agtccattct cacacaaaga actacctagc  34560
caggtgcggt ggctcacgcc tgtaatccca acactttggc aggctgaggc aggcggatca  34620
cttgaggtca ggagtttgat accagcctgg caaacatggt gaaaccccat ctctattaaa  34680
aaatgcataa attagccagg tgtggtggca cacgcctgta atcccggcta ctcgggaggc  34740
tgaggcagga gagtcgcttg aacccgggag gtggaggttg cagtgacccg agatcgcgcc  34800
actgcactcc agcctgggtg acagagtgag actccatctc agaaaaaaat aaaaataaaa  34860
ataaagaact acctgagacc aaatacttta cgaaaaaaaa gaggtttaat tgactcacag  34920
```

```
ctccacaggc ttaacaggaa gcctcaggag acttacaatc atggcagaag gcgaagggga   34980
agcaaacaca tcttaccatg atggagcagg aggcgagttt cggggatgt gccgcacact    35040 tttaaatgat cagatctcgt gagaactcac tcactatcac gagaacagca aggaggaagt   35100
ccgcccccat gattcagtca cctcccacca ggcccctcct ctggcacatg gggattacaa   35160
ttcaagatga gatttgggtg gggacacaga gccaaaccat atcagatctc aagaagggag   35220
aaattcttct tggaggagct ggaggggctt tgtggagagt ttcagaatgc tttgcccact   35280
aggtttgctg tatccatttc tcttcatgta cccaaagac caagccaaga aaccagaagc    35340
ctctggtccc actggcccat gggctccctc ggtccccacc gtcactaatg gccattttgc   35400
atgtctctct cccaggcctg ctctcttgaa cagtgccgaa aacttcactg tgctcatcaa   35460
gaacaatatc gacttccccg ccacaacta caccacgtaa gtgcccaggc tgcctggctg    35520
tcttagttat ctactgctga gtaataaatt atcccaaacc tcagaagcct gaaacaacaa   35580
acgcctattg tctcccacgg tttctgtggg tcaggaatct gggaatgact ttgctgcgtg   35640
gttctggctc aaggtctgtc aggttgtagc caagctgtca accagggctg cagtcatttc   35700
taggcttgac tggggctgga gaacactttt ccaagctctc acacagttgc tcgtgggaga   35760
gctcagttcc tcaccacgtg aacctcgccc tagaccactt gagtatcctt ggtatatggt   35820
ggctggcttc tcccagagca agtgacccaa gagagacaga gcaagcaacc aagagtataa   35880
ccaagatgga agccacagtc tttgggggga gaccccaaca cttctgccat atgccattgg   35940
tcacacagat caaccctggt ccagtgtgag aggccactgc ccaggggtcc caggaggcag   36000
tgatcatttg gggctttcat ggaacctctc caccacactg gctcactcct gggaaagaga   36060
cagatctgtt ttcaatcgag atgtttgttt gtttgctttt aattatgcac aggagaaaca   36120
tcctgccagg tttaaacatc acttgtacct tccacaagac tcagaatcca cagtgtccca   36180
ttttccgact aggagacatc ttccgagaaa caggcgataa ttttcagat gtggcaattc    36240 aggttggtgg tgctttgtac actgggatgt ggggctgtgt gtctagggat ggaggatgtc   36300
aaacagccaa gaggccgggc cactgggtct tcataatgtg gctcacattt actgagcatt   36360
tagtaaatcc acccgctgcg ctaaggtctt tacctacgct acctcgtcaa atcccaaaac   36420
aatccttatg agtgagagct acttggtgta ttcctttcct gtggctgctg tagcaagtta   36480
tcaaagctta gtggcttcaa acaacacata tttgcttatg ttgccagaga tcagaagttg   36540
gagatgattt tccctgagcc agggcggtgc tccctccggg actttaaggg agaatccagt   36600
tcctcagctt ttccaccttc tggagctgca ttccttgcat ttcttcaaag ccagcagcat   36660
aacatcttgc ctcagtggcc actttcactc cctatcctgt gtccaatctc cctttgcctc   36720
tgtcttacaa agagagagag catttacaag aggggggcatt taaggaccaa ctggataatc   36780
caggataatc tcccatctca agatccttca tttaggctgg gcacggtggc tcatgcctgt   36840
aatcccagca ctttgggagg ctgaggtggg tggatcacct gaggtcagga gttcaacacc   36900
agcctggcca acatggtgaa agcccatctt tactaaaaat acaaaaaaaa aaaaaaatag   36960
ccgggcatga ttgcaggctc ctgtaatccc agctactcgg gaggctgaga caggagaatc   37020
gcttgaacct gggaggcaga ggttgcagtg agccgagatc gcaccactgc actccagcct   37080
aggtgacaag agcgaaactc catctcaaaa aaaaaaaaaa aatccttcat gtattcgcat   37140
ctgcaaagag ctttccctag gggagtacta ggaggtaaag cagaaaagat atttgataga   37200
gtgccctgaa ttccagtcta ataagtttgg acttgatctt taatgggggc gtgggggca    37260 ttaaaggtgt ttgggtacag gagtggtctg ttgaaagttg tattttagga caatgagttt   37320
```

```
aacagtgatg tgtcccagac gggggtaggg agagtgagga gatgcgattg tggctgccac    37380
aataacactt gtgcgagtta ggtggggctg tacatatggt tcttcaatca gcattttcc     37440 tctaaaaacc ttaagcaatc ctggctatgc agggagatgt ctggcggttg cgtaactcac    37500
acccagcagc catagagact gtcccttgtt gatccttcag ggcggaataa tgggcattga    37560
gatctactgg gactgcaacc tagaccgttg gttccatcac tgccgtccca aatacagttt    37620
ccgtcgcctt gacgacaaga ccaccaacgt gtccttgtac cctggctaca acttcaggta    37680
actccaaggc ccaggtcaaa ctcacccagt ggctgaatcg cattcccagg aactggtgag    37740
actaattttg gtttccaagg caacaagatg aatgaaaaaa gactttctct aagaactagg    37800
tgataactga attttttcca taattttta aaattctcaa aagagatgca cactctttat     37860 tttttactt attttttttt ttttgaaatg gagtctcact ctgtcaccca ggctgaagtg     37920
cagtggcgcc atctcagtca ctgcaaactt ccgcctccca ggttcaagcg actctcctgc    37980
ctcagcctcc caagtagctg agattacagg cggatgcaca ctgtttataa aacaaaacta    38040
ttgggaaaca gaaaagcata gagggggatc aaaatcaccc ataattcccc taccctgaaa    38100
taatcaataa caaccctcgg gggaatttc tcatctgta ccaattattt catacagctc      38160
ctatgagata atagcatata tatatatatc ttgtggtatt ctgcagggtt tttcatacca    38220
cagccactca aaattctttg taaccatcac attaatgatc ataacattcc attttgtagg    38280
tgaacaaata acaactgcta caattcagga agtgttttct tttctttct tttcttttct    38340 tttttttttt tagatggagt cacactctgc ttgcccaggc tggagtgcag tggcatgatc    38400
tcagctcact gcaacctctg cctcctaggt ccaagcgatc ctcccacctc ccaagtttct    38460
gggaccacag gcatgtgcca ccacacccag ctaattttg tatattcagt agagatgggg     38520
tttcactgtg ttggccagtc tggtctcgaa ctcttgacct caagtgatct tcccaccttg    38580
gcttcccaaa gtgctaggat tacaggcatg agccactgtg cctggcccaa ggagggtttt    38640
ccatatacca agcactcccc atcgccatcc ctaaatctcc caacaaccct ggaaggaaga    38700
tattgtttct ggaagatgat ttgcccaaga cccacagctg atagtacatg ttgcataatt    38760
ctaacccacg tcactctgac cccacactca cactccatcc cttccttccc atctcatgat    38820
tttctcacct acgcctccat gattgaatat ttgagttgct tccagttttt ctattacaag    38880
taaccacagt gtgcatcttt gcacataaac ttctctttga attccaggtt acttccttag    38940
gataaatttc tagacttatt gaatcaaagg ttgtgaacat tttatcatat gcttttatt     39000 tttaaaaata tctatagtta taatgtttca ttttttttc tgagacagag tctcactctg     39060
tcacccaggt tggagtggac cgggtgcaat tatagctcac tgcaacctct gcctcccagg    39120
cccaagtgat cctcccacct cagcctcctg agtagctagg actacaggtg cacgccacca    39180
tgcccagcta atttttaaaa tttttttgta gagtcggggt ctcactatat tgcccaggct    39240
ggtctcaaac tcctggctca agcaatccgc ctgccttggc ctcctaaagc gttgggattg    39300
caggtgtaag ccactgcacc tggcctataa ttttcatttc taggattttt atttggtgct    39360
ttttcaaagt catctattat tgttccagtg agtcccattc ttaccttaag gatcctactc    39420
cttctgtcca ttctactgta tcattccttt cataccgacc tattatctga agtaacttgg    39480
gtgggagttc tcctcgtggg ctttgaaata ctgtcttcag tagaaaagat cttatgcaaa    39540
gttctgcatg tgctgtgtgt tatggagtat tccttatata ttactcaaag cagctccata    39600
aactggcagg cagcccctta aatgtgtttc tgtttctgtt ttttttgtttt ttggtctgca   39660 tgatgtttta aaacttgaga caggccaggt gcggtggctt atgcctgtaa tcccagcact    39720
```

```
ttgggaggcc aaggtgggag gatcacttga acccgggggt tgaggctag cctgggcaac    39780
ataggagac cccatctcta caaataataa tttttaaaac atcagccagg tgtgggggca    39840
tgcacctctg gtcccagcta ctcaggaggc tgaggcagga ggattgcttg aacctgggag   39900
gtggaggctg cagtgaaccg tggttgtgcc actgcactcc agcctgggtg acagagtgag   39960
acccttacat ggtggccact ggctggagct gagtatcagt ggtcctattt agaaaggggc   40020
tgggctttct ggttcatcac tgtccccgcc actccttagt gcttatacct ggcccacatc   40080
actcatttct gtcatctgcc tggcccctgt gtagacattt gagtttgaaa cccttgactc   40140
aaaggcaggc tgatgctttt tgcttcctct ggatcaatgg aatttcatcc aaggcaatgg   40200
aaccagctcc taattgtgat aacttttga tcatcccctg ccactgtgct gaataggctt    40260
atggccatta agaagagagg acaggatgaa tggtcccctg actgactgcc cttccagggt   40320
gttttttag ctgtcagcag aagcatgcgg ggcagtgtac caatcaggtg tcagcaagtg    40380
tccttccagc gactgagttg agcacaaaaa catctgctcc tggagagacc tgagccctct   40440
gaaggcctca gccagttatg atgttaatgt tcttttagaa caaagtggta gagcatttgt   40500
tgtctggaat gagcaccaga agaaatctct ggccaaaaat aaattgttga gggccgggag   40560
cagtggctta tacctgtaat cccaacactt tgggaggccg aagcaggagg atcacctgag   40620
gtcaggagtt cgagaccagc ctggccaaca tggtgaaacc ctgtctctcc taaaaataca   40680
aaaattagct ggacgtggtg acaggtgcct gtaatacagc tactgggagg ctgaggcagg   40740
gagaactgct tgaacccgga aggtggaggt tgcagtgagc cggggtcatg ccacttcact   40800
ccagcctggg caacagagca aagctctgtc tttaaaaaca acttaaataa ataaataaat   40860
tgttgaggtc tgatgagtaa gtggacaagt tattttccag cagacacaca aaagagaagg   40920
aaattacagg ttatacgagg tatttcagaa aatataactt tctaaaacat aggaagttga   40980
agaagttgat cacattacag aattctgttg tttagaaaat gacctgtggc gaaatgtcct   41040
tattcagtga ataggtgatt ccgcttatgc acgacctgtg tgaagtggat caggccaccc   41100
agaatgcacg acgcgcttct caggcccagc aggagtatgt gtctgtgtta atttcctgtg   41160
gctattatga ctaattgcca caaatgtggt ggcttaaaac aacagaaatt aatcttctta   41220
tagttctgga agccagaagt ttggaatcaa gatgtcagca gggccacact cgctctgatg   41280
ctctacggga gggtcctctc ttgcctcttc cagcgtctgg tggctccagg cattccataa   41340
ctttatagca gcgtcccaca aatctctgcc tccatcctca catggccttc tccactgtgt   41400
ctctatgtct tcaatctctt tttttttttt tttttttttt gaggcagggt ttcactccag   41460
tctcctagac tgaagtgcaa tggcgtaatt tcgggtcact gcaacctctg cctcccgggc   41520
tcaagcgatt tgatctctcc tttatcttat aaagatacta gtcattggat ttggggctta   41580
ccctaaatcc aggataatct catcttgaga tgtttaactt aattatatct gcaaacactg   41640
tatttccaaa taaggtcata tcacagccac tagggattag atacttgaac atatcttatt   41700
tgggggctca acccattcca gtgtacgaaa acactcttg ttcaaggccc gatgtttctc     41760
agggcatagc ccactgacta cctgcatcag aataatcact tggtacctgt actgaaaata   41820
cagactccta gaaacatctc agagcttctg caaccactct ttgagtgagg ggctcaggag   41880
tctgcctctg aacacactca ccccaagtga ttctttcttt cttctttttt tttttttttt   41940
tttgagatgg agtcttgctc tgtcccccag gctggagtgc agtggcgtga tctcggctca   42000
ctgcaagctc cgcctcccgg gttcacacga ttctcttgcc tcagcctccc gagtagctgg   42060
gactacaggt gcccgccacc acacccggct aattttttgc attttttagta cagacggggt   42120
```

```
ttcaccatgt tagccaggat ggtctcgatc tcctgacctc gtgatctgcc tgcctcggcc    42180
tcccaaagtg ctgggattac aggcatgagc caccgcgccc agccatcacc ccaagtgatt    42240
cttgccttca gtttaagagc cactgtaaca agactatgga agcagaaatt cacgtgctta    42300
ctacacaatg ttaaccttcc caggcaaacc aactcacata gggagataat gccaatccca    42360
gggcaggcag tggcaatgca tgcttgcttg cgaattaaaa aacaaatcac tgcctgggca    42420
cgttggctca tgcctataat cccaacaatt tgggaggctg aggtgggtgc atcacttgag    42480
ctcaggagtt caagccagcc tgggcaacac agtgagacca tcatctctat aaaaaaattt    42540
taaaaattag tcgggtgtaa tggtttgcac ctgtagtccc agctgccggg aggctgaagt    42600
gggaggatga cttgagcccg ggaggcggag gccacagtga gctgtgttca agccactgca    42660
ctccagcctg gatgacagag ccagatcctg tctcaaaaaa aacaaaaaca aacaacaaca    42720
acaaagataa atcactcaat acatcagcaa gagaaaaagc tctcttgaaa tagtcacatg    42780
caaagaaatt gaattccctc cagtcagaaa gagccactaa agtgcctgag aatatctgat    42840
cgatttcaat gtcaggtttt gagaggtttt ttaaaaacag tttcagatgt ttcttactat    42900
tttttggcag aacatctgcc atctgctttc ttctctccct acatcttgta actagacggt    42960
gaattaataa ctcagaaaaa ataaacatgt atatgtaact ttatctaaaa agaatcatca    43020
aagtgtggtg agaagaaggg gcagatttaa aagtttttatg aagcgttcat tttaagcctc    43080
cttaattatt cttgaaaaac aaaacacacc acttttcctg actgcagcac tggtgagggt    43140
tgcatatcac gggtgactgt gatgatttgt gcctggcgct taatttttaa agttagtact    43200
gagtgatgac agagagaggt caatgccact caaagaatat tttgtttgtt tgtttgtttg    43260
tttgtttgtt tgagaggcag tcttactctc tcactcaggc cggagtgcag tggtgtgata    43320
tcggctcact gcaacctctg cctcctgggt tcaagtgatt ctcctgcctc agcttcctga    43380
gtagctggga ttacaggcgt ctgccaccac atccagctaa ttttttgtatt tttagtagag    43440 atggggtttc atcatgttgg ccaggctggt ctcaaactcc tgacctgagg tgatctgcct    43500
accttggcct cccaaagtgc tgggattaca ggcgtgagcc attgcacctg gccaagaaga    43560
atttattaca tactttttccc aagagatggg gccacaccac accataccag gccacaccag    43620
gccatgccat gctagacagg gccacaggag gaagtaccag atccgctcaa gaggcagaat    43680
aaagggtaaa gaatggtcca gagctttatt gtgttactca gtggaagggc aaggcaggac    43740
tagggaaaca gcttagggtt aactactttg aataatgcca gtaggttctg agttacagga    43800
atggtctcta aatgtctggc cctcacccta cctgtcccta aggagaaata ctggagagtt    43860
agaaaaggag gtggttgagg gattggttgg agggtttgta atatgatttt cacaccctca    43920
caaaagctgg attgcagagg agatgtaaac aacttcagcc ttgggaggcc aagatgaaag    43980
gatggcttga agccaggagt tcaaggctgc aacaagctat gattacacca ctgcactcca    44040
gcctggttga aggaatgaga tcctgattct acaaaacatt tttgaaaaaa acttttttat    44100 tttttcttt cctttctttt tttttttttt ttttgagac agtcttgctc tgtcacccag    44160
gctagagcgc agtgatacga tctcggctca ctgcgacctc catctcctgg gttcaagtga    44220
ttctcgtgcc tcagcgtcct gagtagctgg gattacaggt gcctgccacc atgcacggct    44280 aattttgta ttttttagtag agatgggggtt tcaccatgtt gtccgggctg gtcttgaact    44340
cctgacctca gtgatccac ccgcctcggc ctcccaaagt gctgggatta caggtgtgag    44400
ccacggtgcc cgaccaaaaa atttaaaaat aaaaattagc cacctgtagt ggtgcacgct    44460
tgtagtccca cccagctact tgggaggctg aggtgggagt atcacttggg cccaggaggt    44520
```

```
ggaggctgca gtgagctctg atcatgccag tgctctccaa cctgggtgac agaacaagac    44580
cccacctcaa aacaaaacaa aacaaaaaac acaacttcag cctttagttt ggccctgtga    44640
ttaatgattg ccaaataggc atacacagaa tctaagaaaa tacagtttgc tgaggtgtgc    44700
ctgtctccag tccagtaatt agtatgcaag atttaccacc gcccactccc actttgttct    44760
agatgccaaa cctcttcttc cccttaagg aatagtcata ttgcttgaag tttttttttt    44820
ttaatttctc tgcttgttgt taatcctgtg ttggtttaaa atgtgcattt taatcttaag    44880
cgacaagctg attttccgtc actctgagat gatgcaggta caggtggtga catggggagg    44940
ggggactgct ctttggttcc aggtggttgg agagagaccc agggctttgg attgtgttcc    45000
ttcccctgcc acctgtcaca gagccagggg acagaccagg aggactagac aggccactgt    45060
tttggctttt ccttccataa aataccagca tttttttgcca gatgcagtgg ctcatgcctg    45120
taaccccaaa actttgggag cctgaggcag gcaaatcact tgagctcagg agttcgagac    45180
cagcctgggc aacatggcaa aagcccgtct ctacaaaaaa tacaaaaaat tagccgagca    45240
cggtggtgca tgcctgtagt cccagctacc tgggagactg aggtgggaga atcatctgag    45300
cctagcaagt caaggctgca gtgagtggta atcctgctac tgcactccag cctgggtgac    45360
agcgtgagac cctgtctcaa aaaaaaaaa aaaaaaaaa aaaaaaaaa ccccaaaacc    45420 cagcactttc aaagggatct tacaaataca gatccttttc ttcctacaga tacgccaagt    45480
actacaagga aaacaatgtt gagaaacgga ctctgataaa agtcttcggg atccgttttg    45540
acatcctggt ttttggcacc gtaagtctcg tttcccagct ccgggcaccg gcatcctatg    45600
actgtgtcct aattactgct gtggggcctc catggaggga agggttttgg tctcagcctt    45660
cagctagcac tgggcatttc gcacatggga taaaagagga agaagatgtt ctcgggctgc    45720
tgtccctgaa tgagtcatct gacgagtaca ggagtgggcc tggaaagcaa ttctaacatt    45780
cggctttaaa aatactctga tacttaacaa gagagagaaa gaaatctctc tgtaaaatag    45840
tttgtaagta acagaatcca attcaaattg gcttaagggg aaaaaaaaaa gttttgagtg    45900
ggcttttttg ggttcacgta actgaaaaaa tccagggggtt atttttaagc tacaagcatg    45960
gttggatcca ggtgctcaaa caacaacatc atcatcaaga acttgccacc ttccgtgtct    46020
tatatacgtc ctccttggtc ttggcagcca tctctctatg aaggtatcag gcagcacctt    46080
cgatctgacc agtttagcaa cctcagtgaa aagaaaacac ctctttgcca gaaggttcag    46140
caaaggtctc agacaaatgt cattggctct gattggccca ctatggatga catgcccact    46200
gctgaactaa tcactgtgac cagggtcatg ccatactccc agtggttagt gtcgaaccag    46260
ccctaaccta gcccaggggc cagcagagag gccaacaccc cagccccttc aacacacaca    46320
cacacacaca cacacacaca cacacacaca cactacatgg actgaaaaga aaattggagt    46380
gttgccttct gaagatggaa ggaaaagatg ccagctatgc aaaaatcaac atatcccacg    46440
acatcctgtc caagagcatg ttatctatgt aacacagtga taagcaggac tagaagcaat    46500
aagatatagc tgagagaatg caaagaccgc tgggaataaa aaccacaagg ctgggccggg    46560
cacggtggct catgcctgta atcccagctc tttgggaggc tgaggcaggt ggatcacaag    46620
gtcaggagct caagaccagc ctggccaaca tggtgaaacc ctgtctctac taaaaatgca    46680
aaaaattagc tgggcgtggc ggtgggtact tgtaatccca gctacttggg aggctgaggc    46740
aggagtatct cttgaaccca ggaggcggag cttgcagtga gccgagattg cgccactgca    46800
ctccagcctg gcaaaagtg cgagactctg tctcaaaaaa aaaaaaaaaa aaaaaccccac    46860 gaggccaccc agacattcct tccctctgct tctgaagtaa tgtcaaacct tttggaggag    46920
```

```
aagcttgtct gaaaccctca ccttgtatgg agaaatgata gcccttcagt gggtctcccc    46980
ttaatgtgtg ggccccagtg cttgctcatg taaaacctt  atgggtccaa gcacaccctg    47040
cacggctgaa gcaggatgcc tgagagtcag tttcagtctg cgtagtctct gcctcagcca    47100
gcacttgaac gcatctatcc aagtcacagc atgaggctcc gctccctgat agaaccaaca    47160
attgcacgtt gaagcaaaag agcgttgctc tgaatttcac ctgagtaaac tctcccactc    47220 tgttttagg  gaggaaaatt tgacattatc cagctggttg tgtacatcgg ctcaaccctc    47280
tcctacttcg gtctggtaag agattctctt ttccatgctt taggaaaatg gtttggagaa    47340
ggaagtgact aacgcagcgc ttgtctgcat tctccccagg ccgctgtgtt catcgacttc    47400
ctcatcgaca cttactccag taactgctgt cgctcccata tttatccctg gtgcaagtgc    47460
tgtcagccct gtgtggtcaa cgaatactac tacaggaaga agtgcgagtc cattgtggag    47520
ccaaagccgg tgaggccgct gtgttcacag gacaccaaga catggagaga ttccatgaaa    47580
tcactcagaa atgcacgaaa attaggccca aatcacaggc ttcatcctgt agtggatacg    47640
tcgctgggtt ctaccccgat caaccaactc tcagataaat ttttggtct  tagagaagaa    47700 tggaaacaaa aatggagggg caagatagag ggaaggcaaa tttttatgtc taggacttgc    47760
caattttgtc atttatttat ttatttattt atttatttat ttatttattt atttattttc    47820
agatggagtc ttgctctatc acccaggctg gagtgcagag gcatgatctc ggctcactgc    47880
agcctctgcc tcccaggttt aagtgattct cctgcctcaa cctcccaagt agctgggact    47940 acagggcac  accaccacac ctggctaatt tttgtatttt tagtagagat ggtgtttagc    48000
tatgttggcc aggctggtct caaactcctg acttcaaatg atccaccac  tcggcctccc    48060 acagtgctgg gattataagt gtgagccact gagcccagcc tgttttgtca tttattaaat    48120
tggtatagcc aaaaaagaaa aagaaaaga  aaaataacaa cttggagaa  caatttggca    48180 gtgactaatg tttaaatggg acatacttta cagcctggca ttttcagttc tccatacctg    48240
ccctagagaa acactcacat gagtacccgc agtacatgag tacaagatgt tcaaagcagg    48300
attgtttatt aaattatcaa taatatatga ttattaacag tgaagaaata gcatctaacc    48360
aaatatccaa caggtgaatg gtgaaactat ggtaaatcca tagaaaggaa taccaggcac    48420
cagcttaaaa aaatgagata gataataata atggcaaaca tttacacagc acttctaaat    48480
gctttatcta ttaactcaat cttcacaaca acctgatgta gacagatgct actattatct    48540
ctttctatat atgaggaaat tgagccacag aaaggttaaa taattggccc aaggctgggc    48600
acagtggctc acgcctataa tcccaacact ttgggaggcc gaggcaggca gatcacttga    48660
ggtcaagagt tcgagaccag cctggccaac atggtgaaac cccatctcta ctaaaaatac    48720
aaaaattagc caggcgtggt ggtgcatgcc tgaagtccca gctactggg  aggctgaggc    48780 aggagaattg cttgaacctg gtaggcagag gttgcagtga gctgagatca tgccattgca    48840
ctccagcctg agtgacagag ggaaactctg tctcaaaaaa aaaaaaaaaa aaaaaattat    48900
aggacttgac aagagcagat ctccaagaca ttttgttaaa agaaaaaaag caaactgtag    48960
aacaatatat gttatatgat atataggtta aaaaaaaatc actagacaca gaagctaatc    49020
tgtatatttt ctgcatgtat attctatata tacacaagtg tacacacaca cacacataca    49080
tatacatatg tgtgggtgta tatatgtaca caaaattgta ccagtggctg cttctggaaa    49140
ggagcttagg gtgggggagt aggagtagtc aaagagattt tagcgtcatc tgtattgttt    49200
tgatttgatt aattcagact ttatcaagca ggtcctctgc gttcaactcc atgattttcc    49260
ccaaagataa atctctggta cctaaaaaca aagacgattg gctagacgtg gtggctcacg    49320
```

```
cctgtagtcc cagtactttg ggaggccaag gagggtggat cacctgaggt caggagttca    49380
aaaccagcct ggccaacatg gagaaacccc gtctctacta aaaatacaaa aaattagcca    49440
ggcatggtgg cgcatgcctg taatcccagc ttctctagag gctgaggcag gagaatcgct    49500
tgaacccagg aggtggaggt tgtggtgagc caggattgca ccattgcact ccagcctggg    49560
caacaagagc gaaactccgt ctcaaaaaaa aaaaaaaaac aaagacgatt tctttgtctt    49620
tccctcatcc aagaacatga ttgtcctgtt ccagcagctg atgcacaatt cactgtccat    49680
tgtatatgca ttcacaattt gaaataaaag ttcatctttg cagctaaaac taatcaccac    49740
ttcatggccc aagatgagat gaaatttaac aaacatgtaa ataatttaag ttgcaatagt    49800
acaaatttct ggagatactg aatctagagt tactgaaatt gacagaatac aacaaagaaa    49860
ttttatgcag caactggggg gtccaatgta aaaacattaa gcagtaagct gtggctgtgt    49920
tgaatttaca agttaagatg catggggttc cgcctggcgt ggtggctcac tcctgtaatc    49980
ccagcacttt ggtaggccaa ggcgggcgga tcaactgagg tcaggagttc aagaccagcc    50040
tgaccaacat ggagaaaccc cgtctctact aaaaatacaa aattagctgg gcatgatggt    50100
gcatgcctgt aatcccagct actcaggagg ctgaggcagg agaatcattt gaacctggga    50160
ggcggaggtt gcagtgagcc aagatcatgc cattgcactc cagcctggca acaagagtga    50220
actccaactc aaaaaaaaaa aaaaaaaaaa agcatgggt tccatttctg atttatcttt    50280
agactcagaa atcattaatt cttggttaat gagagttttg agccagcttg ttcaatagtc    50340
tatcatttgg caaataggaa ttacagttgc ctttagatag gcaattcttg ataattctgt    50400
acaaaaatgg gtaaactttc aaaccatctt ttcctagaca ttaaagtatg tgtcctttgt    50460
ggatgaatcc cacattagga tggtgaacca gcagctacta gggagaagtc tgcaagatgt    50520
caagggccaa gaagtcccag taagttaaat cattttgtct ttttttttttt tttaagaaaa    50580 tttactgtta aatataaaca catctagaaa cttgtacaaa tcaaaactga tggattttaa    50640
caaagtaaac atactcatat aaccggcact cagattaaac aattgaaaat tactagcagg    50700
agtccctttt atgcccccct ccaatcacta ccctctcttt ctccttttt aattttttaaa    50760 atttggctgg gcacggtggc tcacacctgc aatcccagca ctttgggagg ccaaggtggg    50820
tggatcactt gaggtcagga gttcgagacc aacctagcca acatggtgaa acctcgtctc    50880
tactaaaaat acaaaaatta gccgggtggt gtggtggcac acatgtaatc ccagctactc    50940
agaagactga ggcaggagaa ctgcttgaac ccaggaggtg gaggttgcag tgagccgaga    51000
ttgtgccatt gcactccagc ctgggtgaca gagcaagact ccatctcaaa aaaaaaaag    51060 aaaaaatgt atattcttaa attacaaacg aggtctcact atgttgtcca ggctggtctc    51120
aagcagtcct cccacctcag ctgtaccaag cccaccaact gccctctctt aaaagtagtc    51180
attatcctgt ttccaaagat taatttact ttggctagaa ttttctaaaa actgaatcac    51240
gtagtatgta agcggtatat acgcggttga gtgtctggct tcctttactc aacattattt    51300
ttgtgagagt tgttcatgat gccatgtata gttcattctc attgtataat tctgttttat    51360
aaatatccaa cttattcagc catcctactg ttgatggaca tttgggtagt gtccagtttg    51420
gggctaatgc caataacgct gctatgctca acatatggca ctctactgga cagttaccta    51480
agagtggaat tgctgagtca taaggcagac atatgttcgg ttttaggaga tactaacaaa    51540
cggtgctgaa aaatggttgt tcacatttgc actctcccca gcagttctgg ttgctgggca    51600
tcttcaattt cctagggctg aattaccaca aactaagtgg cttaaaacaa cagaaatggc    51660
caggcatggt ggctcatgcc tgtaatctca gcactttggg aggctgaggc aggcagatca    51720
```

```
cctgaggtca ggagtttgag accagcctga ccaacatgga gaaacccat  ctctactaaa  51780
aatacaaaaa aatagccagg catggtggca ggcgactgta gtcccagcca ctcaggaggc  51840
tgaggcagga gaatggcatg aacctgggag gcagagcttg cagtgagcca agattgcacc  51900
actttgagag gccaaggtgg gcggatcacc tgaggtcagg agttcaggaa cagcctggcc  51960
aacatggcga aaccctgtct ctattaaaaa tacaaaaatt agccaggcgt ggtggtgcac  52020
acctgtaatc ccagctactc aggacgctga ggtgggagaa ttgcttgaac ctgggaggca  52080
gaggctgcgg ttagctgaga tcacacctct gcactctagc ctgggcaaca gaacaagctc  52140
catctaaaaa aaaaaaaaaa aaaagtcttt ttctgctcct tttgaaatat cagtgagttt  52200
tcttcttttt ttctgttagt tgaattgtac tgattgattt tcaaatatta agccaaactt  52260
gcattcctga agtaaactca atttgaatgt gttgtactat tctttgtatt tattgctgaa  52320
ttccattcac taatatttag gattttttaca tctcttcttg agaaagactg accaaagtgt  52380
ttccattctt gtaatgttct tgttggattt gtgtatgaag tgaactacag tcatgcatca  52440
cttaatgatg gggatatgtt ctgaaaaacg catcagtagc tgattctgtg gttgtctgaa  52500
tatcatggac tctattttaca caaacctaaa tagaatagcc tattatactt aggttatatg  52560
gtgtagtcta ttgctcctag gctgcaaacc tgtacagcat gttactgtac tgaatacggt  52620
aagcaactgt aacagaatgg taagatttgt atatctaaat atagaaaagg tacagtgaaa  52680
atatgatata aaagcttaaa aatggtacat ctgcataggg cacttaccat gaatggagct  52740
tgtaggactg aaagttgctc tgggtgagtc agtgagtagt gagtgaatgt gaaagcctag  52800
gttgttaccg tgcactacag tagacttcat aaacactgta cacttaggct acactaaatt  52860
tacttcaaaa tatttatctt tcttcaataa taaattaatc ttagcttact gtgactgttt  52920
tactttataa attttttaaat tttttaaact ctgtacagtg gtataaaaat attttctttc  52980
tcaccgggag tggtggctca tgcctgtaat cccatcactt tgggaggccg aggcaggcgg  53040
atcacaagat caggagattg agaccatcct ggccaacatg gtgaaacccc atctctacta  53100
aaaatacaaa aaaatagcca ggcatggtgg caggcgcctg tagtcccagc tactcgggag  53160
gctgaggcag gagaatggcg tgaacccagg aggcagagct tgcagtgagc caagatcaca  53220
ccactgcact ccagcctggg cgacagagca agactccatc tcaaaaaaaa aaaaattctt  53280
tctctatatc cttattctat atactttttt ctattttttaa cattttttat ttttattttt  53340
acttttttaaa tattttttgtt aaaaactaag tcatggccgg gtgcagtggc tcacgcttgt  53400
aatctcagta ctttgggagg ctgaggtggg tggatcactc gaggtcagga gttcaacacc  53460
agcctggcca atatggtgaa actctgtctc tactaaaaat ataaaaatta gccgggtgtg  53520
gtggtgcacg cctgtagtcc cagctactca ggaggctgag gcagaagaat cgcttgaacc  53580
caggaggcgg aggttgcagt aagccaagat catgccactg cactccagcc tgggagacag  53640
agcaagactc catctcaaaa aaaaaaaaca acaacaaaca cacacacaca cacacacaca  53700
aaaaccattt ccaatagtgc taagtcctat gaagaatgtg gaataccaca gtgtgataag  53760
ggaatcatgt gggagaaaag ctgctagata gggtggtcag gacaagaggt gacatctcaa  53820
cagaggcctg gcttttctga atttcatttt ccaaaatctg taaaataggc caggtgcagt  53880
ggctcatgcc tgtaatccca gcactttgag aggctgaggc aggtggatca cctgaggtca  53940
ggagttccaa acaagcctgg ccaacatgtt gaaatcctgt ttctactaga aatacgaaag  54000
aattagctgg gcatggtggc atgcacctgt aataccagct acttaggagg ttaaggcatg  54060
aaaattgtct gaacctggga ggtgaaagtt gcagtgagcc aagatcacac cactgtgctc  54120
```

```
cagcctgtgc gacagagtga gaccctctct caaaaaaaaa aaaaaaatct gtaaaataaa   54180
gacaaggata cattatctca caagcgtctt caaaggcctg aatgaggcaa tgcttacaga   54240
acacatgcat ggtcctgata tctacaccta ataaatgacg gctactataa atcatgtaat   54300
attaaacgta actttataag ttaataaaat taaagaacct agaacctgag ggcttgtcat   54360
ggctaatagg tttggaaact tgcttttca gagacctgcg atggacttca cagatttgtc   54420
caggctgccc ctggccctcc atgacacacc cccgattcct ggacaaccag aggagataca   54480
gctgcttaga aaggaggcga ctcctagatc cagggatagc cccgtctggt gccagtgtgg   54540
aagctgcctc ccatctcaac tccctgagag ccacaggtgc ctggaggagc tgtgctgccg   54600
gaaaaagccg ggggcctgca tcaccacctc agagctgttc aggaagctgg tcctgtccag   54660
acacgtcctg cagttcctcc tgctctacca ggagcccttg ctggcgctgg atgtggattc   54720
caccaacagc cggctgcggc actgtgccta caggtgctac gccacctggc gcttcggctc   54780
ccaggacatg gctgactttg ccaacctgcc cagctgctgc cgctggagga tccggaaaga   54840
gtttccgaag agtgaagggc agtacagtgg cttcaagagt ccttactgaa gccaggcacc   54900
gtggctcacg tctgtaatcc cagcgctttg ggaggccgag gcaggcagat cacctgagat   54960
cgggagttgg agaccgcct ggctaacaag gcgaaatcct gtctgtacta aaaatacaaa   55020
aatcagccag acatggtggc atgcacctgc aatcccagct actcgggagg ctgaggcaca   55080
agaatcactt gaacccggga ggcagaggtt gtagtgagcc cagattgtgc cactgctctc   55140
cagcctggga ggcacagcaa actgtcccca aaaaaaaaaa aagagtcctt accaatagca   55200
ggggctgcag tagccatgtt aacatgacat ttaccagcaa cttgaacttc acctgcaaag   55260
ctctgtggcc acattttcag ccaaagggaa atatgctttc atcttctgtt gctctctgtg   55320
tctgagagca aagtgacctg gttaaacaaa ccagaatccc tctacatgga ctcagagaaa   55380
agagattgag atgtaagtct caactctgtc cccaggaagt tgtgtgaccc taggcctctc   55440
acctctgtgc ctctgtctcc ttgttgccca actactatct cagagatatt gtgaggacaa   55500
attgagacag tgcacatgaa ctgtctttta atgtgtaaag atctacatga atgcaaaaca   55560
tttcattatg aggtcagact aggataatgt ccaactaaaa acaaacccctt ttcatcctgg   55620
ctggagaatg tggagaacta aaggtggcca caaattcttt gacactcaag tcccccaaga   55680
cctaagggtt ttatctcctc cccttgaata tgggtggctc tgattgcttt atccaaaagt   55740
ggaagtgaca ttgtgtcagt ttcagatcct gatcttaaga ggctgacagc ttctacttgc   55800
tgtcccttgg aactcttgct atcggggaag ccagacgcca tttaaaagtc tgcctatcct   55860
ggccaggtgt ggtggctcac acctgtaatc ccagcacttt gggagaccaa ggcgggcgga   55920
tcacttaaag tcaggagtcc aagaccagac tcgccaacat ggtgaaaccg tatctctaat   55980
aaaaatacaa aaattagctg ggcatggtgc gggcacctgt agtcctagct atcaagaggc   56040
tgagacagga gaaacacttg aacctgggag gtggaggttg cattgagctg agatcgtgcc   56100
actgcactcc aggctgggtg acagagcgag actccatctc aaaaaaaaaa aaaaagaaa   56160
aaaaaatgt ctgcctatcc tgagactgcc ctgctgtgag gaagcccaag cagtcacgtg   56220
gacagtgcct gaccagcccc agctttcaag ccatccaagc ccagtcacca aacatgagag   56280
agaagaagcc ttcaggtgat tctggactcc actaacatat gactgatacc gcatgataca   56340
tcccaagtga gaactgcccc ataaatccag aaaaccacat tgctatctta agtccctaag   56400
tttggggctt atttgttcca cagcaacagg taactggaac agagggcaag cctgatgaat   56460
```

```
gggcacacag actcagccca taccttccct ggttctaatg ttctcaggga gcccggacca   56520
accctgggag cctcaggaac ttaggtttcc actggacagt tctagaaggg ctatagacca   56580

<210> SEQ ID NO 2
<211> LENGTH: 2164
<212> TYPE: DNA
<213> ORGANISM: Homo sapiens
<220> FEATURE:
<221> NAME/KEY: CDS
<222> LOCATION: (79)..(1863)
<223> OTHER INFORMATION:

<400> SEQUENCE: 2
ggcacgaggg cttgctgtgg ccctgtcagg aagagtagag ctctggtcca gctccgcgca   60
gggagggagg ctgtcacc atg ccg gcc tgc tgc agc tgc agt gat gtt ttc    111
                    Met Pro Ala Cys Cys Ser Cys Ser Asp Val Phe
                     1               5                  10 cag tat gag acg aac aaa gtc act cgg atc cag agc atg aat tat ggc   159
Gln Tyr Glu Thr Asn Lys Val Thr Arg Ile Gln Ser Met Asn Tyr Gly
         15                  20                  25 acc att aag tgg ttc ttc cac gtg atc atc ttt tcc tac gtt tgc ttt   207
Thr Ile Lys Trp Phe Phe His Val Ile Ile Phe Ser Tyr Val Cys Phe
     30                  35                  40 gct ctg gtg agt gac aag ctg tac cag cgg aaa gag cct gtc atc agt   255
Ala Leu Val Ser Asp Lys Leu Tyr Gln Arg Lys Glu Pro Val Ile Ser
 45                  50                  55 tct gtg cac acc aag gtg aag ggg ata gca gag gtg aaa gag gag atc   303
Ser Val His Thr Lys Val Lys Gly Ile Ala Glu Val Lys Glu Glu Ile
 60                  65                  70                  75 gtg gag aat gga gtg aag aag ttg gtg cac agt gtc ttt gac acc gca   351
Val Glu Asn Gly Val Lys Lys Leu Val His Ser Val Phe Asp Thr Ala
                 80                  85                  90 gac tac acc ttc cct ttg cag ggg aac tct ttc ttc gtg atg aca aac   399
Asp Tyr Thr Phe Pro Leu Gln Gly Asn Ser Phe Phe Val Met Thr Asn
             95                 100                 105 ttt ctc aaa aca gaa ggc caa gag cag cgg ttg tgt ccc gag tat ccc   447
Phe Leu Lys Thr Glu Gly Gln Glu Gln Arg Leu Cys Pro Glu Tyr Pro
         110                 115                 120 acc cgc agg acg ctc tgt tcc tct gac cga ggt tgt aaa aag gga tgg   495
Thr Arg Arg Thr Leu Cys Ser Ser Asp Arg Gly Cys Lys Lys Gly Trp
     125                 130                 135 atg gac ccg cag agc aaa gga att cag acc gga agg tgt gta gtg cat   543
Met Asp Pro Gln Ser Lys Gly Ile Gln Thr Gly Arg Cys Val Val His
140                 145                 150                 155 gaa ggg aac cag aag acc tgt gaa gtc tct gcc tgg tgc ccc atc gag   591
Glu Gly Asn Gln Lys Thr Cys Glu Val Ser Ala Trp Cys Pro Ile Glu
                 160                 165                 170 gca gtg gaa gag gcc ccc cgg cct gct ctc ttg aac agt gcc gaa aac   639
Ala Val Glu Glu Ala Pro Arg Pro Ala Leu Leu Asn Ser Ala Glu Asn
             175                 180                 185 ttc act gtg ctc atc aag aac aat atc gac ttc ccc ggc cac aac tac   687
Phe Thr Val Leu Ile Lys Asn Asn Ile Asp Phe Pro Gly His Asn Tyr
         190                 195                 200 acc acg aga aac atc ctg cca ggt tta aac atc act tgt acc ttc cac   735
Thr Thr Arg Asn Ile Leu Pro Gly Leu Asn Ile Thr Cys Thr Phe His
     205                 210                 215 aag act cag aat cca cag tgt ccc att ttc cga cta gga gac atc ttc   783
Lys Thr Gln Asn Pro Gln Cys Pro Ile Phe Arg Leu Gly Asp Ile Phe
220                 225                 230                 235
```

```
cga gaa aca ggc gat aat ttt tca gat gtg gca att cag ggc gga ata         831
Arg Glu Thr Gly Asp Asn Phe Ser Asp Val Ala Ile Gln Gly Gly Ile
                240                 245                 250 atg ggc att gag atc tac tgg gac tgc aac cta gac cgt tgg ttc cat         879
Met Gly Ile Glu Ile Tyr Trp Asp Cys Asn Leu Asp Arg Trp Phe His
            255                 260                 265 cac tgc cat ccc aaa tac agt ttc cgt cgc ctt gac gac aag acc acc         927
His Cys His Pro Lys Tyr Ser Phe Arg Arg Leu Asp Asp Lys Thr Thr
        270                 275                 280 aac gtg tcc ttg tac cct ggc tac aac ttc aga tac gcc aag tac tac         975
Asn Val Ser Leu Tyr Pro Gly Tyr Asn Phe Arg Tyr Ala Lys Tyr Tyr
    285                 290                 295 aag gaa aac aat gtt gag aaa cgg act ctg ata aaa gtc ttc ggg atc        1023
Lys Glu Asn Asn Val Glu Lys Arg Thr Leu Ile Lys Val Phe Gly Ile
300                 305                 310                 315 cgt ttt gac atc ctg gtt ttt ggc acc gga gga aaa ttt gac att atc        1071
Arg Phe Asp Ile Leu Val Phe Gly Thr Gly Gly Lys Phe Asp Ile Ile
                320                 325                 330 cag ctg gtt gtg tac atc ggc tca acc ctc tcc tac ttc ggt ctg gcc        1119
Gln Leu Val Val Tyr Ile Gly Ser Thr Leu Ser Tyr Phe Gly Leu Ala
            335                 340                 345 gct gtg ttc atc gac ttc ctc atc gac act tac tcc agt aac tgc tgt        1167
Ala Val Phe Ile Asp Phe Leu Ile Asp Thr Tyr Ser Ser Asn Cys Cys
        350                 355                 360 cgc tcc cat att tat ccc tgg tgc aag tgc tgt cag ccc tgt gtg gtc        1215
Arg Ser His Ile Tyr Pro Trp Cys Lys Cys Cys Gln Pro Cys Val Val
    365                 370                 375 aac gaa tac tac tac agg aag aag tgc gag tcc att gtg gag cca aag        1263
Asn Glu Tyr Tyr Tyr Arg Lys Lys Cys Glu Ser Ile Val Glu Pro Lys
380                 385                 390                 395 ccg aca tta aag tat gtg tcc ttt gtg gat gaa tcc cac att agg atg        1311
Pro Thr Leu Lys Tyr Val Ser Phe Val Asp Glu Ser His Ile Arg Met
                400                 405                 410 gtg aac cag cag cta cta ggg aga agt ctg caa gat gtc aag ggc caa        1359
Val Asn Gln Gln Leu Leu Gly Arg Ser Leu Gln Asp Val Lys Gly Gln
            415                 420                 425 gaa gtc cca aga cct gcg atg gac ttc aca gat ttg tcc agg ctg ccc        1407
Glu Val Pro Arg Pro Ala Met Asp Phe Thr Asp Leu Ser Arg Leu Pro
        430                 435                 440 ctg gcc ctc cat gac aca ccc ccg att cct gga caa cca gag gag ata        1455
Leu Ala Leu His Asp Thr Pro Pro Ile Pro Gly Gln Pro Glu Glu Ile
    445                 450                 455 cag ctg ctt aga aag gag gcg act cct aga tcc agg gat agc ccc gtc        1503
Gln Leu Leu Arg Lys Glu Ala Thr Pro Arg Ser Arg Asp Ser Pro Val
460                 465                 470                 475 tgg tgc cag tgt gga agc tgc ctc cca tct caa ctc cct gag agc cac        1551
Trp Cys Gln Cys Gly Ser Cys Leu Pro Ser Gln Leu Pro Glu Ser His
                480                 485                 490 agg tgc ctg gag gag ctg tgc tgc cgg aaa aag ccg ggg gcc tgc atc        1599
Arg Cys Leu Glu Glu Leu Cys Cys Arg Lys Lys Pro Gly Ala Cys Ile
            495                 500                 505 acc acc tca gag ctg ttc agg aag ctg gtc ctg tcc aga cac gtc ctg        1647
Thr Thr Ser Glu Leu Phe Arg Lys Leu Val Leu Ser Arg His Val Leu
        510                 515                 520 cag ttc ctc ctg ctc tac cag gag ccc ttg ctg gcg ctg gat gtg gat        1695
Gln Phe Leu Leu Leu Tyr Gln Glu Pro Leu Leu Ala Leu Asp Val Asp
    525                 530                 535 tcc acc aac agc cgg ctg cgg cac tgt gcc tac agg tgc tac gcc acc        1743
Ser Thr Asn Ser Arg Leu Arg His Cys Ala Tyr Arg Cys Tyr Ala Thr
540                 545                 550                 555
```

-continued

```
tgg cgc ttc ggc tcc cag gac atg gct gac ttt gcc atc ctg ccc agc    1791
Trp Arg Phe Gly Ser Gln Asp Met Ala Asp Phe Ala Ile Leu Pro Ser
            560                 565                 570 tgc tgc cgc tgg agg atc cgg aaa gag ttt ccg aag agt gaa ggg cag    1839
Cys Cys Arg Trp Arg Ile Arg Lys Glu Phe Pro Lys Ser Glu Gly Gln
        575                 580                 585 tac agt ggc ttc aag agt cct tac tgaagccagg caccgtggct cacgtctgta   1893
Tyr Ser Gly Phe Lys Ser Pro Tyr
            590                 595 atcccagcgc tttgggaggc cgaggcaggc agatcacctg aggtcgggag ttggagaccc   1953
gcctggctaa caaggcgaaa tcctgtctgt actaaaaata caaaaatcag ccagacatgg   2013
tggcatgcac ctgcaatccc agctactcgg gaggctgagg cacaagaatc acttgaaccc   2073
gggaggcaga ggttgtagtg agcccagatt gtgccactgc tctccagcct gggaggcaca   2133
gcaaactgtc ccaaaaaaaa aaaaaaaaaa a                                  2164
```

<210> SEQ ID NO 3
<211> LENGTH: 595
<212> TYPE: PRT
<213> ORGANISM: Homo sapiens

<400> SEQUENCE: 3

```
Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
    130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255
```

```
Tyr Trp Asp Cys Asn Leu Asp Arg Trp Phe His His Cys His Pro Lys
                260                 265                 270
Tyr Ser Phe Arg Arg Leu Asp Asp Lys Thr Thr Asn Val Ser Leu Tyr
            275                 280                 285
Pro Gly Tyr Asn Phe Arg Tyr Ala Lys Tyr Tyr Lys Glu Asn Asn Val
        290                 295                 300
Glu Lys Arg Thr Leu Ile Lys Val Phe Gly Ile Arg Phe Asp Ile Leu
305                 310                 315                 320
Val Phe Gly Thr Gly Gly Lys Phe Asp Ile Ile Gln Leu Val Val Tyr
                325                 330                 335
Ile Gly Ser Thr Leu Ser Tyr Phe Gly Leu Ala Ala Val Phe Ile Asp
                340                 345                 350
Phe Leu Ile Asp Thr Tyr Ser Ser Asn Cys Cys Arg Ser His Ile Tyr
            355                 360                 365
Pro Trp Cys Lys Cys Gln Pro Cys Val Val Asn Glu Tyr Tyr Tyr
        370                 375                 380
Arg Lys Lys Cys Glu Ser Ile Val Glu Pro Lys Pro Thr Leu Lys Tyr
385                 390                 395                 400
Val Ser Phe Val Asp Glu Ser His Ile Arg Met Val Asn Gln Gln Leu
                405                 410                 415
Leu Gly Arg Ser Leu Gln Asp Val Lys Gly Gln Glu Val Pro Arg Pro
            420                 425                 430
Ala Met Asp Phe Thr Asp Leu Ser Arg Leu Pro Leu Ala Leu His Asp
                435                 440                 445
Thr Pro Pro Ile Pro Gly Gln Pro Glu Glu Ile Gln Leu Leu Arg Lys
            450                 455                 460
Glu Ala Thr Pro Arg Ser Arg Asp Ser Pro Val Trp Cys Gln Cys Gly
465                 470                 475                 480
Ser Cys Leu Pro Ser Gln Leu Pro Glu Ser His Arg Cys Leu Glu Glu
                485                 490                 495
Leu Cys Cys Arg Lys Lys Pro Gly Ala Cys Ile Thr Thr Ser Glu Leu
            500                 505                 510
Phe Arg Lys Leu Val Leu Ser Arg His Val Leu Gln Phe Leu Leu Leu
            515                 520                 525
Tyr Gln Glu Pro Leu Leu Ala Leu Asp Val Asp Ser Thr Asn Ser Arg
            530                 535                 540
Leu Arg His Cys Ala Tyr Arg Cys Tyr Ala Thr Trp Arg Phe Gly Ser
545                 550                 555                 560
Gln Asp Met Ala Asp Phe Ala Ile Leu Pro Ser Cys Cys Arg Trp Arg
                565                 570                 575
Ile Arg Lys Glu Phe Pro Lys Ser Glu Gly Tyr Ser Gly Phe Lys
            580                 585                 590
Ser Pro Tyr
        595

<210> SEQ ID NO 4
<211> LENGTH: 595
<212> TYPE: PRT
<213> ORGANISM: Homo sapiens
<220> FEATURE:
<221> NAME/KEY: DOMAIN
<222> LOCATION: (1)..(20)
<223> OTHER INFORMATION: Intracellular domain
<220> FEATURE:
<221> NAME/KEY: TRANSMEM
<222> LOCATION: (21)..(46)
<223> OTHER INFORMATION:
```

```
<220> FEATURE:
<221> NAME/KEY: DOMAIN
<222> LOCATION: (47)..(320)
<223> OTHER INFORMATION: Extracellular domain
<220> FEATURE:
<221> NAME/KEY: TRANSMEM
<222> LOCATION: (321)..(356)
<223> OTHER INFORMATION:
<220> FEATURE:
<221> NAME/KEY: DOMAIN
<222> LOCATION: (357)..(595)
<223> OTHER INFORMATION: Intracellular domain

<400> SEQUENCE: 4

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys Arg Pro Lys
            260                 265                 270

Tyr Ser Phe Arg Arg Leu Asp Asp Lys Thr Thr Asn Val Ser Leu Tyr
        275                 280                 285

Pro Gly Tyr Asn Phe Arg Tyr Ala Lys Tyr Tyr Lys Glu Asn Asn Val
    290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                325                 330                 335
```

-continued

```
Ile Gly Ser Thr Leu Ser Tyr Phe Gly Leu Ala Ala Val Phe Ile Asp
            340                 345                 350

Phe Leu Ile Asp Thr Tyr Ser Ser Asn Cys Cys Arg Ser His Ile Tyr
        355                 360                 365

Pro Trp Cys Lys Cys Gln Pro Cys Val Val Asn Glu Tyr Tyr
    370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
                405                 410                 415

Leu Gly Arg Ser Leu Gln Asp Val Lys Gly Gln Glu Val Pro Arg Pro
                420                 425                 430

Ala Met Asp Phe Thr Asp Leu Ser Arg Leu Pro Leu Ala Leu His Asp
                435                 440                 445

Thr Pro Pro Ile Pro Gly Gln Pro Glu Glu Ile Gln Leu Leu Arg Lys
        450                 455                 460

Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
                485                 490                 495

Leu Cys Cys Arg Lys Lys Pro Gly Ala Cys Ile Thr Thr Ser Glu Leu
                500                 505                 510

Phe Arg Lys Leu Val Leu Ser Arg His Val Leu Gln Phe Leu Leu Leu
        515                 520                 525

Tyr Gln Glu Pro Leu Leu Ala Leu Asp Val Asp Ser Thr Asn Ser Arg
    530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
                565                 570                 575

Ile Arg Lys Glu Phe Pro Lys Ser Glu Gly Gln Tyr Ser Gly Phe Lys
                580                 585                 590

Ser Pro Tyr
        595

<210> SEQ ID NO 5
<211> LENGTH: 595
<212> TYPE: PRT
<213> ORGANISM: Homo sapiens

<400> SEQUENCE: 5

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
                20                  25                  30

Phe His Val Ile Ile Phe Ser Tyr Val Cys Phe Ala Leu Val Ser Asp
            35                  40                  45

Lys Leu Tyr Gln Arg Lys Glu Pro Val Ile Ser Ser Val His Thr Lys
        50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
                100                 105                 110
```

-continued

```
Gly Gln Glu Gln Trp Leu Cys Pro Glu Tyr Pro Thr Arg Arg Thr Leu
            115                 120                 125
Cys Ser Ser Asp Arg Gly Cys Lys Lys Gly Trp Met Asp Pro Gln Ser
130                 135                 140
Lys Gly Ile Gln Thr Gly Arg Cys Val Val His Glu Gly Asn Gln Lys
145                 150                 155                 160
Thr Cys Glu Val Ser Ala Trp Cys Pro Ile Glu Ala Val Glu Glu Ala
                165                 170                 175
Pro Arg Pro Ala Leu Leu Asn Ser Ala Glu Asn Phe Thr Val Leu Ile
                180                 185                 190
Lys Asn Asn Ile Asp Phe Pro Gly His Asn Tyr Thr Thr Arg Asn Ile
            195                 200                 205
Leu Pro Gly Leu Asn Ile Thr Cys Thr Phe His Lys Thr Gln Asn Pro
210                 215                 220
Gln Cys Pro Ile Phe Arg Leu Gly Asp Ile Phe Arg Glu Thr Gly Asp
225                 230                 235                 240
Asn Phe Ser Asp Val Ala Ile Gln Gly Gly Ile Met Gly Ile Glu Ile
                245                 250                 255
Tyr Trp Asp Cys Asn Leu Asp Arg Trp Phe His His Cys Arg Pro Lys
                260                 265                 270
Tyr Ser Phe Arg Arg Leu Asp Asp Lys Thr Thr Asn Val Ser Leu Tyr
            275                 280                 285
Pro Gly Tyr Asn Phe Arg Tyr Ala Lys Tyr Tyr Lys Glu Asn Asn Val
            290                 295                 300
Glu Lys Arg Thr Leu Ile Lys Val Phe Gly Ile Arg Phe Asp Ile Leu
305                 310                 315                 320
Val Phe Gly Thr Gly Gly Lys Phe Asp Ile Ile Gln Leu Val Val Tyr
                325                 330                 335
Ile Gly Ser Thr Leu Ser Tyr Phe Gly Leu Ala Ala Val Phe Ile Asp
            340                 345                 350
Phe Leu Ile Asp Thr Tyr Ser Ser Asn Cys Cys Arg Ser His Ile Tyr
            355                 360                 365
Pro Trp Cys Lys Cys Cys Gln Pro Cys Val Val Asn Glu Tyr Tyr Tyr
            370                 375                 380
Arg Lys Lys Cys Glu Ser Ile Val Glu Pro Lys Pro Thr Leu Lys Tyr
385                 390                 395                 400
Val Ser Phe Val Asp Glu Ser His Ile Arg Met Val Asn Gln Gln Leu
                405                 410                 415
Leu Gly Arg Ser Leu Gln Asp Val Lys Gly Gln Glu Val Pro Arg Pro
            420                 425                 430
Ala Met Asp Phe Thr Asp Leu Ser Arg Leu Pro Leu Ala Leu His Asp
            435                 440                 445
Thr Pro Pro Ile Pro Gly Gln Pro Glu Glu Ile Gln Leu Leu Arg Lys
            450                 455                 460
Glu Ala Thr Pro Arg Ser Arg Asp Ser Pro Val Trp Cys Gln Cys Gly
465                 470                 475                 480
Ser Cys Leu Pro Ser Gln Leu Pro Glu Ser His Arg Cys Leu Glu Glu
                485                 490                 495
Leu Cys Cys Arg Lys Lys Pro Gly Ala Cys Ile Thr Thr Ser Glu Leu
            500                 505                 510
Phe Arg Lys Leu Val Leu Ser Arg His Val Leu Gln Phe Leu Leu Leu
            515                 520                 525
```

```
Tyr Gln Glu Pro Leu Leu Ala Leu Asp Val Asp Ser Thr Asn Ser Arg
    530                 535                 540
Leu Arg His Cys Ala Tyr Arg Cys Tyr Ala Thr Trp Arg Phe Gly Ser
545                 550                 555                 560
Gln Asp Met Ala Asp Phe Ala Ile Leu Pro Ser Cys Cys Arg Trp Arg
                565                 570                 575
Ile Arg Lys Glu Phe Pro Lys Ser Glu Gly Gln Tyr Ser Gly Phe Lys
            580                 585                 590
Ser Pro Tyr
        595

<210> SEQ ID NO 6
<211> LENGTH: 595
<212> TYPE: PRT
<213> ORGANISM: Homo sapiens

<400> SEQUENCE: 6

Met Pro Ala Cys Cys Ser Cys Ser Asp Val Phe Gln Tyr Glu Thr Asn
1               5                   10                  15
Lys Val Thr Arg Ile Gln Ser Met Asn Tyr Gly Thr Ile Lys Trp Phe
            20                  25                  30
Phe His Val Ile Ile Phe Ser Tyr Val Cys Phe Ala Leu Val Ser Asp
        35                  40                  45
Lys Leu Tyr Gln Arg Lys Glu Pro Val Ile Ser Ser Val His Thr Lys
    50                  55                  60
Val Lys Gly Ile Ala Glu Val Lys Glu Glu Ile Val Glu Asn Gly Val
65                  70                  75                  80
Lys Lys Leu Val His Ser Val Phe Asp Thr Ala Asp Tyr Thr Phe Pro
                85                  90                  95
Leu Gln Gly Asn Ser Phe Phe Val Met Thr Asn Phe Leu Lys Thr Glu
            100                 105                 110
Gly Gln Glu Gln Arg Leu Cys Pro Glu Tyr Pro Thr Arg Arg Thr Leu
        115                 120                 125
Cys Ser Ser Asp Arg Gly Cys Lys Lys Gly Trp Met Asp Pro Gln Ser
130                 135                 140
Lys Gly Ile Gln Thr Arg Arg Cys Val Val His Glu Gly Asn Gln Lys
145                 150                 155                 160
Thr Cys Glu Val Ser Ala Trp Cys Pro Ile Glu Ala Val Glu Glu Ala
                165                 170                 175
Pro Arg Pro Ala Leu Leu Asn Ser Ala Glu Asn Phe Thr Val Leu Ile
            180                 185                 190
Lys Asn Asn Ile Asp Phe Pro Gly His Asn Tyr Thr Thr Arg Asn Ile
        195                 200                 205
Leu Pro Gly Leu Asn Ile Thr Cys Thr Phe His Lys Thr Gln Asn Pro
    210                 215                 220
Gln Cys Pro Ile Phe Arg Leu Gly Asp Ile Phe Arg Glu Thr Gly Asp
225                 230                 235                 240
Asn Phe Ser Asp Val Ala Ile Gln Gly Gly Ile Met Gly Ile Glu Ile
                245                 250                 255
Tyr Trp Asp Cys Asn Leu Asp Arg Trp Phe His His Cys Arg Pro Lys
            260                 265                 270
Tyr Ser Phe Arg Arg Leu Asp Asp Lys Thr Thr Asn Val Ser Leu Tyr
        275                 280                 285
Pro Gly Tyr Asn Phe Arg Tyr Ala Lys Tyr Tyr Lys Glu Asn Asn Val
    290                 295                 300
```

```
Glu Lys Arg Thr Leu Ile Lys Val Phe Gly Ile Arg Phe Asp Ile Leu
305                 310                 315                 320

Val Phe Gly Thr Gly Lys Phe Asp Ile Ile Gln Leu Val Val Tyr
                325                 330                 335

Ile Gly Ser Thr Leu Ser Tyr Phe Gly Leu Ala Ala Val Phe Ile Asp
                340                 345                 350

Phe Leu Ile Asp Thr Tyr Ser Ser Asn Cys Cys Arg Ser His Ile Tyr
                355                 360                 365

Pro Trp Cys Lys Cys Cys Gln Pro Cys Val Val Asn Glu Tyr Tyr Tyr
                370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
                405                 410                 415

Leu Gly Arg Ser Leu Gln Asp Val Lys Gly Gln Glu Val Pro Arg Pro
                420                 425                 430

Ala Met Asp Phe Thr Asp Leu Ser Arg Leu Pro Leu Ala Leu His Asp
                435                 440                 445

Thr Pro Pro Ile Pro Gly Gln Pro Glu Glu Ile Gln Leu Leu Arg Lys
                450                 455                 460

Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
                485                 490                 495

Leu Cys Cys Arg Lys Lys Pro Gly Ala Cys Ile Thr Thr Ser Glu Leu
                500                 505                 510

Phe Arg Lys Leu Val Leu Ser Arg His Val Leu Gln Phe Leu Leu Leu
                515                 520                 525

Tyr Gln Glu Pro Leu Leu Ala Leu Asp Val Asp Ser Thr Asn Ser Arg
                530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
                565                 570                 575

Ile Arg Lys Glu Phe Pro Lys Ser Glu Gly Gln Tyr Ser Gly Phe Lys
                580                 585                 590

Ser Pro Tyr
        595

<210> SEQ ID NO 7
<211> LENGTH: 595
<212> TYPE: PRT
<213> ORGANISM: Homo sapiens

<400> SEQUENCE: 7

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
                20                  25                  30

Phe His Val Ile Ile Phe Ser Tyr Val Cys Phe Ala Leu Val Ser Asp
            35                  40                  45

Lys Leu Tyr Gln Arg Lys Glu Pro Val Ile Ser Ser Val His Thr Lys
        50                  55                  60

Val Lys Gly Ile Ala Glu Val Lys Glu Glu Ile Val Glu Asn Gly Val
65                  70                  75                  80
```

-continued

```
Lys Lys Leu Val His Ser Val Phe Asp Thr Ala Asp Tyr Thr Phe Pro
             85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
            115                 120                 125

Cys Ser Ser Asp Arg Gly Cys Lys Lys Gly Trp Met Asp Pro Gln Ser
    130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Lys Asn Phe Thr Val Leu Ile
            180                 185                 190

Lys Asn Asn Ile Asp Phe Pro Gly His Asn Tyr Thr Thr Arg Asn Ile
195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys Arg Pro Lys
                260                 265                 270

Tyr Ser Phe Arg Arg Leu Asp Asp Lys Thr Thr Asn Val Ser Leu Tyr
            275                 280                 285

Pro Gly Tyr Asn Phe Arg Tyr Ala Lys Tyr Tyr Lys Glu Asn Asn Val
    290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                325                 330                 335

Ile Gly Ser Thr Leu Ser Tyr Phe Gly Leu Ala Ala Val Phe Ile Asp
                340                 345                 350

Phe Leu Ile Asp Thr Tyr Ser Ser Asn Cys Cys Arg Ser His Ile Tyr
            355                 360                 365

Pro Trp Cys Lys Cys Cys Gln Pro Cys Val Val Asn Glu Tyr Tyr Tyr
    370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
                405                 410                 415

Leu Gly Arg Ser Leu Gln Asp Val Lys Gly Gln Glu Val Pro Arg Pro
            420                 425                 430

Ala Met Asp Phe Thr Asp Leu Ser Arg Leu Pro Leu Ala Leu His Asp
            435                 440                 445

Thr Pro Pro Ile Pro Gly Gln Pro Glu Ile Gln Leu Leu Arg Lys
    450                 455                 460

Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
                485                 490                 495
```

```
Leu Cys Cys Arg Lys Lys Pro Gly Ala Cys Ile Thr Thr Ser Glu Leu
            500                 505                 510

Phe Arg Lys Leu Val Leu Ser Arg His Val Leu Gln Phe Leu Leu Leu
        515                 520                 525

Tyr Gln Glu Pro Leu Leu Ala Leu Asp Val Asp Ser Thr Asn Ser Arg
    530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
                565                 570                 575

Ile Arg Lys Glu Phe Pro Lys Ser Glu Gly Gln Tyr Ser Gly Phe Lys
                580                 585                 590

Ser Pro Tyr
        595

<210> SEQ ID NO 8
<211> LENGTH: 595
<212> TYPE: PRT
<213> ORGANISM: Homo sapiens

<400> SEQUENCE: 8

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
    130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Pro Ile
            180                 185                 190

Lys Asn Asn Ile Asp Phe Pro Gly His Asn Tyr Thr Thr Arg Asn Ile
        195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys Arg Pro Lys
            260                 265                 270
```

-continued

```
Tyr Ser Phe Arg Arg Leu Asp Asp Lys Thr Thr Asn Val Ser Leu Tyr
            275                 280                 285

Pro Gly Tyr Asn Phe Arg Tyr Ala Lys Tyr Tyr Lys Glu Asn Asn Val
        290                 295                 300

Glu Lys Arg Thr Leu Ile Lys Val Phe Gly Ile Arg Phe Asp Ile Leu
305                 310                 315                 320

Val Phe Gly Thr Gly Lys Phe Asp Ile Ile Gln Leu Val Val Tyr
                325                 330                 335

Ile Gly Ser Thr Leu Ser Tyr Phe Gly Leu Ala Ala Val Phe Ile Asp
                340                 345                 350

Phe Leu Ile Asp Thr Tyr Ser Asn Cys Cys Arg Ser His Ile Tyr
            355                 360                 365

Pro Trp Cys Lys Cys Gln Pro Cys Val Val Asn Glu Tyr Tyr Tyr
        370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
                405                 410                 415

Leu Gly Arg Ser Leu Gln Asp Val Lys Gly Gln Glu Val Pro Arg Pro
            420                 425                 430

Ala Met Asp Phe Thr Asp Leu Ser Arg Leu Pro Leu Ala Leu His Asp
            435                 440                 445

Thr Pro Pro Ile Pro Gly Gln Pro Glu Glu Ile Gln Leu Leu Arg Lys
        450                 455                 460

Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
                485                 490                 495

Leu Cys Cys Arg Lys Lys Pro Gly Ala Cys Ile Thr Thr Ser Glu Leu
            500                 505                 510

Phe Arg Lys Leu Val Leu Ser Arg His Val Leu Gln Phe Leu Leu Leu
            515                 520                 525

Tyr Gln Glu Pro Leu Leu Ala Leu Asp Val Asp Ser Thr Asn Ser Arg
            530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
                565                 570                 575

Ile Arg Lys Glu Phe Pro Lys Ser Glu Gly Gln Tyr Ser Gly Phe Lys
            580                 585                 590

Ser Pro Tyr
        595

<210> SEQ ID NO 9
<211> LENGTH: 595
<212> TYPE: PRT
<213> ORGANISM: Homo sapiens

<400> SEQUENCE: 9

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
                20                  25                  30

Phe His Val Ile Ile Phe Ser Tyr Val Cys Phe Ala Leu Val Ser Asp
            35                  40                  45
```

```
Lys Leu Tyr Gln Arg Lys Glu Pro Val Ile Ser Ser Val His Thr Lys
 50                  55                  60

Val Lys Gly Ile Ala Glu Val Lys Glu Glu Ile Val Glu Asn Gly Val
 65                  70                  75                  80

Lys Lys Leu Val His Ser Val Phe Asp Thr Ala Asp Tyr Thr Phe Pro
                     85                  90                  95

Leu Gln Gly Asn Ser Phe Phe Val Met Thr Asn Phe Leu Lys Thr Glu
                100                 105                 110

Gly Gln Glu Gln Arg Leu Cys Pro Glu Tyr Pro Thr Arg Arg Thr Leu
                115                 120                 125

Cys Ser Ser Asp Arg Gly Cys Lys Lys Gly Trp Met Asp Pro Gln Ser
    130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
                180                 185                 190

Lys Asn Asn Ile Asp Phe Pro Gly His Asn Tyr Thr Thr Arg Asn Ile
                195                 200                 205

Leu Pro Gly Leu Asn Ile Thr Cys Thr Phe His Lys Thr Gln Asn Pro
210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys Cys Pro Lys
                260                 265                 270

Tyr Ser Phe Arg Arg Leu Asp Asp Lys Thr Thr Asn Val Ser Leu Tyr
                275                 280                 285

Pro Gly Tyr Asn Phe Arg Tyr Ala Lys Tyr Tyr Lys Glu Asn Asn Val
                290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                325                 330                 335

Ile Gly Ser Thr Leu Ser Tyr Phe Gly Leu Ala Ala Val Phe Ile Asp
                340                 345                 350

Phe Leu Ile Asp Thr Tyr Ser Ser Asn Cys Cys Arg Ser His Ile Tyr
                355                 360                 365

Pro Trp Cys Lys Cys Cys Gln Pro Cys Val Val Asn Glu Tyr Tyr Tyr
                370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
                405                 410                 415

Leu Gly Arg Ser Leu Gln Asp Val Lys Gly Gln Glu Val Pro Arg Pro
                420                 425                 430

Ala Met Asp Phe Thr Asp Leu Ser Arg Leu Pro Leu Ala Leu His Asp
                435                 440                 445

Thr Pro Pro Ile Pro Gly Gln Pro Glu Glu Ile Gln Leu Leu Arg Lys
450                 455                 460
```

```
Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
                485                 490                 495

Leu Cys Cys Arg Lys Lys Pro Gly Ala Cys Ile Thr Thr Ser Glu Leu
            500                 505                 510

Phe Arg Lys Leu Val Leu Ser Arg His Val Leu Gln Phe Leu Leu Leu
        515                 520                 525

Tyr Gln Glu Pro Leu Leu Ala Leu Asp Val Asp Ser Thr Asn Ser Arg
    530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
                565                 570                 575

Ile Arg Lys Glu Phe Pro Lys Ser Glu Gly Gln Tyr Ser Gly Phe Lys
            580                 585                 590

Ser Pro Tyr
        595

<210> SEQ ID NO 10
<211> LENGTH: 595
<212> TYPE: PRT
<213> ORGANISM: Homo sapiens

<400> SEQUENCE: 10

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
    130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240
```

-continued

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys Arg Pro Lys
            260                 265                 270

Tyr Ser Phe Arg Arg Leu Asp Asp Lys Thr Thr Asn Val Ser Leu Tyr
        275                 280                 285

Pro Gly Tyr Asn Phe Arg Tyr Ala Lys Tyr Tyr Lys Glu Asn Asn Val
    290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                325                 330                 335

Ile Gly Ser Thr Leu Ser Tyr Phe Gly Leu Ala Ala Val Phe Ile Asp
            340                 345                 350

Phe Leu Ile Asp Thr Tyr Ser Ser Asn Cys Cys Arg Ser His Ile Tyr
        355                 360                 365

Pro Trp Cys Lys Cys Gln Pro Cys Val Val Asn Glu Tyr Tyr Tyr
    370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
                405                 410                 415

Leu Gly Arg Ser Leu Gln Asp Val Lys Gly Gln Glu Val Pro Arg Pro
            420                 425                 430

Ala Met Asp Phe Thr Asp Leu Ser Arg Leu Pro Leu Ala Leu His Asp
        435                 440                 445

Thr Pro Pro Ile Pro Gly Gln Pro Glu Ile Gln Leu Leu Arg Lys
    450                 455                 460

Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
                485                 490                 495

Leu Cys Cys Arg Lys Lys Pro Gly Ala Cys Ile Thr Thr Ser Glu Leu
            500                 505                 510

Phe Arg Lys Leu Val Leu Ser Arg His Val Leu Gln Phe Leu Leu Leu
        515                 520                 525

Tyr Gln Glu Pro Leu Leu Ala Leu Asp Val Asp Ser Thr Asn Ser Arg
    530                 535                 540

Leu Arg His Cys Ala Tyr Arg Cys Tyr Ala Thr Trp Arg Phe Gly Ser
545                 550                 555                 560

Gln Asp Met Ala Asp Phe Ala Asn Leu Pro Ser Cys Cys Arg Trp Arg
                565                 570                 575

Ile Arg Lys Glu Phe Pro Lys Ser Glu Gly Gln Tyr Ser Gly Phe Lys
            580                 585                 590

Ser Pro Tyr
        595

<210> SEQ ID NO 11
<211> LENGTH: 588
<212> TYPE: PRT
<213> ORGANISM: Homo sapiens

<400> SEQUENCE: 11

Met Pro Ala Cys Cys Ser Cys Ser Asp Val Phe Gln Tyr Glu Thr Asn
1               5                   10                  15

-continued

```
Lys Val Thr Arg Ile Gln Ser Met Asn Tyr Gly Thr Ile Lys Trp Phe
             20                  25                  30

Phe His Val Ile Ile Phe Ser Tyr Val Cys Phe Ala Leu Val Ser Asp
             35                  40                  45

Lys Leu Tyr Gln Arg Lys Glu Pro Val Ile Ser Val His Thr Lys
 50                  55                  60

Val Lys Gly Ile Ala Glu Val Lys Glu Ile Val Glu Asn Gly Val
 65                  70                  75                  80

Lys Lys Leu Val His Ser Val Phe Asp Thr Ala Asp Tyr Thr Phe Pro
             85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
            115                 120                 125

Cys Ser Ser Asp Arg Gly Cys Lys Lys Gly Trp Met Asp Pro Gln Ser
130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
            165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
            195                 200                 205

Leu Pro Gly Leu Asn Ile Thr Cys Thr Phe His Lys Thr Gln Asn Pro
            210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
            245                 250                 255

Tyr Trp Asp Cys Asn Leu Asp Arg Trp Phe His His Cys Arg Pro Lys
            260                 265                 270

Tyr Ser Phe Arg Arg Leu Asp Asp Lys Thr Thr Asn Val Ser Leu Tyr
            275                 280                 285

Pro Gly Tyr Asn Phe Arg Tyr Ala Lys Tyr Tyr Lys Glu Asn Asn Val
            290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
            325                 330                 335

Ile Gly Ser Thr Leu Ser Tyr Phe Gly Leu Ala Ala Val Phe Ile Asp
            340                 345                 350

Phe Leu Ile Asp Thr Tyr Ser Ser Asn Cys Cys Arg Ser His Ile Tyr
            355                 360                 365

Pro Trp Cys Lys Cys Cys Gln Pro Cys Val Val Asn Glu Tyr Tyr Tyr
            370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
            405                 410                 415

Leu Gly Arg Ser Leu Gln Asp Val Lys Gly Gln Glu Val Pro Arg Pro
            420                 425                 430
```

```
Ala Met Asp Phe Thr Asp Leu Ser Arg Leu Pro Leu Ala Leu His Asp
        435                 440                 445

Thr Pro Pro Ile Pro Gly Gln Pro Glu Glu Ile Gln Leu Leu Arg Lys
        450                 455                 460

Glu Ala Thr Pro Arg Ser Arg Asp Ser Pro Val Trp Cys Gln Cys Gly
465                 470                 475                 480

Ser Cys Leu Pro Ser Gln Leu Glu Glu Leu Cys Cys Arg Lys Lys Pro
        485                 490                 495

Gly Ala Cys Ile Thr Thr Ser Glu Leu Phe Arg Lys Leu Val Leu Ser
        500                 505                 510

Arg His Val Leu Gln Phe Leu Leu Leu Tyr Gln Glu Pro Leu Leu Ala
        515                 520                 525

Leu Asp Val Asp Ser Thr Asn Ser Arg Leu Arg His Cys Ala Tyr Arg
530                 535                 540

Cys Tyr Ala Thr Trp Arg Phe Gly Ser Gln Asp Met Ala Asp Phe Ala
545                 550                 555                 560

Ile Leu Pro Ser Cys Cys Arg Trp Arg Ile Arg Lys Glu Phe Pro Lys
        565                 570                 575

Ser Glu Gly Gln Tyr Ser Gly Phe Lys Ser Pro Tyr
        580                 585

<210> SEQ ID NO 12
<211> LENGTH: 595
<212> TYPE: PRT
<213> ORGANISM: Homo sapiens

<400> SEQUENCE: 12

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
            85                  90                  95

Leu Gln Gly Asn Ser Phe Phe Val Met Thr Asn Phe Leu Lys Thr Glu
        100                 105                 110

Gly Gln Glu Gln Arg Leu Cys Pro Glu Tyr Pro Thr Arg Arg Thr Leu
    115                 120                 125

Cys Ser Ser Asp Arg Gly Cys Lys Lys Gly Trp Met Asp Pro Gln Ser
130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
            165                 170                 175

Pro Arg Pro Ala Leu Leu Asn Ser Ala Glu Asn Phe Thr Val Leu Ile
        180                 185                 190

Lys Asn Asn Ile Asp Phe Pro Gly His Asn Tyr Thr Thr Arg Asn Ile
    195                 200                 205

Leu Pro Gly Leu Asn Ile Thr Cys Thr Phe His Lys Thr Gln Asn Pro
210                 215                 220
```

```
Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys Arg Pro Lys
                260                 265                 270

Tyr Ser Phe Arg Arg Leu Asp Asp Lys Thr Thr Asn Val Ser Leu Tyr
            275                 280                 285

Pro Gly Tyr Asn Phe Arg Tyr Ala Lys Tyr Tyr Lys Glu Asn Asn Val
        290                 295                 300

Glu Lys Arg Thr Leu Ile Lys Val Phe Gly Ile Arg Phe Asp Ile Leu
305                 310                 315                 320

Val Phe Gly Thr Gly Lys Phe Asp Ile Ile Gln Leu Val Val Tyr
                325                 330                 335

Ile Gly Ser Thr Leu Ser Tyr Phe Gly Leu Ala Ala Val Phe Ile Asp
                340                 345                 350

Phe Leu Ile Asp Thr Tyr Ser Ser Asn Cys Cys Arg Ser His Ile Tyr
            355                 360                 365

Pro Trp Cys Lys Cys Cys Gln Pro Cys Val Val Asn Glu Tyr Tyr Tyr
        370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
                405                 410                 415

Leu Gly Arg Ser Leu Gln Asp Val Lys Gly Gln Glu Val Pro Arg Pro
            420                 425                 430

Ala Met Asp Phe Thr Asp Leu Ser Arg Leu Pro Leu Ala Leu His Asp
        435                 440                 445

Thr Pro Pro Ile Pro Gly Gln Pro Glu Glu Ile Gln Leu Leu Arg Lys
    450                 455                 460

Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
                485                 490                 495

Leu Cys Cys Arg Lys Lys Pro Gly Ala Cys Ile Thr Thr Ser Glu Leu
            500                 505                 510

Phe Arg Lys Leu Val Leu Ser Arg His Val Leu Gln Phe Leu Leu Leu
        515                 520                 525

Tyr Gln Glu Pro Leu Leu Ala Leu Asp Val Asp Ser Thr Asn Ser Arg
    530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
                565                 570                 575

Ile Gln Lys Glu Phe Pro Lys Ser Glu Gly Gln Tyr Ser Gly Phe Lys
            580                 585                 590

Ser Pro Tyr
        595

<210> SEQ ID NO 13
<211> LENGTH: 20
<212> TYPE: DNA
<213> ORGANISM: Homo sapiens
```

```
<400> SEQUENCE: 13
gtaacctcac tgagaacaga                                            20

<210> SEQ ID NO 14
<211> LENGTH: 20
<212> TYPE: DNA
<213> ORGANISM: Homo sapiens

<400> SEQUENCE: 14
tttggtaggc gaaggcgggc                                            20

<210> SEQ ID NO 15
<211> LENGTH: 21
<212> TYPE: DNA
<213> ORGANISM: Homo sapiens

<400> SEQUENCE: 15
ccttgtatgg gctttcgtgc t                                          21

<210> SEQ ID NO 16
<211> LENGTH: 21
<212> TYPE: DNA
<213> ORGANISM: Homo sapiens

<400> SEQUENCE: 16
ttgtgtatcc gtccatcagc t                                          21

<210> SEQ ID NO 17
<211> LENGTH: 20
<212> TYPE: DNA
<213> ORGANISM: Homo sapiens

<400> SEQUENCE: 17
actgccatat gtactattcc                                            20

<210> SEQ ID NO 18
<211> LENGTH: 20
<212> TYPE: DNA
<213> ORGANISM: Homo sapiens

<400> SEQUENCE: 18
aaatctaccc agccacttag                                            20

<210> SEQ ID NO 19
<211> LENGTH: 20
<212> TYPE: DNA
<213> ORGANISM: Homo sapiens

<400> SEQUENCE: 19
tgcagtggcc cacagcacag                                            20

<210> SEQ ID NO 20
<211> LENGTH: 20
<212> TYPE: DNA
<213> ORGANISM: Homo sapiens

<400> SEQUENCE: 20
catcctccaa tgcctgcatc                                            20

<210> SEQ ID NO 21
<211> LENGTH: 20
<212> TYPE: DNA
<213> ORGANISM: Homo sapiens
```

<400> SEQUENCE: 21
tttcccatgt ttgccattta                                              20

<210> SEQ ID NO 22
<211> LENGTH: 20
<212> TYPE: DNA
<213> ORGANISM: Homo sapiens

<400> SEQUENCE: 22
caagagcagt ggttgtgtcc                                              20

<210> SEQ ID NO 23
<211> LENGTH: 20
<212> TYPE: DNA
<213> ORGANISM: Homo sapiens

<400> SEQUENCE: 23
gagcccacag atatctactg                                              20

<210> SEQ ID NO 24
<211> LENGTH: 20
<212> TYPE: DNA
<213> ORGANISM: Homo sapiens

<400> SEQUENCE: 24
tgcctgcctc agtctctggt                                              20

<210> SEQ ID NO 25
<211> LENGTH: 20
<212> TYPE: DNA
<213> ORGANISM: Homo sapiens

<400> SEQUENCE: 25
tctctcgccc aggttgagtt                                              20

<210> SEQ ID NO 26
<211> LENGTH: 20
<212> TYPE: DNA
<213> ORGANISM: Homo sapiens

<400> SEQUENCE: 26
acgtcctctc cgcagttctt                                              20

<210> SEQ ID NO 27
<211> LENGTH: 20
<212> TYPE: DNA
<213> ORGANISM: Homo sapiens

<400> SEQUENCE: 27
attcagaccg aaaggtgtgt                                              20

<210> SEQ ID NO 28
<211> LENGTH: 20
<212> TYPE: DNA
<213> ORGANISM: Homo sapiens

<400> SEQUENCE: 28
tgcctggtgt cccatcgagg                                              20

<210> SEQ ID NO 29
<211> LENGTH: 20
<212> TYPE: DNA
<213> ORGANISM: Homo sapiens

```
<400> SEQUENCE: 29
gttgtaacac tcctgtacca                                              20

<210> SEQ ID NO 30
<211> LENGTH: 20
<212> TYPE: DNA
<213> ORGANISM: Homo sapiens

<400> SEQUENCE: 30
aacagtgcca aaaacttcac                                              20

<210> SEQ ID NO 31
<211> LENGTH: 20
<212> TYPE: DNA
<213> ORGANISM: Homo sapiens

<400> SEQUENCE: 31
tcactgtgcc catcaagaac                                              20

<210> SEQ ID NO 32
<211> LENGTH: 20
<212> TYPE: DNA
<213> ORGANISM: Homo sapiens

<400> SEQUENCE: 32
tgctgcgtgc ttctggctca                                              20

<210> SEQ ID NO 33
<211> LENGTH: 20
<212> TYPE: DNA
<213> ORGANISM: Homo sapiens

<400> SEQUENCE: 33
ctggagaacc cttttccaag                                              20

<210> SEQ ID NO 34
<211> LENGTH: 20
<212> TYPE: DNA
<213> ORGANISM: Homo sapiens

<400> SEQUENCE: 34
caggaggcag ggatcatttg                                              20

<210> SEQ ID NO 35
<211> LENGTH: 20
<212> TYPE: DNA
<213> ORGANISM: Homo sapiens

<400> SEQUENCE: 35
tccacccgct acgctaaggt                                              20

<210> SEQ ID NO 36
<211> LENGTH: 20
<212> TYPE: DNA
<213> ORGANISM: Homo sapiens

<400> SEQUENCE: 36
tgcgctaagg actttaccta                                              20

<210> SEQ ID NO 37
<211> LENGTH: 20
<212> TYPE: DNA
<213> ORGANISM: Homo sapiens
```

```
<400> SEQUENCE: 37
tttacctacc ctacctcgtc                                               20

<210> SEQ ID NO 38
<211> LENGTH: 20
<212> TYPE: DNA
<213> ORGANISM: Homo sapiens

<400> SEQUENCE: 38
ccatcactgc tgtcccaaat                                               20

<210> SEQ ID NO 39
<211> LENGTH: 20
<212> TYPE: DNA
<213> ORGANISM: Homo sapiens

<400> SEQUENCE: 39
tcgccttgat gacaagacca                                               20

<210> SEQ ID NO 40
<211> LENGTH: 20
<212> TYPE: DNA
<213> ORGANISM: Homo sapiens

<400> SEQUENCE: 40
gtaaactctt ccactctgtt                                               20

<210> SEQ ID NO 41
<211> LENGTH: 20
<212> TYPE: DNA
<213> ORGANISM: Homo sapiens

<400> SEQUENCE: 41
accaagacac ggagagattc                                               20

<210> SEQ ID NO 42
<211> LENGTH: 20
<212> TYPE: DNA
<213> ORGANISM: Homo sapiens

<400> SEQUENCE: 42
taatattaaa tgtaacttta                                               20

<210> SEQ ID NO 43
<211> LENGTH: 20
<212> TYPE: DNA
<213> ORGANISM: Homo sapiens

<400> SEQUENCE: 43
aatattaaac ataactttat                                               20

<210> SEQ ID NO 44
<211> LENGTH: 20
<212> TYPE: DNA
<213> ORGANISM: Homo sapiens

<400> SEQUENCE: 44
ccatctcaac tggaggagct                                               20

<210> SEQ ID NO 45
<211> LENGTH: 20
<212> TYPE: DNA
<213> ORGANISM: Homo sapiens
```

```
<400> SEQUENCE: 45
gactttgcca tcctgcccag                                               20

<210> SEQ ID NO 46
<211> LENGTH: 20
<212> TYPE: DNA
<213> ORGANISM: Homo sapiens

<400> SEQUENCE: 46
tggaggatcc agaaagagtt                                               20

<210> SEQ ID NO 47
<211> LENGTH: 20
<212> TYPE: DNA
<213> ORGANISM: Homo sapiens

<400> SEQUENCE: 47
aatcccagca ctttgggagg                                               20

<210> SEQ ID NO 48
<211> LENGTH: 20
<212> TYPE: DNA
<213> ORGANISM: Homo sapiens

<400> SEQUENCE: 48
aaactgtccc aaaaaaaaaa                                               20

<210> SEQ ID NO 49
<211> LENGTH: 20
<212> TYPE: DNA
<213> ORGANISM: Homo sapiens

<400> SEQUENCE: 49
aactgtcccc caaaaaaaaa                                               20

<210> SEQ ID NO 50
<211> LENGTH: 20
<212> TYPE: DNA
<213> ORGANISM: Homo sapiens

<400> SEQUENCE: 50
ctgtccccac aaaaaaaaaa                                               20

<210> SEQ ID NO 51
<211> LENGTH: 20
<212> TYPE: DNA
<213> ORGANISM: Homo sapiens

<400> SEQUENCE: 51
caaggcgggt ggatcactta                                               20

<210> SEQ ID NO 52
<211> LENGTH: 19
<212> TYPE: DNA
<213> ORGANISM: Homo sapiens

<400> SEQUENCE: 52
cgtaggactt ggcgcttct                                                19

<210> SEQ ID NO 53
<211> LENGTH: 21
<212> TYPE: DNA
<213> ORGANISM: Homo sapiens
```

```
<400> SEQUENCE: 53
gagcacgtct cagattcgaa a                                      21

<210> SEQ ID NO 54
<211> LENGTH: 23
<212> TYPE: DNA
<213> ORGANISM: Homo sapiens

<400> SEQUENCE: 54
ccatgaggca ggtatgacta ttc                                    23

<210> SEQ ID NO 55
<211> LENGTH: 20
<212> TYPE: DNA
<213> ORGANISM: Homo sapiens

<400> SEQUENCE: 55
ctcctggatc tcacccagtt                                        20

<210> SEQ ID NO 56
<211> LENGTH: 23
<212> TYPE: DNA
<213> ORGANISM: Homo sapiens

<400> SEQUENCE: 56
ctcgtccagc tttgatatta agc                                    23

<210> SEQ ID NO 57
<211> LENGTH: 22
<212> TYPE: DNA
<213> ORGANISM: Homo sapiens

<400> SEQUENCE: 57
ggtccctagt gctagaacca ga                                     22

<210> SEQ ID NO 58
<211> LENGTH: 18
<212> TYPE: DNA
<213> ORGANISM: Homo sapiens

<400> SEQUENCE: 58
attcatccgt cagtggcc                                          18

<210> SEQ ID NO 59
<211> LENGTH: 22
<212> TYPE: DNA
<213> ORGANISM: Homo sapiens

<400> SEQUENCE: 59
gccatgtgaa ttttctaccg at                                     22

<210> SEQ ID NO 60
<211> LENGTH: 20
<212> TYPE: DNA
<213> ORGANISM: Homo sapiens

<400> SEQUENCE: 60
ttcgttgtgg ttaggatggg                                        20

<210> SEQ ID NO 61
<211> LENGTH: 22
<212> TYPE: DNA
<213> ORGANISM: Homo sapiens
```

```
<400> SEQUENCE: 61
caaggatgct cagggtagta gc                                    22

<210> SEQ ID NO 62
<211> LENGTH: 25
<212> TYPE: DNA
<213> ORGANISM: Homo sapiens

<400> SEQUENCE: 62
cactaggttt gctgtatcca tttct                                 25

<210> SEQ ID NO 63
<211> LENGTH: 20
<212> TYPE: DNA
<213> ORGANISM: Homo sapiens

<400> SEQUENCE: 63
gcaactgtgt gagagcttgg                                       20

<210> SEQ ID NO 64
<211> LENGTH: 19
<212> TYPE: DNA
<213> ORGANISM: Homo sapiens

<400> SEQUENCE: 64
tcaaccctgg tccagtgtg                                        19

<210> SEQ ID NO 65
<211> LENGTH: 25
<212> TYPE: DNA
<213> ORGANISM: Homo sapiens

<400> SEQUENCE: 65
caccaagtag ctctcactca taagg                                 25

<210> SEQ ID NO 66
<211> LENGTH: 24
<212> TYPE: DNA
<213> ORGANISM: Homo sapiens

<400> SEQUENCE: 66
caataacact tgtgcgagtt aggt                                  24

<210> SEQ ID NO 67
<211> LENGTH: 21
<212> TYPE: DNA
<213> ORGANISM: Homo sapiens

<400> SEQUENCE: 67
catcttgttg ccttggaaac c                                     21

<210> SEQ ID NO 68
<211> LENGTH: 23
<212> TYPE: DNA
<213> ORGANISM: Homo sapiens

<400> SEQUENCE: 68
gtgagtggta atcctgctac tgc                                   23

<210> SEQ ID NO 69
<211> LENGTH: 19
<212> TYPE: DNA
<213> ORGANISM: Homo sapiens
```

```
<400> SEQUENCE: 69
aggcccactc ctgtactcg                                                19

<210> SEQ ID NO 70
<211> LENGTH: 19
<212> TYPE: DNA
<213> ORGANISM: Homo sapiens

<400> SEQUENCE: 70
ccaagtcaca gcatgaggc                                                19

<210> SEQ ID NO 71
<211> LENGTH: 18
<212> TYPE: DNA
<213> ORGANISM: Homo sapiens

<400> SEQUENCE: 71
acccagcgac gtatccac                                                 18

<210> SEQ ID NO 72
<211> LENGTH: 19
<212> TYPE: DNA
<213> ORGANISM: Homo sapiens

<400> SEQUENCE: 72
aagcatgggg ttccatttc                                                19

<210> SEQ ID NO 73
<211> LENGTH: 24
<212> TYPE: DNA
<213> ORGANISM: Homo sapiens

<400> SEQUENCE: 73
gcataaaagg gactcctgct agta                                          24

<210> SEQ ID NO 74
<211> LENGTH: 21
<212> TYPE: DNA
<213> ORGANISM: Homo sapiens

<400> SEQUENCE: 74
gcttacagaa cacatgcatg g                                             21

<210> SEQ ID NO 75
<211> LENGTH: 19
<212> TYPE: DNA
<213> ORGANISM: Homo sapiens

<400> SEQUENCE: 75
gcacctgtag gcacagtgc                                                19

<210> SEQ ID NO 76
<211> LENGTH: 21
<212> TYPE: DNA
<213> ORGANISM: Homo sapiens

<400> SEQUENCE: 76
atcaccacct cagagctgtt c                                             21

<210> SEQ ID NO 77
<211> LENGTH: 21
<212> TYPE: DNA
<213> ORGANISM: Homo sapiens
```

```
<400> SEQUENCE: 77
gttaacatgg ctactgcagc c                                          21

<210> SEQ ID NO 78
<211> LENGTH: 21
<212> TYPE: DNA
<213> ORGANISM: Homo sapiens

<400> SEQUENCE: 78
gcttagaaag gaggcgactc c                                          21

<210> SEQ ID NO 79
<211> LENGTH: 22
<212> TYPE: DNA
<213> ORGANISM: Homo sapiens

<400> SEQUENCE: 79
ttgtgacatt tgcaaggctg cc                                         22

<210> SEQ ID NO 80
<211> LENGTH: 20
<212> TYPE: DNA
<213> ORGANISM: Homo sapiens

<400> SEQUENCE: 80
tctgaagctc tgctcctgag                                            20

<210> SEQ ID NO 81
<211> LENGTH: 20
<212> TYPE: DNA
<213> ORGANISM: Homo sapiens

<400> SEQUENCE: 81
ctcaccttct ggcttccagt                                            20

<210> SEQ ID NO 82
<211> LENGTH: 20
<212> TYPE: DNA
<213> ORGANISM: Homo sapiens

<400> SEQUENCE: 82
cttaccactc ccaggactaa                                            20

<210> SEQ ID NO 83
<211> LENGTH: 20
<212> TYPE: DNA
<213> ORGANISM: Homo sapiens

<400> SEQUENCE: 83
gtctgcctgt tcactgccat                                            20

<210> SEQ ID NO 84
<211> LENGTH: 21
<212> TYPE: DNA
<213> ORGANISM: Homo sapiens

<400> SEQUENCE: 84
cagagacctt cagaaacttc g                                          21

<210> SEQ ID NO 85
<211> LENGTH: 20
<212> TYPE: DNA
<213> ORGANISM: Homo sapiens
```

```
<400> SEQUENCE: 85
agatcaccag ggacacagtg                                              20

<210> SEQ ID NO 86
<211> LENGTH: 20
<212> TYPE: DNA
<213> ORGANISM: Homo sapiens

<400> SEQUENCE: 86
ctcaactcca ctttcctcgg                                              20

<210> SEQ ID NO 87
<211> LENGTH: 23
<212> TYPE: DNA
<213> ORGANISM: Homo sapiens

<400> SEQUENCE: 87
cctttcactt ttttggtctc atg                                          23

<210> SEQ ID NO 88
<211> LENGTH: 21
<212> TYPE: DNA
<213> ORGANISM: Homo sapiens

<400> SEQUENCE: 88
gggagaattc tgaaaatgcc c                                            21

<210> SEQ ID NO 89
<211> LENGTH: 20
<212> TYPE: DNA
<213> ORGANISM: Homo sapiens

<400> SEQUENCE: 89
ggaccagagc tctactcttc                                              20

<210> SEQ ID NO 90
<211> LENGTH: 20
<212> TYPE: DNA
<213> ORGANISM: Homo sapiens

<400> SEQUENCE: 90
aggtcataga tcgacctgcc                                              20

<210> SEQ ID NO 91
<211> LENGTH: 20
<212> TYPE: DNA
<213> ORGANISM: Homo sapiens

<400> SEQUENCE: 91
aagaagcgcc aagtcctacg                                              20

<210> SEQ ID NO 92
<211> LENGTH: 21
<212> TYPE: DNA
<213> ORGANISM: Homo sapiens

<400> SEQUENCE: 92
gcaatccaga ctgaagttga c                                            21

<210> SEQ ID NO 93
<211> LENGTH: 20
<212> TYPE: DNA
<213> ORGANISM: Homo sapiens
```

```
<400> SEQUENCE: 93
actctggtct gcagttggtg                                              20

<210> SEQ ID NO 94
<211> LENGTH: 24
<212> TYPE: DNA
<213> ORGANISM: Homo sapiens

<400> SEQUENCE: 94
cctttaaaat cagagacctt caga                                         24

<210> SEQ ID NO 95
<211> LENGTH: 20
<212> TYPE: DNA
<213> ORGANISM: Homo sapiens

<400> SEQUENCE: 95
gcccatcctc tgaacaccat                                              20

<210> SEQ ID NO 96
<211> LENGTH: 21
<212> TYPE: DNA
<213> ORGANISM: Homo sapiens

<400> SEQUENCE: 96
cccttggaac tcttgctatc g                                            21

<210> SEQ ID NO 97
<211> LENGTH: 21
<212> TYPE: DNA
<213> ORGANISM: Homo sapiens

<400> SEQUENCE: 97
ggcagtacag tggcttcaag a                                            21

<210> SEQ ID NO 98
<211> LENGTH: 21
<212> TYPE: DNA
<213> ORGANISM: Homo sapiens

<400> SEQUENCE: 98
gtgggacagt ttgctgtgcc t                                            21

<210> SEQ ID NO 99
<211> LENGTH: 20
<212> TYPE: DNA
<213> ORGANISM: Homo sapiens

<400> SEQUENCE: 99
gagtccttac caatagcagg                                              20

<210> SEQ ID NO 100
<211> LENGTH: 21
<212> TYPE: DNA
<213> ORGANISM: Homo sapiens

<400> SEQUENCE: 100
gtcaaagaat ttgtggccac c                                            21

<210> SEQ ID NO 101
<211> LENGTH: 26
<212> TYPE: DNA
<213> ORGANISM: Homo sapiens
```

```
<400> SEQUENCE: 101
catgaactgt cttttaatgt gtaaag                                          26

<210> SEQ ID NO 102
<211> LENGTH: 22
<212> TYPE: DNA
<213> ORGANISM: Homo sapiens

<400> SEQUENCE: 102
gagatacggt ttcaccatgt tg                                              22

<210> SEQ ID NO 103
<211> LENGTH: 20
<212> TYPE: DNA
<213> ORGANISM: Homo sapiens

<400> SEQUENCE: 103
aattagctgg gcatggtgcg                                                 20

<210> SEQ ID NO 104
<211> LENGTH: 21
<212> TYPE: DNA
<213> ORGANISM: Homo sapiens

<400> SEQUENCE: 104
ttgagatgga gtctcgctct g                                               21

<210> SEQ ID NO 105
<211> LENGTH: 20
<212> TYPE: DNA
<213> ORGANISM: Homo sapiens

<400> SEQUENCE: 105
cactgtccac gtgactgctt                                                 20

<210> SEQ ID NO 106
<211> LENGTH: 25
<212> TYPE: DNA
<213> ORGANISM: Homo sapiens

<400> SEQUENCE: 106
tcctacttcg gtctggtaag agatt                                           25

<210> SEQ ID NO 107
<211> LENGTH: 19
<212> TYPE: DNA
<213> ORGANISM: Homo sapiens

<400> SEQUENCE: 107
gggcctaatt ttcgtgcat                                                  19

<210> SEQ ID NO 108
<211> LENGTH: 23
<212> TYPE: DNA
<213> ORGANISM: Homo sapiens

<400> SEQUENCE: 108
aagaacctag aacctgaggg ctt                                             23

<210> SEQ ID NO 109
<211> LENGTH: 19
<212> TYPE: DNA
<213> ORGANISM: Homo sapiens
```

```
<400> SEQUENCE: 109
ttgagatggg aggcagctt                                              19

<210> SEQ ID NO 110
<211> LENGTH: 17
<212> TYPE: DNA
<213> ORGANISM: Homo sapiens

<400> SEQUENCE: 110
ttcggctccc aggacat                                                17

<210> SEQ ID NO 111
<211> LENGTH: 20
<212> TYPE: DNA
<213> ORGANISM: Homo sapiens

<400> SEQUENCE: 111
cacagagctt tgcaggtgaa                                             20
```

MEANS AND METHODS FOR DIAGNOSING AND TREATING AFFECTIVE DISORDERS

CROSS REFERENCE TO RELATED PATENT APPLICATIONS

This application is a divisional of Ser. No. 10/825,593 filed Apr. 16, 2004, which claims priority to 60/474,232 filed May 30, 2003, and 60/501,011, filed Sep. 9, 2003, the disclosures of which are incorporated by reference herein in their entirety.

BACKGROUND OF THE INVENTION

The present invention relates to nucleic acid molecules, preferably genomic sequences, encoding an ATP-gated ion channel P2X7R which contain a mutation in the 5'UTR or 3'UTR regions, a mutation in exon 3, 5, 6, 8 or 13 or in introns 1, 3, 4, 5, 6, 7, 9, 11 or 12 or a deletion in exon 13, which allow to diagnose affective disorders. The invention further relates to polypeptides encoded by said nucleic acid molecules vectors and host cells comprising said nucleic acid molecules as well as to methods for producing polypeptides encoded by said nucleic acid molecules. The present invention also provides antibodies specifically directed to polypeptides encoded by said nucleic acid molecules and aptamers specifically binding said nucleic acid molecules.

Additionally, primers for selectively amplifying said nucleic acid molecules are provided in the present invention as well as kits, compositions, particularly pharmaceutical and diagnostic compositions comprising said nucleic acid molecules, vectors, polypeptides, aptamers, antibodies and/or primers. Moreover, the present invention relates to methods for diagnosing affective disorders associated with a non-functional P2X7R protein, an altered ATP-gating of the P2X7R protein, an over- or underexpression of the P2X7R protein or associated with the presence of any one of the aforementioned nucleic acid molecules or polypeptides encoded thereby. Additionally, the present invention relates to uses and methods for treating affective disorders employing a functional or non-functional ATP-gated ion-channel P2X7R.

The present invention also relates to uses of modulators of P2X7R activity for treating affective diseases.

Furthermore, the present invention also relates to methods for identifying and characterizing compounds which are capable of specifically interacting with or altering the characteristics of the polypeptides of the present invention as well as to methods for the production of pharmaceutical compositions.

Up to 10% of persons visiting a physician are afflicted with an affective disorder (also known as behavioural disorder, mood disorder). Nonetheless, most cases remain undiagnosed or inadequately treated. Affective disorders include among others, depression, anxiety, and bipolar disorder. These diseases are well described in the literature; see, for example, Diagnostic and Statistical Manual of Mental Disorders—4th Edition Text Revision (DMS-IV-TR), American Psychiatric Press, 2000.

Depression, also known as unipolar affective disorder, is characterized by a combination of symptoms such as lowered mood, loss of energy, loss of interest, feeling of physical illness, poor concentration, altered appetite, altered sleep and a slowing down of physical and mental functions resulting in a relentless feeling of hopelessness, helplessness, guilt, and anxiety. The primary subtypes of this disease are major depression, dysthymia (milder depression), and atypical depression. Other important forms of depression are premenstrual dysphoric disorder and seasonal affective disorder.

Present treatment of depression consists of psychotherapy, antidepressant drugs, or a combination of both. Most antidepressive drugs target the transport of the neurotransmitters serotonin and/or norepinephrine, or the activity of the enzyme monoamine oxidase. They include: Selective serotonin-reuptake inhibitors (e.g., fluoxetine, paroxetine, sertraline, fluvoxamine), tricyclic antidepressants (e.g., amitriptyline, imipramine, desipramine, nortriptyline), monoamine oxidase inhibitors (e.g., phenelzine, isocarboxazid, tranylcypromine), and designer antidepressants such as mirtazapine, reboxetine, nefazodone. However, all existing antidepressive drugs possess shortcomings such as long latency until response, high degree of non-responders and undesirable side effects (Holsboer, Biol. Psychol. 57 (2001), 47-65). Therefore, a need exists in the medical community for new antidepressive drugs with improved pharmacological profile (Baldwin, Hum. Psychopharmacol. Clin. Exp. 16 (2001), S93-S99).

Anxiety disorders are defined by an excessive or inappropriate aroused state characterized by feelings of apprehension, uncertainty, or fear. They are classified according to the severity and duration of their symptoms and specific affective characteristics. Categories include: (1) Generalized anxiety disorder, (2) panic disorder, (3) phobias, (4) obsessive-compulsive disorder, (5) post-traumatic stress disorder, and (6) separation anxiety disorder. The standard treatment for most anxiety disorders is a combination of cognitive-behavioural therapy with antidepressant medication. Additional medications include benzodiazepines and buspirone.

Bipolar disorder, also known as manic-depression, is characterized by mood swings between periods of mania (i.e. mood elevation including exaggerated euphoria, irritability) and periods of depression. Bipolar disorder is classified according to the severity of the symptoms. Patients diagnosed with bipolar disorder type I suffer from manic or mixed episodes with or without major depression. In Bipolar Disorder type II, patients have episodes of hypomania and episodes of major depression. With hypomania the symptoms of mania (euphoria or irritability) appear in milder forms and are of shorter duration. The current drugs used to treat bipolar disorders are lithium, valproate and lamotrigine, which stimulates the release of the neurotransmitter glutamate. As with antidepressive drugs, they take weeks to become effective and can result in undesirable side effects, for example, high levels of lithium in the blood can be fatal.

Compelling evidence suggest that affective disorders are biological diseases. However, there are no laboratory tests or other procedures that a common physician can use to make a definitive diagnosis. Instead, a specially trained physician or psychiatrist must diagnose the illness based on a group of symptoms that occur together. This process is often time consuming and laborious requiring several visits for the physician to perform a careful history of the symptoms that the patient is currently experiencing as well as any symptoms he or she has had in the past. Therefore, an easy and effective method for the accurate diagnosis of affective disorders is of high interest to the medical community (Wittchen et al., J. Clin. Psychiatry 62, suppl. 26 (2001), 23-28).

Most patients afflicted with affective disorders have family antecedents and identical twins studies suggest a strong genetic component. For example, genetic mapping on an isolated population of the central valley of Costa Rica suggests a locus for severe bipolar disorder at chromosome 18q22-q23 (Freimer et al., Nature Genetics 12 (1996), 436-441). Moreover, genetic studies performed on the Old Order Amish population suggest that genes on chromosomes 6, 13, and 15 may contribute to the susceptibility of bipolar affective disorder (Ginns et al., Nature Genetics 12 (1996), 431-435). Recently, a genome-wide search in a homogenous population found in the Saguenay/Lac-St-Jean region of Quebec suggests the presence of a major locus for bipolar disorder on chromosome 12q23-q24 (Morissette et al., Am. J. Med. Genet. (Neuropsychiatr. Genet.) 88 (1999), 567-587). Susceptibility loci on chromosomes 5 and 21 were also found in this study. Other groups report minimal evidence for linkage in the region of 12q23 (Kelsoe et al., Proc. Natl. Acad. Sci. USA 98 (2001), 585-590; Sklar, Annu. Rev. Genomics Hum. Genet. 3 (2002), 371-413). Given the various loci mentioned in the above studies (e.g., links to chromosomes 5, 6, 12, 13, 15, 18, 21), a definite genetic link for affective diseases remains to be found.

Thus, although several genes have been assumed to be linked with affective disorders as mentioned hereinabove, however, no clear correlation has so far been shown. Since no well-suited medication nor diagnosis on a molecular level for affective disorders is available, there is a need for identifying a gene whose mutations cause the whole spectrum of affective disorders as well as for providing medicaments and methods for diagnosis and treatment of affective disorders.

Thus, the technical problem underlying the present invention is to provide means and methods for diagnosis and treating affective disorders.

The solution to said technical problem is achieved by providing the embodiments characterized in the claims.

SUMMARY OF THE INVENTION

Accordingly, the present invention relates to a nucleic acid molecule comprising a nucleic acid sequence selected from the group consisting of:

(a) a genomic nucleotide sequence encoding an ATP-gated ion channel P2X7R and which contains a mutation in the 5'UTR region corresponding to positions 362, 532, 1100, 1122, 1171 or 1702 of the genomic sequence of the wild-type ATP-gated ion channel P2X7R as depicted in SEQ ID NO: 1, wherein at said position said nucleotide is replaced by another nucleotide;

(b) a nucleic acid sequence encoding a polypeptide which has an amino acid sequence of the ATP-gated ion channel P2X7R, wherein in the exon as indicated in column "Exon" of the following Table A the amino acid residue as indicated in column "Amino acid residue" of Table A corresponding to the position as indicated in column "Position in wild-type" of Table A of the wild-type ATP-gated ion channel P2X7R amino acid sequence as depicted in SEQ ID NO: 3 or 4 is replaced by another amino acid residue

TABLE A

| Exon | Amino acid residue | Position in wild-type |
|---|---|---|
| exon 3 | R (Arg) | 117 |
| exon 5 | G (Gly) | 150 |
| exon 6 | E (Glu) | 186 |
| exon 6 | L (Leu) | 191 |
| exon 8 | R (Arg) | 270 |
| exon 13 | I (Ile) | 568 |
| exon 13 | R (Arg) | 578 |

(c) a nucleotide sequence encoding an ATP-gated ion channel P2X7R and which contains a mutation in exon 5 or 8 corresponding to position 32548 or position 37633 of the wild-type ATP-gated ion channel P2X7R nucleotide sequence as depicted in SEQ ID NO: 1, wherein at said position said nucleotide is replaced by another nucleotide (d) a nucleic acid sequence encoding a polypeptide which has an amino acid sequence of an ATP-gated ion channel P2X7R, wherein amino acids corresponding to positions 488 to 494 of the wild-type ATP-gated ion channel P2X7R as depicted in SEQ ID NO: 3 or 4 are deleted;

(e) a genomic nucleotide sequence encoding an ATP-gated ion channel P2X7R, wherein in the intron as indicated in column "Intron" of the following Table B the nucleotide as indicated in column "Replaced nucleotide" of Table B corresponding to the position as indicated in column "Position in wild-type" of Table B of the wild-type ATP-gated ion channel P2X7R nucleotide sequence as depicted in SEQ ID NO: 1 is replaced by another nucleotide

TABLE B

| Intron | REPLACED NUCLEOTIDE | Position in wild-type |
|---|---|---|
| intron 1 | G | 3166 |
| intron 1 | C | 24778 |
| intron 1 | C | 24830 |
| intron 3 | A | 26308 |
| intron 3 | G | 26422 |
| intron 4 | G | 32394 |
| intron 4 | T | 32434 |
| intron 5 | A | 32783 |
| intron 6 | G | 35641 |
| intron 6 | A | 35725 |
| intron 6 | T | 36001 |
| intron 7 | G | 36378 |
| intron 7 | T | 36387 |
| intron 7 | G | 36398 |
| intron 9 | C | 47214 |
| intron 11 | T | 47563 |
| intron 12 | C | 54307 |
| intron 12 | G | 54308 |

(f) a genomic nucleotide sequence encoding an ATP-gated ion channel P2X7R and which contains a mutation in the 3'UTR region corresponding to position 55169, 55170, 55171, 55917 or 54925 of the wild-type ATP-gated ion channel P2X7R nucleotide sequence as depicted in SEQ ID NO: 1, wherein at said position said nucleotide is replaced by another nucleotide;

(g) a nucleotide sequence comprising at least 20 or 21 nucleotides and comprising the mutations or deletions as defined in any one of (a) to (f);

(h) a nucleic acid sequence comprising a nucleotide sequence as shown in any one of SEQ ID NOs: 13 to 51;

(i) a nucleic acid sequence encoding a polypeptide comprising the amino acid sequence of SEQ ID NOs: 5 to 12;

(j) a nucleotide sequence which hybridizes to a nucleotide sequence defined in any one of (a) to (g) or to the nucleotide sequence of (h) and having a mutation as defined in any one of (a) to (f); and (k) a nucleic acid sequence being degenerate as a result of the genetic code to the nucleic acid sequence as defined in (j).

The present invention further relates to a vector and a host cell containing the nucleic acid molecules described herein as well as methods of using such hosts to produce polypeptides encoded by the nucleic acid molecules. In this regard, the present invention also relates to the polypeptides encoded by the nucleic acid molecules and antibodies that specifically bind to the polypeptides.

The present invention additionally relates to an aptamer that specifically binds to a nucleic acid molecule as described herein and a primer or a pair of primers that are capable of specifically amplifying a nucleic acid molecule described herein.

The present invention further relates to methods of diagnosing or diagnosting a susceptibility to an affective disorder or methods of treating an affective disorder as described within the present invention. Diagnostic and pharmaceutical compositions comprising nucleic acid molecules, compounds, modulators and/or agonists as described herein that are useful for these purposes.

It has surprisingly been found that mutations in the P2X7R gene which encodes the ATP-gated ion channel P2X7R can cause the whole spectrum of affective disorders. Six different mutations in the 5'UTR of the P2X7R gene, seven different mutations in exons 3, 5, 6, 8 and 13 of the P2X7R gene leading to an amino acid replacement of the corresponding amino acid in the wild-type sequence of P2X7R depicted in SEQ ID NO: 3 or 4 and two mutations in exons 5 and 8 of said gene, respectively, leading to a replacement of a nucleotide by another nucleotide, a deletion of nucleotides in exon 13 of said gene, 18 mutations in introns 1, 3, 4, 5, 6, 7, 9, 11 and 12 and 5 mutations in the 3'UTR of the P2X7R gene have been identified to co-segregate with the affection status in 41 unrelated families affected with affective disorders. The term "affective disorder" when used in the context of the present invention means to include, but is not limited to, depression, anxiety, unipolar disorder, bipolar disorder type I, bipolar disorder type II, mania, attention deficit hyperactive disorder, substance abuse, and any other disorders affecting the normal behaviour, or mood of an individual.

Each mutation causes alterations that can explain affective disorders as shown in the Examples hereinbelow.

P2X7R is an ATP-gated ion channel belonging to the P2X ionotropic channel family. The gene was first isolated from rat brain (Surprenant et al., (1996), 272, 735-738; Genbank accession number NM_019256) and subsequently from a human monocyte library (Rassendren et al., J. Biol. Chem. 272 (1997), 5482-5486; Genbank accession numbers NM_002562, Y09561) by virtue of its sequence homology with the other members of the P2X family. It was later found that P2X7R corresponded to the unidentified P2Z receptor which mediates the permeabilising action of ATP on mast cells and macrophages (Dahlqvist and Diamant, Acta Physiol. Scand. 34 (1974), 368-384; Steinberg and Silverstein, J. Biol. Chem. 262 (1987), 3118-3122; Gordon, Biochem. J. 233 (1986), 309-319). The P2X7R has two hydrophobic membrane-spanning domains, an extracellular loop, and forms transmembrane ion channels. P2X7 receptors seem to function only in homooligomeric form and bear a pharmacological profile markedly different from other P2X homo- or heteromers (North and Surprenant, Annual Rev. Pharmacology Toxicology 40 (2000), 563-580). P2X7R requires levels of ATP in excess of 1 mM to achieve activation, whereas other P2X receptors activate at ATP concentrations of $\leq 100$ μM (Steinberg et al., J. Biol. Chem. 262 (1987), 8884-8888; Greenberg et al., J. Biol. Chem. 263 (1988), 10337-10343) 32). While all P2X receptors demonstrate non-selective channel-like properties following ligation, the channels formed by the P2X7R can rapidly transform into pores that can allow the passage of molecules of up to 900 Dalton (Virginio et al., J. Physiol. 519 (1999), 335-346).

P2X7R is expressed in hematopoietic cells, mast cells and macrophages (Surprenant et al., Science 272 (1996), 3118-3122), where it is organized in tetrameric or hexameric form (Kim et al., J. Biol. Chem. 276 (2001), 23262-23267). P2X7R is inter alia involved in the regulation of the immune function and inflammatory response. Activation of P2X7R by ATP in macrophages is associated with mitogenic stimulation of T cells (Baricordi et al., Blood 87 (1996), 682-690), the release of cytokines such as interleukin-1β (Griffiths et al., J. Immol. 154 (1995), 2821-2828), and formation of macrophage polykarions (Falzoni et al., J. Clin. Invest. 95 (1995), 1207-1216). Stimulation of the P2X7R with ATP can also result in cell death by triggering massive transmembrane ion fluxes (particularly influx of Ca2+ and Na+, and efflux of K+) and the formation of non-selective plasma membrane pores (Di Virgilio et al., Cell Death Differ. 5 (1998), 191-199).

In the brain, P2X7R was originally thought to be restricted to microglia (resident macrophage of the brain) and ependymal cells rather than neurons (Collo et al., Neuropharmacology 36 (1997), 1277-1283) suggesting a role of P2X7R in neurodegeneration. However, P2X7R has since been found in neurons of the rat retina (Brandle et al, Brain Research Molecular Brain Res. 62 (1998), 106-109), cochlear ganglion cells (Brandle et al, Neuroscience Letters 273 (1999), 105-108), and presynaptic terminals of neurons throughout the brainstem and spinal cord (Deuchards et al., J. Neurosci. 21 (2001), 7143-7152). Subsequent studies also suggest that P2X7R regulates the release of neurotransmitters such as glutamate and GABA in neurons of the hippocampus (Armstrong et al., J. Neuroscience 22 (2002), 5938-5945, Sperlágh et al., J. Neurochem. 81 (2002), 1196-1211). Organisation of P2X7R in glial cells and astrocytes of the brain appears monomeric (Kim et al., J. Biol. Chem. 276 (2001), 23262-23267).

Several agonists and antagonists of P2X7R have been identified. Brilliant Blue (Jiang et al., Mol. Phamacol. 58 (2000), 82-88), the isoquinolines 1-[N,O-Bis(5-isoquinolinesulfonyl)-N-methyl-L-tyrosyl]4-phenylpiperazine and N-[1-[N-methyl-p-(5 isoquinolinesulfonyl) benzyl]-2-(4 phenylpiperazine)ethyl]-5-isoquinolinesulfonamide (Humphreys et al., Mol. Pharmacol., 54 (1998), 22-32), adamantane derivatives (WO 99/29660, WO 99/29661, WO 00/61569, WO 01/42194, WO 01/44170, WO 01/44213), substituted phenyl compounds (WO 00/71529), piperidine and piperazine derivatives (WO 01/46200) are antagonists of P2X7R while Oxidized ATP (oATP) acts as an irreversible inhibitor of the receptor (Chen et al., J. Biol. Chem., 268 (1993), 8199-8203). Some of these antagonists are presently being evaluated for the treatment of inflammatory, immune, and cardiovascular diseases. BzATP (2'-3'-O-(4-Benzoylbenzoyl)adenosine 5'-triphosphate ($C_{24}H_{24}N_5O_{15}P_3$)) acts as agonist of P2X7R (North and Surprenant, Annu. Rev. Pharmacol. Toxicol. 40 (2000), 563-580). WO 99/55901 describes a method for identifying compounds that modulate the activity of a mammalian purinoreceptor selected from the group consisting of P2X2, P2X3, P2X4, P2X5, P2X6 and P2X7 and suggests a role of said purinoreceptors in therapy of behavioural disorders such as epilepsy, depression and aging-associated degenerative diseases.

Mutant mice lacking P2X7R are healthy, fertile and demonstrate no overt phenotype. However, in contrast to their wild-type counterparts, LPS-activated peritoneal macrophages from P2X7R$^{-/-}$ animals fail to generate mature interleukin-1β (IL-1β) when challenged with ATP suggesting an inability of peritoneal macrophages to release IL-1 in response to ATP (Solle et al, J. Biol. Chem. 276 (2001), 125-132). A detailed behavioural study of the P2X7R–/– mice was not performed. In humans, a Glu-496 to Ala polymorphism leads to the loss of P2X7 function (Gu et al., J. Biol. Chem. 276 (2001), 11135-11142) and is associated with B-cell chronic lymphocytic leukaemia (Thunberg, et al, The Lancet 360 (2002), 1935-1939). Additional polymorphs in the putative P2X7R promoter region, and coding region have been reported (Li et al., FEBS Lett. 531 (2002), 127-131; EP 1199372).

Despite the abundant literature concerning P2X7R, a role in affective disorders has never been suggested or alluded to in the prior art.

Before the present invention is described in detail, it is to be understood that this invention is not limited to the particular methodology, protocols, cell lines, vectors, and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

It must be noted that as used herein and in the appended claims, the singular forms "a", "an", and "the", include plural referents unless the context clearly indicates otherwise. Thus, for example, reference to "a reagent" includes one or more of such different reagents, and reference to "the method" includes reference to equivalent steps and methods known to those of ordinary skill in the art that could be modified or substituted for the methods described herein.

In accordance with the present invention, the term "nucleic acid sequence" means the sequence of bases comprising purine- and pyrimidine bases which are comprised by nucleic acid molecules, whereby said bases represent the primary structure of a nucleic acid molecule. Nucleic acid sequences include DNA, cDNA, genomic DNA, RNA, synthetic forms and mixed polymers, both sense and antisense strands, or may contain non-natural or derivatized nucleotide bases, as will be readily appreciated by those skilled in the art.

When used herein, the term "polypeptide" means a peptide, a protein, or a polypeptide which encompasses amino acid chains of a given length, wherein the amino acid residues are linked by covalent peptide bonds. However, peptidomimetics of such proteins/polypeptides wherein amino acid(s) and/or peptide bond(s) have been replaced by functional analogs are also encompassed by the invention as well as other than the 20 gene-encoded amino acids, such as selenocysteine. Peptides, oligopeptides and proteins may be termed polypeptides. The terms polypeptide and protein are often used interchangeably herein. The term polypeptide also refers to, and does not exclude, modifications of the polypeptide, e.g., glycosylation, acetylation, phosphorylation and the like. Such modifications are well described in basic texts and in more detailed monographs, as well as in a voluminous research literature.

The term "position" used in accordance with the present invention means the position of either an amino acid within an amino acid sequence depicted herein or the position of a nucleotide within a nucleic acid sequence depicted herein.

The term "ATP-gated ion channel P2X7R", in accordance with this invention, denotes a polypeptide which can be classified as a member of the P2X ionotropic receptor family. They are also known as purinergic receptors. P2X receptors are ligand-gated ion channels. The ligand for these receptors may be ATP and/or another natural nucleotide such as ADP, UTP and UDP, or a synthetic nucleotide such as 2-methylthio ATP. The criteria for the classification are: (1) a sequence homology that is higher than 39% across the family or different species; (2) signal transduction mechanism involving ion conductance (Khakh et al., Pharmacol Rev. 253 (2001), 107-18). Accordingly, the term "ATP-gated ion channel P2X7R" is interchangeable with the terms "ionotropic receptor" or "purinergic receptor". Preferably, the term "ATP-gated ion channel P2X7R" denotes a polypeptide which can be classified as an ATP-gated ion channel P2X7R on the basis of one or more structural and/or functional characteristics, preferably those described above. Structural characteristics refer to certain structural features which allow to classify a polypeptide as being a P2X7R protein. One such feature is the amino acid sequence. In the context of the present invention a polypeptide is classified as an ATP-gated ion channel P2X7R if it shows a certain degree of sequence identity over its own length to the amino acid sequence of the human P2X7R protein depicted in SEQ ID NO: 3 or 4. This degree of sequence identity is at least 40%, more preferably at least 50%, even more preferably at least 60%, at least 70%, at least 80%, at least 90% or at least 95%. It is particularly preferred that the degree of sequence identity is at least 65%.

Moreover, structural characteristics of P2X7R proteins are two hydrophobic membrane-spanning domains, an extra cellular loop which could be analyzed by using the program TMPRED (Hofmann Biol. Chem. 347 (1993), 166) or TMHMM (Krogh J. Mol. Bio. 305 (2001), 567-580). Additionally, P2X7R may exist as a single polypeptide, as dimer, tetramer or the like.

Thus, in the context of the present invention a protein is preferably classified as a P2X7R protein if it displays at least one of the above-mentioned structural characteristics. Functional characteristics refer to properties related to the biological activity of the P2X7R protein. In particular, P2X7R is an ATP-gated ion channel which allows calcium and sodium ions to pass from extracellular solution to intracellular solution, and allows potassium ions to pass from intracellular to extracellular solution. Moreover, the ATP-gated ion channel P2X7R forms naturally a homooligomeric form. The characteristics of P2X7R receptor proteins can be determined as mentioned hereinbelow. The term "ATP-gated ion channels P2X7R" comprises functional and non-functional forms of the ATP-gated ion channels P2X7R. A functional ATP-gated ion channel P2X7R is understood to be a P2X7R protein which has at least one of the above-mentioned functional characteristics which can be measured by methods known in the art. A non-functional ATP-gated ion channel P2X7R is a protein which can be classified as a P2X7R protein due to structural characteristics as described above but which has lost at least one, preferably all, functional characteristics of a P2X7R protein as described above. Non-functionality of the P2X7R protein can, e.g., be determined by measuring whether calcium and sodium ions can flow into cells or whether potassium ions can exit from cells. Thus, it is possible to determine the occurrence of a mutation in the ATP-gated ion channel P2X7R by measuring either calcium and/or sodium influx or efflux of cells. Cells harbouring a mutation in the P2X7R gene show an altered ion influx and/or efflux in comparison to cells harbouring a wild-type P2X7R protein.

Additionally, there are different methods that could be used to determine whether the P2X7R is functional or non-functional, for example, altered. One method consists of measuring the rate of ATP-induced incorporation of ethidium into cells, e.g. cells isolated from an individual. Ethidium is incorporated into the cells through P2X7R pores, when the pore formation is activated by ATP. Cells are then incubated with or without ATP in the presence of ethidium, then they are analyzed by flow cytometry. Ethidium fluorescence is measured and compared in the presence or absence of ATP. If the P2X7R has lower activity, the ethidium fluorescence induced by ATP will be lower than in control cells. Such a method was used to verify P2X7R activity in isolated B-lymphocytes and T-lymphocytes from leukaemia patients (Wiley et al., Lancet 359 (2002), 1114-1119). Briefly, isolated cells are incubated in 1 ml of Hepes buffered potassium chloride at 37° C. with continuous stirring. Ethidium is then added at a concentration of 25 mol/l, followed 40 seconds later by the addition of 10 µl of 100 mmol/l ATP stock. Cells are analyzed at 1,000 events/s by flow cytometry using a Coulter Elite flow cytometer (Coulter, Hialeah, Fla.) with argon laser excitation at 488 nm. Fluorescent emission was collected using a 590-nm long-pass filter. The linear mean channel fluorescence intensity for each gated subpopulation over successive 5-s intervals was analyzed with the use of Win-MDI software (Joseph Trotter, version 2.7) and plotted against time.

Another method of determining P2X7R activity is to measure calcium entry into isolated cells incubated with fluorescent dyes that emit only upon binding to calcium. The cells have to be loaded with the dye and then the calcium entry has to be stimulated. Examples of such dyes include Fura-2, Calcium green, calcium orange, calcium crimson (all available from Molecular Probes). Methods of measuring calcium transport are well known in the art; see for example, Takahashi et al., Physiol Rev. 79 (1999), 1089-1125. Furthermore, calcium entry into the cells produces changes in the membrane electric potential. This changes can be measured by electrophysiology (patch clamp) or by using dyes which are sensitive to voltage change. Such methods are also well known in the art, see for example, Gonzalez et al., DDT 4 (1999), 431-439; González and Tsien, Chemistry & Biology 4 (1997), 269-277; González and Tsien, Biophysical Journal 69 (1995), 1272-1280.

Yet another method is to measure uptake of 133Ba21. Ba21 is a good surrogate for Ca21 and once inside the cell is neither pumped nor sequestered by transport ATPases. Ba21 uptake can be measured over 60 s using 133BaCl2 (final concentration, 0.2 mM). At time 0, a prewarmed stock solution of 133Ba21 (0.4 mM and 1 µCi/ml) is added in equal volumes to prewarmed isolated cells in 150 mM KCl with HEPES (pH 7.4) at 37° C. ATP (1 mM) is added either 10 minutes before or simultaneously with the 133Ba21 isotope. Aliquots of 0.8 ml are taken at time points between 0 and 60 s and are immediately mixed with 0.2 ml of ice-cold 50 mM MgCl2 (in KCl-HEPES medium) that had been previously layered over 250 µl of oil mixture (di-n-butyl phthalate and di-iso-octyl phthalate, 7:3 vol/vol) and then centrifuged at 8,000 g for 30 s. The supernatants and the oil are aspirated, and the cell pellets are counted in a Wallac Wizard 3 automatic gamma-counter or in any other suitable gamma measuring unit.

The present invention is based on the finding that mutations of different kinds in the P2X7R gene are linked to the occurrence of affective disorders. The first type of mutations are mutations in the 5'UTR. Examples of such mutations are single nucleotide replacements at positions corresponding to positions 362, 532, 1100, 1122, 1171 or 1702 of the genomic sequence of the wild-type ATP-gated ion channel P2X7R as described in SEQ ID NO: 1.

The position with respect to nucleotide sequences mentioned herein refer to the sequence shown in SEQ ID NO: 1. This sequence represents the nucleic acid sequence of the P2X7R gene encoding the ATP-gated ion channel P2X7R. It is possible for the skilled person to identify the position in the genomic sequence corresponding to a position in SEQ ID NO: 1 by aligning the sequences. Moreover, the exact locations of the exons and introns are indicated in SEQ ID NO: 1 hereinbelow. Additionally, the person skilled in the art is able to identify exons and introns of the P2X7R gene by comparing SEQ ID NO: 1 with SEQ ID NO: 2 which shows the cDNA sequence of the P2X7R gene.

Preferably, at position 362 in the 5'UTR of the genomic sequence of the P2X7R gene depicted in SEQ ID NO: 1 a thymine (T) is replaced by another nucleotide, preferably a purine base. More preferably, at said position said thymidine is replaced by a pyrimidine base. Particularly preferred, said thymine is replaced by a cytosine (C).

At position 532 in the 5'UTR of the genomic sequence of the P2X7R gene depicted in SEQ ID NO: 1 a thymine (T) is preferably replaced by another nucleotide, preferably a pyrimidine base. More preferably, at said position said thymine is replaced by a purine base. Particularly preferred, said thymidine is replaced by a guanine (G).

The adenine (A) residues at positions 1100 and 1122, respectively, in the 5'UTR of the genomic sequence of the P2X7R gene is preferably replaced by a pyrimidine base. More preferably, said adenine is replaced by a purine base and particularly preferred said adenine is replaced by a guanine (G).

At position 1171 in the 5'UTR of the genomic sequence of the P2X7R gene depicted in SEQ ID NO: 1 a cytidine (C) is replaced by another nucleotide, preferably by a pyrimidine base. More preferably, said cytidine is replaced by a purine base and even more preferred, said cytidine is replaced by a guanine (G).

The guanine at position 1702 in the 5'UTR of the genomic sequence of the gene P2X7R depicted in SEQ ID NO: 1 is replaced by another nucleotide, preferably by a pyrimidine base. More preferably, said guanine is replaced by a purine base and particularly preferred it is replaced by an adenine (A).

A second type of mutation found in the P2X7R gene are mutations in exons which lead to amino acid substitutions in the corresponding amino acid sequence. These are the mutations listed under item (b), supra. In this context, the term "an amino acid residue as indicated in column 'Amino acid residue' of Table A corresponding to position X of the wild-type ATP-gated ion channel P2X7R as depicted in column 'Position in wild-type'" has the following meaning: The amino acid residue in question would be located at position X in the sequence of SEQ ID NO: 3 or 4 if the sequence in which said amino acid residue occurs is compared and aligned with the amino acid sequence of SEQ ID NO: 3 or 4. The amino acid sequence shown in SEQ ID NO: 3 or 4 is the amino acid sequence of the human P2X7R gene and is used as a reference sequence in the present invention.

In order to determine whether an amino acid residue or nucleotide residue in a given P2X7R sequence corresponds to a certain position in the amino acid sequence or nucleotide sequence of SEQ ID NO: 1, 3 or 4, the skilled person can use means and methods well-known in the art, e.g., alignments, either manually or by using computer programs such as those mentioned further down below in connection with the definition of the term "hybridization" and degrees of homology.

For example, BLAST2.0, which stands for Basic Local Alignment Search Tool (Altschul, Nucl. Acids Res. 25 (1997), 3389-3402; Altschul, J. Mol. Evol. 36 (1993), 290-300; Altschul, J. Mol. Biol. 215 (1990), 403-410), can be used to search for local sequence alignments. BLAST produces alignments of both nucleotide and amino acid sequences to determine sequence similarity. Because of the local nature of the alignments, BLAST is especially useful in determining exact matches or in identifying similar sequences. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

Analogous computer techniques using BLAST (Altschul (1997), loc. cit.; Altschul (1993), loc. cit.; Altschul (1990), loc. cit.) are used to search for identical or related molecules in nucleotide databases such as GenBank or EMBL. This analysis is much faster than multiple membrane-based hybridizations. In addition, the sensitivity of the computer search can be modified to determine whether any particular match is categorized as exact or similar. The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1-2% error; and at 70, the match will be exact. Similar molecules are usually identified by selecting those which show product scores between 15 and 40, although lower scores may identify related molecules.

As mentioned above, the second group of mutations identified in the P2X7R gene are mutations in the exons of the P2X7R gene which lead to amino acid substitutions. In this respect SEQ ID NO 2 shows the cDNA sequence of the P2X7R gene. In exon 3 at position 117 of the corresponding wild-type amino acid sequence of P2X7R depicted in SEQ ID NO: 3 or 4 an arginine (R) residue is replaced by another amino acid residue, preferably by an aliphatic, acidic or basic amino acid residue. More preferably, by an aromatic amino acid residue which is particularly preferred to be a tryptophane (W). The resulting polypeptide is shown in SEQ ID NO: 5.

In exon 5 at position 150 of the wild-type amino acid sequence of P2X7R depicted in SEQ ID NO: 3 or 4 a glycine (G) residue is replaced by another amino acid residue, preferably by an aliphatic, aromatic or acidic amino acid residue. More preferably, by a basic amino acid residue and particularly preferred by an arginine (R). The resulting polypeptide is shown in SEQ ID NO: 6.

At position 186 in exon 6 of the wild-type amino acid sequence of P2X7R depicted in SEQ ID NO: 3 or 4 a glutamate residue (E) is replaced by another amino acid residue, preferably by an aliphatic, aromatic or acidic amino acid residue. More preferably, said glutamate is replaced by a basic amino acid residue which is particularly preferred a lysine (K). The resulting polypeptide is shown in SEQ ID NO: 7.

In exon 6 of the wild-type amino acid sequence of P2X7R depicted in SEQ ID NO: 3 or 4 at position 191 a leucine residue (L) is replaced by another amino acid residue. Said amino acid residue is preferably an aliphatic, acidic or basic amino acid residue. More preferably, said amino acid residue is an aromatic amino acid residue which is particularly preferred to be a proline (P). The resulting polypeptide is shown in SEQ ID NO: 8.

In exon 8 of the wild-type amino acid sequence of P2X7R depicted in SEQ ID NO: 3 or 4 at position 270 an arginine residue (R) is replaced by another amino acid residue. Said amino acid residue is preferably an aromatic, acidic or basic amino acid residue. More preferably, said amino acid residue is an aliphatic amino acid residue which is particularly preferred to be a cysteine (C). The resulting polypeptide is shown in SEQ ID NO: 9.

At position 568 in exon 13 of the wild-type amino acid residue of P2X7R depicted in SEQ ID NO: 3 or 4 an isoleucine (I) residue is replaced by another amino acid residue. More preferably, said isoleucine is replaced by an aromatic, basic or acidic amino acid residue. Even more preferred, said isoleucine is replaced by an aliphatic amino acid residue which is particularly preferred to be an asparagine (N). The resulting polypeptide is shown in SEQ ID NO: 10.

In exon 13 at position 578 in the wild-type amino acid sequence of P2X7R depicted in SEQ ID NO: 3 or 4 an argine residue (R) is replaced by another amino acid residue. Said amino acid residue is preferably an aromatic, acidic or basic amino acid residue. More preferably, it is an aliphatic amino acid residue and particularly preferred it is a glutamine (Q) residue. The resulting polypeptide is shown in SEQ ID NO: 12.

It is envisaged that the above-mentioned mutations in the exons of the P2X7R gene occur due to point mutations caused by, e.g. chemical and/or physical means or inaccuracy of the replication complex followed by a failure of the reparation machinery of a cell, can result in a change of a single codon. Possible types of point mutations are transitions, i.e. change of a purine or pyrimidine base for another purine or pyrimidine base, e.g. adenine to guanine or thymidine to cytosine or transversions, i.e. change of a purine or pyrimidine base for another pyrimide or purine base, e.g., adenine to thymidine or guanine to cytosine. Additionally a point mutation can also be caused by insertion or deletion of one or more nucleotides.

The mutations leading to the replacement of the amino acids as mentioned hereinabove and hereinbelow are indicated in Table 1 hereinbelow.

The third group of mutations in the P2X7R gene has been identified to be in exons 5 and 8 of the P2X7R gene depicted in SEQ ID NO: 1 and to be silent, i.e. they do not lead to amino acid changes. In particular, at position 32548 in exon 5 of the wild-type genomic sequence P2X7R gene depicted in SEQ ID NO: 1 a cytidine residue is replaced by another nucleotide. Said nucleotide is preferably a pyrimidine base and particularly preferred a thymine. The exchange of the cytidine residue at position 32548 in exon 5 of the P2X7R gene by another nucleotide preferably does not lead to the replacement of the amino acid cysteine by another amino acid residue.

In exon 8 of the wild-type P2X7R gene depicted in SEQ ID NO: 1 at position 37633 a cytidine residue is replaced by another nucleotide residue. Said nucleotide residue is preferably a pyrimidine base and particularly preferred thymine. Due to this replacement the amino acid aspartate (D) encoded by the respective codon in which at position 37633 a replacement has taken place is preferably not replaced by another amino acid residue.

The above-mentioned mutations in exons 5 and 8 at positions 32548 and 37633, respectively, of the wild-type P2X7R gene depicted in SEQ ID NO:1 are mutations at the third position of a triplet codon, i.e. at the wobble base, which lead to so-called silent mutations. Silent mutations do normally not lead to a change of the amino acid due to the degeneracy of the genetic code, i.e. 64 triplets encode at all 20 naturally occurring amino acids. However, said silent mutations lead to a change in the codon encoding its respective amino acids insofar that the newly generated codon may not fit so well into the codon usage of an organism. Namely, the newly generated codon is not translated by the ribosome with the same efficiency as the "old" codon. This may lead to insufficient amounts of the corresponding polypeptide causing an distinct phenotype.

The fourth group of mutations in the P2X7R gene described hereinabove in item (d) is a deletion of 7 amino acids corresponding to positions 488 to 494 of the wild-type P2X7R amino acid sequence as depicted in SEQ ID NO: 3 or 4. Thus, the present invention also relates to nucleic acid sequences encoding a P2X7R protein in which amino acids corresponding to positions 488 to 494 of the wild-type ATP-gated ion channel P2X7R as depicted in SEQ ID NO: 3 or 4 are deleted. This means, according to the present invention, that a fragment encompassing amino acid positions 488 to 494 of the corresponding wild-type amino acid sequence depicted in SEQ ID NO: 3 or 4 is deleted which results in a shortened polypeptide. An example for such a shortened polypeptide is depicted in SEQ ID NO: 11. This type of mutation as described herein preferably encodes a non-functional ATP-gated ion channel P2X7R. In the present invention the deletion of a fragment encompassing amino acids 488 to 494 of the wild-type amino acid sequence depicted in SEQ ID NO: 3 or 4 is the result of a deletion in exon 13. The resulting protein depicted in SEQ ID NO: 11 lacks amino acids 488 to 494 of the corresponding wild type amino acid sequence depicted in SEQ ID NO: 3 or 4 such that amino acid position 494 of the deleted polypeptide depicted in SEQ ID NO: 11 corresponds to amino acid position 502 of the wild-type amino acid sequence depicted in SEQ ID NO: 3 or 4. Preferably, the nucleic acid sequence of the invention encodes a P2X7R polypeptide in which exactly amino acids corresponding to positions 488 to 494 of SEQ ID NO: 3 or 4 are deleted. However, also mutants are comprised in which either more or less amino acids within the P2X7R amino acid sequence set forth in SEQ ID NO: 3 or 4 may be deleted due to, for example, atypical splicing or deletion of nucleotides of the nucleic acid molecule encoding P2X7R or wrong post-translational processes, as long as the P2X7R ATP-gated ion channel is non-functional. For example, it is also possible that further amino acids preceding amino acid position 488 or amino acids succeeding amino acid position 494 may be deleted or that less amino acids are deleted.

Preferably at least one, more preferably at least two, even more preferably at least three and most preferably at least 5 amino acid residues are further deleted upstream from the position corresponding to amino acid residue 488 and/or downstream of the position corresponding to amino acid residue 494 of SEQ ID NO: 3 or 4.

However, it is preferred that not more than 20, preferably not more than 15, even more preferably not more than 10 and most preferably not more than 7 amino acid residues are further deleted upstream of the position corresponding to amino acid residue 488 of SEQ ID NO: 3 or 4 or downstream of the position corresponding to amino acid residue 494 of SEQ ID NO: 3 or 4.

Another group of mutation (mentioned in item (e), supra) resides in introns 1, 3, 4, 5, 6, 7, 9, 11 or 12 of the wild-type genomic sequence of P2X7R depicted in SEQ ID NO: 1. Said mutations in said introns are point mutations as shown in Table B hereinabove and in Table 1, hereinbelow.

At the respective position indicated in the column "Position in wild-type" in Table B or indicated in the column "Polymorphism" in Table 1 the position of the nucleotide residue in the respective intron which is replaced by another nucleotide residue is shown. Accordingly, the term "a nucleotide as indicated in column "Intron" of the Table B corresponding to the position as indicated in column "Replaced nucleotide" of Table B corresponding to the position as indicated in column "Position in wild-type" of Table B is replaced by another nucleotide means that a nucleotide residue in a P2X7R encoding sequence would be located at position Y in SEQ ID NO: 1 when the P2X7R sequence is compared and aligned with the sequence of SEQ ID NO: 1.

If the nucleotide at the respective position is a purine base such as adenine or guanine it is preferred that due to a transition it is replaced by another purine base.

For example, an adenine is replaced by a guanine or a guanine is replaced by an adenine. If the nucleotide at the respective position is a pyrimidine base it is preferred that due to a transition it is replaced by another pyrimidine base. For example, thymine is replaced by a cytidine and a cytidine is replaced by a thymine.

It is also preferred that due to a transversion a purine base is replaced by a pyrimidine base or vice versa. For example, an adenine is replaced by a thymine and a guanine is replaced by a cytidine. Particularly preferred, said nucleotide in introns 1, 3, 4, 5, 6, 7, 9, 11 or 12 of the P2X7R gene depicted in SEQ ID NO: 1 is replaced by the nucleotide depicted in column "Polymorphism" of Table 1, hereinbelow.

A last group of mutations that has been identified relates to mutations which reside in the 3'UTR of the wild-type P2X7R gene depicted in SEQ ID NO: 1. The mutations were found at positions 54925, 55169, 55170, 55171 or 55917 respectively, of the wild-type P2X7R gene depicted in SEQ ID NO: 1.

At position 54925 a guanine residue was found to be replaced by another nucleotide. Preferably, said guanine residue is replaced by a pyrimidine base, more preferably by a purine base and particularly preferred by an adenine.

At position 55169 a cytidine residue is replaced by another nucleotide, preferably by a pyrimidine base. More preferably, it is replaced by a purine base and particularly preferred, it is replaced by an adenine.

At positions 55170 and 55171 an adenine residue is replaced by another nucleotide residue, preferably by a purine base. More preferably, said adenine residue is replaced by a pyrimidine base and particularly preferred said adenine residue is replaced by a cytidine residue. It was also found that at position 55917 a cytidine residue is replaced by another nucleotide. Preferably, said nucleotide residue is a purine base, more preferably a pyrimidine base and particularly preferable a thymine.

As is evident from the above, not all identified mutations are located in exons or lead to a change in the amino acid sequence. Some of the mutations are located in the 5'UTR, the 3'UTR or in introns.

It is known that polymorphisms in promoter and enhancer regions can affect gene function by modulating transcription, particularly if they are situated at recognition sites for DNA binding proteins (Fishman et al., J. Clin. Invest. 102 (1998), 1369-1376). The term "polymorphism" which is used in the present invention means single nucleotide substitution, nucleotide insertion and nucleotide deletion which in the case of insertion and deletion includes insertion or deletion of one or more nucleotides at a position of a gene and corresponding alterations in expressed proteins. Polymorphisms in the 5' untranslated region (5'UTR) of genes can affect the efficiency with which proteins are translated. A representative example of this is in the c-myc gene where a C-G SNP that creates an internal ribosome entry site is associated with increased efficiency of c-myc translation and myeloma (Chappell et al., Oncogene 19 (2000), 4437-4440). Polymorphisms in the 3'UTR can affect gene function by altering the secondary structure of RNA and efficiency of translation or by affecting motifs in the RNA that bind proteins which regulate RNA degradation. Polymorphisms within introns can affect gene function by affecting RNA splicing resulting in aberrant polypeptides. Another way in which intronic polymorphisms can affect gene function is when they affect regulatory motifs within introns. Examples are the Sp1 binding site polymorphism within intron 1 of the COL1A1 gene (Mann et al., J. Clin. Invest 107 (2001), 899-907) and a repeat polymorphisms within the IL-1Ra gene (Keen et al., Bone 23 (1998), 367-371). Further examples between intronic SNPs and gene function are described in Caceres and Kornblihtt, Trends Genet. 4 (2002), 186-93. Example 4 on page 52, line 30 to page 53, line 51 of the text describes potential alternative splicing events and aberrant protein production associated with three SNPs disclosed in the application.

The nucleic acid sequences described hereinabove may comprise at least 56580 nucleotides, preferably at least 10000 nucleotides, at least 5000 nucleotides, at least 1000 nucleotides, at least 500 nucleotides, at least 100 nucleotides. More preferably, said nucleic acid sequences comprise at least 50 nucleotides and particularly preferred they comprise at least 20 or 21 nucleotides comprising the mutations or deletions as described hereinabove. Most preferably such a nucleic acid sequence has a sequence as depicted in any one of SEQ ID NOs: 13 to 51.

The nucleic acid sequences described hereinabove which comprise mutations in exons leading to a replacement of the corresponding amino acid sequence of the P2X7R wild-type polypeptide depicted in SEQ ID NO: 3 or 4 encode polypeptides shown in SEQ ID NOs: 5 to 10 and 12

Additionally, the nucleic acid sequences described hereinabove which comprise a deletion leading to a truncated polypeptide in comparison to the full-length polypeptide of the wild-type P2X7R polypeptide shown in SEQ ID NO: 3 or 4 is shown in SEQ ID NO: 11.

The present invention also relates to nucleic acid molecules which hybridize to one of the above described nucleic acid molecules and which shows a mutation as described hereinabove.

The term "hybridizes" as used in accordance with the present invention may relate to hybridizations under stringent or non-stringent conditions. If not further specified, the conditions are preferably non-stringent. Said hybridization conditions may be established according to conventional protocols described, for example, in Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989), or Higgins and Hames (Eds.) "Nucleic acid hybridization, a practical approach" IRL Press Oxford, Washington D.C., (1985). The setting of conditions is well within the skill of the artisan and can be determined according to protocols described in the art. Thus, the detection of only specifically hybridizing sequences will usually require stringent hybridization and washing conditions such as 0.1×SSC, 0.1% SDS at 65° C. Non-stringent hybridization conditions for the detection of homologous or not exactly complementary sequences may be set at 6×SSC, 1% SDS at 65° C. As is well known, the length of the probe and the composition of the nucleic acid to be determined constitute further parameters of the hybridization conditions. Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. Hybridizing nucleic acid molecules also comprise fragments of the above described molecules. Such fragments may represent nucleic acid sequences which code for a non-functional ATP-gated ion channel P2X7R or a non-functional fragment thereof, and which have a length of at least 12 nucleotides, preferably at least 15, more preferably at least 18, more preferably of at least 21 nucleotides, more preferably at least 30 nucleotides, even more preferably at least 40 nucleotides and most preferably at least 60 nucleotides. Furthermore, nucleic acid molecules which hybridize with any of the aforementioned nucleic acid molecules also include complementary fragments, derivatives and allelic variants of these molecules. Additionally, a hybridization complex refers to a complex between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed). The terms complementary or complementarity refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between single-stranded molecules. The degree of complementarity between nucleic acid strands has significant effects on the efficiency and strength of hybridization between nucleic acid strands. This is of particular importance in amplification reactions, which depend upon binding between nucleic acids strands.

The term "hybridizing sequences" preferably refers to sequences which display a sequence identity of at least 40%, preferably at least 50%, more preferably at least 60%, even more preferably at least 70%, particularly preferred at least 80%, more particularly preferred at least 90%, even more particularly preferred at least 95% and most preferably at least 97% identity with a nucleic acid sequence as described above encoding a P2X7R protein having a described mutation. Moreover, the term "hybridizing sequences" preferably refers to sequences encoding a P2X7R protein having a sequence identity of at least 40%, preferably at least 50%, more preferably at least 60%, even more preferably at least 70%, particularly preferred at least 80%, more particularly preferred at least 90%, even more particularly preferred at least 95% and most preferably at least 97% identity with an amino acid sequence of a P2X7R mutant as described herein above.

In accordance with the present invention, the term "identical" or "percent identity" in the context of two or more nucleic acid or amino acid sequences, refers to two or more sequences or subsequences that are the same, or that have a specified percentage of amino acid residues or nucleotides that are the same (e.g., 60% or 65% identity, preferably, 70-95% identity, more preferably at least 95% identity), when compared and aligned for maximum correspondence over a window of comparison, or over a designated region as measured using a sequence comparison algorithm as known in the art, or by manual alignment and visual inspection. Sequences having, for example, 60% to 95% or greater sequence identity are considered to be substantially identical. Such a definition also applies to the complement of a test sequence. Preferably the described identity exists over a region that is at least about 15 to 25 amino acids or nucleotides in length, more preferably, over a region that is about 50 to 100 amino acids or nucleotides in length. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art.

Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul Nucl. Acids Res. 25 (1977), 3389-3402). The BLASTN program for nucleic acid sequences uses as defaults a word length (W) of 11, an expectation (E) of 10, M=5, N=4, and a comparison of both strands. For amino acid sequences, the BLASTP program uses as defaults a wordlength (W) of 3, and an expectation (E) of 10. The BLOSUM62 scoring matrix (Henikoff Proc. Natl. Acad. Sci., USA, 89, (1989), 10915) uses alignments (B) of 50, expectation (E) of 10, M=5, N=4, and a comparison of both strands.

Moreover, the present invention also relates to nucleic acid molecules the sequence of which is degenerate in comparison with the sequence of an above-described hybridizing molecule. When used in accordance with the present invention the term "being degenerate as a result of the genetic code" means that due to the redundancy of the genetic code different nucleotide sequences code for the same amino acid.

The present invention also related to nucleic acid molecules which comprise one or more of the above-described mutations or deletions.

The nucleic acid molecules according to the invention may be derived from any organism encoding corresponding P2X7R ATP-gated ion channels. For example, P2X7R ATP-gated ion channels have been reported in various organisms, for example, rat (see, Suprenant (1996), loc. cit.), mouse (Genbank Accession No. AJ 489297), xenopus (Genbank Accession No. AJ 345114), chicken (Genbank Accession No. BM 491404) or *Bos Taurus* (Genbank Accession No. AF 083073). In a preferred embodiment the nucleic acid molecule of the invention is derived from a vertebrate, preferably from a mammal, even more preferably the nucleic acid molecule is derived from rabbit or guinea pig, and most preferably the nucleic acid is derived from mouse, rat or human.

The nucleic acid molecule according to the invention may be any type of nucleic acid, e.g. DNA, RNA or PNA (peptide nucleic acid).

For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by Nielsen et al., Science 254:1497 (1991); and Egholm et al., Nature 365:666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNA/DNA 15-mer lowers the melting point (T.sub.m) by 8°-20° C., vs. 4°-16° C. for the DNA/DNA 15-mer duplex. Also, the absence of charge groups in PNA means that hybridization can be done at low ionic strengths and reduce possible interference by salt during the analysis.

The DNA may, for example, be cDNA. In a preferred embodiment it is a genomic DNA. The RNA may be, e.g., mRNA. The nucleic acid molecule may be natural, synthetic or semisynthetic or it may be a derivative, such as peptide nucleic acid (Nielsen, Science 254 (1991), 1497-1500) or phosphorothioates. Furthermore, the nucleic acid molecule may be a recombinantly produced chimeric nucleic acid molecule comprising any of the aforementioned nucleic acid molecules either alone or in combination.

Preferably, the nucleic acid molecule of the present invention is part of a vector. Therefore, the present invention relates in another embodiment to a vector comprising the nucleic acid molecule of this invention. Such a vector may be, e.g., a plasmid, cosmid, virus, bacteriophage or another vector used e.g. conventionally in genetic engineering, and may comprise further genes such as marker genes which allow for the selection of said vector in a suitable host cell and under suitable conditions.

The nucleic acid molecules of the present invention may be inserted into several commercially available vectors. Nonlimiting examples include plasmid vectors compatible with mammalian cells, such as pUC, pBluescript (Stratagene), pET (Novagen), pREP (Invitrogen), pCRTopo (Invitrogen), pcDNA3 (Invitrogen), pCEP4 (Invitrogen), pMC1 neo (Stratagene), pXT1 (Stratagene), pSG5 (Stratagene), EBO-pSV2neo, pBPV-1, pdBPVMMTneo, pRSVgpt, pRSVneo, pSV2-dhfr, pUCTag, pIZD35, pLXIN and pSIR (Clontech) and pIRES-EGFP (Clontech). Baculovirus vectors such as pBlueBac, BacPacz Baculovirus Expression System (CLONTECH), and MaxBac™ Baculovirus Expression System, insect cells and protocols (Invitrogen) are available commercially and may also be used to produce high yields of biologically active protein. (see also, Miller (1993), Curr. Op. Genet. Dev., 3, 9; O'Reilly, Baculovirus Expression Vectors: A Laboratory Manual, p. 127). In addition, prokaryotic vectors such as pcDNA2; and yeast vectors such as pYes2 are non-limiting examples of other vectors suitable for use with the present invention. For vector modification techniques, see Sambrook and Russel (2001), loc. cit. Vectors can contain one or more replication and inheritance systems for cloning or expression, one or more markers for selection in the host, e.g., antibiotic resistance, and one or more expression cassettes.

The coding sequences inserted in the vector can be synthesized by standard methods, isolated from natural sources, or prepared as hybrids. Ligation of the coding sequences to transcriptional regulatory elements (e.g., promoters, enhancers, and/or insulators) and/or to other amino acid encoding sequences can be carried out using established methods.

Furthermore, the vectors may, in addition to the nucleic acid sequences of the invention, comprise expression control elements, allowing proper expression of the coding regions in suitable hosts. Such control elements are known to the artisan and may include a promoter, translation initiation codon, translation and insertion site or internal ribosomal entry sites (IRES) (Owens, Proc. Natl. Acad. Sci. USA 98 (2001), 1471-1476) for introducing an insert into the vector. Preferably, the nucleic acid molecule of the invention is operatively linked to said expression control sequences allowing expression in eukaryotic or prokaryotic cells. Particularly preferred are in this context control sequences which allow for correct expression in neuronal cells and/or cells derived from nervous tissue.

Control elements ensuring expression in eukaryotic and prokaryotic cells are well known to those skilled in the art. As mentioned above, they usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in for example mammalian host cells comprise the CMV-HSV thymidine kinase promoter, SV40, RSV-promoter (Rous sarcoma virus), human elongation factor 1α-promoter, CMV enhancer, CaM-kinase promoter or SV40-enhancer.

For the expression for example in nervous tissue and/or cells derived therefrom, several regulatory sequences are well known in the art, like the minimal promoter sequence of human neurofilament L (Charron, J. Biol. Chem. 270 (1995), 25739-25745). For the expression in prokaryotic cells, a multitude of promoters including, for example, the tac-lac-promoter, the lacUV5 or the trp promoter, has been described. Beside elements which are responsible for the initiation of transcription such regulatory elements may also comprise transcription termination signals, such as SV40-poly-A site or the tk-poly-A site, downstream of the polynucleotide. In this context, suitable expression vectors are known in the art such as Okayama-Berg cDNA expression vector pcDV1 (Pharmacia), pRc/CMV, pcDNA1, pcDNA3 (in-Vitrogene, as used, inter alia in the appended examples), pSPORT1 (GIBCO BRL) or pGEMHE (Promega), or prokaryotic expression vectors, such as lambda gt11.

An expression vector according to this invention is at least capable of directing the replication, and preferably the expression, of the nucleic acids and protein of this invention. Suitable origins of replication include, for example, the Col E1, the SV40 viral and the M 13 origins of replication. Suitable promoters include, for example, the cytomegalovirus (CMV) promoter, the iacZ promoter, the gai10 promoter and the *Autographa californica* multiple nuclear polyhedrosis virus (AcMNPV) polyhedral promoter. Suitable termination sequences include, for example, the bovine growth hormone, SV40, iacZ and AcMNPV polyhedral polyadenylation signals. Examples of selectable markers include neomycin, ampicillin, and hygromycin resistance and the like. Specifically-designed vectors allow the shuttling of DNA between different host cells, such as bacteria-yeast, or bacteria-animal cells, or bacteria-fungal cells, or bacteria invertebrate cells.

Beside the nucleic acid molecules of the present invention, the vector may further comprise nucleic acid sequences encoding for secretion signals. Such sequences are well known to the person skilled in the art. Furthermore, depending on the expression system used leader sequences capable of directing the expressed polypeptide to a cellular compartment may be added to the coding sequence of the nucleic acid molecules of the invention and are well known in the art. The leader sequence(s) is (are) assembled in appropriate phase with translation, initiation and termination sequences, and preferably, a leader sequence capable of directing secretion of translated protein, or a part thereof, into, inter alia, the extracellular membrane. Optionally, the heterologous sequence can encode a fusion protein including an C- or N-terminal identification peptide imparting desired characteristics, e.g., stabilization or simplified purification of expressed recombinant product. Once the vector has been incorporated into the appropriate host, the host is maintained under conditions suitable for high level expression of the nucleotide sequences, and, as desired, the collection and purification of the proteins, antigenic fragments or fusion proteins of the invention may follow. Of course, the vector can also comprise regulatory regions from pathogenic organisms.

Furthermore, said vector may also be, besides an expression vector, a gene transfer and/or gene targeting vector. Gene therapy, which is based on introducing therapeutic genes (for example for vaccination) into cells by ex-vivo or in-vivo techniques is one of the most important applications of gene transfer. Suitable vectors, vector systems and methods for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Wang, Nature Medicine 2 (1996), 714-716; WO 94/29469; WO 97/00957; Schaper, Current Opinion in Biotechnology 7 (1996), 635-640 or Verma, Nature 389 (1997), 239-242 and references cited therein.

The nucleic acid molecules of the invention and vectors as described herein above may be designed for direct introduction or for introduction via liposomes, or viral vectors (e.g. adenoviral, retroviral) into the cell. Additionally, baculoviral systems or systems based on vaccinia virus or Semliki Forest Virus can be used as eukaryotic expression system for the nucleic acid molecules of the invention. In addition to recombinant production, fragments of the protein, the fusion protein or antigenic fragments of the invention may be produced by direct peptide synthesis using solid-phase techniques (cf Stewart et al. (1969) Solid Phase Peptide Synthesis; Freeman Co, San Francisco; Merrifield, J. Am. Chem. Soc. 85 (1963), 2149-2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments may be chemically synthesized separately and combined using chemical methods to produce the full length molecule.

The present invention in addition relates to a host transformed with a vector of the present invention or to a host comprising the nucleic acid molecule of the invention. Said host may be produced by introducing said vector or nucleotide sequence into a host cell which upon its presence in the cell mediates the expression of a protein encoded by the nucleotide sequence of the invention or comprising a nucleotide sequence or a vector according to the invention wherein the nucleotide sequence and/or the encoded polypeptide is foreign to the host cell.

By "foreign" it is meant that the nucleotide sequence and/or the encoded polypeptide is either heterologous with respect to the host, this means derived from a cell or organism with a different genomic background, or is homologous with respect to the host but located in a different genomic environment than the naturally occurring counterpart of said nucleotide sequence. This means that, if the nucleotide sequence is homologous with respect to the host, it is not located in its natural location in the genome of said host, in particular it is surrounded by different genes. In this case the nucleotide sequence may be either under the control of its own promoter or under the control of a heterologous promoter. The location of the introduced nucleic acid molecule or the vector can be determined by the skilled person by using methods well-known to the person skilled in the art, e.g., Southern Blotting. The vector or nucleotide sequence according to the invention which is present in the host may either be integrated into the genome of the host or it may be maintained in some form extrachromosomally. In this respect, it is also to be understood that the nucleotide sequence of the invention can be used to restore or create a mutant gene via homologous recombination.

Said host may be any prokaryotic or eukaryotic cell. Suitable prokaryotic/bacterial cells are those generally used for cloning like *E. coli, Salmonella typhimurium, Serratia marcescens* or *Bacillus subtilis*. Said eukaryotic host may be a mammalian cell, an amphibian cell, a fish cell, an insect cell, a fungal cell, a plant cell or a bacterial cell (e.g., *E coli* strains HB101, DH5a, XL1 Blue, Y1090 and JM101). Eukaryotic recombinant host cells are preferred. Examples of eukaryotic host cells include, but are not limited to, yeast, e.g., *Saccharomyces cerevisiae, Schizosaccharomyces pombe, Kluyveromyces lactis* or *Pichia pastoris* cells, cell lines of human, bovine, porcine, monkey, and rodent origin, as well as insect cells, including but not limited to, *Spodoptera frugiperda* insect cells and *Drosophila*-derived insect cells as well as zebra fish cells. Mammalian species-derived cell lines suitable for use and commercially available include, but are not limited to, L cells, CV-1 cells, COS-1 cells (ATCC CRL 1650), COS-7 cells (ATCC CRL 1651), HeLa cells (ATCC CCL 2), C1271 (ATCC CRL 1616), BS-C-1 (ATCC CCL 26) and MRC-5 (ATCC CCL 171).

In a particularly preferred embodiment said mammalian cell is a neuronal cell and/or a cultured cell like, inter alia, a HEK 293 (human embryonic kidney) cell, a CHO, HeLa, NIH3T3, BHK, PC12 cell or a neuronal stem cell preferably derived from a mammal and more preferably from a human.

In another more preferred embodiment said amphibian cell is an oocyte. In an even more preferred embodiment said oocyte is a frog oocyte, particularly preferred a *Xenopus laevis* oocyte.

In a more preferred embodiment, the host according to the invention is a non-human transgenic organism. Said non-human organism may be a mammal, amphibian, a fish, an insect, a fungus or a plant. Particularly preferred non-human transgenic animals are *Drosophila* species, *Caenorhabditis elegans, Xenopus* species, zebra fish, *Spodoptera frugiperda, Autographa californica*, mice and rats. Transgenic plants comprise, but are not limited to, wheat, tobacco, parsley and *Arabidopsis*. Transgenic fungi are also well known in the art and comprise, inter alia, yeasts, like *S. pombe* or *S. cerevisae*, or *Aspergillus, Neurospora* or *Ustilago* species or *Pichia* species.

In another embodiment, the present invention relates to a method for producing the polypeptide encoded by a nucleic acid molecule of the invention comprising culturing/raising the host of the invention and isolating the produced polypeptide.

A large number of suitable methods exist in the art to produce polypeptides in appropriate hosts. If the host is a unicellular organism or a mammalian or insect cell, the person skilled in the art can revert to a variety of culture conditions that can be further optimized without an undue burden of work. Conveniently, the produced protein is harvested from the culture medium or from isolated (biological) membranes by established techniques. Furthermore, the produced polypeptide may be directly isolated from the host cell. Said host cell may be part of or derived from a part of a host organism, for example said host cell may be part of the CNS of an animal or the harvestable part of a plant. Additionally, the produced polypeptide may be isolated from fluids derived from said host, like blood, milk or cerebrospinal fluid.

Additionally the present invention relates to polypeptides depicted in SEQ ID NOs: 5 to 12 which are encoded by the nucleic acid molecules of the invention or produced by the method of the invention. The polypeptide of the invention may accordingly be produced by microbiological methods or by transgenic mammals. It is also envisaged that the polypeptide of the invention is recovered from transgenic plants. Alternatively, the polypeptide of the invention may be produced synthetically or semi-synthetically.

For example, chemical synthesis, such as the solid phase procedure described by Houghton Proc. Natl. Acad. Sci. USA (82) (1985), 5131-5135, can be used. Another method is in vitro translation of mRNA. A preferred method involves the recombinant production of protein in host cells as described above. For example, nucleotide acid sequences comprising all or a portion of any one of the nucleotide sequences according to the invention can be synthesized by PCR, inserted into an expression vector, and a host cell transformed with the expression vector. Thereafter, the host cell is cultured to produce the desired polypeptide, which is isolated and purified. Protein isolation and purification can be achieved by any one of several known techniques; for example and without limitation, ion exchange chromatography, gel filtration chromatography and affinity chromatography, high pressure liquid chromatography (HPLC), reversed phase HPLC, preparative disc gel electrophoresis. In addition, cell-free translation systems can be used to produce the polypeptides of the present invention. Suitable cell-free expression systems for use in accordance with the present invention include rabbit reticulocyte lysate, wheat germ extract, canine pancreatic microsomal membranes, *E. coli* S30 extract, and coupled transcription/translation systems such as the TNT-system (Promega). These systems allow the expression of recombinant polypeptides or peptides upon the addition of cloning vectors, DNA fragments, or RNA sequences containing coding regions and appropriate promoter elements. As mentioned supra, protein isolation/purification techniques may require modification of the proteins of the present invention using conventional methods. For example, a histidine tag can be added to the protein to allow purification on a nickel column. Other modifications may cause higher or lower activity, permit higher levels of protein production, or simplify purification of the protein.

In a further embodiment, the present invention relates to an antibody specifically directed to a polypeptide of the invention, wherein said antibody specifically reacts with an epitope generated and/or formed by the mutation in the ATP-gated ion channel P2X7R selected from the group consisting of:

(i) an epitope specifically presented by a polypeptide which has an amino acid sequence of an ATP-gated ion channel P2X7R, wherein the R (Arg), G (Gly), E (Glu), L (Leu), R (Arg), I (Ile) or R (Arg) residue corresponding to position 117, 150, 186, 191, 270, 568 or 578 of the wild-type ATP-gated ion channel P2X7R as depicted in SEQ ID NO: 3 or 4 is replaced by another amino acid residue; and (ii) an epitope specifically presented by a polypeptide which has an amino acid sequence of an ATP-gated ion channel P2X7R, wherein amino acids corresponding to positions 488 to 494 of the wild-type ATP-gated ion channel P2X7R as depicted in SEQ ID NO: 3 or 4 are deleted.

With respect to preferred embodiments of (i) and (ii) the same applies as described above in connection with the nucleic acid molecules. The term "specifically" in this context means that the antibody reacts with the mutant P2X7R protein but not with a wild-type P2X7R protein. Preferably this term also means that such an antibody does not bind to other mutant forms of the P2X7R protein, in particular those described herein. Whether the antibody specifically reacts as defined herein above can easily be tested, inter alia, by comparing the reaction of said antibody with a wild-type ATP-gated ion channel P2X7R (or a subunit or a fragment thereof) with the reaction of said antibody with a mutant P2X7R polypeptide of the invention.

The antibody of the present invention can be, for example, polyclonal or monoclonal. The term "antibody" also comprises derivatives or fragments thereof which still retain the binding specificity. Techniques for the production of antibodies are well known in the art and described, e.g. in Harlow and Lane "Antibodies, A Laboratory Manual", CSH Press, Cold Spring Harbor, 1988. These antibodies can be used, for example, for the immunoprecipitation and immunolocalization of the polypeptides of the invention as well as for the monitoring of the presence of such polypeptides, for example, in recombinant organisms or in diagnosis. They can also be used for the identification of compounds interacting with the proteins according to the invention (as mentioned herein below). For example, surface plasmon resonance as employed in the BIAcore system can be used to increase the efficiency of phage antibodies which bind to an epitope of the polypeptide of the invention (Schier, Human Antibodies Hybridomas 7 (1996), 97-105; Malmborg, J. Immunol. Methods 183 (1995), 7-13).

The present invention furthermore includes chimeric, single chain and humanized antibodies, as well as antibody fragments, like, inter alia, Fab fragments. Antibody fragments or derivatives further comprise F(ab')2, Fv or scFv fragments; see, for example, Harlow and Lane, loc. cit. Various procedures are known in the art and may be used for the production of such antibodies and/or fragments. Thus, the (antibody) derivatives can be produced by peptidomimetics. Further, techniques described for the production of single chain antibodies (see, inter alia, U.S. Pat. No. 4,946,778) can be adapted to produce single chain antibodies to polypeptide(s) of this invention. Also, transgenic animals may be used to express humanized antibodies to polypeptides of this invention. Most preferably, the antibody of this invention is a monoclonal antibody. For the preparation of monoclonal antibodies, any technique which provides antibodies produced by continuous cell line cultures can be used. Examples for such techniques include the hybridoma technique (Köhler and Milstein Nature 256 (1975), 495-497), the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). Techniques describing the production of single chain antibodies (e.g., U.S. Pat. No. 4,946,778) can be adapted to produce single chain antibodies to immunogenic polypeptides as described above. Furthermore, transgenic mice may be used to express humanized antibodies directed against said immunogenic polypeptides. It is in particular preferred that the antibodies/antibody constructs as well as antibody fragments or derivatives to be employed in accordance with this invention or capable to be expressed in a cell. This may, inter alia, be achieved by direct injection of the corresponding proteineous molecules or by injection of nucleic acid molecules encoding the same. Furthermore, gene therapy approaches are envisaged. Accordingly, in context of the present invention, the term "antibody molecule" relates to full immunoglobulin molecules as well as to parts of such immunoglobulin molecules. Furthermore, the term relates, as discussed above, to modified and/or altered antibody molecules, like chimeric and humanized antibodies. The term also relates to monoclonal or polyclonal antibodies as well as to recombinantly or synthetically generated/synthesized antibodies. The term also relates to intact antibodies as well as to antibody fragments thereof, like, separated light and heavy chains, Fab, Fab/c, Fv, Fab', F(ab')2. The term "antibody molecule" also comprises bifunctional antibodies and antibody constructs, like single chain Fvs (scFv) or antibody-fusion proteins. It is also envisaged in context of this invention that the term "antibody" comprises antibody constructs which may be expressed in cells, e.g. antibody constructs which may be transfected and/or transduced via, inter alia, viruses or vectors. It is in particular envisaged that such antibody constructs specifically recognize the polypeptides of the present invention. It is, furthermore, envisaged that said antibody construct is employed in gene therapy approaches.

The present invention relates also to an aptamer specifically binding to a polypeptide according to the invention wherein said aptamer reacts with an epitope of a polypeptide of the present invention. The present invention furthermore relates to an aptamer specifically directed to a corresponding nucleic acid molecule according to the invention.

In accordance with the present invention, the term "aptamer" means nucleic acid molecules that can bind to target molecules. Aptamers commonly comprise RNA, single stranded DNA, modified RNA or modified DNA molecules. The preparation of aptamers is well known in the art and may involve, inter alia, the use of combinatorial RNA libraries to identify binding sides (Gold, Ann. Rev. Biochem. 64 (1995), 763-797).

Furthermore, the present invention relates to a primer or pair of primers capable of specifically amplifying the nucleic acid molecules of the present invention. The term "primer" when used in the present invention means a single-stranded nucleic acid molecule capable of annealing the nucleic acid molecule of the present application and thereby being capable of serving as a starting point for amplification. Said term also comprises oligoribo- or deoxyribonucleotides which are complementary to a region of one of the strands of a nucleic acid molecule of the present invention. According to the present invention the term "pair of primers" means a pair of primers that are with respect to a complementary region of a nucleic acid molecule directed in the opposite direction towards each other to enable, for example, amplification by polymerase chain reaction (PCR).

The term "amplifying" refers to repeated copying of a specified sequence of nucleotides resulting in an increase in the amount of said specified sequence of nucleotides. and allows the generation of a multitude of identical or essentially identical (i.e. at least 95% more preferred at least 98%, even more preferred at least 99% and most preferred at least 99.5% such as 99.9% identical) nucleic acid molecules or parts thereof. Such methods are well established in the art; see Sambrook et al. "Molecular Cloning, A Laboratory Manual", $2^{nd}$ edition 1989, CSH Press, Cold Spring Harbor. They include polymerase chain reaction (PCR) and modifications thereof, ligase chain reaction (LCR) to name some preferred amplification methods.

When used in the context of primers the term "specifically" means that only the nucleic acid molecules as described herein above are amplified and nucleic acid molecules encoding the wild-type P2X7R ATP-gated receptor as depicted in SEQ ID NO: 1 are not amplified. Thus, a primer according to the invention is preferably a primer which binds to a region of a nucleic acid molecule of the invention which is unique for this molecule and which is not present in the wild-type P2X7R encoding sequence, i.e. the primer binds in a region in which one of the above described mutations occur. In connection with a pair of primers according to the invention it is possible that one of the primers of the pair is specific in the above described meaning or both of the primers of the pair are specific. In both cases, the use of such a pair of primers would allow to specifically amplify a mutant of the invention as described herein-above but not the wild-type P2X7R encoding sequence.

The 3'-OH end of a primer is used by a polymerase to be extended by successive incorporation of nucleotides. The primer or pair of primers of the present invention can be used, for example, in primer extension experiments on template RNA according to methods known by the person skilled in the art. Preferably, the primer or pair of primers of the present invention are used for amplification reactions on template RNA or template DNA, preferably cDNA or genomic DNA. The terms "template DNA" or "template RNA" refers to DNA or RNA molecules or fragments thereof of any source or nucleotide composition, that comprise a target nucleotide sequence as defined above. The primer or pair of primers can also be used for hybridization experiments as known in the art. Preferably, the primer or pair of primers are used in polymerase chain reactions to amplify sequences corresponding to a sequence of the nucleic acid molecule of the present invention. It is known that the length of a primer results from different parameters (Gillam, Gene 8 (1979), 81-97; Innis, PCR Protocols: A guide to methods and applications, Academic Press, San Diego, USA (1990)). Preferably, the primer should only hybridize or bind to a specific region of a target nucleotide sequence. The length of a primer that statistically hybridizes only to one region of a target nucleotide sequence can be calculated by the following formula: $(1/4)^x$ (whereby x is the length of the primer). For example a hepta- or octa-nucleotide would be sufficient to bind statistically only once on a sequence of 37 kb. However, it is known that a primer exactly matching to a complementary template strand must be at least 9 base pairs in length, otherwise no stable-double strand can be generated (Goulian, Biochemistry 12 (1973), 2893-2901). It is also envisaged that computer-based algorithms can be used to design primers capable of amplifying the nucleic acid molecules of the invention. Preferably, the primers of the invention are at least 10 nucleotides in length, more preferred at least 12 nucleotides in length, even more preferred at least 15 nucleotides in length, particularly preferred at least 18 nucleotides in length, even more particularly preferred at least 20 nucleotides in length and most preferably at least 25 nucleotides in length. The invention, however, can also be carried out with primers which are shorter or longer.

It is also envisaged that the primer or pair of primers is labeled. The label may, for example, be a radioactive label, such as $^{32}P$, $^{33}P$ or $^{35}S$. In a preferred embodiment of the invention, the label is a non-radioactive label, for example, digoxigenin, biotin and fluorescence dye or a dye.

In another preferred embodiment said primers are selected from the group consisting of SEQ ID NOs: 52 to 111.

In yet another embodiment, the present invention relates to a composition comprising a nucleic acid molecule, a vector, a polypeptide, an antibody, an aptamer and/or a primer or pair of primers of the invention.

The term "composition", as used in accordance with the present invention, relates to compositions which comprise at least one nucleic acid molecule, vector, polypeptide, an antibody and/or primer or pair of primers of this invention. It may, optionally, comprise further molecules capable of altering the characteristics of the component of the invention thereby, for example, suppressing, blocking, modulating and/or activating their function which have neuroprotective, nootropic, antidepressive and/or cell-protective properties as will also be described herein below. The composition may be in solid, liquid or gaseous form and may be, inter alia, in the form of (a) powder(s), (a) tablet(s), (a) solution(s) or (an) aerosol(s).

In a preferred embodiment the composition according to the invention is a diagnostic composition, optionally further comprising suitable means for detection. As described above, the present invention is based on the surprising finding that mutations in the P2X7R protein are connected with affective disorders. Thus, this knowledge now allows to diagnose affective disorders in an easy way. The diagnostic composition comprises at least one of the aforementioned compounds of the invention. The diagnostic composition may be used, inter alia, for methods for determining the presence and/or expression of the nucleic acids and/or polypeptides of the invention. This may be effected by detecting, e.g., the presence of a corresponding gene in the genetic material of an individual or the presence of the corresponding mRNA which comprises isolation of DNA or RNA from a cell derived from said individual, contacting the DNA or RNA so obtained with a nucleic acid probe as described above under hybridizing conditions, and detecting the presence of mRNAs hybridized to the probe. Alternatively, the diagnostic composition may also be used for detecting the presence of a nucleic acid molecule of the invention by PCR. Furthermore, polypeptides of the invention can be detected with methods known in the art, which comprise, inter alia, immunological methods, like, RIA, FIA, ELISA, FACS or Western blotting.

Furthermore, the diagnostic composition of the invention may be useful, inter alia, in detecting the prevalence, the onset or the progress of a disease related to the expression of a polypeptide of the invention. Accordingly, the diagnostic composition of the invention may be used, inter alia, for assessing the prevalence, the onset and/or the disease status of affective disorders, as defined herein above. It is also contemplated that the diagnostic composition of the invention may be useful in discriminating (the) stage(s) of a disease.

The diagnostic composition optionally comprises suitable means for detection. The nucleic acid molecule(s), vector(s), host(s), antibody(ies), aptamer(s), polypeptide(s) described above are, for example, suitable for use in immunoassays in which they can be utilized in liquid phase or bound to a solid phase carrier. Examples of well-known carriers include glass, polystyrene, polyvinyl ion, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention.

Solid phase carriers are known to those in the art and may comprise polystyrene beads, latex beads, magnetic beads, colloid metal particles, glass and/or silicon chips and surfaces, nitrocellulose strips, membranes, sheets, duracytes and the walls of wells of a reaction tray, plastic tubes or other test tubes. Suitable methods of immobilizing nucleic acid molecule(s), vector(s), host(s), antibody(ies), aptamer(s), polypeptide(s), etc. on solid phases include but are not limited to ionic, hydrophobic, covalent interactions or (chemical) crosslinking and the like. Examples of immunoassays which can utilize said compounds of the invention are competitive and non-competitive immunoassays in either a direct or indirect format. Commonly used detection assays can comprise radioisotopic or non-radioisotopic methods. Examples of such immunoassays are the radioimmunoassay (RIA), the sandwich (immunometric assay) and the Northern or Southern blot assay. Furthermore, these detection methods comprise, inter alia, IRMA (Immune Radioimmunometric Assay), EIA (Enzyme Immuno Assay), ELISA (Enzyme Linked Immuno Assay), FIA (Fluorescent Immuno Assay), and CLIA (Chemiluminescent Immune Assay). Furthermore, the diagnostic compounds of the present invention may be are employed in techniques like FRET (Fluorescence Resonance Energy Transfer) assays.

Appropriate labels and methods for labeling are known to those of ordinary skill in the art. Examples of the types of labels which can be used in the present invention include inter alia, fluorochromes (like fluorescein, rhodamine, Texas Red, etc.), enzymes (like horse radish peroxidase, β-galactosidase, alkaline phosphatase), radioactive isotopes (like 32P, 33P, 35S or 125I), biotin, digoxygenin, colloidal metals, chemi- or bioluminescent compounds (like dioxetanes, luminol or acridiniums).

A variety of techniques are available for labeling biomolecules, are well known to the person skilled in the art and are considered to be within the scope of the present invention and comprise, inter alia, covalent coupling of enzymes or biotinyl groups, phosphorylations, biotinylations, random priming, nick-translations, tailing (using terminal transferases). Such techniques are, e.g., described in Tijssen, "Practice and theory of enzyme immunoassays", Burden and von Knippenburg (Eds), Volume 15 (1985); "Basic methods in molecular biology", Davis L G, Dibmer M D, Battey Elsevier (1990); Mayer, (Eds) "Immunochemical methods in cell and molecular biology" Academic Press, London (1987); or in the series "Methods in Enzymology", Academic Press, Inc.

Detection methods comprise, but are not limited to, autoradiography, fluorescence microscopy, direct and indirect enzymatic reactions, etc.

Said diagnostic composition may be used for methods for detecting the presence and/or abundance of a nucleic acid molecule of the invention in a biological and/or medical sample and/or for detecting expression of such a nucleic acid molecule (e.g. by determining the mRNA or the expressed polypeptide). Furthermore, said diagnostic composition may also be used in methods of the present invention, inter alia, for the detection of specific antagonists or agonists for P2X7R ATP-gated ion channels (see herein below).

In a further embodiment the present invention provides a method of diagnosing an affective disorder or a susceptibility to an affective disorder comprising the step of determining in a sample obtained from an individual whether the P2X7R protein expressed in the cells of said individual is non-functional, shows an altered ATP-gating in comparison to the wild-type P2X7R protein or is over- or under-expressed in comparison to the P2X7R protein level of an unaffected individual.

The term "over- or under-expressed in comparison to the P2X7R protein level" in the context of the present invention means that the P2X7R protein level is higher or lower than the P2X7R level of an healthy individual, i.e. an individual not affected with an affective disorder. The over-expression may result, e.g. from an increased amount of P2X7R mRNA caused by enhanced transcription rates due to increased activity of the RNA-polymerase II. The amount of mRNA may accordingly lead to an increased translation and, thus, to an higher protein level of P2X7R. It may also be possible that a higher amount of P2X7R protein is caused by increased stability of the protein. An under-expression of P2X7R protein may be caused by low transcription rates of the P2X7R gene and, thus, insufficient amounts of P2X7R mRNA give only rise to a low P2X7R protein amount. Another reason may be that the P2X7R protein is unstable and, thus, is not present in amounts comparable to the wild-type protein level.

The under- or over-expression of P2X7R protein may be determined by methods well-known to the person skilled in the art. These include, but are not limited, to methods for determining the amount of mRNA or the amount and/or activity of the protein. Examples are Northern Blot analysis or immuno based techniques, such as Western Blotting.

"Non-functional" means that the P2X7R protein has lost at least one functional property displayed by the wild-type P2X7R protein as described herein above. Preferably, "non-functional" means that the P2X7R protein does no longer function as a channel. Non-functionality may, e.g., be caused by the fact that one allele occurring in an individual codes for a P2X7R protein which leads to non-functional dimers (dominant negative mutation). Whether a P2X7R protein in an individual is functional or non-functional can be determined by the methods described herein above and in the examples.

The term "altered ATP-gating" means that the respective P2X7R protein reacts in a different way to ATP than the wild-type P2X7R protein. This can be determined as described in the appended examples or as described hereinabove.

In the context of diagnosis, not only the activity of the P2X7R could be of diagnostic value but also the amount of expression. For example, if a polymorphism affects RNA stability or translation efficiency, this could lead to lower expression of the P2X7 protein not only in the hippocampus but also in the blood. Therefore, one could speculate that a lower amount of P2X7 detected by western blot in blood cells could be related to depression.

Another aspect of the present invention is a method for diagnosing an affective disorder or a susceptibility to an affective disorder comprising the step of determining in a sample obtained from an individual whether the P2X7R gene sequence or encoded protein thereof comprises a mutation in comparison to the wild-type P2X7R sequence.

A preferred embodiment of the present invention is a method, wherein a mutation is a mutation in a P2X7R sequence as defined hereinabove and/or a nucleotide replacement or deletion selected from the following Table C indicating in column "Region of P2X7R" the region of the P2X7R genomic nucleotide sequence in which the replacement or deletion occurs, in column "Nucleotide" of Table C the nucleotide which is replaced by another nucleotide or the nucleotides which are deleted and in column "Position in wild-type" of Table C the corresponding position in the nucleotide sequence of the wild-type ATP-gated ion channel P2X7R as depicted in SEQ ID NO: 1

TABLE C

| Region of P2X7R | Nucleotide | Position in wild-type |
|---|---|---|
| 5'UTR | T | 362 |
| 5'UTR | T | 532 |
| 5'UIR | A | 1100 |
| 5'UTR | A | 1122 |
| 5'UTR | C | 1171 |
| 5'UTR | T | 1351 |
| 5'UTR | G | 1702 |
| 5'UTR | T | 1731 |
| 5'UTR | C | 1860 |
| 5'UTR | C | 2162 |
| 5'UTR | C | 2238 |
| 5'UTR | A | 2373 |
| 5'UTR | G | 2569 |
| 5'UTR | G | 2702 |
| intron 1 | G | 3166 |
| intron 1 | C | 24778 |
| intron 1 | C | 24830 |
| exon 2 | T | 24942 |
| exon 3 | C | 26188 |
| exon 3 | A | 26308 |
| exon 3 | G | 26422 |
| intron 4 | G | 32394 |
| intron 4 | T | 32434 |
| exon 5 | G | 32493 |
| exon 5 | G | 32506 |
| exon 5 | C | 32507 |
| exon 5 | C | 32548 |
| intron 5 | A | 32783 |
| intron 5 | T | 35309 |
| intron 5 | C | 35374 |
| intron 5 | A | 35378 |
| exon 6 | G | 35438 |
| exon 6 | T | 35454 |
| intron 6 | T | 35549 |
| intron 6 | G | 35641 |
| intron 6 | A | 35725 |

TABLE C-continued

| Region of P2X7R | Nucleotide | Position in wild-type |
|---|---|---|
| intron 6 | T | 36001 |
| intron 6 | A | 36064 |
| intron 6 | deletion of GTTT | 36091 to 36094 |
| intron 6 | C | 36108 |
| intron 7 | C | 36374 |
| intron 7 | G | 36378 |
| intron 7 | T | 36387 |
| intron 7 | G | 36398 |
| intron 7 | C | 37439 |
| intron 7 | T | 37513 |
| exon 8 | C | 37604 |
| exon 8 | G | 37605 |
| exon 8 | G | 37623 |
| exon 8 | C | 37633 |
| intron 9 | C | 47214 |
| exon 11 | G | 47383 |
| exon 11 | C | 47411 |
| intron 11 | T | 47563 |
| intron 12 | C | 54307 |
| intron 12 | G | 54308 |
| exon 13 | C | 54399 |
| exon 13 | A | 54480 |
| exon 13 | C | 54523 |
| exon 13 | deletion of CCCTGAGAGCCACAGGTGCCT | 54562 to 54582 |
| exon 13 | A | 54588 |
| exon 13 | C | 54664 |
| exon 13 | G | 54703 |
| exon 13 | A | 54804 |
| exon 13 | G | 54834 |
| exon 13 | G | 54847 |
| 3'UTR | G | 54925 |
| 3'UTR | C | 55169 |
| 3'UTR | A | 55170 |
| 3'UTR | A | 55171 |
| 3'UTR | C | 55917 |

As indicated hereinabove, if the respective nucleotide which is replaced by another nucleotide is a purine base, it is preferred to be replaced by another purine base. If it is a pyrimidine base, it is preferred to be replaced by another pyrimidine base. It is also preferred that a purine base is replaced by a pyrimidine base and that a pyrimidine base is replaced by a purine base. Most preferably, the nucleotides indicated in Table C are replaced by the nucleotides indicated at the respective position in Table 12 hereinbelow (see Example 3).

In a preferred embodiment the present invention relates to diagnostic composition designed for use in a method in which the occurrence of the mutation in the ATP-gated ion channel P2X7R gene is determined by PCR, immunological methods and/or electrophysiological methods as described herein below and in the appended Examples. Additionally, it is possible to determine the occurrence of a mutation in the ATP-gated ion channel P2X7R as described hereinabove.

In yet another aspect the present invention relates to the use of a nucleic acid molecule, a vector, a polypeptide, an antibody, aptamer and/or a primer or pair of primers of the present invention for the preparation of a diagnostic composition for the detection of an affective disorder.

It is also envisaged that the present invention relates to methods of diagnosing an affective disorder of an individual comprising:
(a) isolating DNA from cells obtained from an individual;
(b) determining all or part of the nucleotide composition of the P2X7R gene; and
(c) analyzing said nucleotide composition of P2X7R for the presence of one or more polymorphism, mutation or allelic variation.

The term "gene" means a nucleotide sequence associated with the production of a protein, including promoter sequences, enhancer sequences, intron sequences, exon sequences, coding regions, 5' untranslated region (5'UTR), 3' untranslated region (3'UTR), and splice variants.

In a preferred embodiment of the described method the individual is a mammal and more preferably human. Moreover, the cells are preferably derived from skin, blood, urine or cerebral spinal fluid.

The method of the present invention allows for the diagnosis of an affective disorder according to the composition of a genetic marker corresponding to the P2X7R gene. As is demonstrated by the appended examples, polymorphisms in the P2X7R are genetically linked to patients suffering from an affective disorder.

In accordance with this embodiment of the present invention, the diagnosis of an affective disorder can, e.g., be effected by isolating cells from an individual, and isolating the genomic DNA of said cells. Such cells can be collected from body fluids, skin, hair, biopsies and other sources. Collection and analysis of cells from bodily fluids such as blood, urine and cerebrospinal fluid is well known to the art; see for example, Rodak, "Haematology: Clinical Principles & Applications" second ed., WB Saunders Co, 2002; Brunzel, "Fundamentals of Urine and Body Fluids Analysis", WB Saunders Co, 1994; Herndon and Brumback (Ed.), "Cerebrospinal Fluid", Kluwer Academic Pub., 1989. In addition, methods for DNA isolation are well described in the art; see, for example, Sambrook et al., "Molecular Cloning: A Laboratory Manual", 3$^{rd}$ edition, Cold Spring Harbor Laboratory, 2001.

Once DNA has been isolated, various oligonucleotide primers spanning the P2X7R locus may be designed in order to amplify the genetic material by Polymerase Chain Reaction (PCR). Conventional methods for designing, synthesizing, producing said oligonucleotide primers and performing PCR amplification may be found in standard textbooks, see, for example Agrawal (Ed.), "Protocols for Oligonucleotides and Analogs: Synthesis and Properties (Methods in Molecular Biology, 20)", Humana Press, 1993; Innis et al. (Ed.), "PCR Applications: Protocols for Functional Genomics", Academic Press, 1999; Chen and Janes (Ed.), "PCR Cloning Protocols: From Molecular Cloning to Genetic", 2$^{nd}$ edition, Humana Press, 2002. Primers for the detection of P2X7R polymorphisms are also given in, but not limited to, SEQ ID NO: 52 to SEQ ID NO: 111. Once DNA has been amplified, nucleotide structure can be analysed by sequencing methods and compared to normal P2X7R DNA. Sequencing may be performed manually by any molecular biologist of ordinary skills or by an automated sequencing apparatus. These procedures are common in the art, see, for example, Adams et al. (Ed.), "Automated DNA Sequencing and Analysis", Academic Press, 1994; Alphey, "DNA Sequencing: From Experimental Methods to Bioinformatics", Springer Verlag Publishing, 1997.

Detection and analysis of polymorphisms in P2X7R can also be performed using amplification refractory mutation system (ARMS™), amplification refractory mutation system linear extension (ALEX™), single-strand conformation polymorphism (SSCP), heteroduplex analysis, PCR-SSCP, fluorescent SSCP in an automated DNA sequencer, denaturing gradient gel electrophoresis, RNase protection assays, detection of mutations by sequence specific oligonucleotide hybridization, chemical cleavage methods, enzyme mismatch cleavage methods, cleavage fragment length methods, allele-specific oligonucleotide hybridization on DNA chips, and other such methods known in the art, see, for example Nollau et al, Clin. Chem. 43 (1997), 1114-1128; Burczak and Mardis (Ed.), "Polymorphism Detection & Analysis Techniques", Eaton Pub Co, 2000; Cotton et al. (Ed.), "Mutation Detection: A Practical Approach", Irl Press, 1998; Taylor (Ed.), "Laboratory Methods for the Detection of Mutations and Polymorphisms in DNA", CRC Press, 1997.

The present invention also relates to a method of diagnosing an affective disorder in an individual comprising:
(a) isolating RNA from cells obtained from an individual;
(b) converting the RNA into cDNA;
(c) determining all or part of the nucleotide composition of the cDNA so obtained; and
(c) analyzing said nucleotide composition for the presence of one or more polymorphism(s) or allelic variation.

With respect to the preferred embodiments the same applies as already described above.

Detection and analysis of polymorphisms in the P2X7R RNA can be performed according to the methods described above.

The present invention also relates to a method for diagnosing an affective disorder in an individual comprising:
(a) isolating RNA or proteins from cells obtained from an individual;
(b) determining the levels of P2X7R RNA or protein; and
(c) comparing the levels of P2X7R RNA or protein with the corresponding levels from a normal individual not afflicted with an affective disorder.

With respect to the preferred embodiments the same applies as already described above.

As is demonstrated by the appended examples, a relationship exists between the expression, or protein level of P2X7R and an affective disorder. This and other embodiments of the present invention will readily occur to those of ordinary skill in the art in view of the disclosure herein.

According to another aspect on the invention, there is provided a polynucleotide comprising at least 20 bases of the human P2X7R gene and comprising a mutation or polymorphism selected from any of the following:

TABLE 1

Novel polymorphisms in the human P2X7R

| Region in P2X7 | Polymorphism | Protein Modification |
|---|---|---|
| 5'UTR | 362 T-C | |
| 5'UTR | 532 T-G | |
| 5'UTR | 1100 A-G | |
| 5'UTR | 1122 A-G | |
| 5'UTR | 1171 C-G | |
| 5'UTR | 1702 G-A | |
| Intron01 | 3166 G-C | |
| Intron01 | 24778 C-T | |
| Intron01 | 24830 6C-T | |
| Exon03 | 26188 C-T | Arg117Trp |
| Intron03 | 26308 A-G | |
| Intron03 | 26422 G-A | |
| Intron04 | 32394 G-A | |
| Intron04 | 32434 T-C | |
| Exon05 | 32493 G-A | Gly150Arg |
| Exon05 | 32548 C-T | Silent Cys168 |
| Intron05 | 32783 A-C | |
| Exon06 | 35438 G-A | Glu186Lys |
| Exon06 | 35454 T-C | Leu191Pro |
| Intron06 | 35641 G-C | |
| Intron06 | 35725 A-C | |
| Intron06 | 36001 T-G | |
| Intron07 | 36378 G-A | |
| Intron07 | 36387 T-A | |
| Intron07 | 36398 G-C | |
| Exon08 | 37604 C-T | Arg270Cys |
| Exon08 | 37633 C-T | Silent Asp279 |
| Intron09 | 47214 C-T | |
| Intron11 | 47563 T-C | |
| Intron12 | 54307 C-T | |
| Intron12 | 54308 G-A | |
| Exon13 | 54562-54582 deletion of CCCTGAGA GCCACAGGTGCCT | deletion of 7aa 488 to 494 (PESHRCL) |
| Exon13 | 54804 A-T | Ile568Asn |
| Exon13 | 54834 G-A | Arg578Gln |
| 3'UTR | 55169 C-A | |
| 3'UTR | 55170 A-C | |
| 3'UTR | 55171 A-C | |
| 3'UTR | 55917 C-T | |
| 3'UTR | 54925 G-A | |

The polymorphism describes the position and the variation observed. The position and numbering of the polymorphism corresponds to the human P2X7R gene as defined in SEQ ID No 1. Primers used for SNP amplification and sequencing are shown in Table 1a and listed in SEQ ID NO: 52 to SEQ ID NO: 111.

TABLE 1a

Primer sequences for SNP amplification and sequencing

| Primer Name | Orientation | Sequence | Begin | End |
|---|---|---|---|---|
| P2RX7_01.for | Sense | cgtaggacttggcgcttct | 2785 | 2803 |
| P2RX7_01.rev | Antisense | gagcacgtctcagattcgaaa | 3224 | 3244 |
| P2RX7_02.for | Sense | ccatgaggcaggtatgactattc | 24665 | 24687 |
| P2RX7_02.rev | Antisense | ctcctggatctcacccagtt | 25168 | 25187 |
| P2RX7_03.for | Sense | ctcgtccagctttgatattaagc | 25966 | 25988 |
| P2RX7_03.rev | Antisense | ggtccctagtgctagaaccaga | 26426 | 26447 |
| P2RX7_04.for | Sense | attcatccgtcagtggcc | 30794 | 30811 |
| P2RX7_04.rev | Antisense | gccatgtgaattttctaccgat | 31277 | 31298 |
| P2RX7_05.for | Sense | ttcgttgtggttaggatggg | 32314 | 32333 |
| P2RX7_05.rev | Antisense | caaggatgctcagggtagtagc | 32805 | 32826 |

TABLE 1a-continued

Primer sequences for SNP amplification and sequencing

| Primer Name | Orientation | Sequence | Begin | End |
|---|---|---|---|---|
| P2RX7_06.for | Sense | cactaggtttgctgtatccatttct | 35277 | 35301 |
| P2RX7_06.rev | Antisense | gcaactgtgtgagagcttgg | 35731 | 35750 |
| P2RX7_07.for | Sense | tcaaccctggtccagtgtg | 35950 | 35968 |
| P2RX7_07.rev | Antisense | caccaagtagctctcactcataagg | 36424 | 36448 |
| P2RX7_08.for | Sense | caataacacttgtgcgagttaggt | 37380 | 37403 |
| P2RX7_08.rev | Antisense | catcttgttgccttggaaacc | 37750 | 37770 |
| P2RX7_09.for | Sense | gtgagtggtaatcctgctactgc | 45321 | 45343 |
| P2RX7_09.rev | Antisense | aggcccactcctgtactcg | 45743 | 45761 |
| P2RX7_10_11.for | Sense | ccaagtcacagcatgaggc | 47119 | 47137 |
| P2RX7_10_11.rev | Antisense | acccagcgacgtatccac | 47632 | 47649 |
| P2RX7_12.for | Sense | aagcatggggttccatttc | 50252 | 50268 |
| P2RX7_12.rev | Antisense | gcataaaagggactcctgctagta | 50691 | 50714 |
| P2RX7_13a.for | Sense | gcttacagaacacatgcatgg | 54232 | 54252 |
| P2RX7_13a.rev | Antisense | gcacctgtaggcacagtgc | 54739 | 54757 |
| P2RX7_13b.for | Sense | atcaccacctcagagctgttc | 54620 | 54640 |
| P2RX7_13b.rev | Antisense | gttaacatggctactgcagcc | 55203 | 55223 |
| P2XR7_13d.for | Sense | gcttagaaaggaggcgactcc | 54484 | 54504 |
| P2XR7_Pro13.for | Sense | ttgtgacatttgcaaggctgcc | 2617 | 2638 |
| P2XR7_Pro7.rev | Antisense | tctgaagctctgctcctgag | 1955 | 1974 |
| P2XR7_Pro8.rev | Antisense | ctcaccttctggcttccagt | 1611 | 1630 |
| P2XR7_Pro9.for | Sense | cttaccactcccaggactaa | 1496 | 1515 |
| P2XR7_Pro10.for | Sense | gtctgcctgttcactgccat | 1149 | 1168 |
| P2XR7_Pro1.for | Sense | cagagaccttcagaaacttcg | 1841 | 1861 |
| P2XR7_Pro2.rev | Antisense | agatcaccagggacacagtg | 2261 | 2280 |
| P2XR7_Pro3.for | Sense | ctcaactccactttcctcgg | 2133 | 2152 |
| P2XR7_Pro4.rev | Antisense | cctttcacttttttggtctcatg | 2655 | 2677 |
| P2XR7_Pro5.for | Sense | gggagaattctgaaaatgccc | 2691 | 2711 |
| P2XR7_Pro6.rev | Antisense | ggaccagagctctactcttc | 2951 | 2970 |
| P2XR7_Pro11.for | Sense | aggtcatagatcgacctgcc | 2296 | 2315 |
| P2XR7_Pro12.rev | Antisense | aagaagcgccaagtcctacg | 2785 | 2804 |
| P2XR7_Pro14.for | Sense | gcaatccagactgaagttgac | 2051 | 2071 |
| P2XR7_Pro15.rev | Antisense | actctggtctgcagttggtg | 2428 | 2447 |
| P2XR7_Pro21.for | Sense | cctttaaaatcagagaccttcaga | 1831 | 1854 |
| P2XR7_Pro22.for | Sense | gcccatcctctgaacaccat | 2708 | 2727 |
| P2XR7_3UTR10.for | Sense | cccttggaactcttgctatcg | 55804 | 55824 |
| P2XR7_3UTR1.for | Sense | ggcagtacagtggcttcaaga | 54858 | 54878 |
| P2XR7_3UTR2.rev | Antisense | gtgggacagtttgctgtgcct | 55150 | 55170 |
| P2XR7_3UTR3.for | Sense | gagtccttaccaatagcagg | 55183 | 55202 |

TABLE 1a-continued

Primer sequences for SNP amplification and sequencing

| Primer Name | Orientation | Sequence | Begin | End |
| --- | --- | --- | --- | --- |
| P2XR7_3UTR4.rev | Antisense | gtcaaagaatttgtggccacc | 55643 | 55663 |
| P2XR7_3UTR5.for | Sense | catgaactgtcttttaatgtgtaaag | 55515 | 55540 |
| P2XR7_3UTR6.rev | Antisense | gagatacggtttcaccatgttg | 55955 | 55976 |
| P2XR7_3UTR7.for | Sense | aattagctgggcatggtgcg | 55992 | 56011 |
| P2XR7_3UTR8.rev | Antisense | ttgagatggagtctcgctctg | 56122 | 56140 |
| P2XR7_3UTR9.rev | Antisense | cactgtccacgtgactgctt | 56208 | 56227 |
| P2RX7_11.For | Sense | tcctacttcggtctggtaagagatt | 47281 | 47305 |
| P2RX7_11.Rev | Antisense | gggcctaattttcgtgcat | 47591 | 47609 |
| P2RX7_13G.For | Sense | aagaacctagaacctgagggctt | 54333 | 54355 |
| P2RX7_13G.Rev | Antisense | ttgagatgggaggcagctt | 54541 | 54559 |
| P2RX7_13H.For | Sense | ttcggctcccaggacat | 54773 | 54789 |
| P2RX7_13H.Rev | Antisense | cacagagctttgcaggtgaa | 55248 | 55267 |

Another aspect of the present invention is in the form of a diagnostic kit for affective disorders comprising a specific oligonucleotide probe, or primer corresponding to P2X7R polymorphisms. The diagnostic kit may comprise appropriate packaging and instructions for the use in the method of the invention. Said kit may further comprise appropriate buffer, and enzymes such as reverse transcriptase, and thermostable polymerases.

In a preferred embodiment of the invention, diagnosis can be performed on a mouse, rat or human. The invention is generally applied in vitro, e.g. using cells or other material obtained from an individual. However, it can also be applied on a living individual, or post mortem.

In accordance with the embodiments of the present invention, diagnosis of an affective disorder may be followed by prescription, or administration of an antidepressant drug. Administration and dosage of antidepressive drugs can vary between patients and are well know in the medical art, see, for example Benkert and Hippius, "Kompendium der Psychiatrischen Pharmakotherapie", Springer Verlag Publishing, 2000; Albers, "Handbook of Psychiatric Drugs: 2001-2002 Edition", Current Clinical Strategies Publishing, 2000. Preferred examples include between 5 mg and 80 mg per day, preferably 20 mg, fluoxetine; between 5 mg and 50 mg per day, preferably 20 mg, paroxetine; between 5 mg and 200 mg per day, preferably 50 mg, sertraline; between 5 mg and 300 mg per day, preferably 100 mg, fluvoxamine; between 5 mg and 100 mg per day, preferably 30 mg, mirtazapine; between 4 mg and 50 mg, preferably 8 mg, reboxetine; between 5 mg and 600 mg per day, preferably 200 mg, nefazodone; between 450 mg and 1800 mg per day, preferably 900 mg, lithium carbonate.

The P2X7R protein is also useful for monitoring the efficacy and/or dosing of a drug or the likelihood of a patient to respond to a drug. Thus, in yet another embodiment the invention relates to a method for, monitoring the efficacy and/or dosing of a drug, e.g. an antidepressive drug, and/or the likelihood of a patient to respond to said drug which comprises determining the level of expression and/or activity of the P2X7R protein in a patient before and after administration of the respective drug. As presented in the examples below, treatment with an antidepressive drug results in an upregulation in P2X7R activity. In humans, P2X7R activity can be monitored by Positron Emission Tomography (PET) or Single Photon Emission Computerised Tomography (SPECT) using a radiolabelled ligand tracer for P2X7R. Examples of P2X7R ligands can be, but are not limited to, ATP, an antagonist binding P2X7R, an agonist binding P2X7R, or a small polynucleotide comprising at least 20 bases of the human P2X7R gene. A modulation of P2X7R activity, membrane distribution or expression levels would reflect the activity and potency of the antidepressive drug. Methods and techniques required for PET analysis are well known in the art, see, for example Paans and Vaalburg, Curr. Pharmac. Design 6 (2000), 1583-1591; van Waarde, Curr. Pharmac. Design. 6 (2000), 1593-1610; Paans et al, Methods 27 (2002), 195-207; Passchier et al., Methods 27 (2002), 278-286; Laruelle et al., Methods 27 (2002), 287-299.

In accordance with the present invention by the term "sample" is intended any biological sample obtained from an individual, cell line, tissue culture, or other source containing polynucleotides or polypeptides or portions thereof. As indicated, biological samples include body fluids (such as blood, sera, plasma, urine, synovial fluid and spinal fluid) and tissue sources found to express the polynucleotides of the present invention. Methods for obtaining tissue biopsies and body fluids from mammals are well known in the art. A biological sample which includes genomic DNA, mRNA or proteins is preferred as a source.

As described herein above, mutations of the P2X7R encoding gene can occur on DNA level or on mRNA level and may result in an altered expression of P2X7R or in the expression of P2X7R ATP-gated ion channels which show either an altered function or no function when compared to the wild-type P2X7R ATP-gated ion channel as described herein. Thus, various methods on DNA level, RNA level or protein level exist for determining whether the ATP-gated ion channel P2X7R gene shows a mutation as described herein above. Consequently, mRNA, cDNA, DNA and genomic DNA are the preferred nucleic acid molecules to be used in the below mentioned methods. Also polypeptides or fragments thereof are preferred if a mutation in the P2X7R ATP-gated ion channel protein as described herein is to be determined.

Preferably, a point mutation leading to the replacement of an amino acid residue at the positions as indicated in Table 1 of the corresponding wild-type P2X7R amino acid sequence depicted in SEQ ID NO: 3 or 4 by another amino acid can be determined by PCR. Said PCR is followed by a restriction fragment length polymorphism (RFLP) analysis if due to the point mutation a recognition site for a restriction endonuclease is generated which is not present in the wild-type nucleotide sequence or a recognition site for a restriction enzyme is created which does not occur in the wild-type P2X7R. More preferably said mutation can be determined by PCR using primers and conditions that allow only an amplification of the wild-type nucleotide sequence encoding the corresponding wild-type amino acid at the respective position, but not of the nucleotide sequence of a nucleic acid molecule encoding a different amino acid residue at the corresponding position. It is even more preferred that PCR is performed to determine a mutation using primers and conditions that allow no amplification if the wild-type nucleotide sequence is present, but only if another amino acid residue is encoded at the respective position. Particularly preferred is a method using PCR and primers under conditions that allow amplification of a fragment comprising at least the nucleotide residues encoding the amino acid residue corresponding to positions of SEQ ID NO: 1.

Said PCR is followed by e.g., sequencing and/or single strand conformation analysis (SSCA). Said fragment is preferably of at least 25 nucleotides in length, more preferred of at least 50 nucleotide in length, even more preferred of at least 75 nucleotides in length, particularly preferred of at least 100 nucleotides in length, more particularly preferred of at least 200 nucleotides in length, also more particularly preferred at least 250 nucleotides in length, even more particularly preferred at least 300 nucleotides in length and most particularly preferred at least 600 nucleotides in length. Said primers are preferably of at least 12 nucleotides in length, more preferred of at least 15 nucleotides in length, even more preferred of at least 18 nucleotides in length and most preferred of at least 21 nucleotides in length as depicted in SEQ ID NOs: 52 to 111. The temperature for annealing said primers is preferably at least 50° C., more preferred at least 55° C. and most preferred at least 58° C. The temperature for denaturation is preferably at least 95° C. for preferably at least 10 sec, more preferably at least 20 sec, even more preferred at least 30 sec and most preferred at least 60 sec. However, depending on the length and the G-C content of the nucleic acid sequence to be amplified the temperature for denaturation may be shorter or longer. The temperature for extension of the annealed primers is preferably at least 10 sec, more preferably at least 20 sec, even more preferred at least 30 sec and most preferred at least 60 sec. A PCR reaction comprising the aforementioned conditions is exemplified in the Examples herein below. The subsequent sequencing and/or SSCA is carried out as known in the art. Preferably, the PCR fragments are separated on a 10% polyacrylamide gel at 4° C. or also preferred at room temperature. PCR fragments showing a SSCA band shift are amplified with the primers under conditions as mentioned above and are subsequently sequenced. Alternatively, it is also possible to directly sequence genomic DNA in order to determine whether a mutation in the CLCN2 gene has occurred. A direct genomic sequencing approach is, for example, demonstrated for baker's yeast in Horecka, Yeast 16 (2000), 967-970.

Preferably, a deletion is determined by using hybridization techniques as known in the art. In particular, a primer is designed as mentioned herein above that is capable to only hybridize to wild-type genomic DNA as depicted in SEQ ID NO: 1 but not to a nucleotide sequence comprising a deletion of a fragment between nucleotides 54562 and 54582 of SEQ ID NO: 1. Also preferred is the method of fluorescent in situ hybridization (FISH) for determining on whole chromosomes, in particular on chromosome 12q23-q24 that said chromosome has the above mentioned deletion. Even more preferred is that a deletion of nucleotide residues as described herein may be determined by using PCR, wherein one primer of a pair of primers is located within the region of genomic DNA comprising said deletion. Preferably, said deletion is between nucleotide positions 54562 and 54582 as depicted in SEQ ID NO: 1. Thus, under the appropriate conditions no PCR fragment will result if the genomic DNA comprises said deletion. It is particularly preferred that PCR using primers which are located upstream or downstream of the deletion is performed to determine said deletion. Under appropriate conditions as mentioned herein above, both a fragment of genomic DNA of the wild-type nucleotide sequence as set forth in SEQ ID NO: 1 and a fragment of the nucleotide sequence comprising a deletion of preferably the nucleotides between positions 54562 and 54582 as depicted in SEQ ID NO: 1 will be amplified.

It is also possible to determine the above-described P2X7R mutations on the protein level. Some of the mutations described above lead to shortened versions of the P2X7R protein. Thus, it is conceivable to determine the occurrence of these mutations by determining the length or molecular weight of the P2X7R protein expressed in an individual, e.g. by SDS PAGE.

It is also possible to determine the mutations of the P2X7R ATP-gated channel as described herein by using the antibodies of the present invention. Said antibodies specific for said mutations of P2X7R proteins will be determined by assay techniques such as radioimmunoassays, competitive-binding assays, Western blot analysis and ELISA assay. Also preferred are classical immunohistological methods.

The finding, described in the present invention, that certain mutations in the P2X7R encoding gene and/or the corresponding protein are connected with affective disorder is indicative that the non- or dysfunction of the P2X7R protein is responsible for various forms of affective disorders. Thus, the finding of these mutations not only allows the diagnosis of affective disorders by determining whether the above-described mutations occur in an individual. It also allows to develop a treatment of affective disorders which has been diagnosed to be the result of a mutation in the P2X7R encoding gene. Such a treatment can, e.g., comprise the introduction of a nucleic acid molecule encoding a non-functional or functional wild-type P2X7R protein thereby restoring in said individual the P2X7R activity or the activation or repression of (a) P2X7R gene(s) in vivo. The term "activation or repression" in this context means that the expression of the gene is either enhanced (activation) or reduced (repression). An enhancement of expression can, e.g., be achieved by increasing the efficiency of transcription initiation, for example, by using suitable compounds which have an activating effect on transcription. Alternatively, an enhancement can be achieved by replacing the naturally occurring promoter by a more efficient promoter.

A repression may be achieved by suppressing expression of the gene, e.g., by specifically suppressing transcription from the respective promoter by suitable compounds or by rendering the promoter less efficient or non-functional.

In another embodiment the present invention also relates to a pharmaceutical composition. In accordance with the present invention the term "pharmaceutical composition" relates to a composition comprising a nucleic acid molecule comprising a nucleotide sequence which encodes an ATP-gated ion channel P2X7R and which is selected from the group consisting of:
(a) a nucleotide sequence encoding a polypeptide comprising the amino acid sequence as depicted in SEQ ID NO: 3 or 4;
(b) a nucleotide sequence comprising the nucleotide sequence as depicted in SEQ ID NO: 1 or SEQ ID NO: 2;
(c) a nucleotide sequence which hybridizes to the nucleotide sequence of (a) or (b); and
(d) a nucleotide sequence which is degenerated as a result of the genetic code to the nucleotide sequence of (c).

Such pharmaceutical compositions comprise a therapeutically effective amount of a nucleic acid molecule encoding a functional P2X7R protein and, optionally, a pharmaceutically acceptable carrier. The pharmaceutical composition may be administered with a physiologically acceptable carrier to a patient, as described herein. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium ion, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the aforementioned compounds, preferably in purified form, together with a suitable amount of carrier so as to provide the form for proper administration to the patient. The formulation should suit the mode of administration.

In another preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical composition of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. Preferably, the pharmaceutical composition is administered directly or in combination with an adjuvant.

The pharmaceutical composition is preferably designed for the application in gene therapy. The technique of gene therapy has already been described above in connection with the nucleic acid molecules of the invention and all what has been said there also applies in connection with the pharmaceutical composition. For example, the nucleic acid molecule in the pharmaceutical composition is preferably in a form which allows its introduction, expression and/or stable integration into cells of an individual to be treated.

For gene therapy, various viral vectors which can be utilized, for example, adenovirus, herpes virus, vaccinia, or, preferably, an RNA virus such as a retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can also incorporate multiple genes. All of these vectors can transfer or incorporate a gene for a selectable marker so that transduced cells can be identified and generated. By inserting a P2X7R sequence of interest encoding a functional P2X7R protein into the viral vector, along with another gene which encodes, for example, the ligand for a receptor on a specific target cell, for example, the vector is now target specific.

Retroviral vectors can be made target specific by inserting, for example, a polynucleotide encoding a sugar, a glycolipid, or a protein. Those of skill in the art will know of, or can readily ascertain without undue experimentation, specific polynucleotide sequences which can be inserted into the retroviral genome to allow target specific delivery of the retroviral vector containing the inserted polynucleotide sequence.

Since recombinant retroviruses are preferably defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to w2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for P2X7R polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2-4.0 pm can encapsulate a substantial percentage of an aqueous buffer containing large macromolecules. RNA, DNA and intact virions can be encapsulated within the aqueous interior and be delivered to cells in a biologically active form (Fraley, et al., Trends Biochem. Sci., 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine. The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries.

In another aspect the present invention relates to a method of treating an affective disorder comprising administering a therapeutically effective amount of the pharmaceutical composition comprising a nucleotide sequence encoding a functional ATP-gated ion channel as described herein above to a subject suffering from said disorder.

In the context of the present invention the term "subject" means an individual in need of a treatment of an affective disorder. Preferably, the subject is a vertebrate, even more preferred a mammal, particularly preferred a human.

The term "administered" means administration of a therapeutically effective dose of the aforementioned nucleic acid molecule encoding a functional P2X7R protein to an individual. By "therapeutically effective amount" is meant a dose that produces the effects for which it is administered. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

The methods are applicable to both human therapy and veterinary applications. The compounds described herein having the desired therapeutic activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1-100 wt %. The agents may be administered alone or in combination with other treatments.

The administration of the pharmaceutical composition can be done in a variety of ways as discussed above, including, but not limited to, orally, subcutaneously, intravenously, intraarterial, intranodal, intramedullary, intrathecal, intraventricular, intranasally, intrabronchial, transdermally, intranodally, intrarectally, intraperitoneally, intramuscularly, intrapulmonary, vaginally, rectally, or intraocularly. In some instances, for example, in the treatment of wounds and inflammation, the candidate agents may be directly applied as a solution dry spray.

The attending physician and clinical factors will determine the dosage regimen. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg; however, doses below or above this exemplary range are envisioned, especially considering the aforementioned factors.

The dosages are preferably given once a week, however, during progression of the treatment the dosages can be given in much longer time intervals and in need can be given in much shorter time intervals, e.g., daily. In a preferred case the immune response is monitored using herein described methods and further methods known to those skilled in the art and dosages are optimized, e.g., in time, amount and/or composition. Dosages will vary but a preferred dosage for intravenous administration of DNA is from approximately $10^6$ to $10^{12}$ copies of the DNA molecule. If the regimen is a continuous infusion, it should also be in the range of 1 µg to 10 mg units per kilogram of body weight per minute, respectively. Progress can be monitored by periodic assessment. The pharmaceutical composition of the invention may be administered locally or systemically. Administration will preferably be parenterally, e.g., intravenously. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium ion solution, Ringer's dextrose, dextrose and sodium ion, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

It is also envisaged that the pharmaceutical compositions are employed in co-therapy approaches, i.e. in co-administration with other medicaments or drugs, for example other drugs for preventing, treating or ameliorating affective disorders.

Another aspect of the present invention is a pharmaceutical composition comprising a compound, the administration of which to cells leads to a reduction or increase of the expression of a nucleic acid encoding an ATP-gated ion channel P2X7R in the cells or comprising a nucleic acid molecule the expression of which in cells or the administration of which to cells leads to a reduction or increase of the expression of a nucleic acid encoding an ATP-gated ion channel P2X7R in the cells. Said pharmaceutical composition may be useful for treating individuals having an increased or reduced amount of the P2X7R protein or expression level as described hereinabove. Preferably, said pharmaceutical composition leads to in increase of the expression of a nucleic acid encoding an ATP-gated ion channel P2X7R in the cells.

It is envisaged that the above-mentioned pharmaceutical composition, the administration of which to cells leads to a reduction of the expression of a nucleic acid encoding an ATP-gated ion channel P2X7R is an antisense nucleic acid, a ribozyme, a co-suppressive nucleic acid, iRNA or siRNA.

An siRNA approach is, for example, disclosed in Elbashir ((2001), Nature 411, 494-498)). It is also envisaged in accordance with this invention that for example short hairpin RNAs (shRNAs) are employed in accordance with this invention as pharmaceutical composition. The shRNA approach for gene silencing is well known in the art and may comprise the use of st (small temporal) RNAs; see, inter alia, Paddison (2002) Genes Dev. 16, 948-958.

As mentioned above, approaches for gene silencing are known in the art and comprise "RNA"-approaches like RNAi or siRNA. Successful use of such approaches has been shown in Paddison (2002) loc. cit., Elbashir (2002) Methods 26, 199-213; Novina (2002) Mat. Med. Jun. 3, 2002; Donze (2002) Nucl. Acids Res. 30, e46; Paul (2002) Nat. Biotech 20, 505-508; Lee (2002) Nat. Biotech. 20, 500-505; Miyagashi (2002) Nat. Biotech. 20, 497-500; Yu (2002) PNAS 99, 6047-6052 or Brummelkamp (2002), Science 296, 550-553. These approaches may be vector-based, e.g. the pSUPER vector, or RNA polIII vectors may be employed as illustrated, inter alia, in Yu (2002) loc. cit.; Miyagishi (2002) loc. cit. or Brummelkamp (2002) loc. cit.

A compound which leads to a reduction of the expression of the P2X7R gene may, e.g., be a compound which acts on the regulatory region of the gene and thereby reduces the level of transcription. Such compounds can be identified by methods as described herein below.

The invention also relates to the use of a nucleic acid molecule encoding a functional P2X7R protein as described herein above in connection with the pharmaceutical composition for the preparation of a pharmaceutical composition for treating an affective disorder.

Furthermore, the present invention relates to a method of treating an affective disorder comprising administering a therapeutically effective amount of the nucleic acid molecule according to the invention or a therapeutically effective amount of the corresponding encoded polypeptide to a subject suffering from said disorder.

In another preferred embodiment the present invention relates to a pharmaceutical composition comprising, inter alia, the polynucleotides according to the present invention, i.e. polynucleotides having mutations and/or deletions as described hereinabove. Such pharmaceutical compositions may, e.g., be useful for treating individuals having an increased or decreased amount of the P2X7R protein or having a P2X7R protein showing an increased or decreased activity which can be determined as described hereinabove. Preferably, such a pharmaceutical composition may be useful for treating individuals having a decreased amount of the P2X7R protein or having a P2X7R protein showing a decreased activity which can be determined as described hereinabove It is envisaged that, e.g. a non-functional or preferably a hyper-functional P2X7R protein comprised by said pharmaceutical composition is incorporated in a P2X7R complex which naturally exists in cells as described hereinabove. It is also envisaged that the above-described techniques for gene therapy can be used for treating an individual with the nucleic acid molecules of the present invention, mutatis mutandis.

With respect to the possible modes of administration and preferred embodiments the same applies as has been set forth above.

Additionally, the present invention also envisages the use of the nucleic acid molecules, the vectors, the polypeptides, the antibody and/or the aptamer according to the invention for the preparation of a pharmaceutical composition for the treatment of an affective disorder.

A further aspect of the present invention is the use of a modulator of P2X7R activity or expression for the preparation of a pharmaceutical composition for treating an affective disorder. In the context of the present invention the term "modulator" means (a) compound(s), a complex of compounds, (a) substance(s) or complex of substances which can modify, i.e. modulate the activity of P2X7R or the expression of P2X7R either directly or indirectly. The modulation can, for example, occur at the protein level. Particularly, the P2X7R protein may interfere with the modulator such that it is either more active or less active. The modulation can also occur on nucleic acid level. Namely, the gene is transcribed more frequently or less frequently giving rise to more or less protein. Modulation can also influence RNA or protein stability. Since it was surprisingly found that agonists of P2X7R improve the symptoms of mice selected for anxiety and depressive behaviour, the modulator of P2X7R activity used for the preparation of a pharmaceutical composition for treating an affective disorder is preferably an agonist. The term "agonist" means an agent or a compound that can interact with a receptor and initiate a physiological or a pharmacological response characteristic of that receptor. Examples of P2X7R agonist include but are not restricted to ATP, ATP-4, BzATP (2'-3'-O-(4-Benzoylbenzoyl)adenosine 5'-triphosphate ($C_{24}H_{24}N_5O_{15}P_3$)) and tenidap (5-chloro-2,3-dihydro-2-oxo-3-(2-thienylcarbonyl)-indole-1-carboxamide, i.e. $C_{15}H_{11}ClN_2O_2S$) or a derivative thereof. Particularly preferred, said agonist used to treat depression or anxiety is BzATP is as demonstrated in Example 9 hereinbelow.

Although it was reported that activation of P2X7R could induce apoptosis and cell death in vitro (Di Virgilio et al., Cell Death Differ. 5 (1988), 191-199; Virginio et al., J. Physiol. 519 (1999), 335-346), the present application demonstrates in Example 9 hereinbelow that treatment of the brain of mice selected for anxiety and depressive behaviour with BzATP revealed no significant difference in the numbers of apoptotic cells between control mice and mice treated with BzATP. This result indicates that activation of P2X7R did not result in cerebral cell death in vivo which, thus, renders BzATP to be a candidate drug for treatment of affective disorders.

It is furthermore envisaged that said modulator is selected from the group consisting of piperidine and piperazine derivatives, adamantane derivatives, substituted phenyl compounds, oxidized ATP, 2-O-(4-benzoylbenzoyl)adenosine-5-triphosphate and 3-O-(4-benzoylbenzoyl)adenosine-5-triphosphate as, for example, described in WO 99/29660, WO 99/29661; WO 99/296896; WO 00/61569; WO 01/42194; WO 01/44170; WO 01/44213; WO 00/71529; WO 01/46200. The following compounds illustrate compounds which are also preferred to be used as modulators of P2X7R activity.

A compound of general formula:

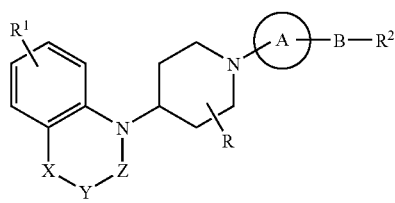

where A is phenyl or a 5- or 6-membered heterocyclic ring containing one or two heteroatoms selected from O, N or S; and optionally substituted by $C_{1-6}$alkyl, halogen, nitro, amino, alkylamino, $CF_3$, $SO_2Me$, $NHSO_2Me$ or cyano; B is C=O, NH or $SO_2$; X is C=O, CH(Me), O or $(CH_2)p$ where p is 0 or 1; Y is O, $CH_2$, NH or S; Z is C=O or $SO_2$, provided that when Z is C=O, then Y is O, $CH_2$ or S; R is hydrogen or $C_{1-6}$alkyl; $R^1$ is hydrogen, halogen; $R^2$ is phenyl optionally substituted by $CO_2H$, $CO_2$alkyl, $CONH_2$ or $R^2$ is OH, $NHR^3$, $NHCH(R^4)(CHR^5)_nR^6$, $NH-R^7-R^8$, $SO_2NH$alkyl, NHCOalkyl, $NHSO_2$alkyl, morpholine, $NR^9R^{10}$, piperazine substituted by phenyl, alkoxyphenyl, pyridyl or fluorophenyl; n is 0, 1 or 2; $R^3$ is hydrogen, a bi- or tricyclic saturated ring system optionally containing a nitrogen atom, piperidinyl, alkylpyrollidine, ethynylcyclohexyl, a 5-membered aromatic ring containing 2 or 3 heteroatoms, $C_{4-6}$ cycloalkyl optionally substituted by alkyl, cyano or hydroxy, or $C_{1-8}$ alkyl optionally containing an oxygen atom in the alkyl chain and being optionally substituted by one or more substituents selected from ethynyl, cyano, fluoro, dialkylamino, hydroxy, thioalkyl, $CO_2R^{11}$ or $CONH_2$; $R^4$ is hydrogen or alkyl optionally substituted by hydroxy or alkoxy; $R^5$ is hydrogen or hydroxy; $R^6$ is $CO_2R^{11}$, $NHCO_2R^{12}$, $CONH_2$ or a 5 or 6-membered saturated ring containing an oxygen atom, a 5-membered heterocyclic ring containing one or two heteroatoms selected from O, N or S, or phenyl optionally substituted by one or more groups selected from alkyl, hydroxy, amino, alkoxy, or nitro; $R^6$ is alkyl; $R^7$ is a cyclopentane ring; $R^8$ is phenyl; $R^9$ and $R^{10}$ are independently hydrogen, benzyl, alkenyl, cycloalkyl, alkyl optionally substituted by hydroxy, alkoxy, cyano, dialkylamino, phenyl, pyridyl or $CO_2R^{11}$ or $R^9$ and $R^{10}$ together form a 5- to 7-membered saturated or partially saturated ring optionally containing a further heteroatom and optionally substituted by one or more groups selected from alkyl (optionally containing an oxygen atom in the chain and optionally substituted 14 by hydroxy), COalkyl, $CO_2R^{11}$, $COR^{13}R^{14}$, CHO or piperidine, $R^{11}$ is hydrogen or alkyl; $R^{12}$ is alkyl; and $R^{13}$ and $R^{14}$ are independently hydrogen or alkyl, is or a pharmaceutically acceptable salt or solvate thereof.

A compound of general formula:

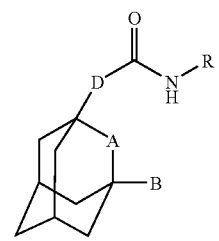

wherein A represents a group $CH_2$ or an oxygen atom; B represents a hydrogen or halogen atom; D represents a group $CH_2$, $OCH_2$, $NHCH_2$ or $CH_2CH_2$; R represents a phenyl, benzothiazolyl, indolyl, indazolyl, purinyl, pyridyl, pyrimidinyl or thiophenyl group, each of which may be optionally substituted by one or more substituents independently selected from a halogen atom or a cyano, carboxyl, hydroxyl, nitro, halo-$C_1$-$C_6$-alkyl, —$N(R^1)$—C(=O)—$R^2$, —C(O)—$NR^3R^4$, —$NR^5R^6$, $C_3$-C8-cycloalkyl, 3- to 8-membered heterocyclyl, $C_3$-$C_8$-cycloalkyloxy, $C_1$-$C_6$-alkylcarbonyl, phenoxy, benzyl, $C_1$-$C_6$-alkylthio, phenylthio, $C_1$-$C_6$-alkoxycarbonyl, $C_1$-$C_6$-alkylsulphinyl or $C_1$-$C_6$-alkylsulphonyl group, or a $C_1$-$C_6$-alkyl or $C_1$-$C_6$-alkoxy group optionally substituted by one or more substituents independently selected from a halogen atom or an amino, carboxyl, hydroxyl, $C_1$-$C_6$-alkoxy, (di)$C_1$-$C_6$-alkylamino, $C_1$-$C_6$-alkoxycarbonyl, imidazolyl, morpholinyl, piperidinyl or pyrrolidinyl group; $R^1$ represents a hydrogen atom or a $C_1$-$C_6$-alkyl or $C_3$-$C_8$-cycloalkyl group; $R^2$ represents a $C_1$-$C_6$-alkyl or $C_3$-$C_8$-cycloalkyl group; and $R^3$, $R^4$, $R^5$ and $R^6$ each independently represent a hydrogen atom or a $C_1$-$C_6$-alkyl or $C_3$-$C_8$-cycloalkyl group; with the provisos that when A is $CH_2$, B is H and D is $CH_2$, then R does not represent a phenyl, ortho-carboxyphenyl, methylphenyl or para-phenoxyphenyl group, and that when A is $CH_2$, D is $CH_2$ or $CH_2CH_2$ and R represents a substituted phenyl group, the substituent or substituents present do not comprise, in an ortho position, a $C_1$-$C_6$-alkoxy group substituted by an amino, (di)$C_1$-$C_6$-alkylamino, imidazolyl, morpholinyl, piperidinyl or pyrrolidinyl group; or a pharmaceutically acceptable salt or solvate thereof.

A compound of general formula:

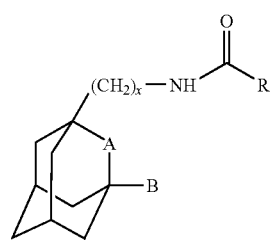

wherein x represents 1 or 2; A represents a group $CH_2$ or an oxygen atom; B represents a hydrogen or halogen atom; R represents a phenyl, pyridyl, indolyl, indazolyl, pyrimidinyl or thiophenyl group, each of which may be optionally substituted by one or more substituents independently selected from a halogen atom or an amino, cyano, carboxyl, hydroxyl, nitro, $C_1$-$C_6$-alkyl, halo-$C_1$-$C_6$-alkyl, —$N(R^1)$—C(=O)—

$R^2$, —C(O)NR$^3$R$^4$, —NR$^5$R$^6$, $C_3$-$C_8$-cycloalkyl, 3- to 8-membered heterocyclyl, $C_3$-$C_8$-cycloalkyloxy, $C_1$-$C_6$-alkylcarbonyl, $C_1$-$C_6$-alkoxycarbonyl, $C_1$-$C_6$-alkylsulphinyl or $C_1$-$C_6$-alkylsulphonyl group, or a $C_1$-$C_6$-alkoxy, $C_1$-$C_6$-alkylamino, phenoxy, benzyl, $C_1$-$C_6$-alkylthio or phenylthio group optionally substituted by one or more substituents independently selected from a 15 halogen atom or an amino, cyano, carboxyl, hydroxyl, nitro, 1-pyrrolidinyl, 1-piperidinyl, $C_1$-$C_6$-alkyl, $C_1$-$C_6$-alkoxy, (di)$C_1$-$C_6$-alkylamino, halo-$C_1$-$C_6$-alkyl, $C_1$-$C_6$-alkoxycarbonyl or one of the following groups:

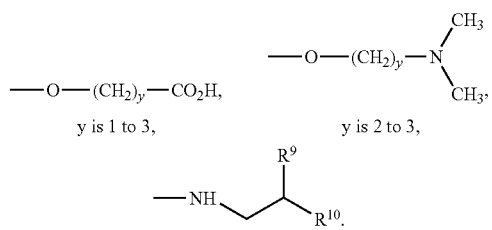

$R^1$ represents a hydrogen atom or a $C_1$-$C_6$-alkyl or $C_3$-$C_8$-cycloalkyl group; $R^2$ represents a $C_1$-$C_6$-alkyl or $C_3$-$C_8$-cycloalkyl group; $R^3$ and $R^4$ each independently represent a hydrogen atom or a $C_1$-$C_6$-alkyl or $C_3$-$C_8$-cycloalkyl group; $R^5$ represents a-hydrogen atom or a $C_1$-$C_6$-alkyl or $C_3$-$C_8$-cycloalkyl group; $R^6$ represents a $C_3$-$C_8$-cycloalkyl group and, additionally, a $C_1$-$C_6$-alkyl group when $R^5$ is not a hydrogen atom; $R^7$ represents a hydrogen atom or a $C_1$-$C_6$-alkyl or $C_3$-$C_8$-cycloalkyl group; $R^8$ represents a $C_1$-$C_6$-alkyl or $C_3$-$C_8$-cycloalkyl group; $R^9$ represents a hydrogen atom or a hydroxyl group; and $R^{10}$ represents a hydrogen atom or a phenyl or imidazolyl group; with the provisos that R does not represent an unsubstituted pyridyl group when A represents a group CH$_2$ and B represents a hydrogen atom, and that when R represents a substituted phenyl, indolyl or indazolyl group, the substituent or substituents present do not comprise an amido, carboxyl, (di)$C_1$-$C_6$-alkylamido or $C_1$-$C_6$-alkoxycarbonyl group in an ortho position; or a pharmaceutically acceptable salt or solvate thereof.

A compound of general formula:

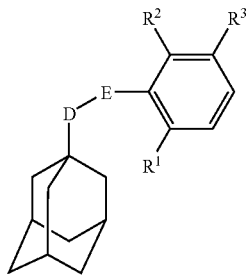

wherein D represents CH$_2$ or CH$_2$CH$_2$; E represents C(O)NH or NHC(O); $R^1$ and $R^2$ each independently represent a hydrogen or halogen atom, or an amino, nitro, $C_1$-$C_6$-alkyl or trifluoromethyl group; $R^3$ represents a group of formula:

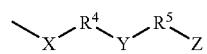

X represents an oxygen or sulphur atom or a group NH, SO or SO$_2$; Y represents an oxygen or sulphur atom or a group NR$^{11}$, SO or SO$_2$; Z represents a group —OH, —SH, —CO$_2$H, $C_1$-$C_6$-alkoxy, $C_1$-$C_6$-alkylthio, $C_1$-$C_6$-alkylsulphinyl, $C_1$-$C_6$-alkylsulphonyl, —NR$^6$R$^7$, —C(O)NR$^8$R$^9$, imidazolyl, 1-methylimidazolyl, —N(R$^{10}$)C(O)—$C_1$-$C_6$-alkyl, $C_1$-$C_6$-alkylcarbonyloxy, $C_1$-$C_6$-alkoxycarbonyloxy, —OC(O)NR$^{12}$R$^{13}$, —OCH$_2$OC(O)R$^{14}$OCHOC(O)OR$^{15}$ or —OC(O)OCH)OR$^{16}$, $R^4$ represents a $C_2$-$C_6$-alkyl group; $R^5$ represents a $C_1$-$C_6$-alkyl group; $R^6$, $R^7$, $R^8$, $R^9$, $R^{10}$, $R^{12}$, and $R^{13}$ each independently represent a hydrogen atom, or a $C_1$-$C_6$-alkyl group optionally substituted by at least one hydroxyl group; $R^{11}$ represents a hydrogen atom, or a $C_1$-$C_6$-alkyl group optionally substituted by at least one substituent independently selected from hydroxyl and $C_1$-$C_6$-alkoxy; and $R^{14}$, $R^{15}$ and $R^{16}$ each independently represent a $C_1$-$C_6$-alkylgroup; with the provisos that (i) when E represents NEC(O), X represents O, S or NH and Y represents O, then Z represents —NR$^6$R$^7$ where R$^6$ represents a hydrogen atom and R$^7$ represents either a hydrogen atom or a $C_1$-$C_6$-alkyl group substituted by at least one hydroxyl group, and (ii) when E represents NHC(O), X represents O, S or NH, Y represents NH, and R$^5$ represents CH$_2$CH$_2$, then Z is not —OH or imidazolyl; or a pharmaceutically acceptable salt or solvate thereof.

A compound of general formula:

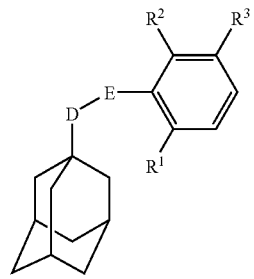

wherein D represents CH$_2$ or CH$_2$CH$_2$; E represents C(O)NH or NHC(O); $R^1$ and $R^2$ each independently represent hydrogen, halogen, amino, nitro, $C_1$-$C_6$-alkyl or trifluoromethyl, but $R^1$ and $R^2$ may not both simultaneously represent hydrogen; $R^3$ represents a group of formula

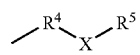

$R^4$ represents a $C_1$-$C_6$-alkyl group; X represents an oxygen or sulphur atom or a group NR$^{13}$, SO or SO$_2$; $R^5$ represents hydrogen, or $R^5$ represents $C_1$-$C_6$-alkyl or $C_2$-$C_6$-alkenyl, each of which may be optionally substituted by at least one substituent selected from halogen, hydroxyl, (di)$C_1$-$C_6$-alkylamino, —Y—R$^6$,

and a 5- or 6-membered heteroaromatic ring comprising from 1 to 4 heteroatoms independently selected from nitrogen, oxygen and sulphur which heteroaromatic ring may itself be optionally substituted by at least one substituent selected from halogen, hydroxyl and $C_1$-$C_6$-alkyl; Y represents an oxygen or sulphur atom or a group NH, SO or $SO_2$; $R^6$ represents a group —$R^7Z$ where $R^7$ represents a $C_2$-$C_6$-alkyl group and Z represents an —OH, —$CO_2H$. —$NR^8R^9$, —C(O)$NR^{10}R^{11}$ or —N($R^{12}$)C(O)—$C_1$-$C_6$-alkyl group, and, in the case where Y represents an oxygen or sulphur atom or a group NH, $R^6$ additionally represents hydrogen, $C_1$-$C_6$-alkyl, $C_1$-$C_6$-alkylcarbonyl, $C_1$-$C_6$-alkoxycarbonyl, —C(O)$NR^{14}R^{15}$, —$CH_2OC(O)R^{16}$, —CH2OC(O)$OR^{17}$ or —C(O)OCH2O$R^{18}$; $R^8$, $R^9$, $R^{10}$, $R^{11}$ and $R^{12}$ each independently represent a hydrogen atom or a $C_1$-$C_6$-alkyl group; $R^{13}$ represents hydrogen, $C_3$-$C_8$-cycloalkyl, $C_3$-$C_8$-cycloalkylmethyl, or $R^{13}$ represents a $C_1$-$C_6$-alkyl group optionally substituted by at least one substituent selected from hydroxyl to and $C_1$-$C_6$-alkoxy; and $R^{14}$, $R^{15}$, $R^{16}$, $R^{17}$, and $R^{18}$ each independently represent a $C_1$-$C_6$-alkyl group; with the proviso that when E is C(O)NH, X is O, NH or N($C_1$-$C_6$-alkyl), then $R^5$ is other than a hydrogen atom or an unsubstituted $C_1$-$C_6$-alkyl group; or a pharmaceutically acceptable salt or solvate thereof.

A compound of general formula:

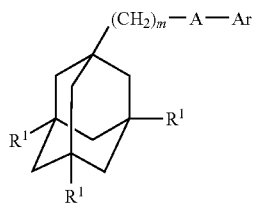

wherein m represents 1, 2 or 3; each $R^1$ independently represents a hydrogen or halogen atom; A represents C(O)NH or NHC(O); Ar represents a group

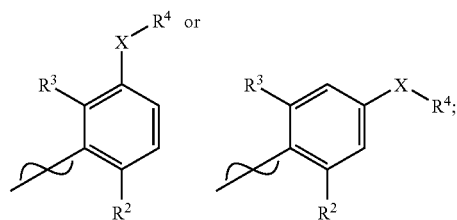

X represents a bond, an oxygen atom or a group CO, $(CH_2)_{1-6}$, CH=, $(CH_2)_{1-6}O$, $O(CH_2)_{1-6}$, $O(CH_2)_{2-6}O$, $O(CH_2)_{2-3}O(CH_2)_{1-3}$, CR'(OH), $(CH_2)_{1-3}O(CH_2)_{1-3}$, $(CH_2)_{1-3}O(CH_2)_{2-3}O$, $NR^5$, $(CH_2)_{1-6}NR^5$, $NR^5(CH_2)_{1-6}$, $(CH_2)_{1-3}NR^5(CH_2)_{1-3}$, $O(CH_2)_{2-6}NR^5$, $O(CH_2)_{2-3}NR^5(CH_2)_{1-3}$, $(CH_2)_{1-3}NR^5(CH_2)_{2-3}O$, $NR^5(CH_2)_{2-6}O$, $NR^5(CH_2)_{2-3}O(CH_2)_{1-3}$, $CONR^5$, $NR^5CO$, $S(O)_n$, $S(O)_nCH_2$, $CH_2S(O)_n$, $SO_2NR^5$ or $NR^5SO_2$; n is 0, 1 or 2; $R^1$ represents a hydrogen atom or a $C_1$-$C_6$-alkyl group; one of $R^2$ and $R^3$ represents a halogen, cyano, nitro, amino, hydroxyl, or a group selected from (i) $C_1$-$C_6$-alkyl optionally substituted by at least one $C_3$-$C_6$-cycloalkyl, (ii) $C_3$-$C_8$-cycloalkyl, (iii) $C_1$-$C_6$-alkyloxy optionally substituted by at least one $C_3$-$C_6$-cycloalkyl, and (iv) $C_3$-$C_8$-cycloalkyloxy, each of these groups being optionally substituted by one or more fluorine atoms, and the other of $R^2$ and $R^3$ represents a hydrogen or halogen atom; either $R^4$ represents a 3- to 9-membered saturated or unsaturated aliphatic heterocyclic ring system containing one or two nitrogen atoms and optionally an oxygen atom, the heterocyclic ring system being optionally substituted by one or more substituents independently selected from fluorine atoms, hydroxyl, carboxyl, cyano, $C_1$-$C_6$-alkyl, $C_1$-$C_6$-hydroxyalkyl, —$NR^6R^7$, $(CH_2)_rNR^6R^7$ and CON$R^6R^7$, r is 1, 2, 3, 4, 5 or 6; $R^5$ represents a hydrogen atom or a $C_1$-$C_6$-alkyl or $C_3$-$C_8$-cycloalkyl group; $R^6$ and $R^7$ each independently represent a hydrogen atom or a $C_1$-$C_6$-alkyl, $C_2$-$C_6$-hydroxyalkyl or $C_3$-$C_8$-cycloalkyl group, or $R^6$ and $R^7$ together with the nitrogen atom to which they are attached form a 3- to 8-membered saturated heterocyclic ring; with the provisos that, (a) when A represents C(O)NH and $R^4$ represents an unsubstituted 3- to 8-membered saturated aliphatic heterocyclic ring system containing one nitrogen atom, then X is other than a bond, and (b) when A represents C(O)NH and X represents a group $(CH_2)_{1-6}$ or $O(CH_2)_{1-6}$, then $R^4$ does not represent an unsubstituted imidazolyl, unsubstituted morpholinyl, unsubstituted piperidinyl or unsubstituted pyrrolidinyl group, and (c) when A represents NHC(O) and $R^4$ represents an unsubstituted 3- to 8-membered saturated aliphatic heterocyclic ring system containing one nitrogen atom, then X is other than a bond, and (d) when A represents NHC(O) and X represents $O(CH_2)_{1-6}$, $NH(CH_2)_{1-6}$ or $SCH_2$, then $R^4$ does not represent an unsubstituted 1-piperidinyl or unsubstituted 1-pyrrolidinyl group, and (e) when A represents NHC(O) and X represents $O(CH_2)_{2-3}NH(CH_2)_2$, then $R^4$ does not represent an imidazolyl group; or a pharmaceutically acceptable salt or solvate thereof.

A compound of general formula:

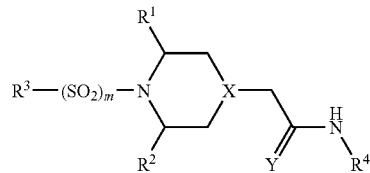

X represents a nitrogen atom or a group C($R^5$); Y represents an oxygen or sulphur atom or a group $NR^6$; either $R^1$ and $R^2$ each independently represent a hydrogen atom or a $C_1$-$C_4$-alkyl group but do not both simultaneously represent a hydrogen atom, or $R^1$ and $R^2$ together represent a group —$CH_2ZCH_2$—; Z represents a bond, an oxygen or sulphur atom or a group $CH_2$ or $NR^7$; m is 0 or 1; $R^3$ represents a 5- to 10-membered unsaturated ring system which may comprise from 1 to 4 ring heteroatoms independently selected from nitrogen, oxygen and sulphur, the ring system being optionally substituted by one or more substituents independently selected from halogen, nitro, cyano, $NR^8R^9$, $C_1$-$C_4$-alkyl-C(O)NH—, $NHR^{12}C(O)$—, $C_1$-$C_4$-alkyl-$SO_2$—, $C_1$-$C_4$-alkyl-$SO_2NH$—, $C_1$-$C_4$-alkyl-$NHSO_2$—, $C_1$-$C_4$-alkoxy, and $C_1$-$C_4$-alkyl optionally substituted by one or more fluorine atoms; $R^4$ represents a phenyl or pyridinyl group, each of which is substituted in an ortho position with a substituent selected from halogen, $C_1$-$C_4$-alkoxy, $C_1$-$C_4$-alkylthio, and $C_1$-$C_4$-alkyl optionally substituted by one or more fluorine atoms, the phenyl or pyridinyl group being optionally further substituted by one or more substituents independently selected from halogen, cyano, hydroxyl, $C_1$-$C_4$-alkylthio, $C_1$-$C_4$-alkyl-NH—, $NHR^{13}$—$C_1$-$C_4$-alkyl-, $C_1$-$C_4$-alkyl-$SO_2$—, $C_1$-$C_4$-alkyl-$SO_2NH$—, $C_1$-$C_4$-alkyl-$NHSO_2$—, $C_1$-$C_4$-alkyl-C(O)NH—, $C_1$-$C_4$-alkyl-NHC(O)—, -D-G, $C_1$-$C_4$-alkoxy optionally substituted by —$NR^{14}R^{15}$ or by $R^{16}$, and $C_1$-$C_4$-alkyl optionally substituted by one or more fluorine atoms or by one or more hydroxyl groups, or $R^4$ represents a 9- or 10-membered unsaturated bicyclic ring system which may comprise from 1 to 4 ring heteroatoms independently selected from nitrogen, oxygen and sulphur, the bicyclic ring system being optionally substituted by one or more substituents independently selected from halogen, oxo, $C_1$-$C_4$-alkyl, $C_1$-$C_4$-alkoxy, $C_1$-$C_4$-alkylthio and —$NR^{10}R^{11}$; D represents an oxygen atom or a group $(CH_2)_n$ or $CH_2NH$; n is 1, 2 or 3; G represents a piperazinyl, morpholinyl or 2,5-diazabicyclo[2.2.1]heptyl group, or G represents a piperidinyl group optionally substituted by amino; $R^5$ represents a hydrogen atom, or a hydroxyl or $C_1$-$C_4$-alkoxy group; $R^6$ represents a hydrogen atom, or a cyano, nitro, hydroxyl, $C_1$-$C_4$-alkyl or $C_1$-$C_4$-alkoxy group; $R^7$, $R^8$ and $R^9$ each independently represent a hydrogen atom or a $C_1$-$C_4$-alkyl group; $R^{10}$ and $R^{11}$ each independently represent a hydrogen atom or a $C_1$-$C_4$-alkyl group, or $R^{10}$ and $R^{11}$ together with the nitrogen atom to which they are attached form a 5- or 6-membered saturated heterocyclic ring comprising one or two ring nitrogen atoms; $R^{12}$ represents a hydrogen atom, or a $C_1$-$C_4$-alkyl group optionally substituted by amino; $R^{13}$ represents a hydrogen atom, or a $C_1$-$C_4$-alkyl group optionally substituted by hydroxyl; $R^{14}$ and $R^{15}$ each independently represent a hydrogen atom or a $C_1$-$C_4$-alkyl group optionally substituted by hydroxyl, or $R^{14}$ and $R^{15}$ together with the nitrogen atom to which they are attached form a 5- or 6-membered saturated heterocyclic ring comprising one or two ring nitrogen atoms; and $R^{16}$ represents a 1-($C_1$-$C_4$-alkyl)-piperidinyl group; with the proviso that when m is 0, X is N and Y is O, then $R^4$ does not represent 2-benzothiazolyl; or a pharmaceutically acceptable salt or solvate thereof.

A compound of general formula:

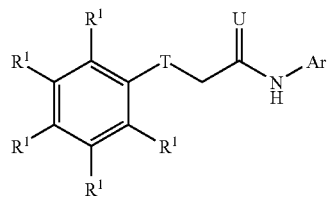

wherein: each $R^1$ independently represents a hydrogen or halogen atom, or a trifluoromethyl, cyano, nitro, $C_1$-$C_6$-alkyl or $C_1$-$C_6$-alkoxy group; T represents an oxygen atom or a group NH; U represents an oxygen or sulphur atom or a group NH; Ar represents a group:

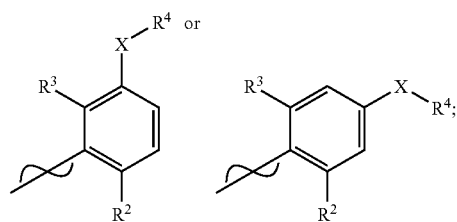

X represents a bond, an oxygen atom or a group CO, $CH_2$, $CH_2O$, $O(CH_2)_m$, $CH_2OCH_2$, $NR^5$, $CH_2NR^5$, $NR^5CH_2$, $CH_2NR^5CH_2$, $CONR^5$, $S(O)_n$ or $SO_2NR^5$, m is 1, 2 or 3; n is 0, 1 or 2; one of $R^2$ and $R^3$ represents a halogen, cyano, nitro, amino, hydroxyl, or a group selected from $C_1$-$C_6$-alkyl optionally substituted by at least one $C_3$-$C_6$-cycloalkyl, $C_3$-$C_8$-cycloalkyl, $C_1$-$C_6$-alkyloxy optionally substituted by at least one $C_3$-$C_6$-cycloalkyl, $C_3$-$C_8$-cycloalkyloxy, $S(O)_p$ $C_1$-$C_6$-alkyl or $S(O)_q C_3$-$C_8$-cycloalkyl, each of these groups being optionally substituted by one or more fluorine atoms, and the other of $R^2$ and $R^3$ represents a hydrogen or halogen atom or a methyl group; p is 0, 1 or 2; q is 0, 1 or 2; R4 represents di($C_{1-2}$alkyl)N(CH2)$_t$ where t is 0, 1 or 2 or imidazolyl, or $R^4$ represents a 3- to 9-membered saturated heterocyclic ring system containing one or two nitrogen atoms, the heterocyclic ring system being optionally substituted by one or more substituents independently selected from fluorine atoms, hydroxyl, $C_1$-$C_6$-alkyl, acetyl, hydroxy$C_1$-$C_6$-alkyl, —$NR^6R^7$, —$(CH2)_rNR^6R^7$, $CONR^6R^7$ and pyrimidinyl, or $R^4$ represents a 3- to 8-membered saturated carbocyclic ring system substituted by one or more substituents independently selected from —$NR^6R^7$, —$(CH_2)_r$ $NR^6R^7$, —$CONR^6R^7$ the ring system being optionally further substituted by one or more substituents independently selected from fluorine atoms, hydroxyl and $C_1$-$C_6$-alkyl; r is 1, 2, 3, 4, 5 or 6; $R^5$ represents a hydrogen atom or a $C_1$-$C_6$-alkyl or $C_3$-$C_8$-cycloalkyl group; and $R^6$ and $R^7$ each independently represent a hydrogen atom or a $C_1$-$C_6$-alkyl or $C_3$-$C_8$-cycloalkyl group, or $R^6$ and $R^7$ together with the nitrogen atom to which they are attached form a 3- to 8-membered saturated heterocyclic ring, provided that when $R^3$ represents a cyano group, then X is other than a bond; or a pharmaceutically acceptable salt or solvate thereof.

A compound of general formula:

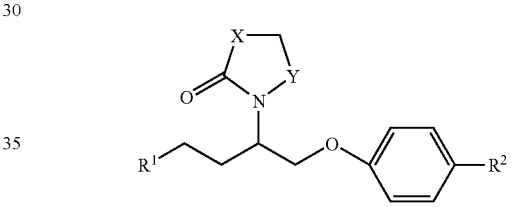

wherein X represents an oxygen or sulphur atom or a group NH, $CH_2$, $CH_2CH_2$ or $OCH_2$; Y represents a group $CH_2$ or C=O; $R^1$ represents a pyridyl or pyrimidinyl group; $R^2$ represents a phenyl, pyridyl or pyrimidinyl group, each of which may be optionally substituted by one or more substituents independently selected from a halogen atom or an amino, cyano, hydroxyl, nitro, $C_1$-$C_6$-alkyl, halo-$C_1$-$C_6$-alkyl, $C_1$-$C_6$-alkoxy, $C_1$-$C_6$-alkylthio, (di)$C_1$-$C_6$-alkylamino, $C_1$-$C_6$-alkylcarbonyl, $C_1$-$C_6$-alkoxycarbonyl, $C_1$-$C_6$-alkylsulphinyl, $C_1$-$C_6$-alkylsulphonyl, —$NR^3SO_2R^4$ or —$SO_2NR^5R^6$ group, or a group -Z-$(CH_2)_p$-Z-$(CH_2)_q$—H wherein each Z independently represents a nitrogen or oxygen atom, p is an integer from 2 to 5 and q is 0 or an integer from 1 to 5; $R^3$ and $R^4$ each independently represent a hydrogen atom or a $C_1$-$C_6$-alkyl group; and $R^5$ and $R^6$ each independently represent a hydrogen atom or a $C_1$-$C_6$-alkyl group, or together with the nitrogen atom to which they are attached form a pyrrolidinyl or piperidinyl group; or a pharmaceutically acceptable salt or solvate thereof.

An additional embodiment of the invention provides a method for treating affective disorders by administrating an agent modulating the activity of P2X7R, such as an antagonist of the P2X7R. The term "antagonist" means an agent or drug or a compound that opposes the physiological effects of another. Examples of P2X7R antagonists include, but are not restricted to, adamantane derivatives, isoquinolines and their derivatives, substituted phenyl compounds, piperidine derivatives, piperazine derivatives. P2X7R antagonists are described in the art and include the compounds found in Chen et al., Bioconjugate Chem. 13 (2002), 1100-1111; WO 99/29660; WO 99/29661; WO 99/296896; WO 00/61569; WO 01/42194; WO 01/44170; WO 01/44213; WO 00/71529; WO 01/46200. P2X7R activity can also be modulated by RNA-based interference mechanisms and methods such as, but not limited to, small interference RNA (siRNA) molecules, and long double-stranded RNA (dsRNA).

Since it was unexpectedly found that agonists of P2X7R improve the symptoms of mice selected for anxiety and depressive behaviour, the present invention relates in a further embodiment to a method for treating affective disorders such as anxiety and depressive behaviour by administrating an agent modulating the activity of P2X7R such as an agonist of the P2X7R. What is even more striking is the finding of the present application shown in Example 10 that antagonists of P2X7R have no antidepressive effects although this is being taught by the prior art, for example, WO 03/042190, WO 03/042191, WO 03/049353 or US 2004/0029841. WO 03/042190, WO 03/042191, WO 03/059353 or US 2004/0029841 describe compositions of P2X7R antagonists and methods of treating P2X7 mediated diseases by administering these compounds. However, while the prior art may make a link between P2X7R and, e.g., treating depression, it is generally implied that antagonists of P2X7R have to be used in the treatment of, e.g., depression. Thus, the finding of the present invention that antagonists have no antidepressive effects, but rather agonists of P2X7R have an antidepressive effect could not have been expected and is, thus, even more surprising. The present application, therefore, provides, inter alia, the basis for the development of effective medicaments having therapeutic benefits against, e.g., depression. In particular, said medicaments comprising an agonist of P2X7R are effective in treating affective disorders, in particular for treating those disorders mentioned herein, and in particular for treating depression. Examples of P2X7R agonists include but are not restricted to ATP, ATP-4, and BzATP (2'-3'-O-(4-Benzoylbenzoyl)adenosine 5'-triphosphate $(C_{24}H_{24}N_5O_{15}P_3)$). Preferably, the P2X7R agonist to be used for treating affective disorders is BzATP. More preferably, BzATP is used to treat depression or anxiety as demonstrated in Example 9 hereinbelow.

The present application provides another unexpected finding in that the chemical compound called tenidap or a derivative thereof also functions as a modulator of P2X7R which can thus be used for treating affective disorders. So far, various medical applications are described for tenidap or a derivative thereof. However, the use of tenidap or a derivative thereof for treating affective disorders is neither known nor suggested in the prior art. Accordingly, the present application relates to the use of tenidap or a derivative thereof or 3-substituted-2-oxindole-1-carboxamides for the preparation of a pharmaceutical composition for treating an affective disorder. Of course, also a method of treatment of an affective disorder comprising administering a therapeutically effective amount of tenidap or a derivative thereof or 3-substituted-2-oxindole-1-carboxamides to a subject suffering from said disorder is envisaged.

The composition of tenidap (5-chloro-2,3-dihydro-2-oxo-3-(2-thienylcarbonyl)-indole-1-carboxamide, i.e. $C_{15}H_{11}ClN_2O_2S$)) having the following structural formula

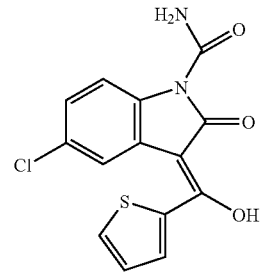

and other 3-substituted-2-oxindole-1-carboxamides and their use as anti-inflammatory and analgesic agents, and as inhibitors of both the cyclooxygenase (Cox) and lipoxygenase (5-LPO) enzymes was first disclosed in U.S. Pat. No. 4,556,672. Of course, various modifications of, e.g., side groups or atoms which are well known in the art can be made to the composition of tenidap.

Derivatives of tenidap or 3-substituted-2-oxindole derivatives are described, for example, in U.S. Pat. Nos. 4,556,672; 4,658,037; 4,721,712; 5,290,802; 5,118,703; 5,270,331; 5,298,522; 5,086,186, 5,449,788 and 5,795,902. Various processes for the synthesis of tenidap and other 3-substituted-2-oxindole-1-carboxamides are well known in the art, see for example U.S. Pat. Nos. 4,652,658; 4,665,194; 4,952,703; EP-B1 155 828, WO 90/04393, WO 94/07488, WO 94/17061, WO 95/20574; WO 97/36895; van Deurzen et al., J. Mol. Catal. B-Enzym., 2 (1996), 33-42; Porcs-Makkay and Simig, Org. Process. Res. Dev., 4 (2000), 10-16; Kumar et al., Org. Process. Res. Dev., 5 (2001), 61-64. The anhydrous crystalline form of the sodium salt of tenidap is described in U.S. Pat. No. 5,036,099 and WO 88/05656. Injectable composition and pharmaceutical composition for rectal administration of tenidap are mentioned in EP-B1 508 311 and EP-B1 508 310, respectively. It is also described in the prior art that tenidap or a derivative thereof can be administered in combination with tetracycline (U.S. Pat. No. 5,308,839) or methotrexate (WO 96/35419) for the treatment of rheumatoid arthritis. Inhibition of the photodecomposition of tenidap and other 3-substituted-2-oxindole-1-carboxamides is disclosed in WO 96/33701.

Further applications of tenidap or a derivative thereof and other 3-substituted-2-oxindole-1-carboxamides have been described for the inhibition of interleukin-1 biosynthesis in mammals and for the treatment interleukin-1 mediated disorders (U.S. Pat. No. 4,861,794); for the inhibition of elastase release from neutrophils (U.S. Pat. No. 5,006,547); for the suppression of T-cell function in mammals and to treat T-cell mediated autoimmune disorders of the systemic or organ specific type (U.S. Pat. No. 4,853,409; Dolhain et al., Scand. J. Immunol. 42 (1995), 686-693). Tenidap is also used for the treatment of Alzheimer's disease (WO 96/31209; U.S. Pat. No. 5,545,656).

Tenidap or a derivative thereof or its pharmaceutically base salts have also been shown to inhibit activation of collagenase, treat collagenase mediated disorders and diseases, and inhibit the activity of myeloperoxidase in mammals (U.S. Pat. No. 5,008,283). Tenidap can reduce total serum cholesterol, LDL cholesterol and triglycerides (U.S. Pat. No. 5,122,534), and can be used for the treatment of ischemia induced myocardial injury and cytokine mediated myocardial injury (EP-B1 679 396). However, none of the aforementioned documents discloses a use of tenidap or derivatives thereof or 3-substituted-2-oxindole-1-carboxamides thereof for treating, for example, affective disorders such as depression.

Sanz et al., Eur. J. Pharmacol. 355 (1998), 235-244 suggest that tenidap can enhance the activity of the P2X7 receptor. It is suggested that tenidap may act by increasing ATP levels or improving the effect of ATP on P2X7. ATP is the natural ligand of P2X7R. Accordingly, tenidap or a derivative thereof is a modulator of P2X7R as is described herein since a modulator is defined as either directly or indirectly modulating the activity or expression of P2X7R. By making use of the teaching of the present invention that modulators of P2X7R are useful for treating affective disorders, it is envisaged that tenidap or a derivative thereof is used as a modulator of P2X7R activity for the preparation of a pharmaceutical composition for the treatment of an affective disorder, examples of which are described herein. The preparation of pharmaceutical compositions, the modes of administration etc. are described supra and infra and apply to the use of tenidap or a derivative thereof for the preparation of a pharmaceutical composition, mutatis mutandis. Moreover, also the embodiments relating to the uses of and methods for treating affective disorders described herein apply to the use of tenidap or a derivative thereof for treating affective disorders or the corresponding method of treatment, mutatis mutandis.

The present application moreover envisages that modulators of P2X7R activity can be used in any combinations thereof for treating an affective disorder. For example, BzATP and tenidap or a derivative thereof or 3-substituted-2-oxindole-1-carboxamides may be used together, e.g., simultaneously or by successive administration for treating an affective disorder.

In a preferred embodiment the pharmaceutical composition described herein optionally comprises further molecules which have cell protective properties capable of altering the characteristics of the components of the invention thereby, for example, modulating, preferably blocking possible undesired, adverse or negative side effects of these components. One such possible undesired, adverse or negative side effect is the formation of pores in the cell membrane of treated cells which ultimately leads to apoptosis. Accordingly, said further molecules belong to the class of beta-adrenergic receptor modulators including agonists or antagonists having membrane-stabilizing properties. Beta-adrenergic receptor modulators including agonists and antagonists are compounds which decrease or increase the positive chronotropic, positive inotropic, bronchodilator and vasodilator responses caused by beta-adrenergic receptor agonists or antagonists. The magnitude of this decreased or increased response is proportional to the existing sympathetic tone and the concentration of beta-adrenergic receptor blocking agent which reaches the receptor sites. A beta-adrenergic receptor modulator in the context of the present invention is thus an antagonist or agonist. The activity of a beta-adrenergic receptor antagonist or agonist can be determined as is well known in the art. The activity of beta-adrenergic receptors can be determined by measuring the accumulation of cyclic adenosine mono-phosphate (cAMP) in Chinese hamster ovary (CHO) cells. CHO cells can be uniquely transfected with the cDNA coding for the human beta1-, beta2-, or beta3-adrenergic receptor under the control of the CMV promoter or any other suitable promoter element. Transfection of the cells is performed using standard cell transfection methods, see for example, Joyner, "Gene Targeting: A Practical Approach", Oxford University Press, New York, 1993. Cells overexpressing one of the beta-adrenergic gene are then grown to confluence in Ham's F12 media (Gibco BRL) containing 10% fetal bovine serum, 500 mg/ml Geneticin, 100 U/ml penicillin, 100 mg/ml streptomycin and 250 ng/ml fungizone according to the procedure described in American Type Culture Collection Catalogue of Cell Lines and Hybridomas, Seventh Edition, 1992, p. 36, ATCC CCL 61 CHO-K1. Beta-adrenergic modulator compounds can be prepared as 10 mM stock solutions in DMSO (0.1% DMSO, final concentration), diluted in Ham's F12 media and added to the cells at $10^{-10}$ to $10^{-5}$ M along with $10^{-3}$ M isobutylmethylxanthine to inhibit phosphodiesterase activity. The media and cells are then incubated for 5 minutes at 37° C. At the end of this period, the media is aspirated and the cells lysed in 0.01N HCl. The cellular content of cAMP can then be determined by radioimmunoassay (RIA) using a kit from New England Nuclear (Burlington, Mass.). There is a direct correlation between the cellular content of cAMP and the activation/inhibition of the beta-adrenergic receptor. Other methods for determining the activity of a beta-adrenergic receptors are well described in the art, see for example, Vansal and Feller, J. Recept. Signal. Transduct. Res. 19 (1999) 853-863; Durocher et al., Anal. Biochem. 284 (2000) 316-326.

Examples of compounds which fit the definition of a beta-adrenergic receptor modulating agent include but are not limited to known beta-adrenergic receptor antagonist such as timolol, sotalol, esmolol, cateolol, propranolol, betaxolol, penbutolol, metoprolol, acebutolol, atenolol, metoprolol, pindolol, and bisoprolol, and their salts, hydrates, solvates and any crystal forms in which they may occur. Further examples of beta-adrenergic receptor blocking agents are described in U.S. Pat. No. 5,776,930. Preferred examples of beta-adrenergic receptor antagonists are DL-propanolol, D-propanolol and labetolol. DL-propanolol and labetolol are beta-adrenergic receptor antagonists with membrane-stabilizing properties, while D-propanolol is an optical isomer with poor beta-adrenergic blocking activity. The optional addition of beta-adrenergic receptor antagonists or agonists to the pharmaceutical composition of the present invention for treating an affective disorder may be useful in the context of administering P2X7R agonists. This is because the prior art suggests that the activation of P2X7R by agonists may result in cell death by triggering the formation of pores within the cell membrane. However, as is demonstrated in Example 9 of the present application the pore-forming activity effect described for P2X7R agonists by the prior art was only observed for very few cells. Recently, Alzola et al., Cell Signal. 13 (2001), 465-473 have shown that concentrations of 10 to 300 μM DL-propanolol, D-propanolol or labetolol can inhibit the pore-forming activity of P2X7R without affecting the opening of the cation channel activity of P2X7R. From FR 2768626 it is also known that beta-adrenergic modulators, e.g. agonists are useful as apoptosis inhibiting agents. Accordingly, in a preferred embodiment of the present invention, beta-adrenergic receptor modulators including antagonists or agonists are administered in combination with P2X7R agonists for the treatment of affective disorders. Said beta-adrenergic receptor antagonists or agonists are preferably administered in a concentration of 10 to 300 μM.

Dosage, pharmaceutical preparation and delivery of P2X7R modulating agent for use in accordance with the present invention may be formulated in conventional manner according to methods found in the art, using one or more physiological carriers or excipient, see, for example Ansel et al., "Pharmaceutical Dosage Forms and Drug Delivery Systems", 7th edition, Lippincott Williams & Wilkins Publishers, 1999. Thus, the P2X7R modulating agent and its physiologically acceptable salts and solvates may be formulated for administration by inhalation, insufflation (either through the mouth, or nose), oral, buccal, parenteral, or rectal administration.

For oral administration, the pharmaceutical composition of the P2X7 modulating agent may take the form of, for example, tablets or capsules prepared by conventional means with pharmaceutical acceptable excipients such as binding agents (e.g., pregelatinised maize starch, polyvinylpyrrolidone, hydroxypropyl methylcellulose), fillers (e.g., lactose, microcrystalline cellulose, calcium hydrogen phosphate), lubricants (e.g., magnesium stearate, talc, silica), disintegrants (e.g., potato starch, sodium starch glycolate), or wetting agents (e.g., sodium lauryl sulphate). Liquid preparations for oral administration may take the form of, for example, solutions, syrups, or suspensions, or may be presented as a dry product for constitution with water or other suitable vehicle before use. Such liquid preparation may be prepared by conventional means with pharmaceutically acceptable additives such as suspending agents (e.g., sorbitol, syrup, cellulose derivatives, hydrogenated edible fats), emulsifying agents (e.g., lecithin, acacia), non-aqueous vehicles (e.g., almond oil, oily esters, ethyl alcohol, fractionated vegetable oils), preservatives (e.g., methyl or propyl-p-hydroxycarbonates, soric acids). The preparations may also contain buffer salts, flavouring, coloring and sweetening agents as deemed appropriate. Preparations for oral administration may be suitably formulated to give controlled release of the agent modulating P2X7R activity.

For administration by inhalation, the agent modulating P2X7R activity for use according to the present invention is conveniently delivered in the form of an aerosol spray presentation from a pressurised pack or a nebulizer, with the use of a suitable propellant (e.g., dichlorodifluoromethane, trichlorofluoromethane, dichlorotetrafluoroethane, carbon dioxide or other suitable gas). In the case of a pressurised aerosol, the dosage unit may be determined by providing a valve to deliver a metered amount. Capsules and cartridges of, for example, gelatine, for use in an inhaler or insufflator may be formulated containing a powder mix of the P2X7R activity modulating agent and a suitable powder base such as lactose or starch.

An agent modulating P2X7R activity may be formulated for parenteral administration by injection, for example, by bolus injection or continuous infusion. Site of injections include intra-venous, intra-peritoneal or sub-cutaneous. Formulations for injection may be presented in units dosage form (e.g., in phial, in multi-dose container), and with an added preservative. The agent modulating P2X7R activity may take such forms as suspensions, solutions or emulsions in oily or aqueous vehicles, and may contain formulatory agents such as suspending, stabilizing, or dispersing agents. Alternatively, the agent may be in powder form for constitution with a suitable vehicle (e.g., sterile pyrogen-free water) before use.

An agent modulating P2X7R activity may, if desired, be presented in a pack, or dispenser device which may contain one or more unit dosage forms containing the said agent. The pack may for example comprise metal or plastic foil, such as blister pack. The pack or dispenser device may be accompanied with instruction for administration.

In a more preferred embodiment the aforementioned methods or uses are envisaged to treat affective disorders selected from the group consisting of major depression, generalized anxiety disorder and bipolar disorder.

In a particularly preferred embodiment said major depression is selected from the group consisting of major depression, dysthymia, atypical depression, premenstrual dysphoric disorder and seasonal affective disorder.

In another particularly preferred embodiment said generalized anxiety disorder is selected from the group consisting of panic disorder, phobias, agoraphobia, social phobia, specific phobia, obsessive-compulsive disorder, post-traumatic stress disorder, separation anxiety disorder, mania, hypomania and cyclothymic disorder.

A still also particularly preferred embodiment is that said bipolar disorder is bipolar disorder type I or bipolar disorder type II.

Additionally, the present invention relates to a kit comprising the nucleic acid molecule, the vector, the host, the polypeptide, the antibody or the aptamer, the primer or pair of primers of the invention or the molecule as identified or characterized in a method herein below of the present invention.

Advantageously, the kit of the present invention further comprises, optionally (a) reaction buffer(s), storage solutions and/or remaining reagents or materials required for the conduct of scientific or diagnostic assays or the like. Furthermore, parts of the kit of the invention can be packaged individually in vials or bottles or in combination in containers or multicontainer units.

The kit of the present invention may be advantageously used, inter alia, for carrying out the method of producing a polypeptide of the invention, the method(s) of identification and/or characterization of molecules specifically interacting with P2X7R ATP-gated ion channels as described herein below and/or it could be employed in a variety of applications referred herein, e.g., as diagnostic kits, as research tools or therapeutic tools. Additionally, the kit of the invention may contain means for detection suitable for scientific, medical and/or diagnostic purposes. The manufacture of the kits follows preferably standard procedures which are known to the person skilled in the art.

Furthermore, the present invention relates to a method for identifying compounds or mixtures of compounds which are capable of specifically interacting with a polypeptide of the present invention, comprising the steps of (a) contacting a polypeptide of the present invention with a candidate compound or mixture of compounds to be tested; and (b) determining whether said is capable of specifically interacting with said polypeptide. The polypeptide may be provided directly or by expression of a corresponding nucleic acid molecule or vector of the invention, e.g., in vitro or in a suitable host cell.

Additionally, the present invention relates to a method for the characterization of compounds which are capable of altering characteristics of the polypeptides of the present invention, comprising the steps of (a) contacting a polypeptide of the invention with said compound; and (b) determining whether the compound alters a characteristic of said polypeptide.

The term "altering characteristic of the polypeptide of the present invention" means that the functional characteristics to the polypeptides of the present invention in comparison to functional characteristics which they had before being contacted with the compounds identified by the above-described method: as described hereinabove are altered; i.e. changed.

Said identification and/or characterization of which are capable of interacting with or altering characteristics of the polypeptide of this invention, may be, inter alia, achieved by transfecting an appropriate host with a nucleic acid molecule of invention. Said hosts comprise, but are not limited to, HEK 293 cells or are injected into frog oocytes, preferably a *Xenopus* oocyte for functional expression (Goldin, Methods Enzymol. 207 (1992), 266). Expressed P2X7R ATP-gated channels can be examined using standard two-electrode voltage clamp techniques (Stuhmer, Methods Enzymol. 207 (1992), 319; Kohler, Science 273 (1996), 1709). After expression of a P2X7R ATP-gated ion channel as defined herein, membrane currents may be deduced in the absence and/or presence of the molecule to be identified and/or characterized. Methods for the deduction of membrane currents are well known in the art and comprise, e.g., patch clamp methods as described in Hamill, Pfluger's Arch. 391 (1981), 85-100 or two-electrode voltage clamp in oocytes, as described in Methfessel, Pflügers Archive 407 (1986), 577-588. In accordance with the present invention the term "interacting with the polypeptides of the present invention" means that the polypeptides of the present invention interact directly and/or indirectly with compounds identified by the method described above.

Furthermore, the present invention relates to a method of screening for molecules which are capable of interacting with the polypeptide of this invention, comprising the steps of (a) contacting a polypeptide of the invention with a molecule; and (b) measuring and/or detecting a response; and (c) comparing said response to a standard response as measured in the absence of said candidate molecule.

The present invention also relates to a method for identifying a compound which is capable of enhancing or reducing the expression of the P2X7R gene comprising the steps of contacting a cell which expresses the P2X7R gene from its natural promoter or a reporter gene driven by the P2X7R promoter and determining whether the expression of the gene is increased or reduced when compared to conditions in which the compound is not present.

Potential candidate molecules or candidate mixtures of molecules may be, inter alia, substances, compounds or compositions which are of chemical or biological origin, which are naturally occurring and/or which are synthetically, recombinantly and/or chemically produced or compounds or compositions described hereinabove. Thus, candidate molecules may be proteins, protein-fragments, peptides, amino acids and/or derivatives thereof or other compounds, such as ions, which bind to and/or interact with wild-type P2X7R ATP-gated ion channels. Such binding and/or interacting candidate compounds may be found employing, inter alia, yeast two-hybrid systems or modified yeast two-hybrid systems as described, for example in Fields, Nature 340 (1989), 245-246; Gyuris, Cell 75 (1993), 791-801; or Zervos, Cell 72 (1993), 223-232.

Furthermore, potential candidate molecules may be contacted with a cell, such as an oocyte or a HEK 293 cell, which expresses a polypeptide of the invention or with a membrane patch comprising a polypeptide of the invention and a corresponding response (inter alia, a dose-response response, a current-response, or single current channel response) may be measured in order to elucidate any effect said candidate molecule causes.

Within the scope of the present invention are also methods for identifying, characterizing and for screening of molecules which are capable of interacting with the P2X7R ATP-gated ion channels according to the invention which comprise so-called high-throughput screening methods and similar approaches which are known in the art (Spencer, Biotechnol. Bioeng. 61 (1998), 61-67; Oldenburg, Annu. Rev. Med. Chem. 33 (1998), 301-311) carried out using 96-well, 384-well, 1536-well (and other) commercially available plates. Further methods to be employed in accordance with the present invention comprise, but are not limited to, homogenous fluorescence readouts in high-throughput screenings (as described, inter alia, in Pope, Drug Discovery Today 4 (1999), 350-362). The method of the present invention for identification, characterization and/or screening of molecules capable of interacting with P2X7R ATP-gated ion channels can, inter alia, employ hosts as defined herein which express the polypeptide of the present invention. Cell-based assays, instrumentation for said assays and/or measurements are well-known in the art and described, inter alia, in Gonzalez, Drug Discovery Today 4 (1999), 431-439 or Ramm, Drug Discovery Today 4 (1999), 401-410. It is also envisaged that the high through put screens described herein are conducted by using, for example cRNA, i.e. synthetic RNA from a cDNA construct) that can be introduced in host cells, such as Xenopus oocytes using routine methods in the art. As an example, direct nucleic acid injection can be employed, such as the Eppendorf microinjection system (Micromanipulator 5171 and Transjector 5242). The injected/transformed cells can be analyzed for ion currents about 4 hours later using patch-clamp techniques which are commonly practiced in the art.

Additionally, the present invention relates to a method for the production of a pharmaceutical composition comprising the steps of a method of the invention for identifying, characterizing and/or screening of molecules which are capable of interacting with and/or altering the characteristics of a P2X7R ATP-gated ion channel of the invention and further comprising a step, wherein a derivative of said identified, characterized and/or screened molecule is generated. Such a derivative may be generated by, inter alia, peptidomimetics.

The invention furthermore relates to a method for the production of a pharmaceutical composition comprising the steps of a method of the invention for identifying, characterizing, screening and/or derivatizing of molecules which are capable of interacting with and/or altering the characteristics of a P2X7R ATP-gated ion channel and formulating the molecules identified, characterized, screened and/or derivatized in pharmaceutically acceptable form.

In a more preferred embodiment the present invention relates to a method wherein said molecule(s) comprise(s) (a) neuroprotective, (a) nootropic and/or (a) antiepileptic molecule(s).

Yet another embodiment of the invention is the use of a P2X7R polypeptide, in particular those according to the present invention, to identify biological, chemical, or pharmacological agents that can have an antidepressive effect. The term 'agent' refers to a chemical compound or composition capable of inducing a desired therapeutic or prophylactic effect when properly administered to a subject or cell. For example, the present invention allows the generation of cells expressing P2X7R for the identification and characterization of agents which modulate ionic influx and efflux. For example, HEK293 cells, or other cell lines (e.g., HCN-1A, HCN-2, HIT-T15, RIN-m5F, betaTC3, PC12, HT22, SH-SY5Y, Neuro2A or CA77), can be stably transfected with cDNA encoding the human P2X7R and plated in 12, 96 and 384 well plates. Said cells are cultured in appropriate medium. Examples of such medium are well known in the art, see, for example Freshney, "Culture of Animal Cells: A Manual of Basic Technique, 4th edition, Wiley-Liss Publishing, 2000.

Said cells can then be pre-incubated with said agents for 15 min prior to stimulation with 3 mM ATP for 10 minutes. Reactions are then terminated by rapid aspiration of the extracellular medium in each well. The cells in each well are subsequently extracted overnight with 1 ml 10% $HNO_3$. Potassium ($K^+$) content in the extracts can be determined by atomic absorbance spectrophotometry. Agent function is then measured by the percent inhibition or stimulation of the $K^+$ release triggered by 3 mM ATP and compared to $K^+$ release in the absence of the agents. P2X7R activity can also be monitored according to the movement of calcium (Ca2+; see Denyer et al., Drug Discov. Today 7 (1998), 323-332; González et al., Drug Discov. Today 9 (1999), 431-439; Helmchen and Waters, Eur. J. Pharmacol. 447 (2002), 119-129). Agents can also be verified in the absence of ATP.

P2X7R activity can also be monitored according to secretion of neurotransmitters such as glutamate and GABA. Neurotransmitter levels in treated cells can be quantified by suitable methods, e.g., Enzyme Linked Immunoabsorbent Assay (ELISA), Radio Immuno Assay (RIA), High Performance Liquid Chromatography (HPLC). Using these methods, a large number of compounds can be screened for increase in neurotransmitter (for example, glutamate) secretion. The release of glutamate can be measured for example by Fluorometric glutamate release assays (e.g., Amplex Red Glutamic Acid/Glutamate Oxidase Assay Kit, Molecular Probes) or High-Throughput ElectroPhysiology.

In a further aspect the present invention uses the P2X7R polypeptides disclosed herein or polypeptides of the present invention in a method for identifying compounds or agents having agonist activity to said P2X7R polypeptides or to the polypeptides of the present invention. Agents and compounds are defined and described hereinabove and hereinbelow. In particular, cells that express the P2X7 gene are contacted with candidate agents, molecules or compounds as described hereinabove and either calcium influx or ethidium bromide entry is measured by methods known in the art, described hereinabove and in particular described in Example 8 hereinbelow. The cells used in the method for identifying agonists to P2X7R are preferably cells of a hippocampal cell line. Hippocampal cell lines are prepared by methods known in the art, for example, described in EP 0 773 287 or EP 0 773 292. Non limiting examples of hippocampal cell lines are rat H19-7 hippocampal cells (ATCC-2526) described in Eves et al. Proc. Natl. Acad. Sci. USA 89 (1992), 4373-4377, mouse HN9.10 hippocampal cells described in Lee et al. J. Neurosci. 10 (1992), 1779-1787 or rat Hi5B hippocampal cells described in Renfranz et al., Cell 66 (1991), 713-729. Preferably, the hippocampal cells used in accordance with the aforementioned method are cells of the HT-series (see Davis and Maher (1994), Brain Res. 652, 169-173), Morimoto and Koshland (1990), Neuron 5, 875-880). It is also preferred that the hippocampal cells express the endogenous P2X7R gene. However, it is also envisaged that such cells may be genetically modified by introducing an exogenous P2X7R gene using methods commonly known in the art. More preferably, HT-22 cells are used for identifying agonists to the P2X7R polypeptides described herein or to the polypeptides of the present invention and HT-39 cells are used as a negative control as described in Example 8 hereinbelow.

In another embodiment, cells are transfected with nucleic acid constructs encoding a reporter gene regulated by the P2X7R promoter (see above), an increase or decrease in the expression of the reporter gene in response to biological or pharmaceutical agents can be analyzed using methods that detect levels or status of protein or mRNA present in the corresponding cell or detect biological activities of the reporter gene. Suitable reporter molecules or labels, which may be used, include radionucleotides, enzymes, fluorescent, chemiluminescent or chromogenic agents as well as substrates, co-factors, inhibitors, magnetic particles, and the like. Designing such drug screening assays are well known in the art; see Harvey ed., 'Advances in drug discovery techniques', John Wiley and Sons, 1998; Vogel and Vogel eds., 'Drug discovery and evaluation: Pharmaceutical assays', Springer-Verlag Berlin, 1997). For example, drug screening in animal models, in vitro tests using animal cells, or in vivo tests involving toxicology tests in animals. An in vitro model can be used for screening libraries of compounds in any of a variety of drug screening techniques.

Candidate agents encompass numerous chemical classes, though typically they are organic molecules, preferably small organic compounds having a molecular weight of more than 50 and less than about 2,500 Daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise carbocyclic or heterocyclic structures and/or aromatic or polyaromatic structures substituted with one or more of the above functional groups.

Candidate agents are also found among biomolecules including peptides, amino acids, saccharides, fatty acids, steroids, purines, pyrimidines, nucleic acids and derivatives, structural analogs or combinations thereof. Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Another technique for drug screening, which may be used, provides for high throughput screening of compounds having suitable binding affinity to the protein of interest as described in published PCT application WO 84/03564. In this method, as applied to the proteins of the invention large numbers of different small test compounds, e.g. aptamers, peptides, low-molecular weight compounds etc., are provided or synthesized on a solid substrate, such as plastic pins or some other surface. The test compounds are reacted with the proteins or fragments thereof, and washed. Bound proteins are then detected by methods well known in the art. Purified proteins can also be coated directly onto plates for use in the aforementioned drug screening techniques. Alternatively, non-neutralizing antibodies can be used to capture the peptide and immobilize it on a solid support. In another embodiment, one may use competitive drug screening assays in which neutralizing antibodies capable of binding the protein specifically compete with a test compound for binding the protein. In this manner, the antibodies can be used to detect the presence of any peptide, which shares one or more antigenic determinants with the protein.

The present invention further particularly provides a method, wherein the pharmaceutical composition to be produced further comprises neuroprotective substances, nootrophic substances, brilliant blue, piperidine or derivatives thereof, adamantine derivatives, substituted phenyl compounds, oxidized ATP, 2-O-(4-benzoylbenzoyl)adenosine-5-triphosphate or 3-O-(4-benzoylbenzoyl)adenosine-5-triphosphate. It is also envisaged that the pharmaceutical compositions to be produced further comprise antidepressants such as fluoxetine, paroxetine, sertraline, fluoroxamine, mirtazapine, reoretine, nefazodone or lithium carbonate.

In a preferred embodiment of the present invention, the compounds of the aforementioned methods comprise antagonist(s), partial antagonist(s), partial agonist(s) and/or agonist(s) for an altered ATP-gated ion channel P2X7R.

In accordance with the present invention, the term "antagonist" denotes molecules/substances, which are capable of inhibiting and/or reducing an agonistic effect. The term "antagonist" comprises competitive, non-competitive, functional and chemical antagonists as described, inter alia, in Mutschler, "Arzneimittelwirkungen" (1986), Wissenschaftliche Verlagsgesellschaft mbH, Stuttgart, Germany. The term "partial antagonist" in accordance with the present invention means a molecule/substance that is capable of incompletely blocking the action of agonists through, inter alia, a non-competitive mechanism.

In the context of the present invention, an antagonist is preferably a drug that does not provoke a response itself, but blocks agonist-mediated responses. It is a chemical entity that opposes the receptor-associated responses normally induced by another bioactive agent. For the P2X7R, the antagonists have an IC50 between 10 nanomolar and 300 micromolar.

As "agonist", in accordance with this invention, molecules/substances are denoted which have an affinity as well as an intrinsic activity. Mostly, said intrinsic activity ($\alpha$) is defined as being proportional to the quotient of the effect, triggered by said agonist (EA) and the effect which can be maximally obtained in a given biological system (Emax): therefore, the intrinsic activity can be defined as $$\alpha \sim \frac{E_A}{E_{max}}$$

The highest relative intrinsic activity results from EA/Emax=1. Agonists with an intrinsic activity of 1 are full agonists, whereas substances/molecules with an intrinsic activity of >0 and <1 are partial agonists. Partial agonists show a dualistic effect, i.e. they comprise agonistic as well as antagonistic effects.

Preferably, in the context of the present invention, an agonist (or full agonist) is an endogenous substance or a drug that can interact with a receptor and initiate a maximal or complete physiological or a pharmacological response characteristic of that receptor. ATP, the natural ligand for the P2X7R, is an agonist with an EC50 of 300 micromolar while the synthetic P2X7R agonist Bz-ATP has an EC50 of 8 micromolar. Thus, agonists of P2X7R have an EC50 equal or below 300 micromolar. The EC50 is defined as the concentration of agonist that provokes a response half way between the baseline response and maximum response on a dose response curve where the X-axis plots concentration of an agonist and the Y-axis plots ion current. An inverse agonist (also called negative antagonist) is a drug which acts at the same receptor as that of an agonist, yet produces an opposite effect. A partial agonist is an endogenous substance or a drug that also provokes physiological or a pharmacological response but, the maximum response is less than the maximum response to a full agonist, regardless of the amount of drug applied. In the case of P2X7R, partial agonists have EC50s higher than 300 micromolar.

The person skilled in the art can, therefore, easily employ the compounds and the methods of this invention in order to elucidate the agonistic and/or antagonistic effects and/or characteristics of a compound/molecule/substance to be identified and/or characterized in accordance with any of the above described methods. Preferably, an identified antagonist of the ATP-gated ion channel P2X7R comprising the mutation(s) and/or deletion(s) described hereinabove may be useful to reestablish the properties normally shown by wild-type P2X7R ATP-gated ion channels. An identified agonist of the ATP-gated ion channel P2X7R comprising the mutation(s) and/or deletion(s) described hereinabove may be useful to reestablish the lost functionality of the P2X7R ATP-gated ion channel.

The Figures show:

FIG. 1a. Genomic map of the region on the human chromosome 12 associated to bipolar affective disorder. Genes found between markers NBG11 and NBG2 are depicted.

Figure 1B:
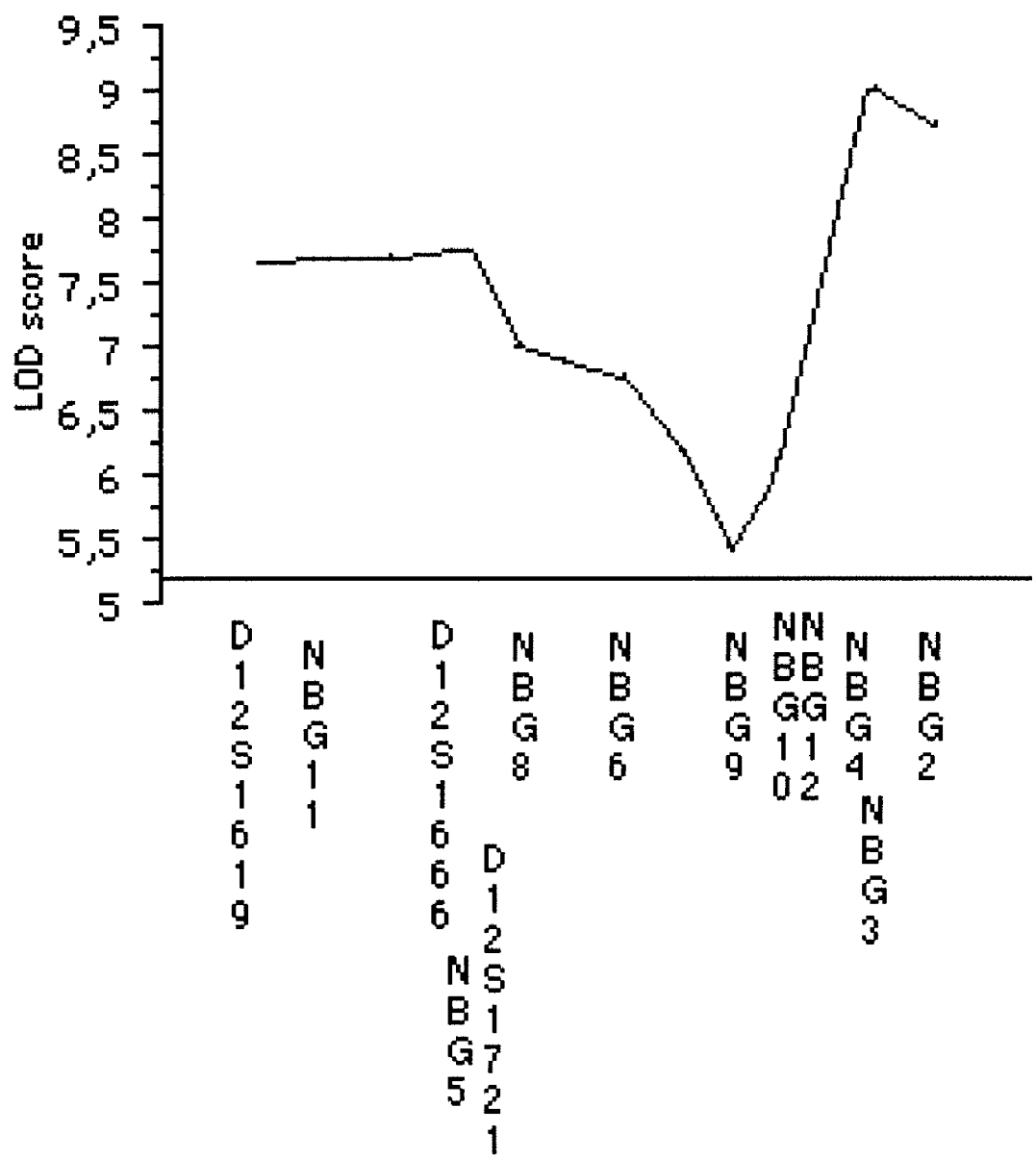

FIG. 1b. Graphic illustrating the multipoint analysis using ASPEX on independent sib-pairs.

Figure 1C:
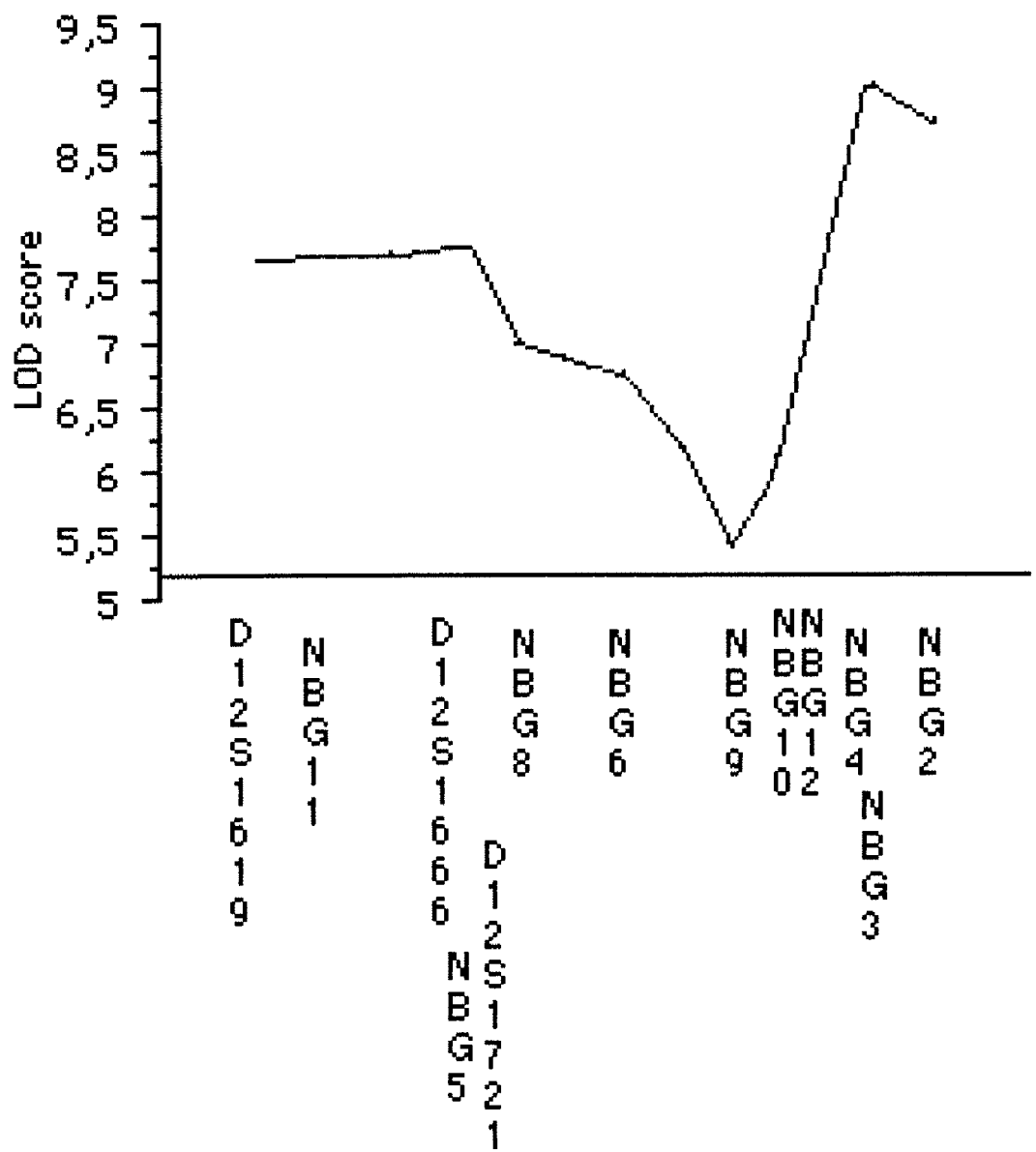

FIG. 1c. Graphic illustrating the multipoint analysis using ASPEX on all sib-pairs FIG. 1d. Graphic illustrating the ASPEX sib_phase by considering only independent sib-pairs FIG. 1e. Graphic illustrating the ASPEX sib_phase by considering all sib-pairs FIG. 1f. Effect of the P2XR7v13A polymorphism on basal cortisol levels before and after administration of dexamethasone (DST test). Individuals were subjected to the test within the first ten days of admission. Individuals with the AG and GG genotypes have significantly lower cortisol levels pre- and post-dexamethasone administration.

Figure 1D:
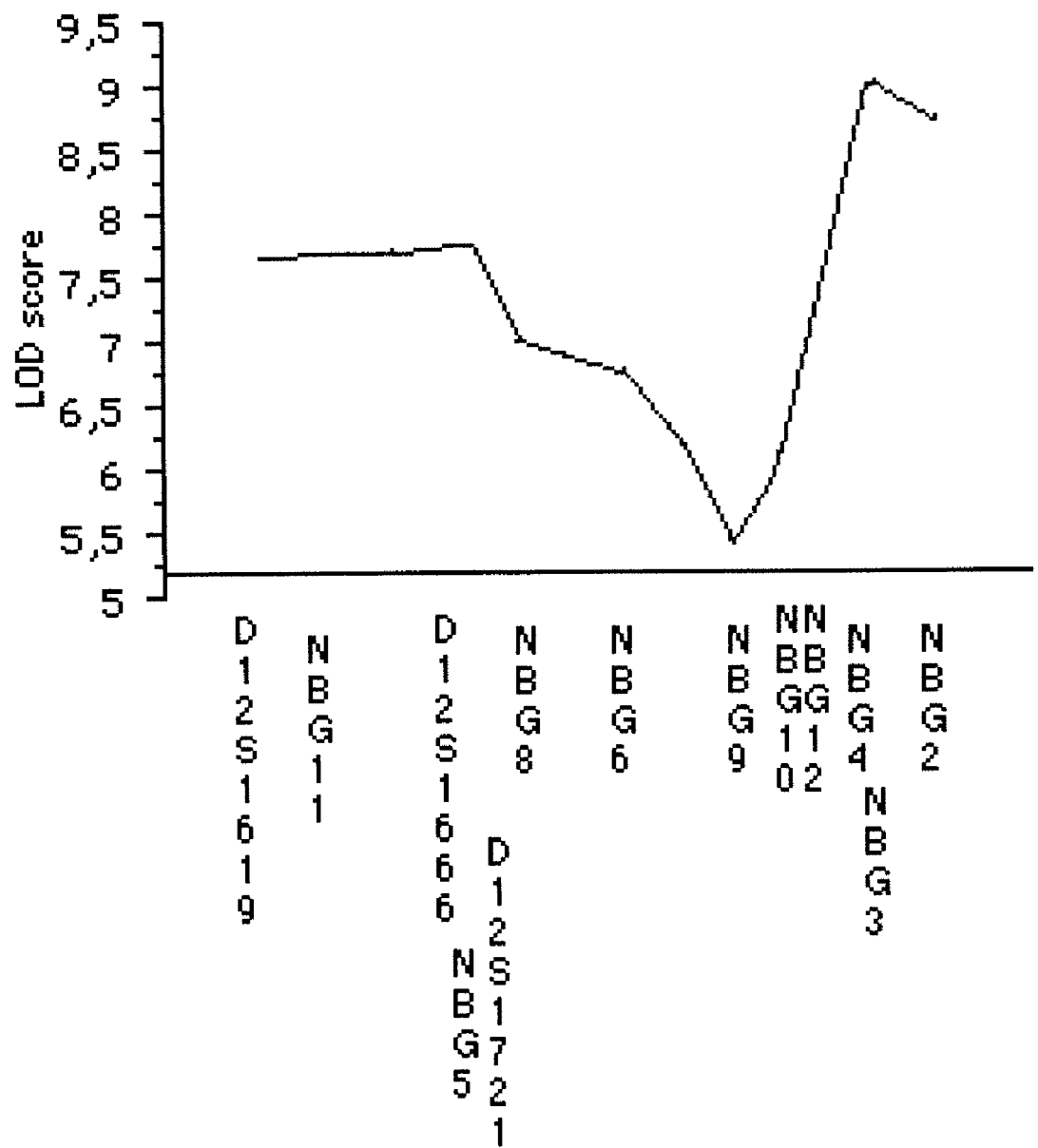
Figure 1E:
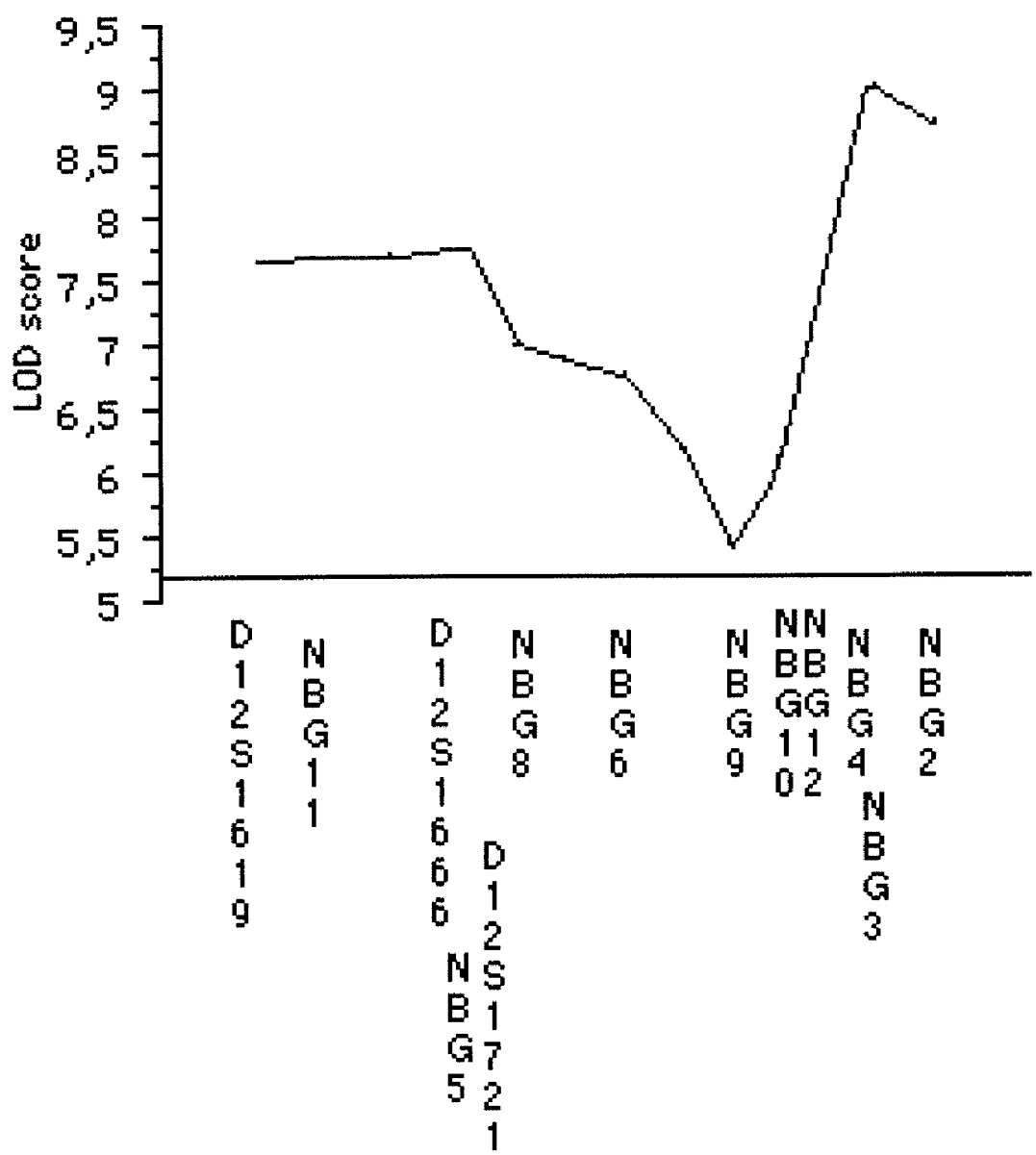
Figure 1F:
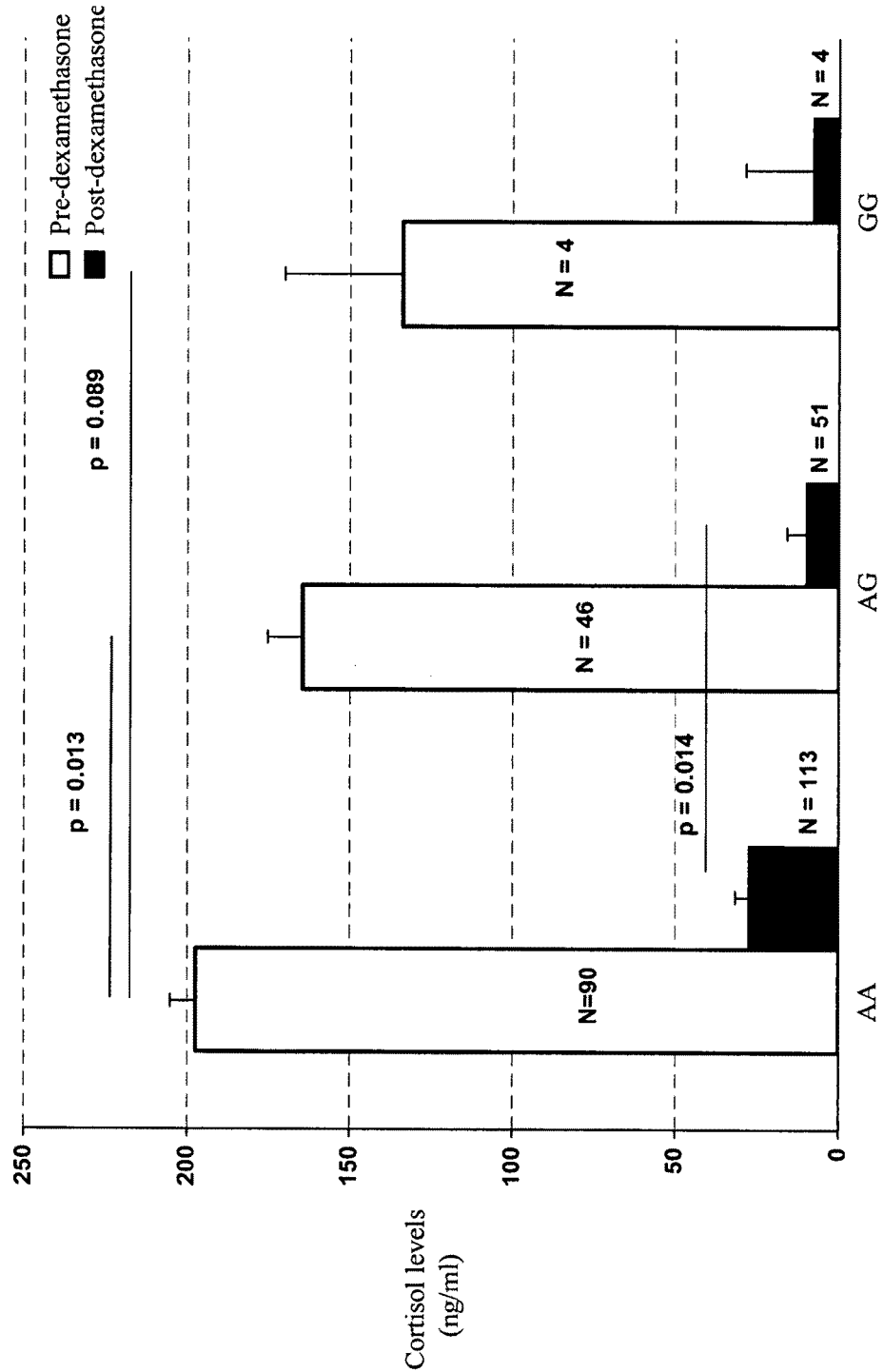
Figure 1G:
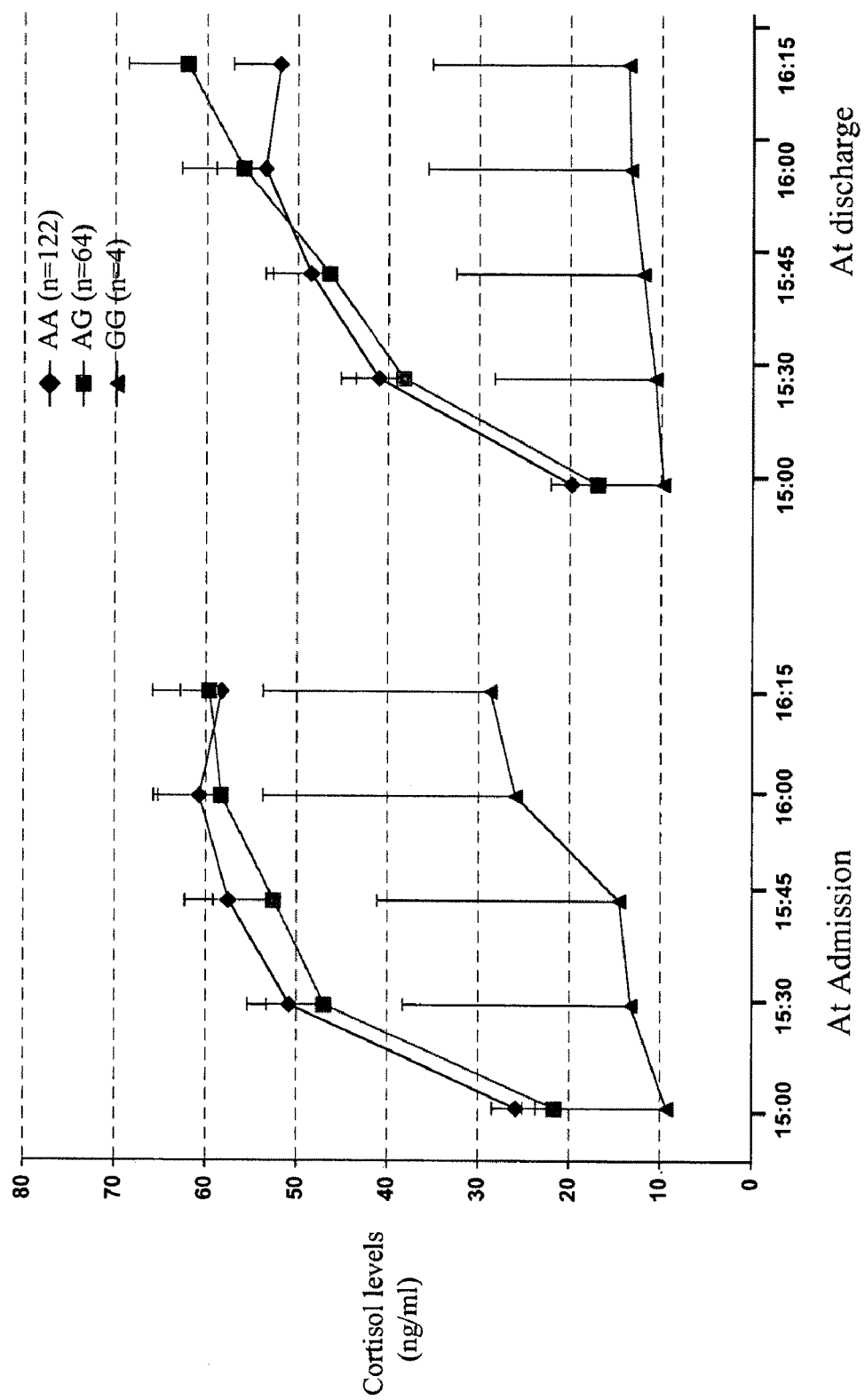

FIG. 1g. Effect of the P2XR7v13A polymorphism on cortisol response during the Dex/CRH test. Individuals were subjected to the test within the first ten days of admission (i.e. At admission) and at the last ten days before discharge (i.e. at discharge). Individuals with the GG genotype have lower cortisol levels in response to the Dex/CRH test at admission and at discharge. These results are indicative of an abnormal HPA axis.

Figure 1H:
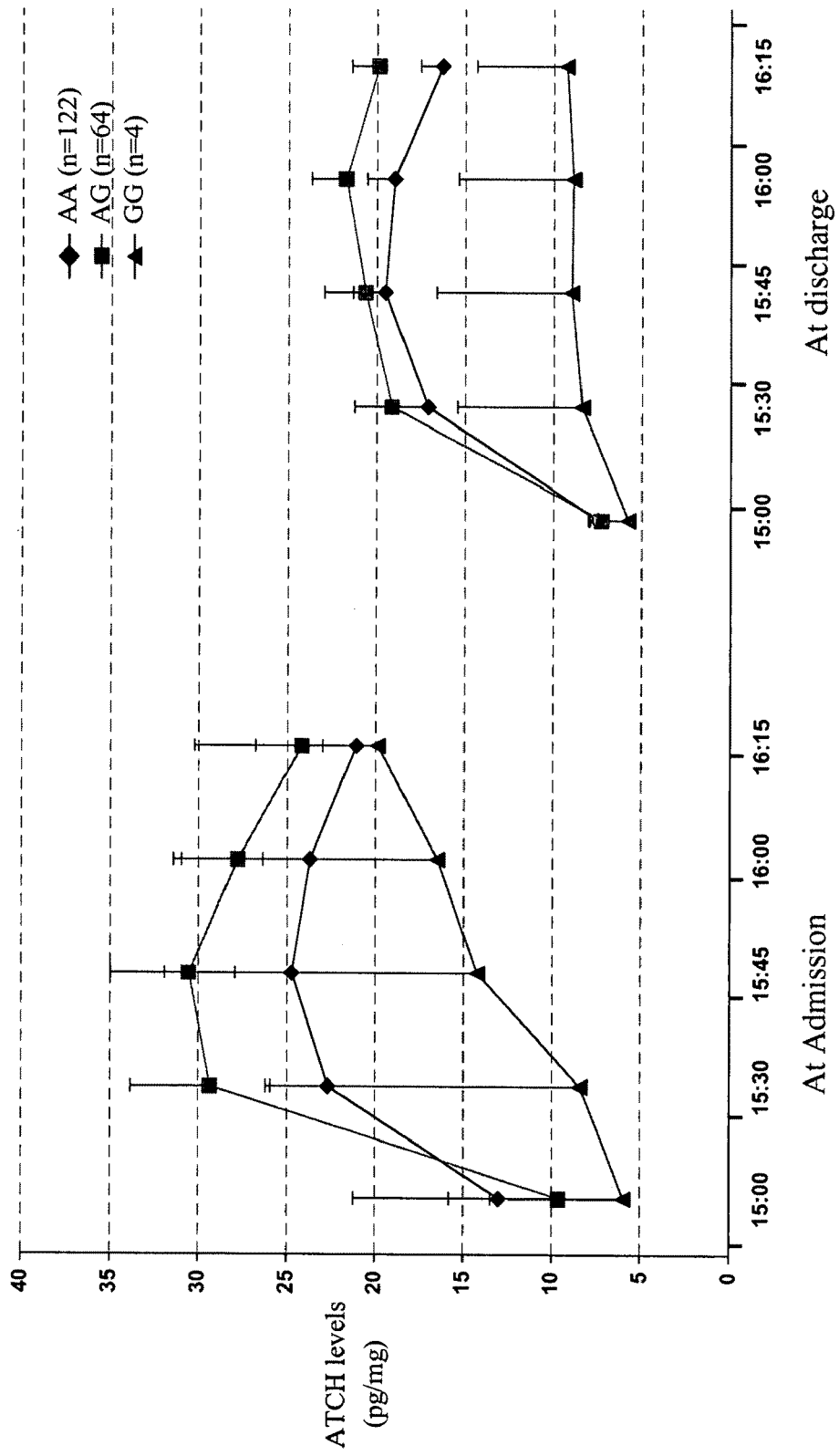

FIG. 1h. Effect of the P2XR7v13A polymorphism on ACTH response during the Dex/CRH test. Individuals were subjected to the test within the first ten days of admission (i.e. at admission) and at the last ten days before discharge (i.e. at discharge). Individuals with the GG genotype have lower ACTH levels in response to the Dex/CRH test, at admission and at discharge. These results are indicative of an abnormal HPA axis.

Figure 1I:
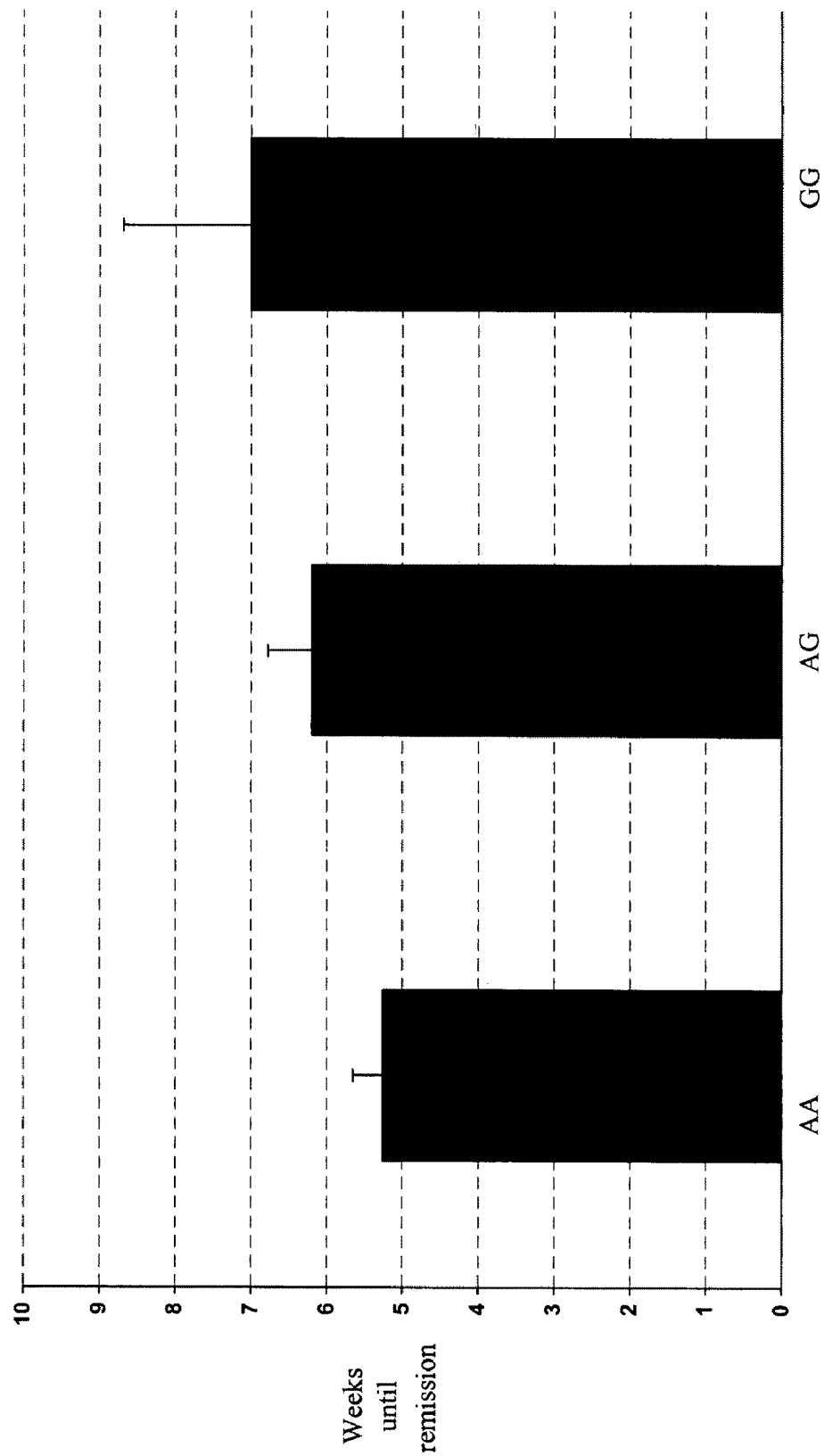

FIG. 1i. Duration of antidepressant treatment until remission. Depression is diagnosed according to the Hamilton Depression Rating Scale (HAM-D; Hamilton, Br. J. Soc. Clin. Psychol. 6 (1967) 278-296). A HAM-D score of 10 or below is regarded as remission of the depressive symptoms.

Figure 1J:
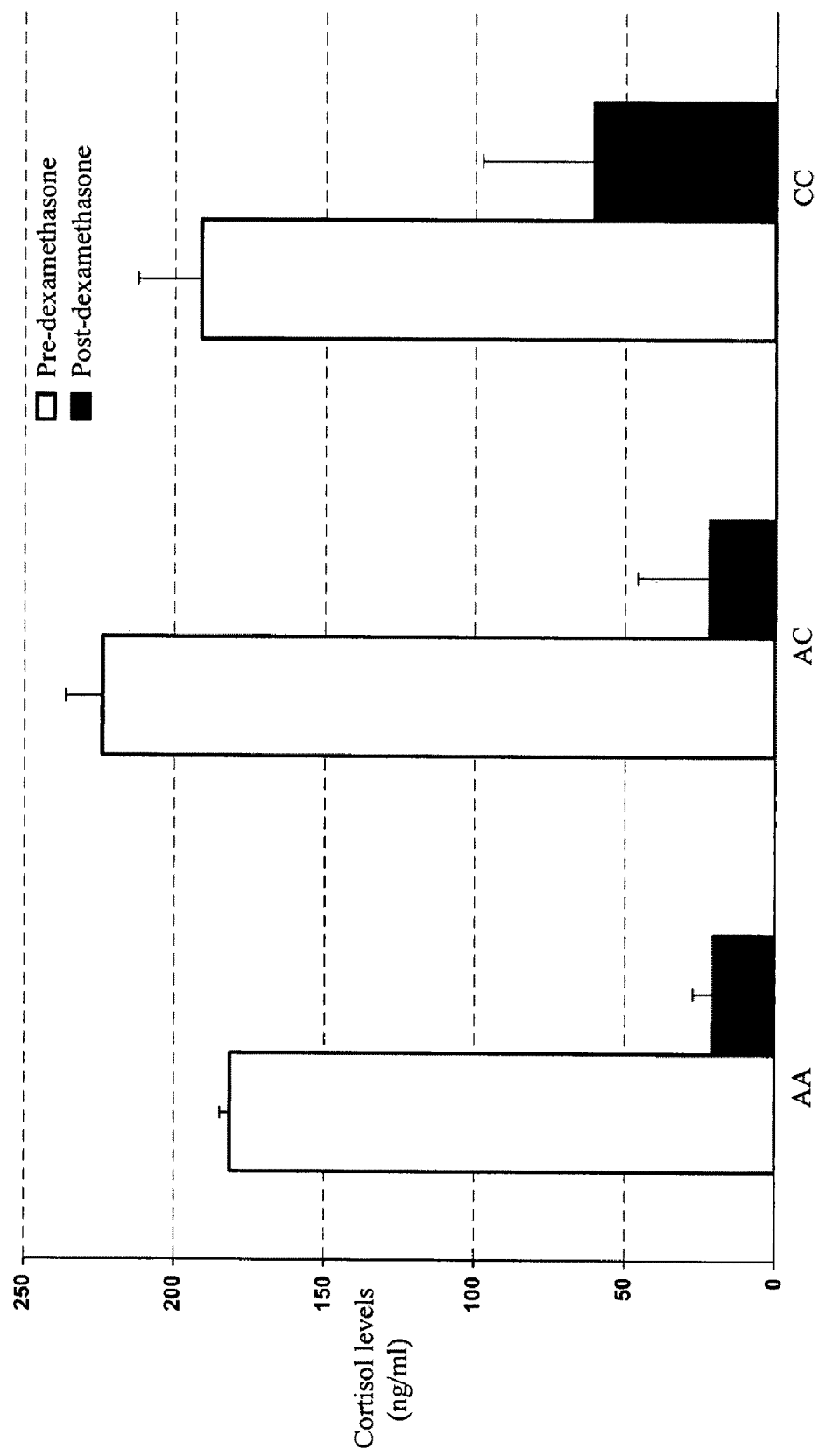

FIG. 1j. Effect of the P2XR7v13C polymorphism on basal cortisol levels before and after administration of dexamethasone (DST test). Individuals were subjected to the test within the first ten days of admission. Individuals with the CC genotypes have elevated cortisol levels post-dexamethasone administration.

Figure 1K:
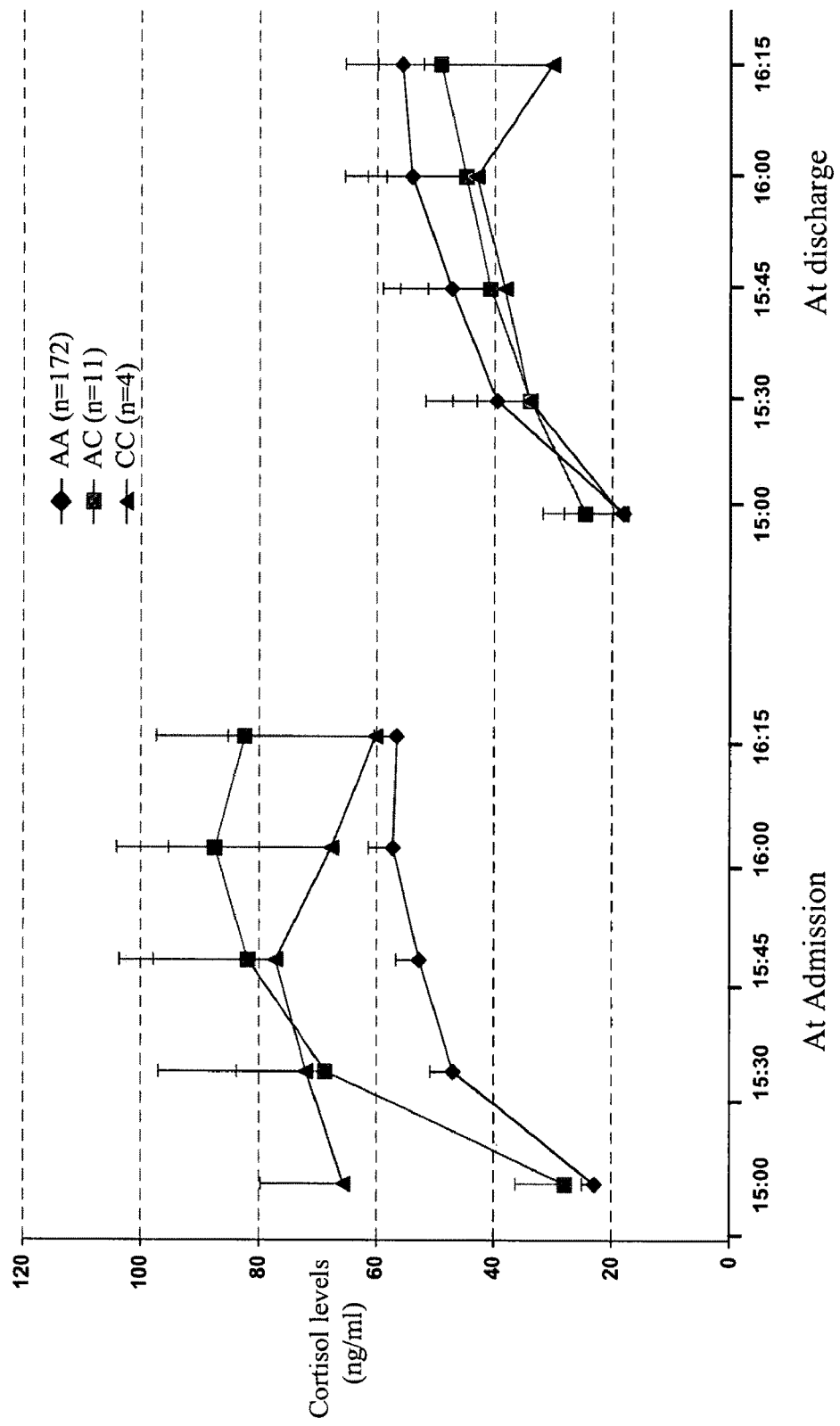

FIG. 1k. Effect of the P2XR7v13C polymorphism on cortisol response during the Dex/CRH test. Individuals were subjected to the test within the first ten days of admission (i.e. at admission) and at the last ten days before discharge (i.e. at discharge). Individuals with the AC or CC genotype have elevated cortisol levels in response to the Dex/CRH test at admission, indicating an abnormal HPA axis.

Figure 1L:
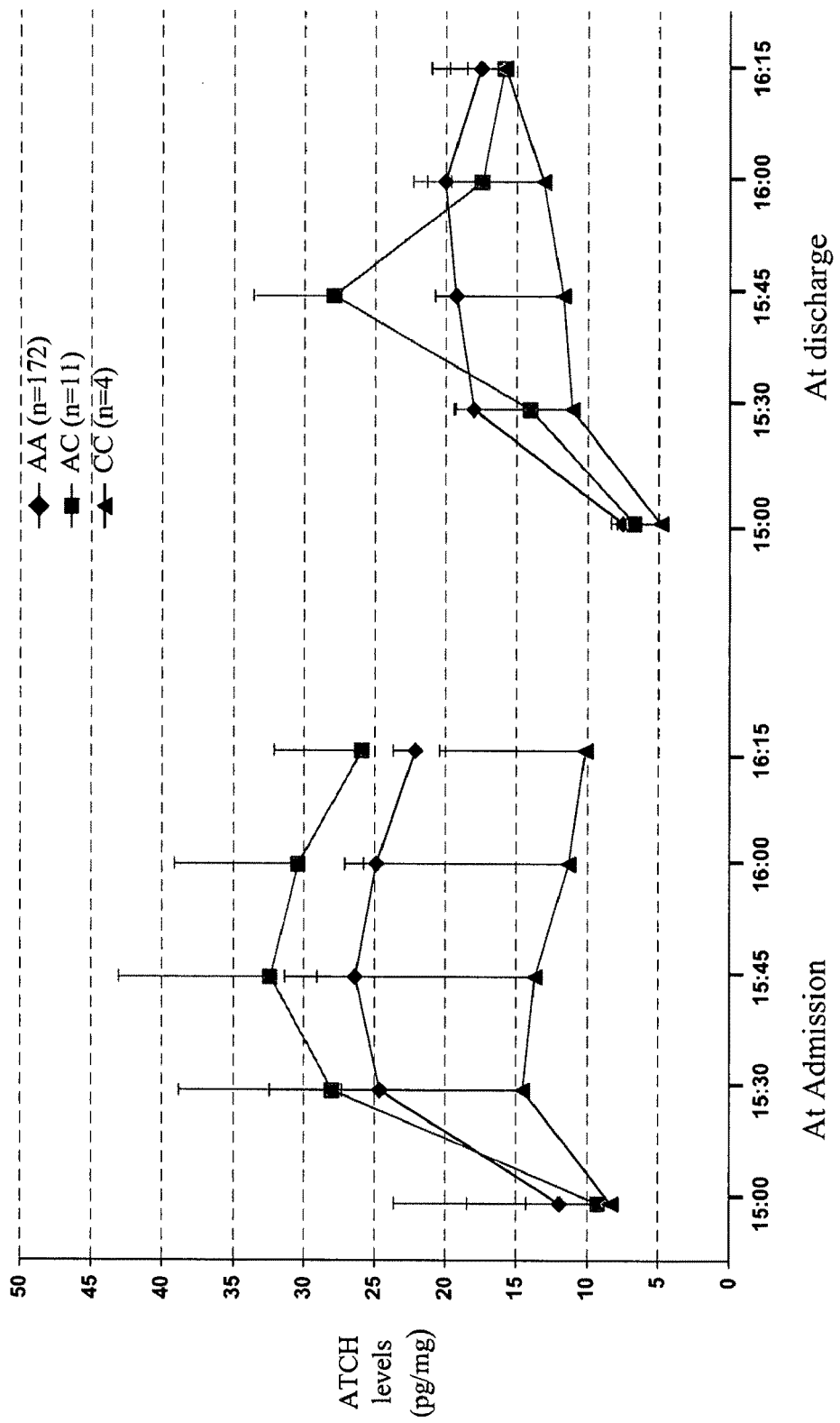

FIG. 1l. Effect of the P2XR7v13C polymorphism on ACTH response during the Dex/CRH test. Individuals were subjected to the test within the first ten days of admission (i.e. at admission) and at the last ten days before discharge (i.e. at discharge). Individuals with the CC genotype have lower ACTH levels in response to the Dex/CRH test, at admission and at discharge. These results are indicative of an abnormal HPA axis.

Figure 2:
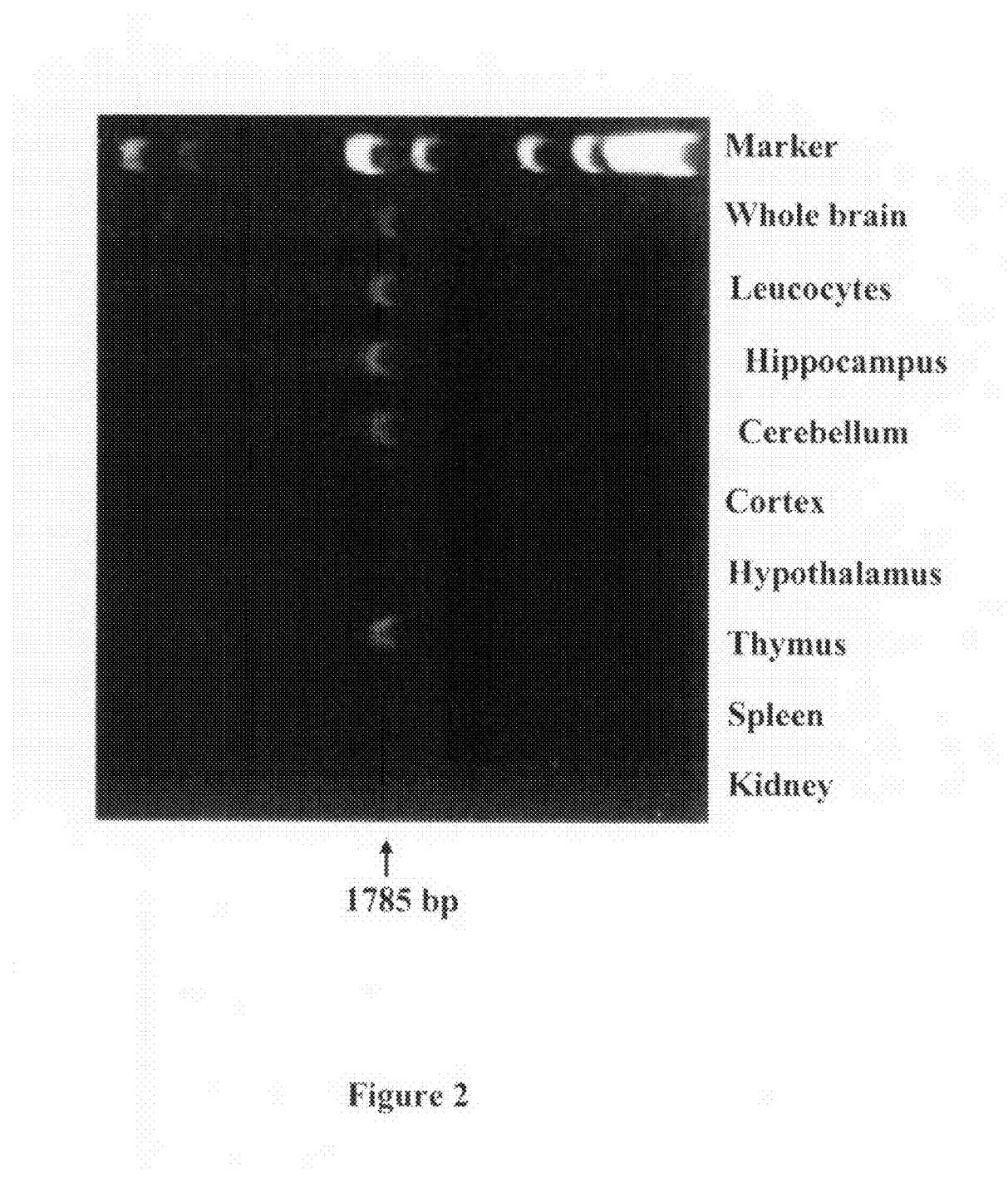

FIG. 2. RT-PCR analysis of the complete coding sequence of P2X7R in different tissues FIG. 3. P2X7R expression in the olfactory bulb, hypothalamus and ependymal cells in the brain of a stress-free mouse. Magnification 100×.

Figure 4:
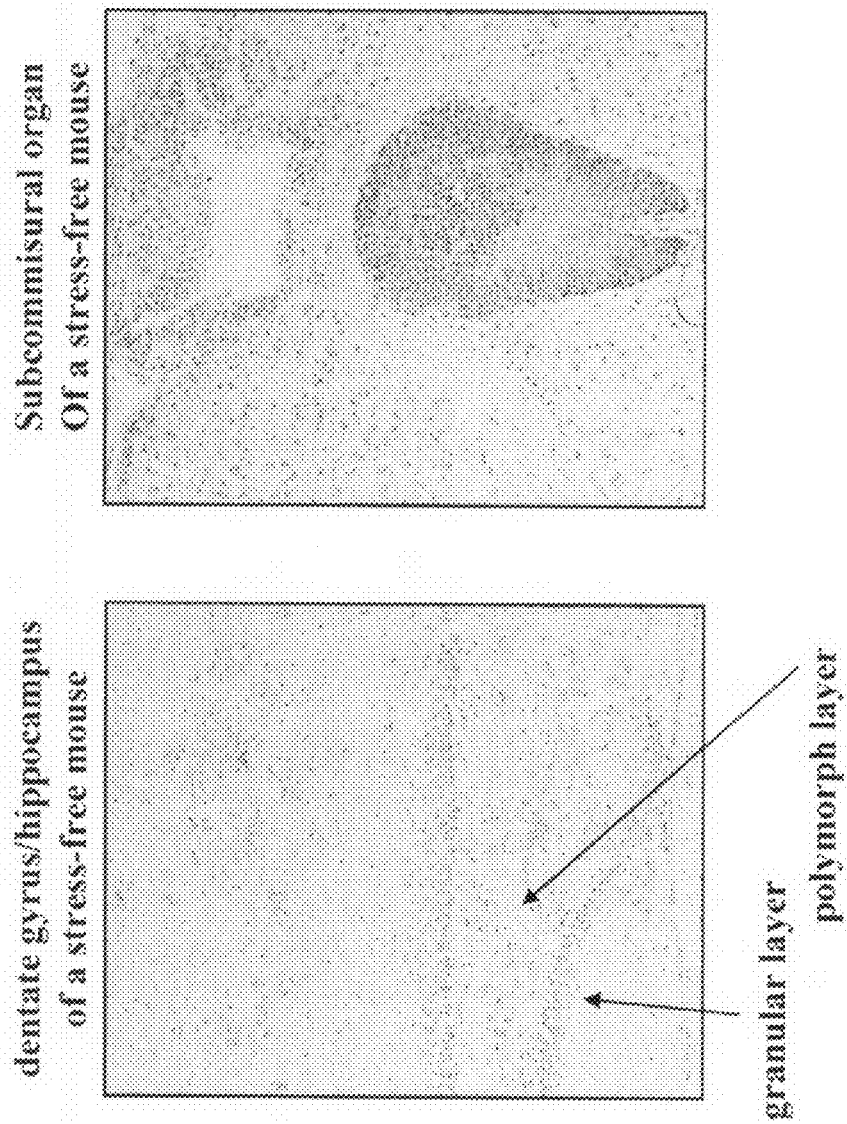

FIG. 4. P2X7R expression in the hippocampus/dentate gyrus and subcommisural organ in the brain of a stress-free mouse. Magnification 100×.

Figure 5:
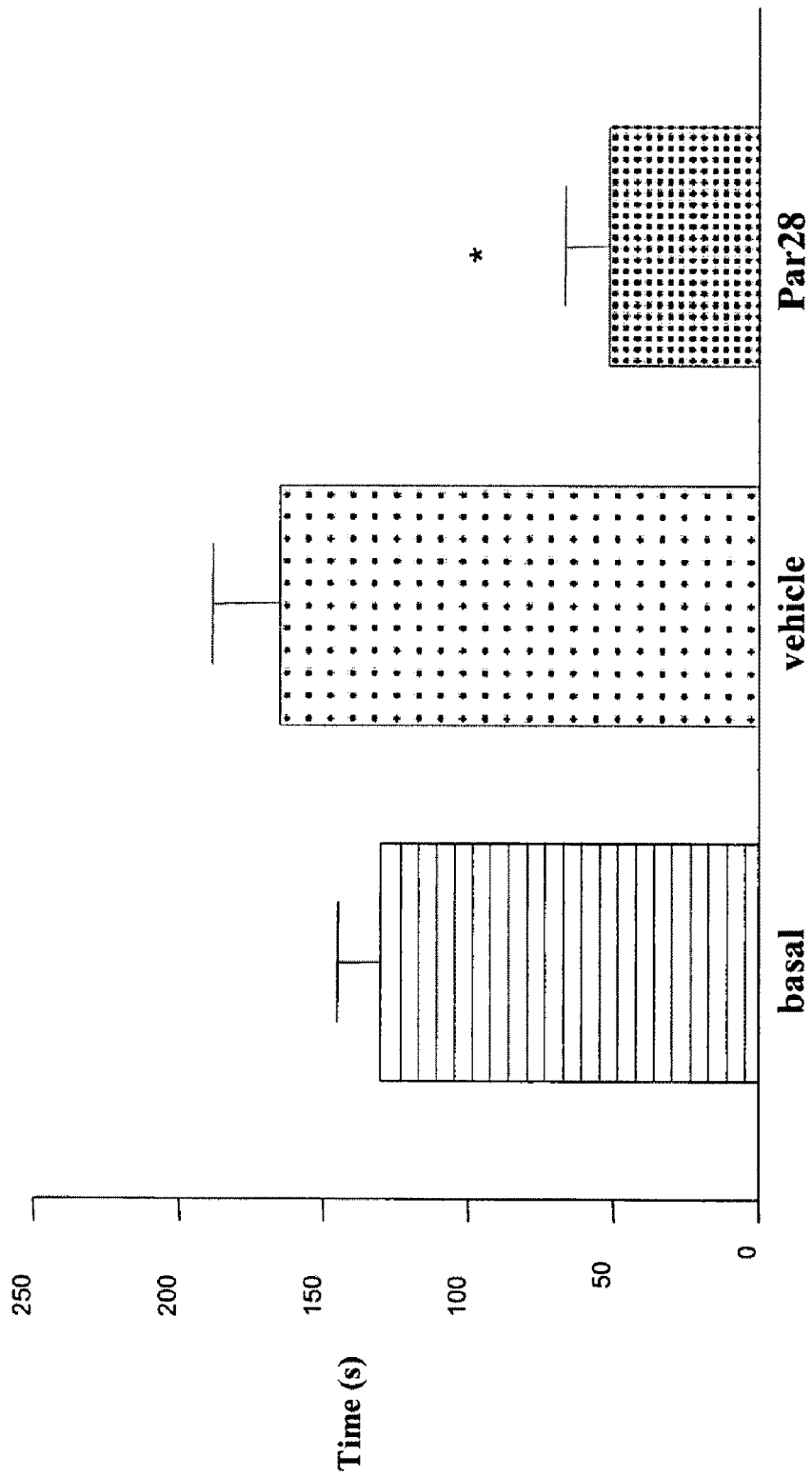

FIG. 5. Floating behaviour in the forced swim test. Passive stress coping behaviour decreased after long-term treatment with the antidepressant paroxetine (Par28: treated with paroxetine for 28 days, per os). Basal n=8; vehicle n=8; Par28 n=8.

Figure 6:
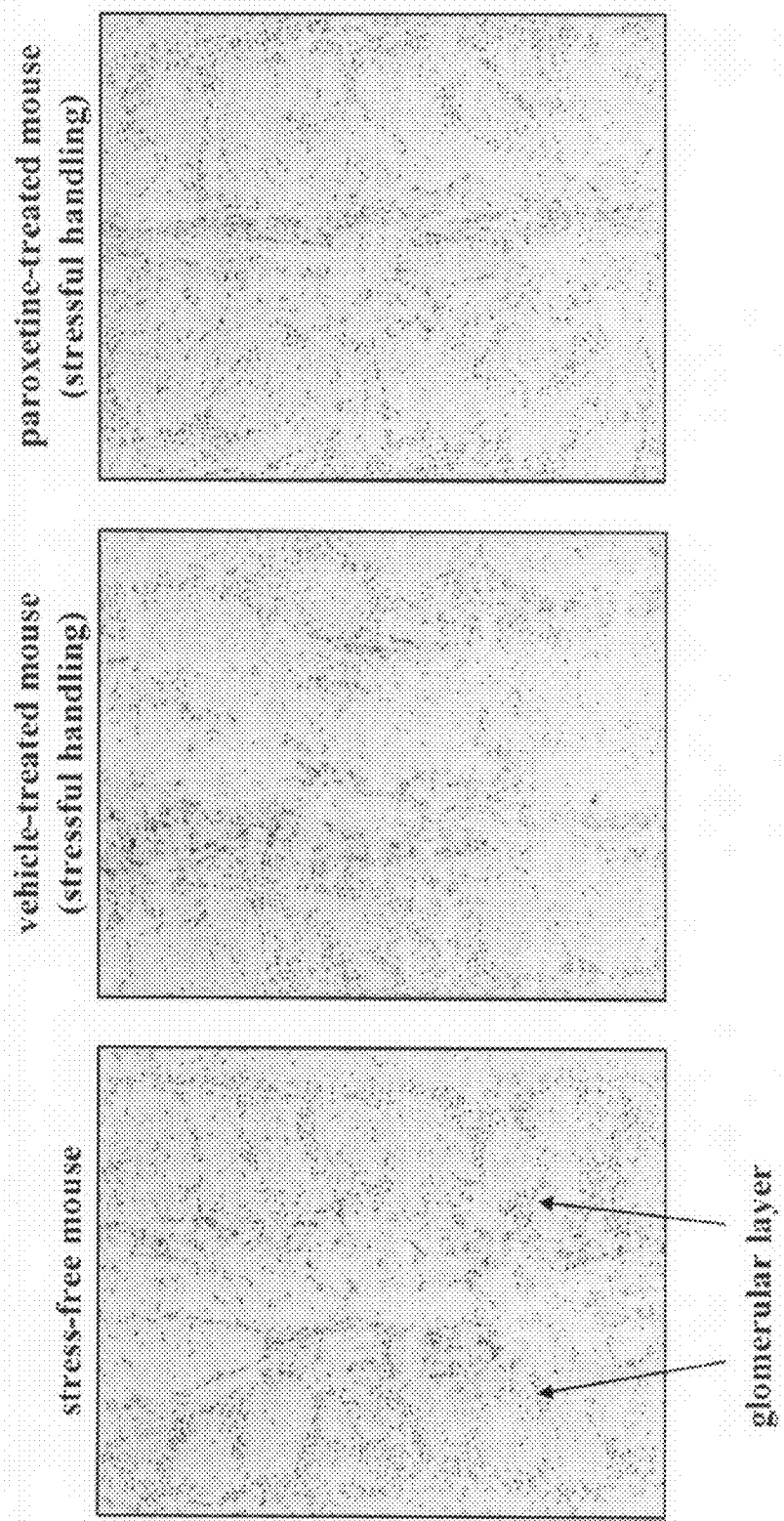

FIG. 6. Comparative analysis of P2X7R expression in the olfactory bulb of stress-free, vehicle-treated and antidepressant-treated mice. Magnification 100×.

Figure 7:
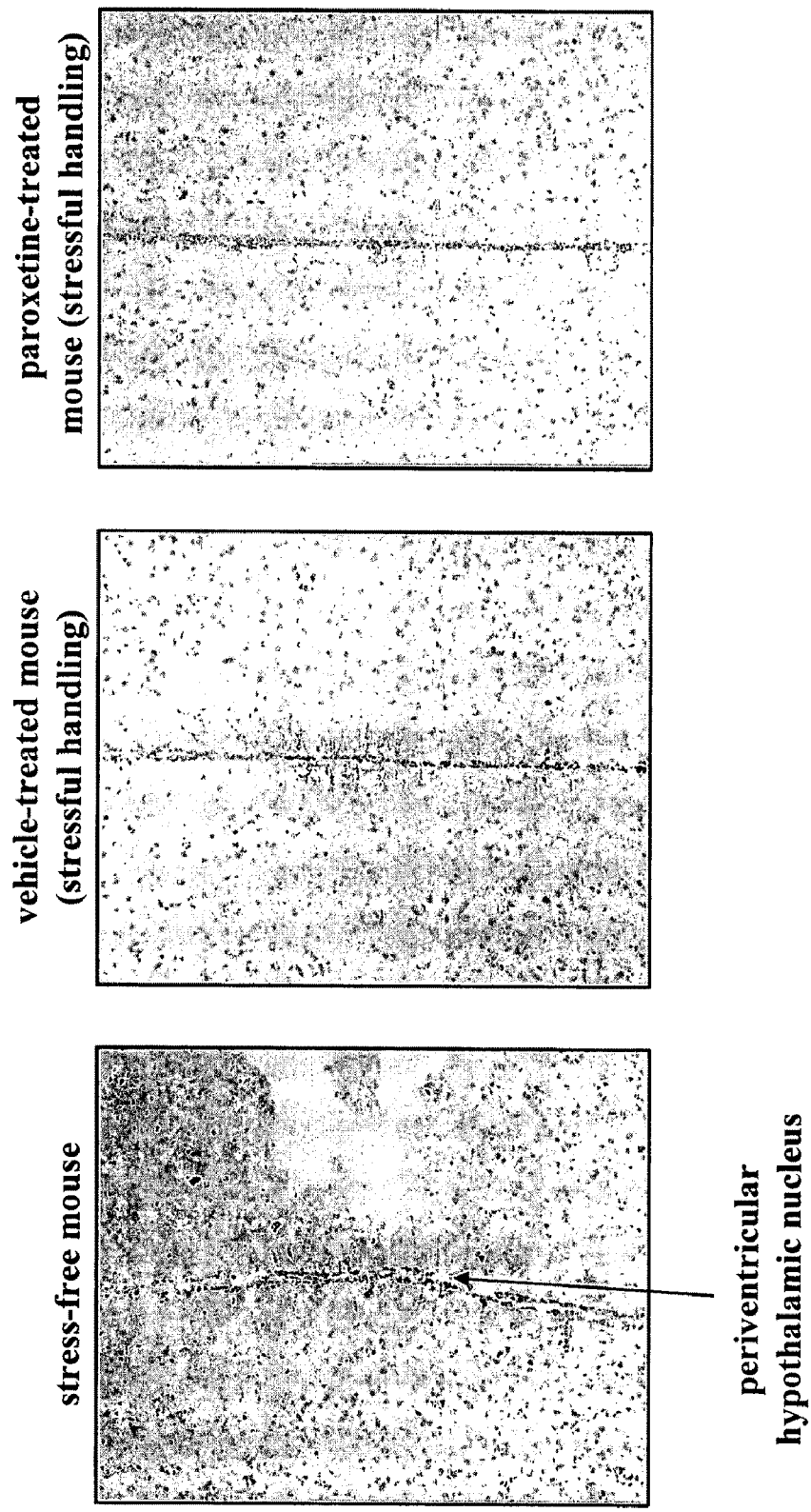

FIG. 7. Comparative analysis of P2X7R expression in the hypothalamus of stress-free, treated-treated and antidepressant-treated mice. Magnification 100×.

Figure 8:
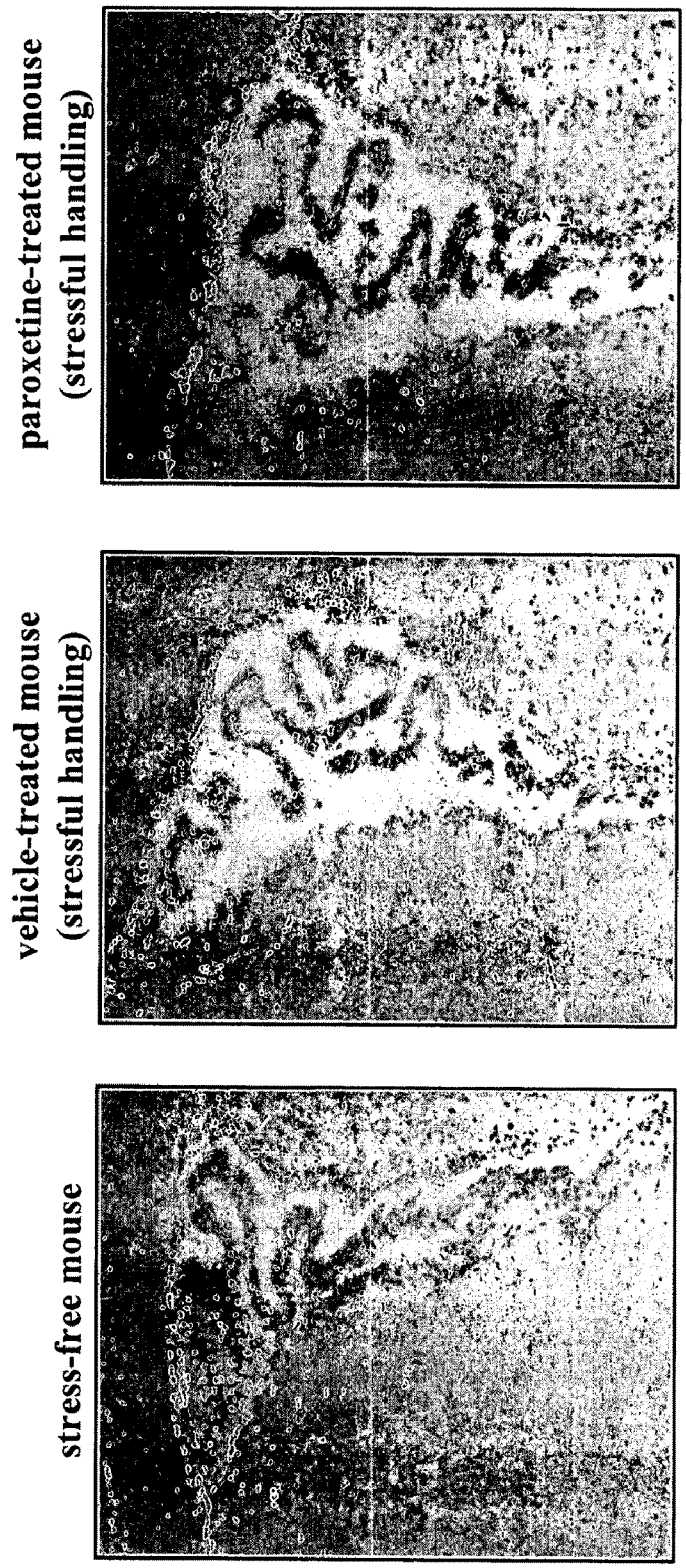

FIG. 8. Comparative analysis of P2X7R expression in ependymal cells of stress-free, vehicle-treated and antidepressant-treated mice. Magnification 100×.

Figure 9:
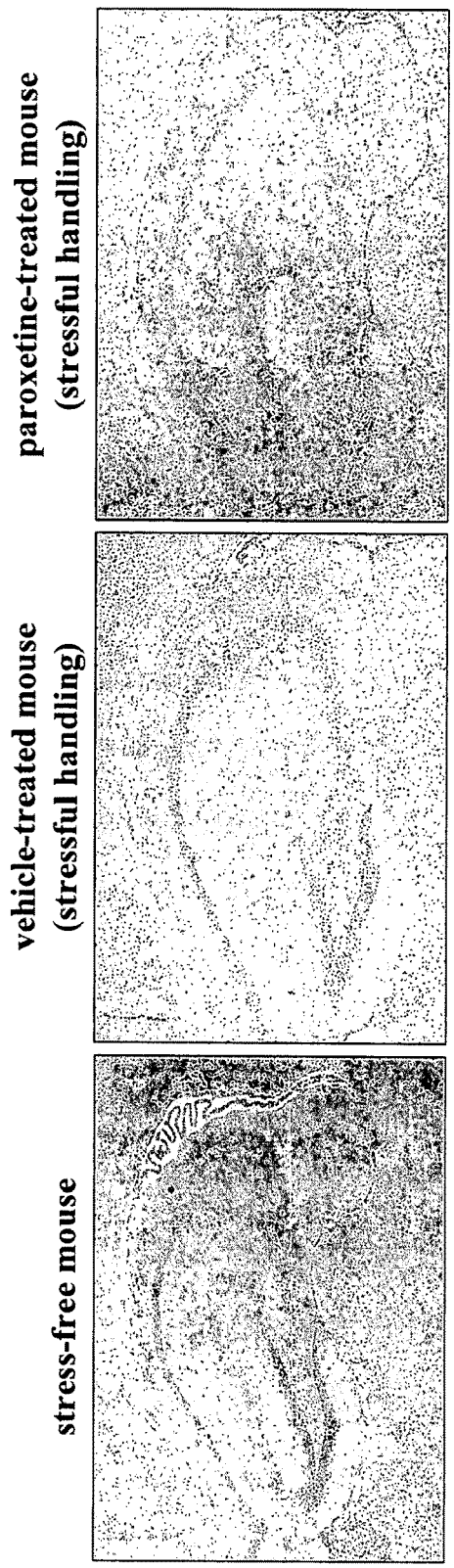

FIG. 9. Comparative analysis of P2X7R expression in the hippocampus of stress-free, vehicle-treated and antidepressant-treated mice. Magnification 25×.

Figure 10:
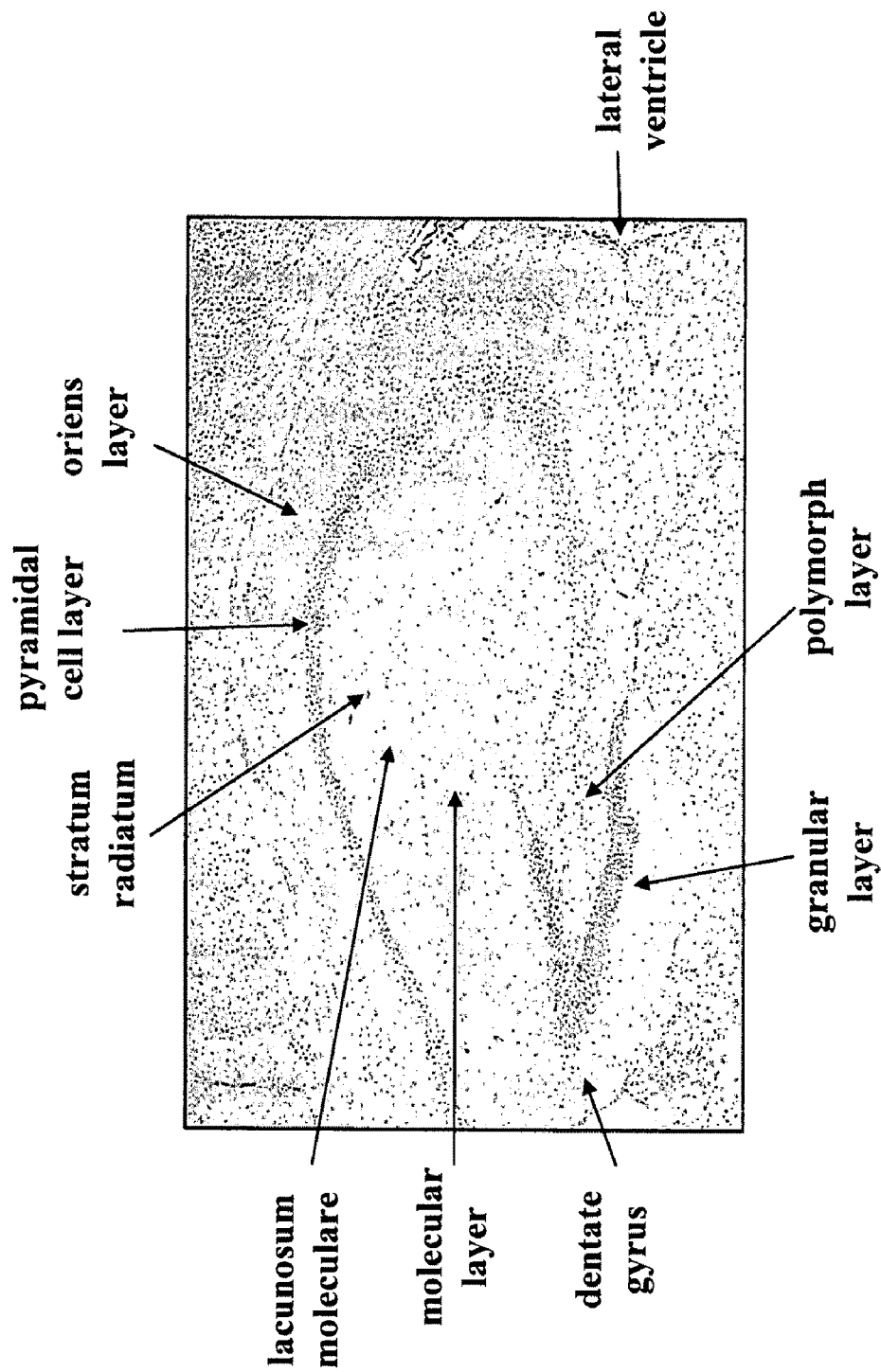

FIG. 10. P2X7R expression in the hippocampus of a vehicle treated mouse. Magnification 25×.

Figure 11:
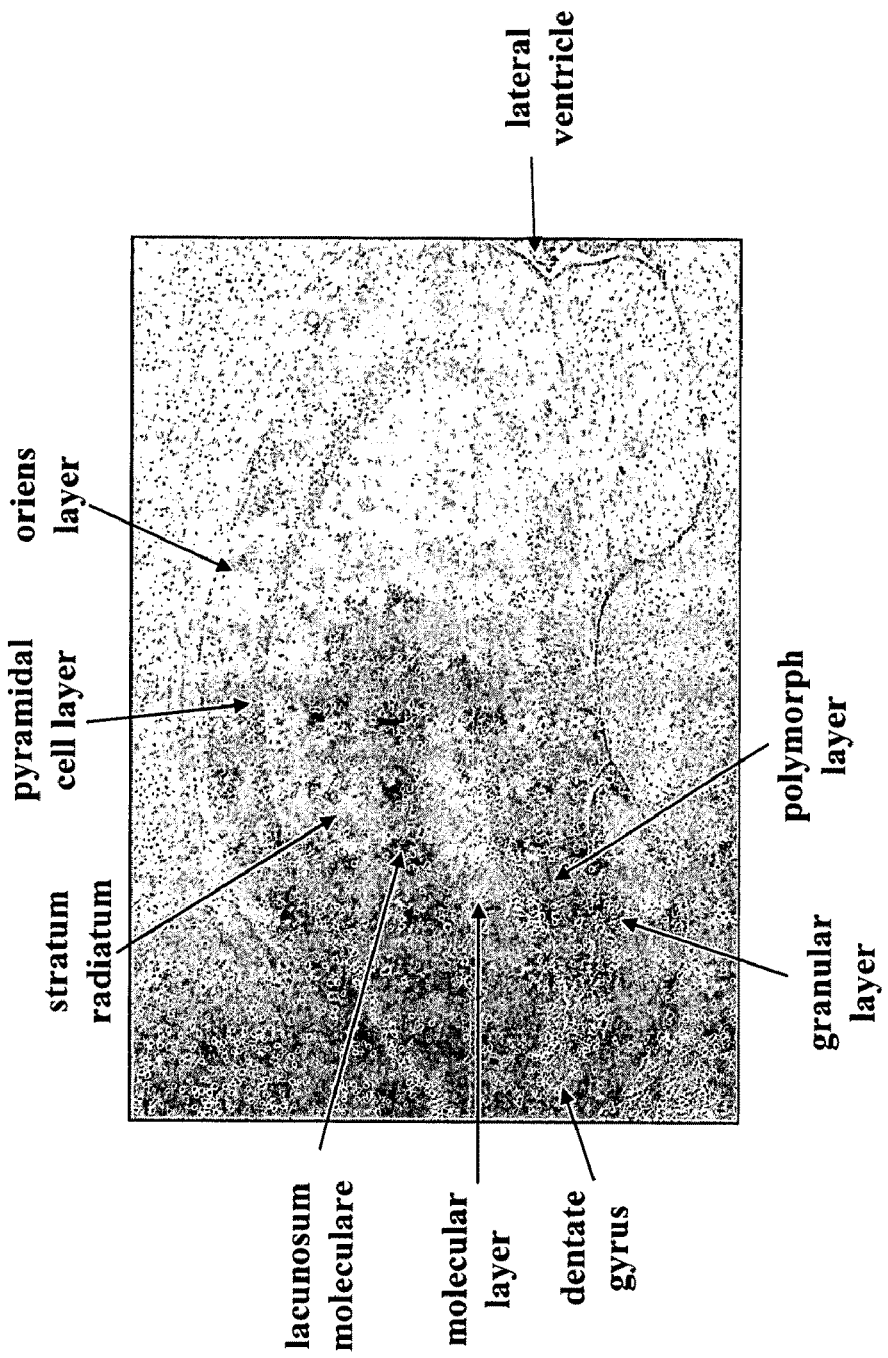

FIG. 11. P2X7R expression in the hippocampus of a mouse treated with the antidepressant paroxetine. Magnification 25×.

Figure 12:
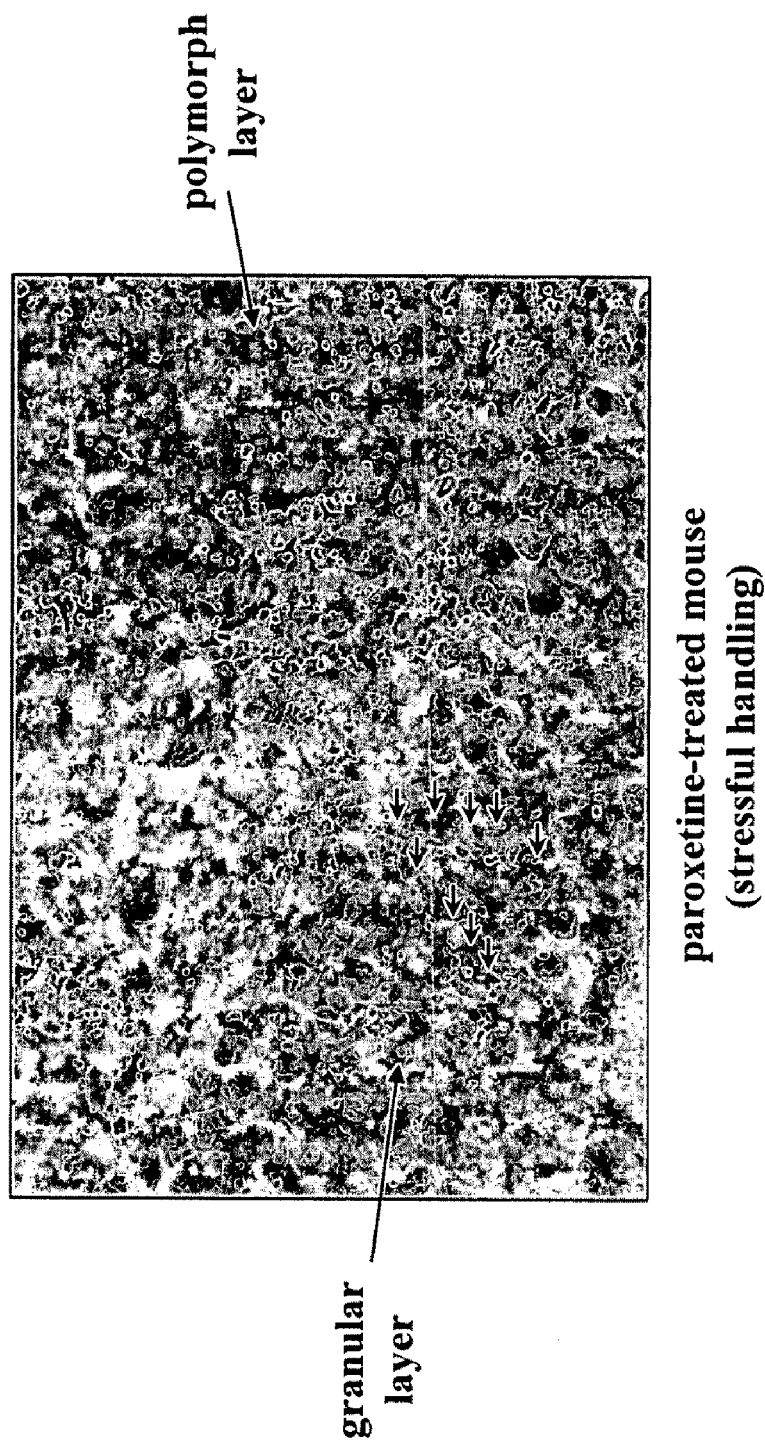

FIG. 12. Detailed expression of P2X7R in the dentate gyrus of a mouse treated with the antidepressant paroxetine. Magnification 400×.

Figure 13:
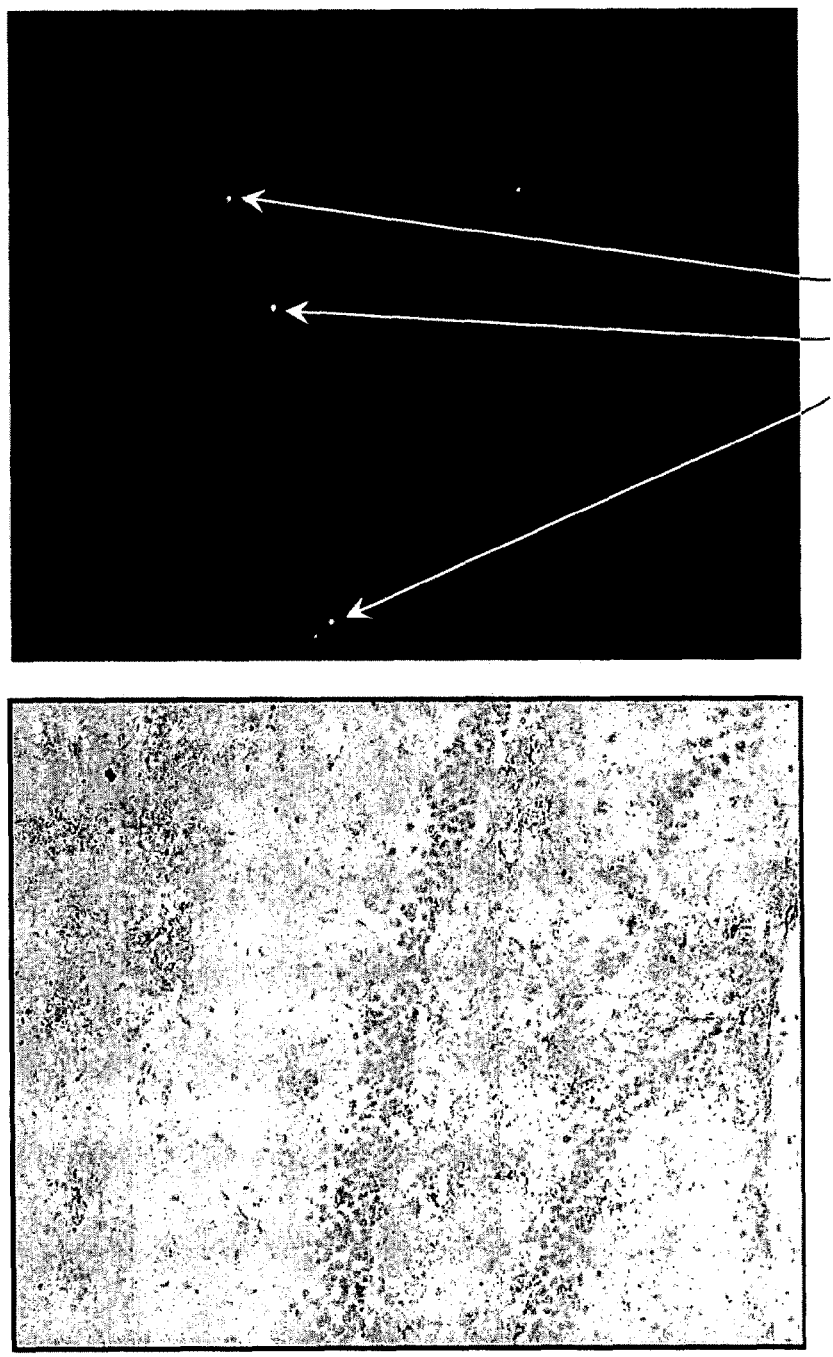

FIG. 13. Comparative analysis of P2X7R expression and apoptotic cells in the hippocampus of a mouse treated with the antidepressant paroxetine. Magnification 100×.

Figure 14:
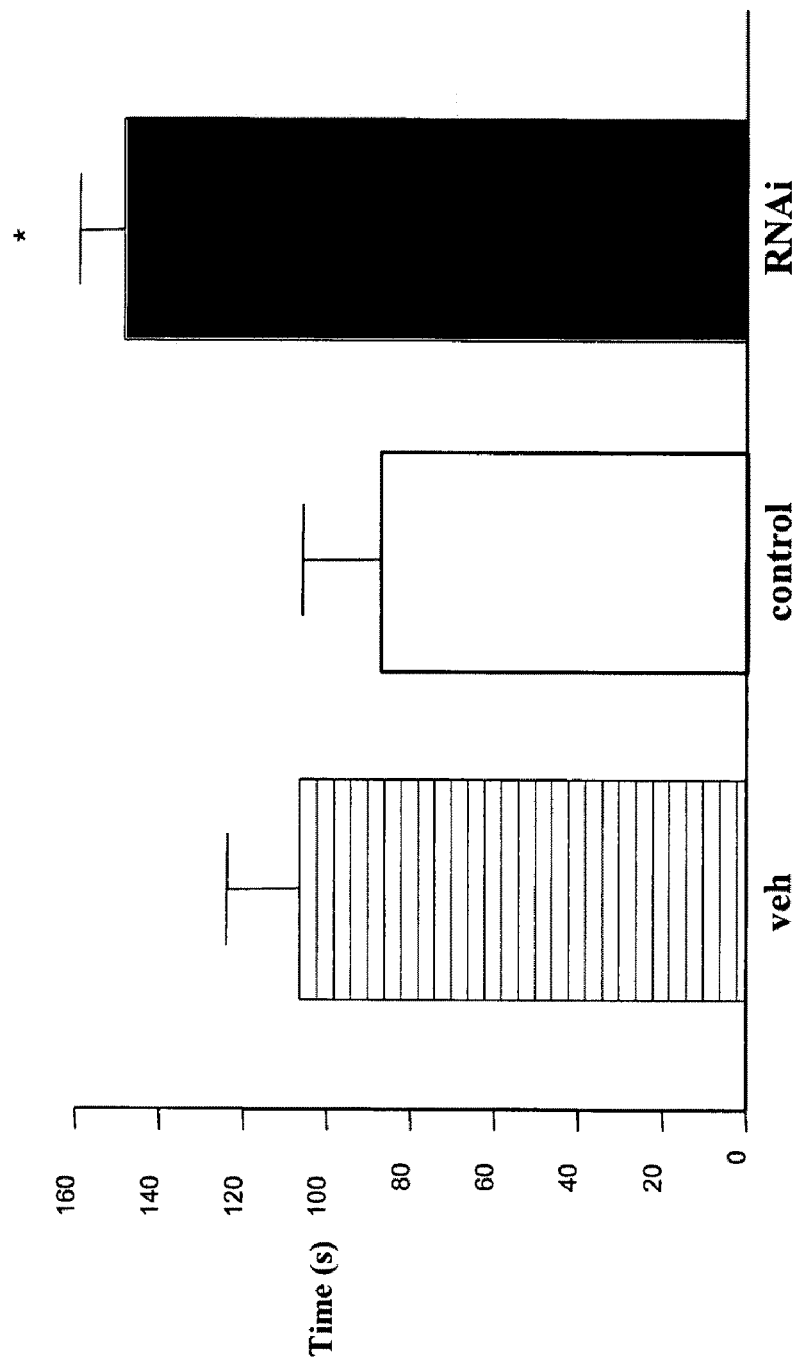

FIG. 14. Floating behaviour in the forced swim test. Passive stress coping behaviour increased after acute intrahippocampal (bilateral, dentate gyrus) of siRNA targeting P2X7R. Vehicle n=7; control RNA n=10; P2X7R siRNA n=9.

Figure 15:
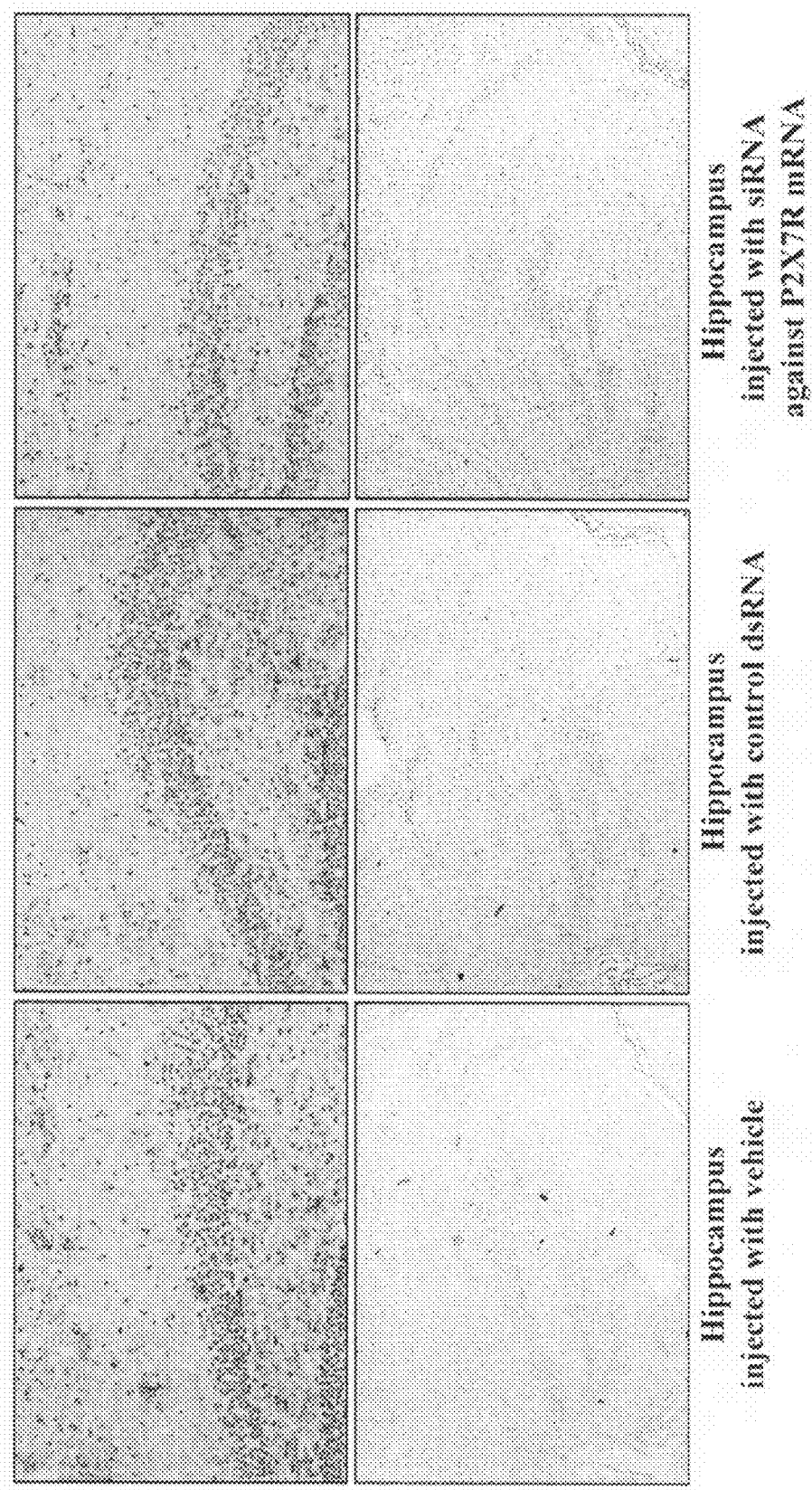

FIG. 15. Comparative analysis of P2X7R expression in the hippocampus of mice treated with vehicle, control RNA and of siRNA targeting P2X7R. Magnification 100× upper row, 25× lower row.

FIG. 16a, b, c, d, e. Three splicing variants caused by polymorphisms in the introns of P2X7R.

Figure 17:
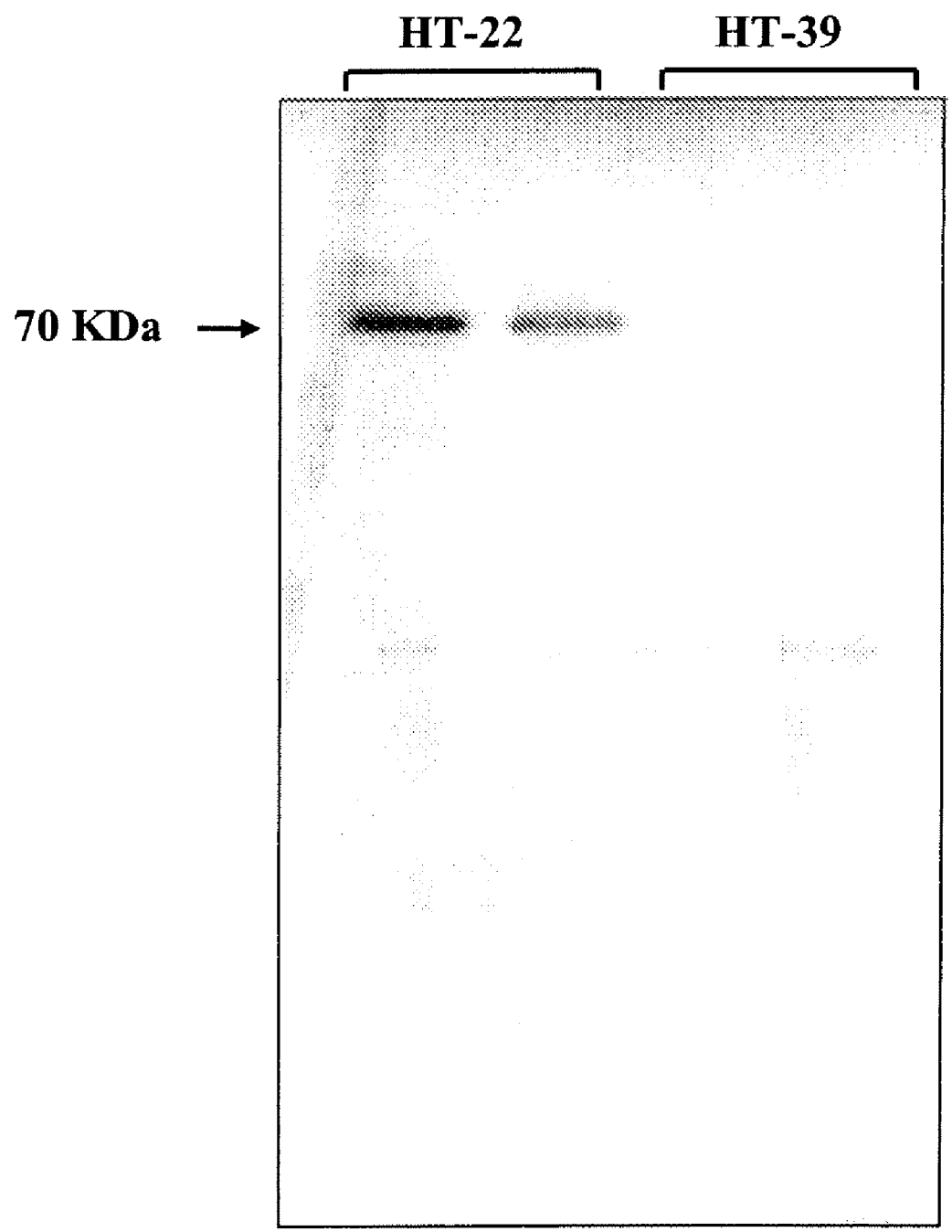

FIG. 17. Expression of P2X7R in immortalized hippocampal cell lines.

Figure 18:
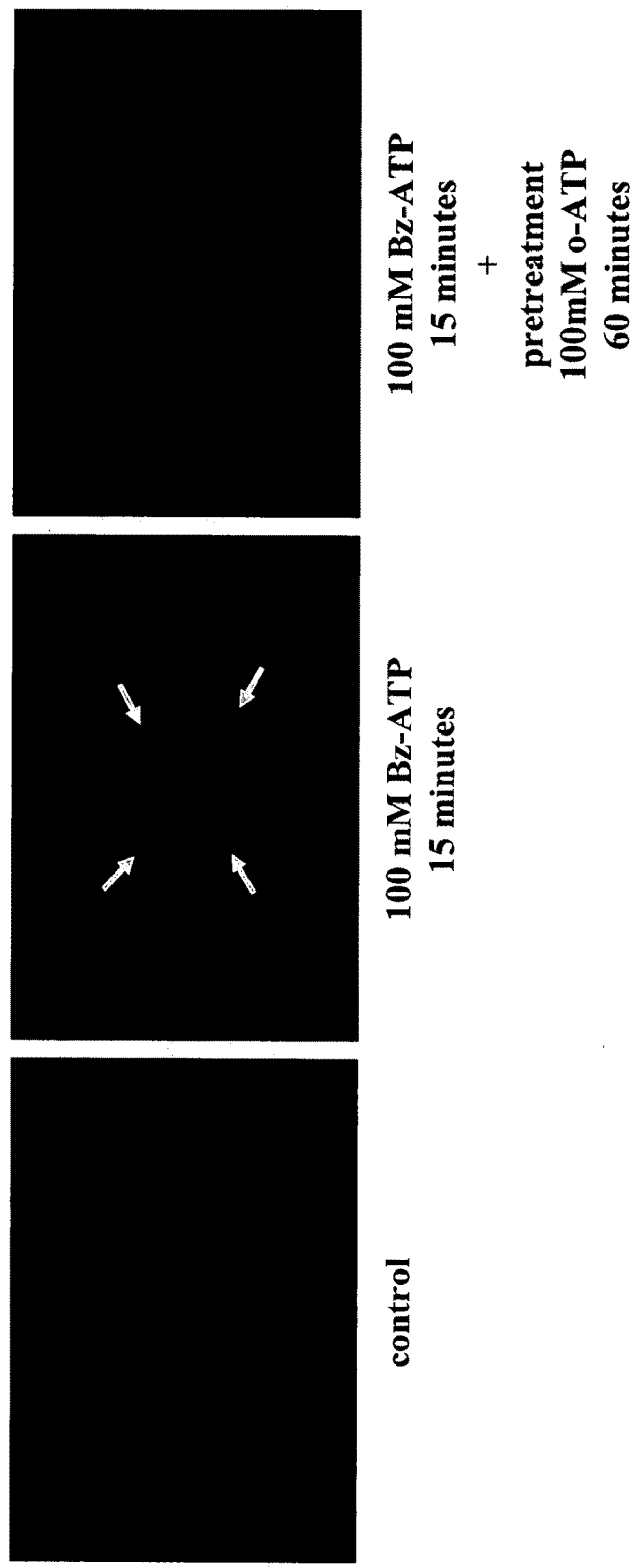

FIG. 18. Increase calcium influx in hippocampal cells treated with a P2X7R agonist compound (BzATP).

Figure 19A:
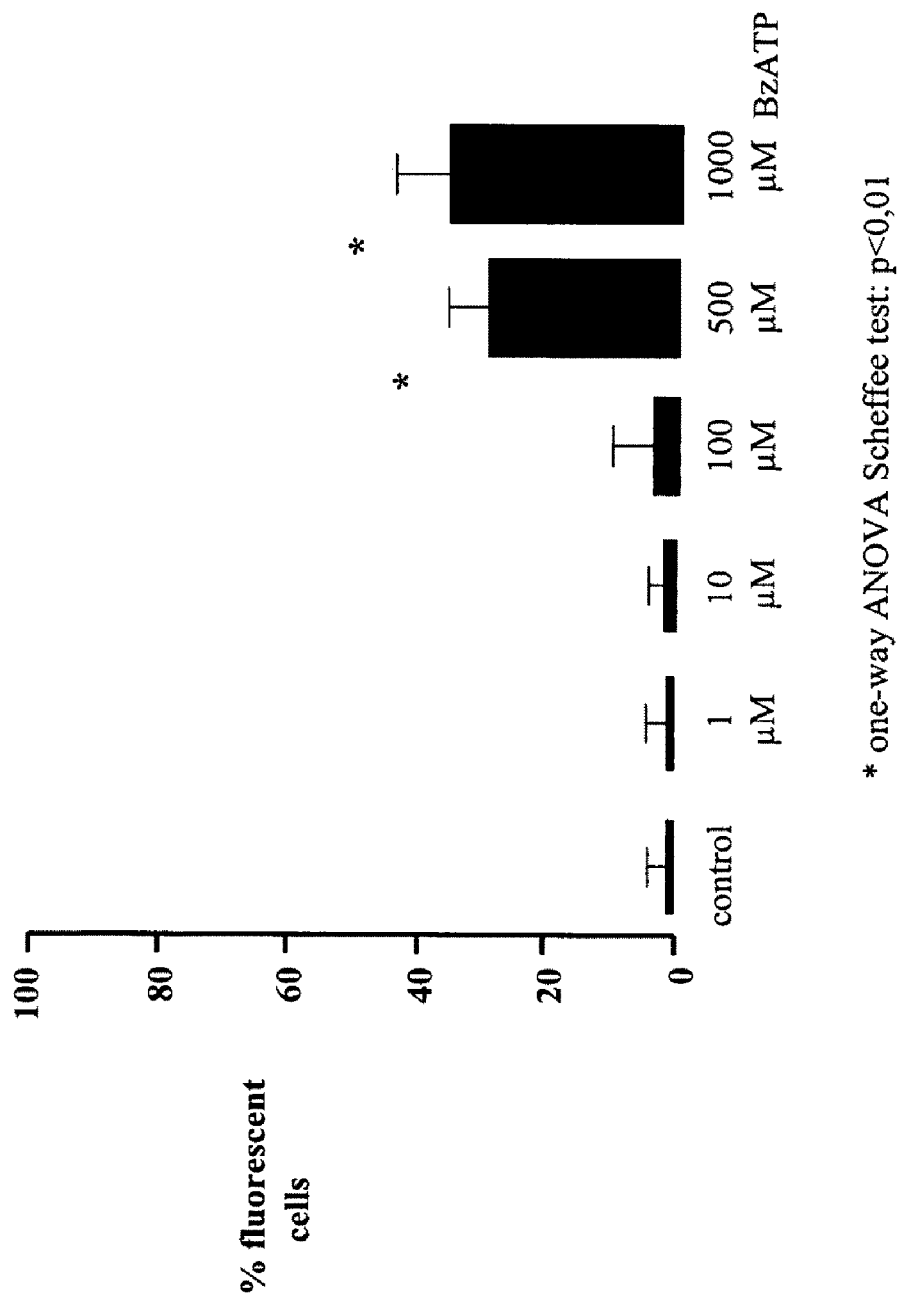

FIG. 19a, b. Entry of ethidium bromide dye into hippocampal cells (a) treated with P2X7R agonist compound (BzATP) or (b) pre-treated with a P2X7R antagonist compound.

Figure 19B:
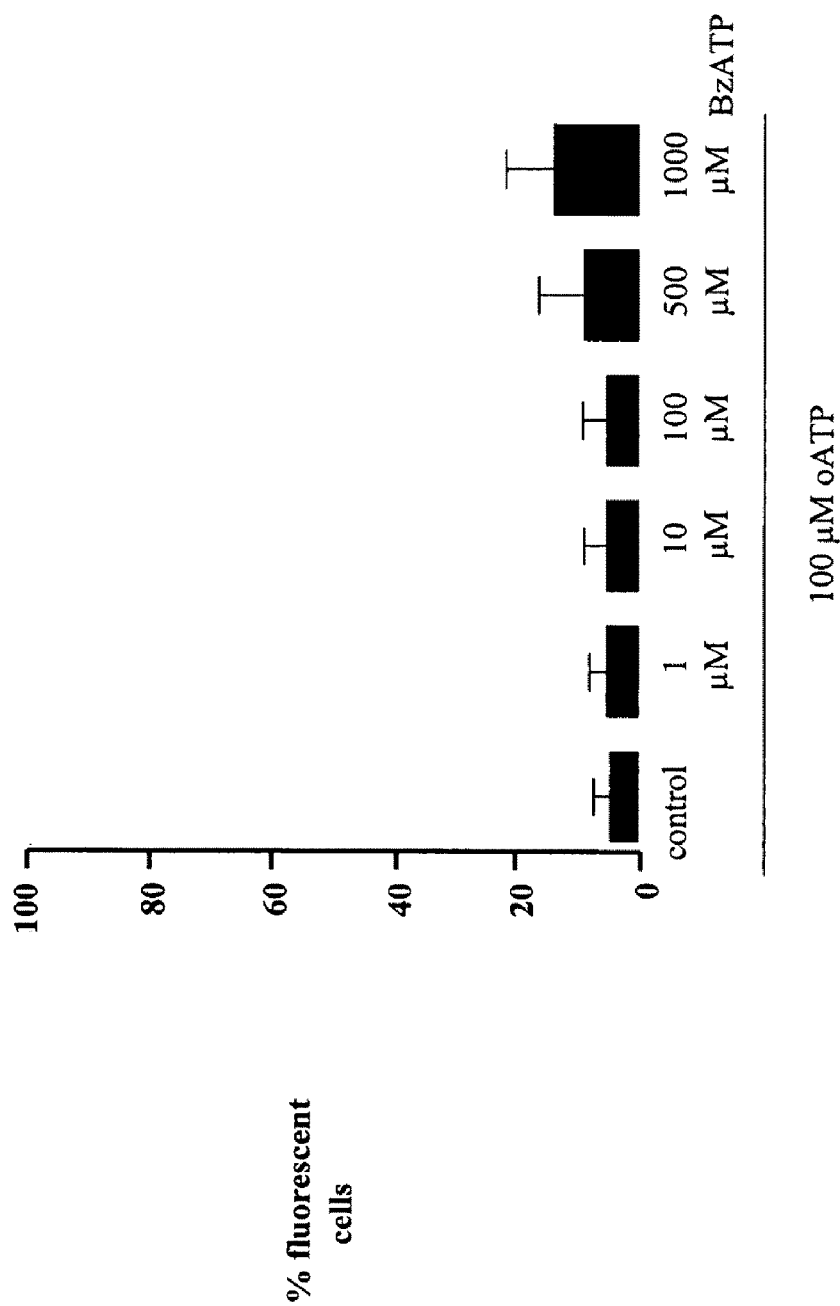
Figure 19C:
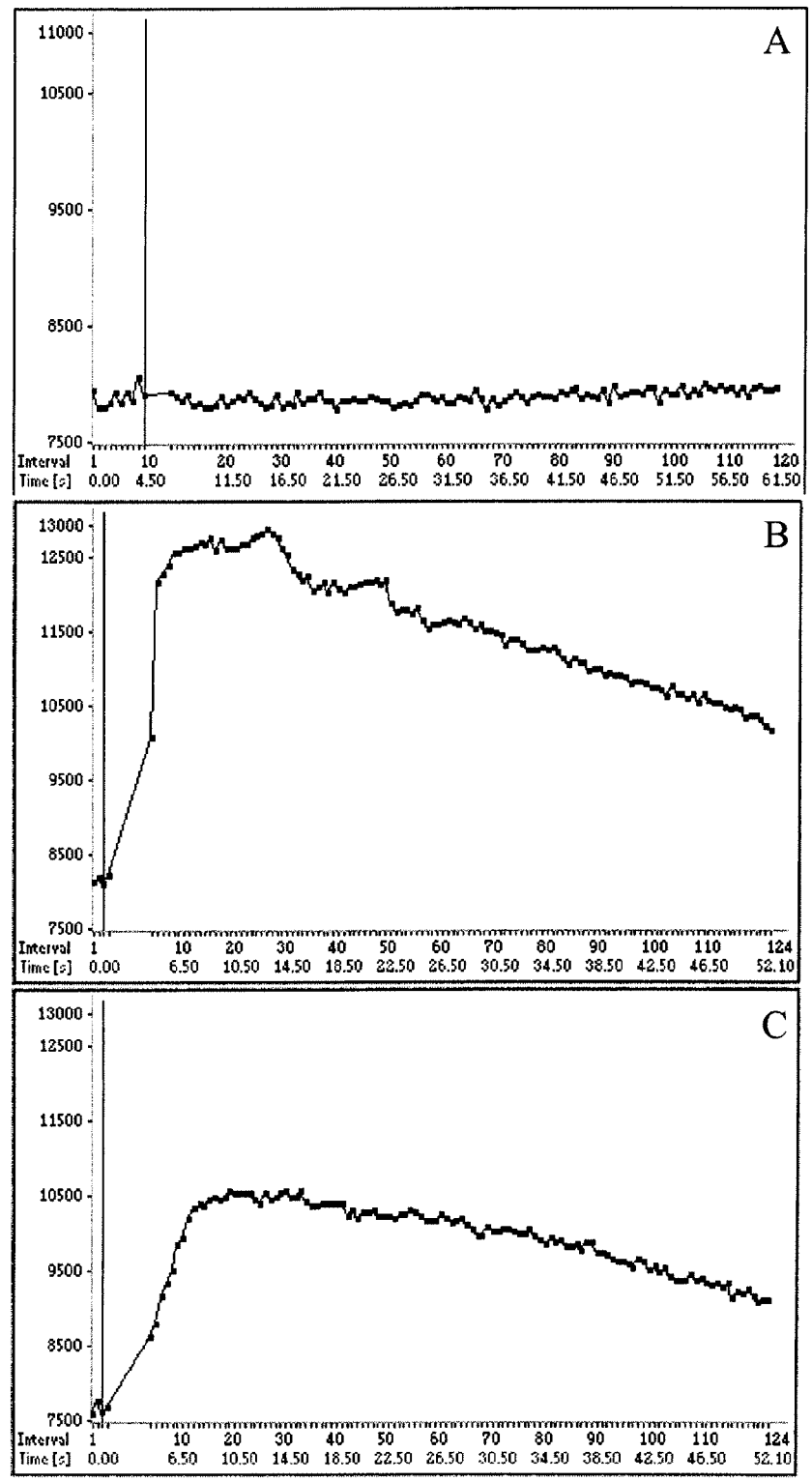

FIG. 19c. Agonist action of BzATP and tenidap on P2X7R activity. The calcium channel activity of human P2X7R was measured under basal conditions for four seconds to 10 seconds. A. Negative control consisting of cells loaded with 10 µM Fluo-4-AM without further treatment. B. Cells treated with 20 µM BzATP after four seconds of basal measurement. C. Cells treated with 50 µM tenidap after four seconds of basal measurement.

Figure 20:
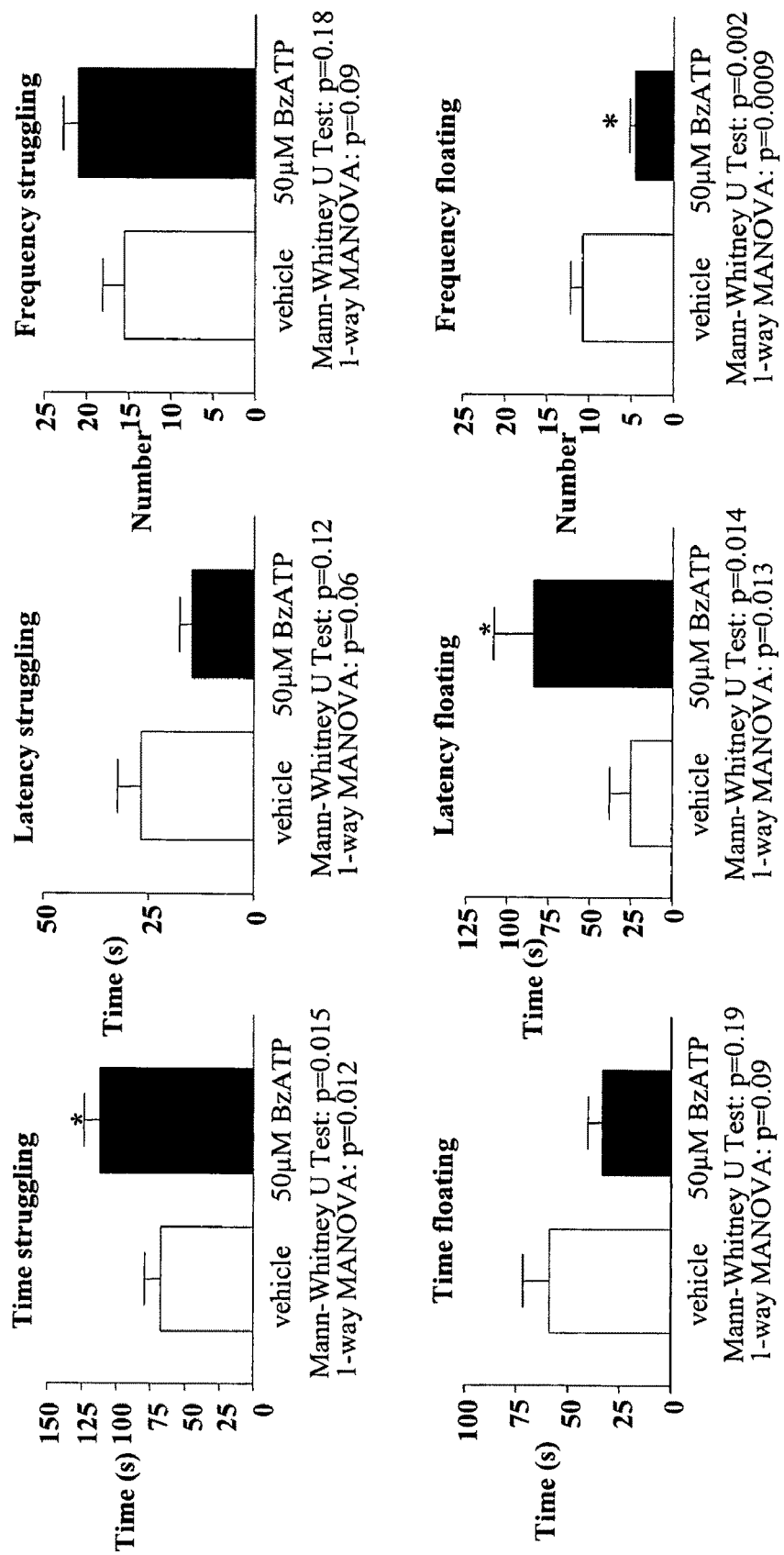

FIG. 20. Effect of intrahippocampal injection of a P2X7R agonist compound (BzATP) on behaviour in the forced swim test.

Figure 21:
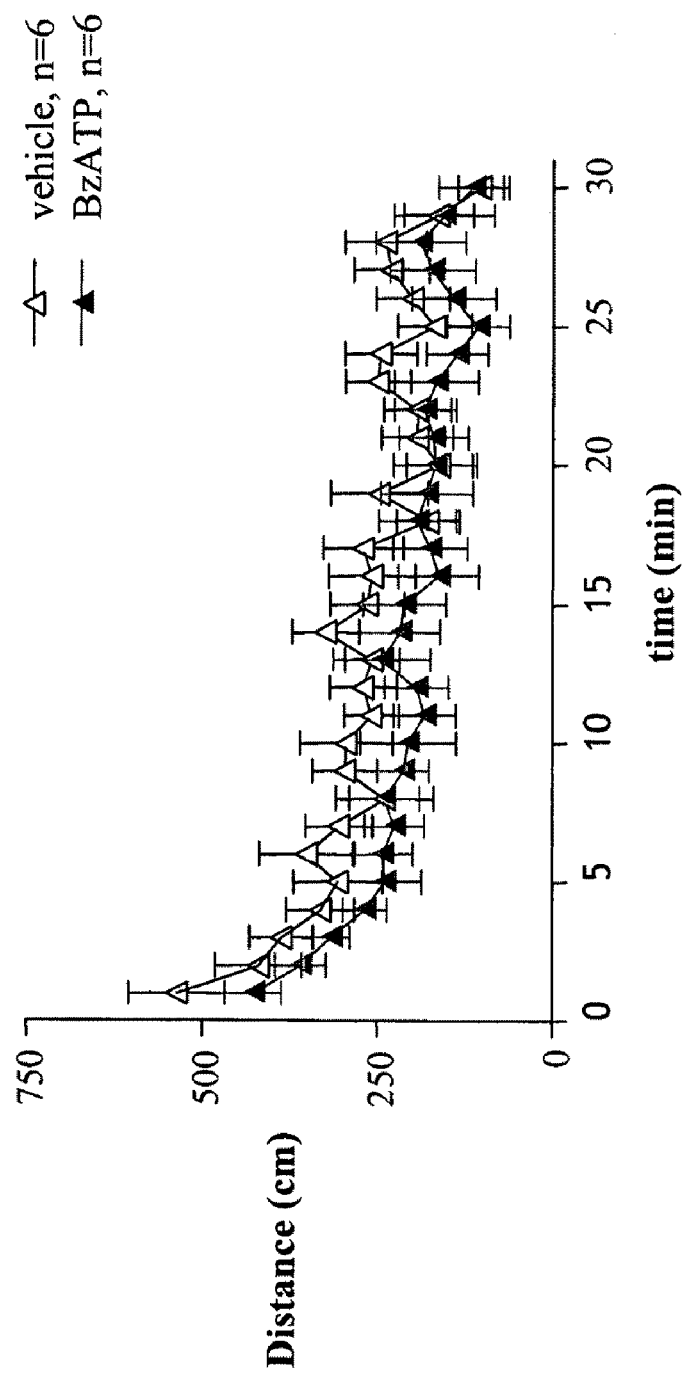

FIG. 21. Open field test measuring locomotor activity of mice treated with a P2X7R agonist compound (BzATP).

Figure 22:
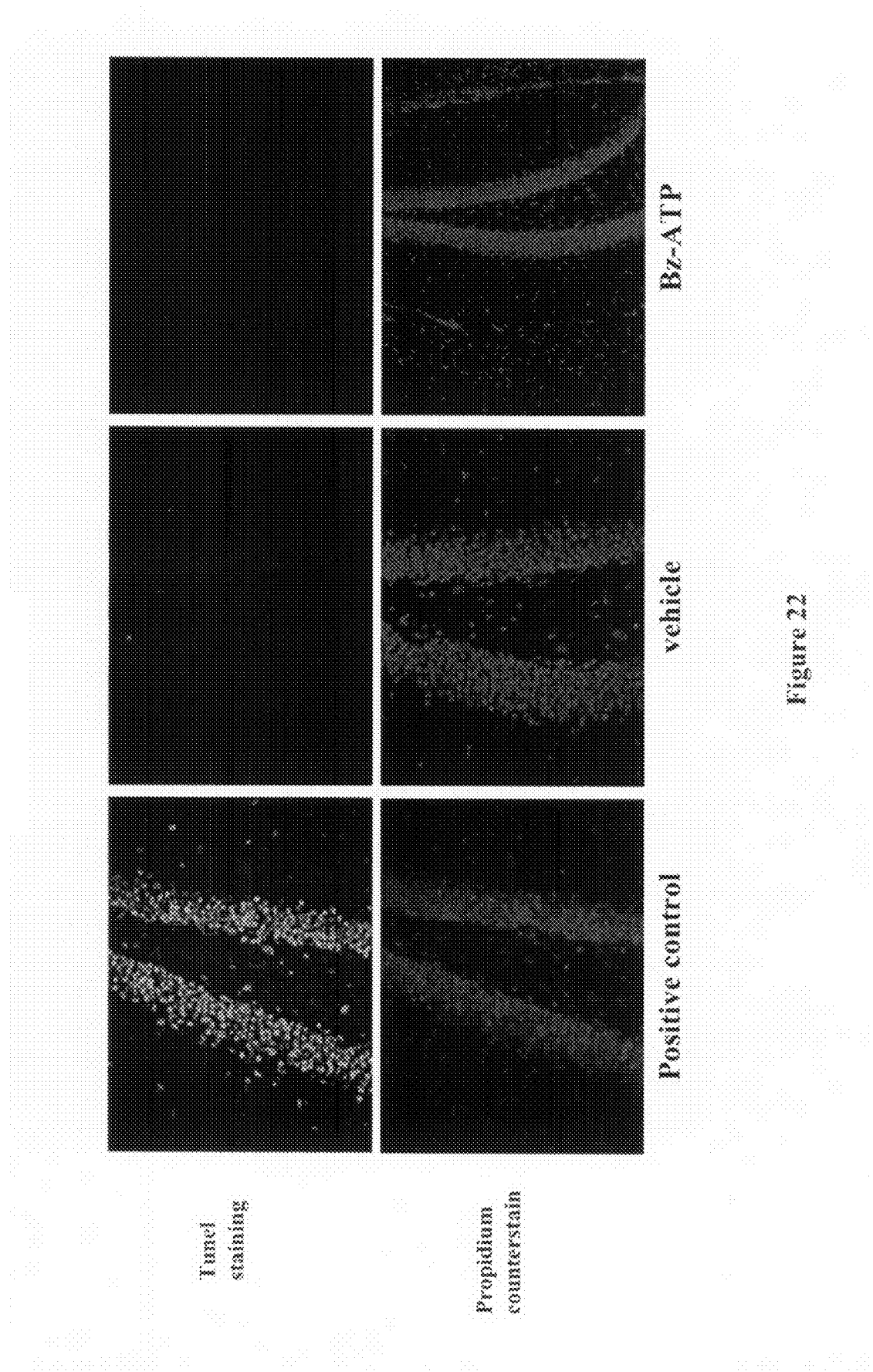

FIG. 22. Comparative analysis of apoptotic cells in the hippocampus of a mouse treated with control vehicle solution or a P2X7R agonist compound (BzATP).

Figure 23:
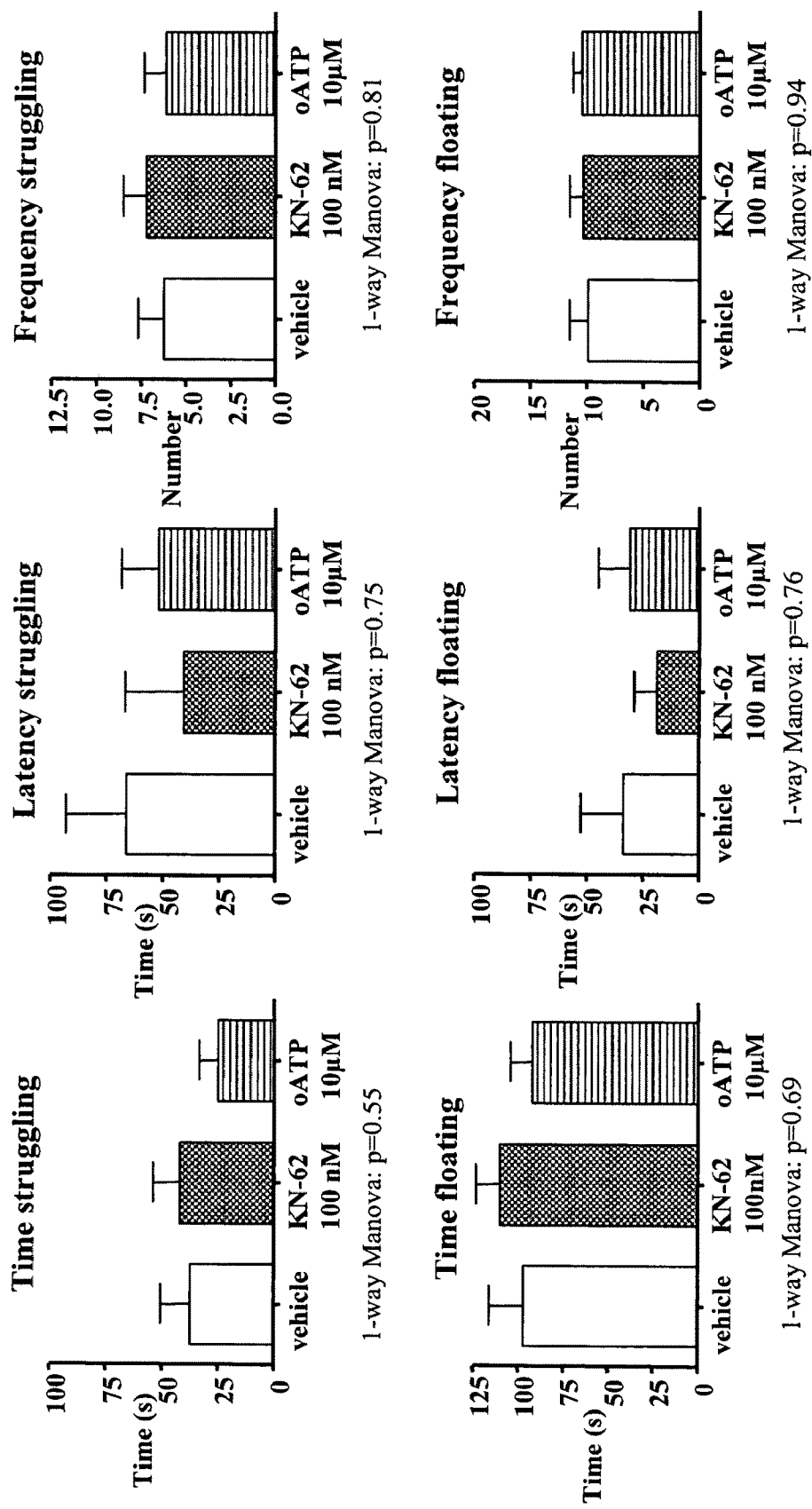

FIG. 23. Effect of intrahippocampal injection of the P2X7R antagonist KN-62 and oATP on behaviour during the forced swim test FIG. 24. Open field test measuring locomotor activity of mice treated with the P2X7R antagonist KN-62 and oATP.

A better understanding of the present invention and of its many advantages will be had from the following examples, offered for illustrative purposes only, and are not intended to limit the scope of the present invention in any way.

EXAMPLE 1

Linkage Analysis of Bipolar Affective Disorder in a Homogeneous Human Population 41 families of different sizes containing a total of 485 sampled individuals from the region of Saguenay/Lac St-Jean were used in the linkage analysis. Individuals were distributed according to their diagnoses as follows: 105 individuals afflicted with Bipolar Disorder type I (BPI) or schizoaffective disorder bipolar type; 42 individuals diagnosed with Bipolar Disorder type II (BPII); 54 individuals with recurrent major depression; and 57 individuals with single episode major depression. The remaining 227 individual were unaffected and normal. For the purpose of the calculation, the following classification was used: individuals diagnosed with either BPI, schizoaffective disorder, bipolar type, BPII and recurrent major depression were considered as affected (n=201); individuals with a single major depression episode were scored as unknown phenotype (n=57); and all others diagnoses as unaffected (n=227).

Blood samples from each individual were collected in 10-ml K3 EDTA Vacutainer tube (Becton-Dickinson) and genomic DNA was isolated by Puregene DNA Isolation kit (Gentra Systems). Blood was poured into 50 ml conical tube and diluted with four volume of Red Blood Cell Lysis Solution. After an incubation of 10 minutes at room temperature, the tube was centrifuged for 10 minutes at 2,000 g and supernatant was removed leaving behind cell pellet and 200-400 µl of the residual liquid. Cells were resuspended by vortexing the tube and 9 ml of Cell Lysis Solution were added with up and down pipetting. 40 µl of RNAse A Solution (20 mg/ml) were added and the sample was mixed by inverting the tube several times. Sample was incubated at 37° C. for 15 minutes and cooled to room temperature. 3 ml of Protein Precipitation Solution were added to cell lysate. Tube was vigorously vortexed for 30 seconds and centrifuged at 2,000 g for 10 minutes. Supernatant was poured into a new tube containing 9 ml of 100% isopropanol. Sample was mixed by inverting gently several times. Tube was centrifuged at 2,000 g for 5 minutes. The DNA white pellet was washed with 10 ml 70% ethanol and the tube was centrifuged at 2,000 g for 3 minutes. Ethanol was poured off and pellet allowed to partially air dry. DNA was solubilized in 500 µl of DNA Hydration Solution. Final concentration was adjusted to 300-400 µg/ml.

A fluorescent-based method was used for the genotyping of microsatellite markers. Briefly, the region encompassing each repeated sequence was amplified by PCR using an unlabeled primer and a fluorescent-labeled primer (Applied biosystems inc, CA, USA). The marker-associated dyes and the corresponding PCR product length are listed in table 2. The PCR reaction was performed using 10 ng of DNA sample, 0.2 unit of Taq platinum DNA polymerase (Invitrogene, CA, USA), 20 mM Tris-Cl (pH 8.4), 50 mM KCl, 1.5 mM $MgCl_2$, 100 µM of dNTP, and 1.5 µM of each primer in a final volume of 7 µl. The samples were incubated at 95° C. for 3 minutes to activate the Taq platinum DNA polymerase, then 10 cycles of PCR amplification were performed as follows: 95° C. for 15 seconds; 58° C. for 15 seconds; 72° C. for 30 seconds; after that 15 cycles were performed as follow: 89° C. for 15 seconds; 58° C. for 15 seconds; 72° C. for 30 seconds. Finally, the samples were incubated at 72° C. for 30 min. Following the PCR amplification samples were pooled according to their dye-labeled primer and their PCR product length (pool of four samples). Pooled sample were separated on an ABI 3100 DNA analyzer (Applied Biosystems inc, CA, USA). The resulting data were analysed using Genemapper2 (Applied Biosystems inc, CA, USA), and compiled in a 4D database (ACIUS) designed in a Macintosh environment as previously described (Morissette et al., Am. J. Med. Genet. (Neuropsychiatr. Genet.) 88 (1999), 567-587)

Markers used in the following linkage analysis are shown in table 2. Recombination fraction (q) between successive markers was computed according to the analyzed families.

TABLE 2

Genomic markers used for the linkage analysis

| Locus | Associated dye | Allele length (bp) | Distance (q) | Cumulative distance (cM) | Heterozygosity (%) |
|---|---|---|---|---|---|
| D12S1619 | VIC | 170-210 | 0.0135 | 0.00 | 74.5 |
| NBG11 | VIC | 204-218 | 0.006 | 1.37 | 65.5 |
| D12S1666 | FAM | 241-281 | 0.001 | 1.97 | 66.9 |
| NBG5 | VIC | 253-261 | 0.001 | 2.07 | 38.3 |
| D12S1721 | VIC | 263-299 | 0.005 | 2.17 | 72.1 |
| NBG8 | VIC | 166-188 | 0.011 | 2.67 | 73.3 |
| NBG6 | NED | 182-218 | 0.0115 | 3.79 | 73.9 |
| NBG9 | VIC | 156-180 | 0.0035 | 4.95 | 68.9 |
| NBG10 | FAM | 174-186 | 0.001 | 5.30 | 49.7 |
| NBG12 | NED | 165-207 | 0.009 | 5.40 | 64.2 |
| NBG4 | NED | 171-199 | 0.001 | 6.31 | 66.4 |
| NBG3 | VIC | 182-206 | 0.006 | 6.41 | 64.8 |
| NBG2 | VIC | 171-199 |  | 7.01 | 54.2 |

Haldane's map function was used for cumulative distance in cMorgans.

For bipoint parametric analysis, MOD score analysis were used where parametric LOD score were maximized over genetic models.

The following results were obtained under MOD score analysis for recessive models.

TABLE 3

MOD score analysis for recessive models

| Locus | Distance (q) | Cumulative distance (cM) | LOD score ($q_{max}$) |
|---|---|---|---|
| D12S1619 | 0.0135 | 0.00 | 3.46 (0.10) |
| NBG11 | 0.006 | 1.37 | 4.06 (0.04) |
| D12S1666 | 0.001 | 1.97 | 1.22 (0.14) |
| NBG5 | 0.001 | 2.07 | 0.66 (0.16) |
| D12S1721 | 0.005 | 2.17 | 2.82 (0.10) |
| NBG8 | 0.011 | 2.67 | 1.51 (0.00) |
| NBG6 | 0.0115 | 3.79 | 4.77 (0.06) |
| NBG9 | 0.0035 | 4.95 | 0.75 (0.22) |
| NBG10 | 0.001 | 5.30 | 0.74 (0.00) |
| NBG12 | 0.009 | 5.40 | 1.41 (0.16) |
| NBG4 | 0.001 | 6.31 | 3.56 (0.08) |
| NBG3 | 0.006 | 6.41 | 3.96 (0.08) |
| NBG2 |  | 7.01 | 2.59 (0.10) |

Model-free LOD score studies using ANALYZE, sib_phase from the ASPEX V1.85 package (David Hinds and Neil Risch 1999; ftp://lahmed.stanford.edu/pub/aspex, see also http://watson.hgen.pitt.edu/docs/usage.html) and SIMWALK2 (Sobel and Lange, Am J Hum Genet 58 (1996), 1323-1337) were performed to analyze the allele sharing among affected sib-pairs. The ANALYZE program weights sibships according to their size. The ASPEX sib_phase program uses allele frequencies to reconstruct missing information, and is tailored for data sets where parents are missing, but additional typed children may be used to reconstruct and phase the parents. SimWalk2 is a statistical genetics computer application for haplotype, parametric linkage, non-parametric linkage (NPL), identity by descent (IBD) and mistyping analyses on any size of pedigree. SimWalk2 uses Markov chain Monte Carlo (MCMC) and simulated annealing algorithms to perform these multipoint analyses.

ASPEX sib_phase was used with two computational strategies: First, by using strictly independent sib pairs; secondly, by using all affected sib-pair combinations. ASPEX was performed for bi-point and multipoint calculations.

The bi-point results observed with ANALYZE and ASPEX are shown in Table 4.

TABLE 4

Bi-point results observed with ANALYZE and ASPEX

| Locus | Distance (q) | Cumulative distance (cM) | Sib-pair from ANALYZE LOD score | sib_phase LOD score indep. sib-pairs | sib_phase LOD score all sib-pairs |
|---|---|---|---|---|---|
| D12S1619 | 0.0135 | 0.00 | 2.31 | 2.55 | 3.14 |
| NBG11 | 0.006 | 1.37 | 2.83 | 2.72 | 3.27 |
| D12S1666 | 0.001 | 1.97 | 1.01 | 2.52 | 3.14 |
| NBG5 | 0.001 | 2.07 | 0.50 | 2.52 | 3.13 |
| D12S1721 | 0.005 | 2.17 | 1.57 | 2.51 | 3.12 |
| NBG8 | 0.011 | 2.67 | 0.51 | 2.24 | 2.75 |
| NBG6 | 0.0115 | 3.79 | 2.55 | 2.11 | 2.64 |
| NBG9 | 0.0035 | 4.95 | 0.49 | 1.65 | 1.97 |
| NBG10 | 0.001 | 5.30 | 0.77 | 1.45 | 2.10 |
| NBG12 | 0.009 | 5.40 | 0.47 | 1.44 | 2.17 |
| NBG4 | 0.001 | 6.31 | 1.21 | 1.29 | 3.07 |
| NBG3 | 0.006 | 6.41 | 1.84 | 1.29 | 3.07 |
| NBG2 |  | 7.01 | 1.24 | 1.22 | 3.00 |

SIMWALK2 computed four different statistics based on descent trees. These statistics measure the degree of clustering among the marker alleles descending from the founders. Statistic A is the number of different founder-alleles contributing alleles to the affected it is most powerful at detecting linkage to a recessive trait. Statistic B is the maximum number of alleles among the affected descended from any one founder-allele and most powerful at detecting linkage to a dominant trait. Statistic C is the 'entropy' of the marker alleles among the affected. Statistic D is the extent of allele sharing among all affected pairs as measured by their IBD kinship coefficient. Statistics C and D are more general statistics indicating whether a few founder-alleles are overly represented among the affected.

Table 5 shows the results observed with SIMWALK2. The authors signal that p-values should be generally conservative. They are expressed as −Log(p-values). For correspondence purpose, −Log(0.05)=1.30, −Log(0.01)=2, −Log(0.001)=3 etc.

TABLE 5

SIMWALK2 analysis

| Locus | Distance (q) | Cumul. Distance (cM) | STAT(A) −Log(p-value) | STAT(B) −Log(p-value) | STAT(C) −Log(p-value) | STAT(D) −Log(p-value) |
|---|---|---|---|---|---|---|
| D12S1619 | 0.0135 | 0.00 | 1.4550 | 0.4103 | 1.1306 | 1.1310 |
| NBG11 | 0.006 | 1.37 | 2.0157 | 1.4375 | 1.5955 | 1.9845 |
| D12S1666 | 0.001 | 1.97 | 2.0236 | 0.9765 | 1.4727 | 1.4614 |
| NBG5 | 0.001 | 2.07 | 1.7596 | 0.8558 | 1.3866 | 1.3602 |
| D12S1721 | 0.005 | 2.17 | 1.6628 | 1.1692 | 1.4235 | 1.6384 |
| NBG8 | 0.011 | 2.67 | 1.5374 | 0.6940 | 1.0623 | 1.1552 |
| NBG6 | 0.0115 | 3.79 | 1.5896 | 0.4452 | 1.0935 | 1.1786 |
| NBG9 | 0.0035 | 4.95 | 1.2677 | 0.3815 | 0.8412 | 0.9133 |
| NBG10 | 0.001 | 5.30 | 1.1117 | 0.3642 | 0.6987 | 0.7554 |
| NBG12 | 0.009 | 5.40 | 1.0809 | 0.3485 | 0.6694 | 0.7179 |
| NBG4 | 0.001 | 6.31 | 1.1024 | 0.4148 | 0.6368 | 0.8544 |
| NBG3 | 0.006 | 6.41 | 1.1040 | 0.4146 | 0.6373 | 0.8559 |
| NBG2 | | 7.01 | 1.0963 | 0.5380 | 0.6587 | 0.9356 |

Multipoint result observed with ASPEX when only independent sib-pairs were used (FIG. 1b). The maximum LOD score value was observed at NBG11.

Multipoint result observed with ASPEX when all sib-pairs were considered (FIG. 1c). The maximum LOD score value was observed at NBG11 but a second peak appeared at NBG4 and NBG3.

Multipoint and bi-point LOD score values computed by ASPEX were similar. The second peak, observed when all sib-pairs are used, may be explained by the presence of a recombinant affected individual, with many affected sibs, sharing the chromosomal region telomeric to NBG12. This kind of individuals has a large impact on LOD score values when all sib-pairs are used instead of one sib-pair. This situation was observed in two sibships.

Strata analysis was subsequently performed. Although HOMOG did not detect evidence for heterogeneity, a homogeneity test was constructed based on allele sharing found in selected chromosomal regions. Only 20 of the 41 families were used for this analysis since the others were not genotyped in all these regions. For each marker within the selected regions, the proportion of alleles shared IBD by affected sib-pairs was estimated with ASPEX (sib_phase). For each region retained, the proportion of shared alleles was used as variable for a Principal Component Analysis and the first principal component as an index of linkage. Correlation analysis was done on these indexes to detect heterogeneity (correlation <0) or epistasis (correlation >0). Fisher algorithm was used to classify into two groups of families as linked or unlinked to a particular locus. A negative correlation was observed between the chromosome 12 region and the chromosome 15 area (r=−0.51; p=0.023). Cluster analysis suggested that 11 families out of 20 were linked to chromosome 12. This sub-sample was called the strata.

This strata included 11 families (266 sampled individuals) that include 52 BPI or schizoaffective disorder, bipolar type, 20 BPII and 28 recurrent major depression The following MOD score values illustrated in Table 6 were obtained under recessive models.

TABLE 6

MOD scores under recessive models

| Locus | Distance (q) | Cumulative distance (cM) | LOD score ($q_{max}$) |
|---|---|---|---|
| D12S1619 | 0.0135 | 0.00 | 4.03 (0.08) |
| NBG11 | 0.006 | 1.37 | 4.98 (0.00) |
| D12S1666 | 0.001 | 1.97 | 1.49 (0.12) |
| NBG5 | 0.001 | 2.07 | 0.79 (0.14) |
| D12S1721 | 0.005 | 2.17 | 4.23 (0.06) |
| NBG8 | 0.011 | 2.67 | 2.79 (0.00) |
| NBG6 | 0.0115 | 3.79 | 5.06 (0.06) |
| NBG9 | 0.0035 | 4.95 | 1.57 (0.14) |
| NBG10 | 0.001 | 5.30 | 1.73 (0.00) |
| NBG12 | 0.009 | 5.40 | 1.65 (0.12) |
| NBG4 | 0.001 | 6.31 | 4.60 (0.08) |
| NBG3 | 0.006 | 6.41 | 4.84 (0.06) |
| NBG2 | | 7.01 | 2.80 (0.06) |

Model-free LOD score results obtained with ANALYZE and ASPEX applied to the strata are shown in Table 7.

TABLE 7

Model-free LOD score obtained with ANALYZE and ASPEX

| Locus | Distance (q) | Cumulative distance (cM) | ANALYZE LOD score | sib_phase LOD score independent sib-pairs | sib_phase LOD score all sib-pairs |
|---|---|---|---|---|---|
| D12S1619 | 0.0135 | 0.00 | 4.54 | 5.29 | 7.65 |
| NBG11 | 0.006 | 1.37 | 4.29 | 5.34 | 7.70 |
| D12S1666 | 0.001 | 1.97 | 2.77 | 5.36 | 7.74 |
| NBG5 | 0.001 | 2.07 | 0.67 | 5.36 | 7.74 |
| D12S1721 | 0.005 | 2.17 | 4.48 | 5.35 | 7.74 |
| NBG8 | 0.011 | 2.67 | 2.97 | 4.87 | 7.00 |
| NBG6 | 0.0115 | 3.79 | 4.05 | 4.59 | 6.76 |
| NBG9 | 0.0035 | 4.95 | 2.03 | 3.72 | 5.41 |
| NBG10 | 0.001 | 5.30 | 2.00 | 3.42 | 5.89 |
| NBG12 | 0.009 | 5.40 | 0.89 | 3.44 | 6.11 |
| NBG4 | 0.001 | 6.31 | 2.84 | 3.71 | 9.00 |
| NBG3 | 0.006 | 6.41 | 3.89 | 3.71 | 9.01 |
| NBG2 | | 7.01 | 1.91 | 3.52 | 8.73 |

Model-free results observed with SIMWALK2 are illustrated in Table 8.

TABLE 8

Model-free LOD score obtained with SIMWALK2

| Locus | Distance (q) | Cumulative Distance (cM) | STAT(A) −Log(p-value) | STAT(B) −Log(p-value) | STAT(C) −Log(p-value) | STAT(D) −Log(p-value) |
|---|---|---|---|---|---|---|
| D12S1619 | 0.0135 | 0.00 | 2.5963 | 0.9565 | 3.2156 | 2.3584 |
| NBG11 | 0.006 | 1.37 | 3.0698 | 1.7400 | 3.7747 | 3.0103 |
| D12S1666 | 0.001 | 1.97 | 2.9340 | 1.6546 | 3.5812 | 2.7223 |
| NBG5 | 0.001 | 2.07 | 2.9781 | 1.2722 | 3.6505 | 2.7846 |
| D12S1721 | 0.005 | 2.17 | 2.9680 | 1.2630 | 3.6844 | 2.7752 |
| NBG8 | 0.011 | 2.67 | 3.0954 | 1.0804 | 3.4399 | 2.5654 |
| NBG6 | 0.0115 | 3.79 | 3.1632 | 1.0672 | 3.2670 | 2.5956 |
| NBG9 | 0.0035 | 4.95 | 2.2106 | 1.0137 | 2.7765 | 2.4456 |
| NBG10 | 0.001 | 5.30 | 2.5513 | 1.0251 | 2.7625 | 2.1914 |
| NBG12 | 0.009 | 5.40 | 2.4893 | 0.9868 | 2.6841 | 2.0920 |
| NBG4 | 0.001 | 6.31 | 2.9028 | 1.1312 | 3.4063 | 2.8156 |
| NBG3 | 0.006 | 6.41 | 2.9070 | 1.1326 | 3.4637 | 2.8300 |
| NBG2 | | 7.01 | 2.8430 | 1.1108 | 3.3135 | 2.7978 |

Multipoint results on the strata with ASPEX sib_phase by considering only independent sib-pairs (FIG. 1b) or all sib-pairs (FIG. 1c) are shown in FIGS. 1d and 1e. As previously reported a second peak appeared when all sib-pairs were observed.

A confidence interval was calculated. GENEFINDER (Liang et al., Am. J. Hum. Genet. 66 (2000), 1631-1641) was used to estimate the location of the susceptibility gene (say t). The method is based on the IBD (Identity by Descent) sharing of affected sib-pairs for multiple markers. For the purpose of our analysis, pedigrees were divided into sibship. 56 nuclear families and 183 sib-pairs were used. Liang K Y, Huang C Y, Beaty T H (2000) A unified sampling approach for multipoint analysis of qualitative and quantitative traits in sib pairs. Am J Hum Genet 66:1631-1641

The GENEFINDER results points to localization of a susceptibility gene for affective disorders at 3.19±0.446 cM telomeric to the marker D12S1721 (D12S1721 is approximately located at 136.82 cM on the sex-averaged Marshfield chromosome 12 map).

| | |
|---|---|
| 95% | C.I.: [2.32, 4.06]; |
| 99% | C.I.: [2.03, 4.35] |
| 99.9% | C.I.: [1.71, 4.67] |

From the strata, 24 nuclei, and 107 sib-pairs were obtained, and the location of the susceptibility gene was estimated at 3.07±0.57 (see map above). The following confidence interval (C.I.) was obtained:

| | |
|---|---|
| 95% | C.I.: [1.95, 4.19]; |
| 99% | C.I.: [1.59, 4.55] |
| 99.9% | C.I.: [1.18, 4.96] |

An association study using the NBG microsatellite markers was done with CLUMP (Sham & Curtis, Ann. Hum. Genet. 59 (1995), 97-105). Samples were distributed as follow: 83 male/case; 124 female/case; 95 male/control; and 101 female/control. One thousand simulations were used to estimate p-values. The observed results are summarized in Table 9.

TABLE 9

Association study using the NBG microsatellite

| | Sample | | T1 statistic (p-value) | T2 statistic (p-value) | T3 statistic (p-value) | T4 statistic (p-value) |
|---|---|---|---|---|---|---|
| Locus | Case | Control | | | | |
| NBG11 | 204 | 129 | 0.226 | 0.562 | 0.410 | 0.421 |
| NBG5 | 206 | 194 | 0.972 | 0.980 | 0.948 | 0.971 |
| NBG8 | 206 | 194 | 0.983 | 1.000 | 0.994 | 0.978 |
| NBG6 | 206 | 194 | 0.147 | 0.074 | 0.759 | 0.485 |
| NBG9 | 206 | 190 | 0.512 | 0.940 | 0.786 | 0.583 |
| NBG10 | 206 | 190 | 0.594 | 0.480 | 0.403 | 0.709 |
| NBG12 | 206 | 190 | 0.002 | 0.019 | 0.003 | 0.117 |

T1 statistic is the usual chi-squared statistic on the raw contingency table
T2 statistic is the usual chi-squared statistic apply on he contingency table obtained after collapsing columns with small expected values together
T3 statistic is the largest chi-squared statistic got by comparing one column of the original table against the total of the others columns
T4 statistic is the largest chi-squared statistic got by comparing any combination of alleles against the rest.

Only the NBG12 marker gave significant association at the 1% level. For the others markers, there was no single alleles that seems to be associated with bipolar disorder. It seems that no founder-alleles was overly represented among the affected. There is no significant result for association of genotypes with the NBG markers.

Further microsatellite marker based association studies using CLUMP was performed on samples containing additional control and case individuals. One thousand simulations were used to estimate p-values.

TABLE 9a

Empirical p-values observed with CLUMP for statistics T1 and T3 for allelic and genotypic analyses of microsatellite markers

| | | | Alleles | | Genotypes | |
|---|---|---|---|---|---|---|
| Name | Effective case | controls | T1 (p-value) | T3 (p-value) | T1 (p-value) | T3 (p-value) |
| NBG11 | 204 | 98 | 0.250 | 0.421 | 0.680 | 0.553 |
| D12S1666 | 208 | 175 | 0.366 | 0.543 | 0.393 | 0.476 |
| NBG5 | 213 | 179 | 0.969 | 0.934 | 0.997 | 1.000 |
| D12S1721 | 210 | 176 | 0.693 | 0.463 | 0.805 | 0.838 |
| NBG8 | 213 | 179 | 0.754 | 0.921 | 0.973 | 0.929 |
| NBG6 | 213 | 179 | 0.008 | 0.356 | 0.172 | 0.449 |

TABLE 9a-continued

Empirical p-values observed with CLUMP for statistics
T1 and T3 for allelic and genotypic analyses of microsatellite markers

| | | | | Alleles | Genotypes | |
|---|---|---|---|---|---|---|
| Name | Effective case | controls | T1 (p-value) | T3 (p-value) | T1 (p-value) | T3 (p-value) |
| NBG9 | 213 | 175 | 0.759 | 0.768 | 0.690 | 0.606 |
| NBG10 | 213 | 175 | 0.521 | 0.178 | 0.122 | 0.173 |
| D12S1349 | 212 | 180 | 0.887 | 0.864 | 0.782 | 0.816 |
| NBG12 | 213 | 175 | 0.002 | <10$^{-3}$ | 0.018 | 0.552 |
| NBG4 | 207 | 178 | 0.418 | 0.506 | 0.813 | 0.545 |
| NBG3 | 209 | 175 | 0.171 | 0.829 | 0.601 | 0.897 |
| D12S378 | 211 | 180 | 0.171 | 0.405 | 0.540 | 0.560 |
| NBG2 | 210 | 170 | 0.896 | 0.749 | 0.210 | 0.613 |
| D12S1614 | 210 | 179 | 0.803 | 0.692 | 0.710 | 0.831 |
| D12S342 | 211 | 180 | 0.394 | 0.740 | 0.445 | 0.622 |
| D12S340 | 209 | 179 | 0.890 | 0.869 | 0.895 | 0.838 |
| D12S1639 | 209 | 180 | 0.087 | 0.170 | 0.652 | 0.295 |
| D12S1634 | 211 | 181 | 0.361 | 0.248 | 0.505 | 0.590 |
| D12S2075 | 203 | 181 | 0.023 | 0.157 | 0.085 | 0.451 |

HWE hypothesis was satisfied at the 5% level for each microsatellite marker after application of the conservative Bonferroni corrections for multiple testing (Bland & Altman, Brit. J. Med. 310 (1995) 170). Table 9a lists empirical p-values observed with CLUMP for allele and genotype association analyses. Empirical p-values less than 0.005 were observed at marker NBG12 for T1 and T3 statistics under allelic association analysis. T1 statistic suggested allelic association between bipolar affective disorders and NBG6 (empirical p-value=0.008). Moreover, a barely significant empirical p-value of 0.023 was observed at the most distal marker D12S2075.

In conclusion, the parametric and model-free multipoint results suggest to investigate genes located between D12S1619 and D12S1666. Moreover, according to GENEFINDER results, genes situated centromeric to NBG9 should be considered for association and linkage disequilibrium analysis. Moreover, positive association was seen with the NBG6 marker, which is located in intron 9 of the P2X7R gene.

EXAMPLE 2

Physical Mapping and Mutation Analysis of Chromosome 12 Associating the P2X7R to Bipolar Affective Disorders The most conservative prediction for the disease-associated region is included between markers NBG11 and NBG2 (see FIG. 1a). This region was delimited according to linkage and association analysis described in Example 1, using genethon markers and NBG markers. The approximate length of this region is 5.2 Mb. Two major gaps (between FLJ10701 and FLJ32372, and between FLJ1466 and MONDOA) were included in this region. At least 73 genes were listed in this area, where 48 are known genes and 25 are unknown but associated to mRNA and/or EST clusters based on the last genome assembly available at UCSC (November 2002). Predicted genes were not listed. However, the estimation of CI 99% (confidence interval) using GENEFINDER has limited the most interesting region between markers D12S1666 and NBG9. This genomic region covers 1.6 Mb and includes at least 28 genes, and has no major gap. Thus, the term fBAD (familial Bipolar Affective Disorders) region was used to describe the genomic segment between D12S1666 and NBG9. Genes found within this region include CaMKK2, CABP, P2X7, P2X4, PIN, PLA2, G1B, CIT, PXN, Rab35, and APC5. However, given the present art, it would not have been obvious to an ordinary person skilled in the art to select P2X7R as the gene associated with affective diseases. Other genes from the ones listed above would be obvious.

For example, the CaMKK2 gene (also known as $Ca^{2+}$/Calmodulin-dependent protein kinase kinase beta, or CaMKKb) is a serine/threonine protein kinase involved in $Ca^{2+}$ dependent signalling pathways. CaMKK2 can activate in vitro the downstream kinases CaMKIV and CaMKI, which modulate gene transcription through phosphorylation of transcription factors (e.g., CREB, SRF, MEF2; Corcoran and Means, J. Biol. Chem. 276 (2001), 2975-2978; Soderling, Trends Biochem. Sci. 24 (1999), 232-236). Its role in the $Ca^{2+}$ cascade is not critical. Some studies suggest that CaMKs could be activated without the CaMKKs phosphorylation (Matsushita and Nairn, J. Biol. Chem. 274 (1998), 10086-10093). However, CaMKK phosphorylation step would contribute to amplification of the $Ca^{2+}$ signal since CaMKK is more sensitive to activation by $Ca^{2+}$/Calmodulin, therefore CaMKK would be an important mediator when the levels of intracellular $Ca^{2+}$ are low (Anderson et al., J. Biol. Chem. 273 (1998), 31880-31889).

CaMKK2 is an obvious target for depression since prior art suggest that cAMP-dependent signaling pathways (mediated by PKA activation) is affected in brain from patients with Bipolar Affective Disorders (Field et al., J. Neurochem. 73 (1997), 1704-1710; Rahman et al., J. Neurochem. 68 (1997), 297-304; Takahashi et al., J. Neurosci. 19 (1999), 610-618). According to a study using lymphoblastic cell lines, Bipolar disorder could be related to a elevated intracellular calcium levels (Yoon et al., Mol. Psychiatry 6 (2001), 678-683). Moreover, some groups found relations between antidepressant drugs and CaMK activation (Budziszewska et al., Br. J. Pharmacol. 130 (2000), 1385-1393; Consogno et al., Neuropsychopharmacology 24 (2001), 21-30; Mori et al., Neuropharmacology 40 (2001), 448-456; Zanotti et al., Neuropharmacology 37 (1998), 1081-1089). Furthermore, inhibition of CaMKK by PKA-mediated phosphorylation suggest a close relationship between both pathways (Matsushita et al., J. Biol. Chem. 273 (1999), 21473-21481). These observations would suggest to a person skilled in the art that CaMKK2 is the gene responsible for bipolar affective disease.

Another obvious candidate for affective disorders would have been the CABP1 gene which generates four neuronal $Ca^{2+}$-binding protein by alternative usage of the 9 coding exons, which are L-CABP, S-CABP, calbrain, and caldendrin (Haeseleer et al., J. Biol. Chem. 275 (2000), 1247-1260). Their expression is almost totally restricted to brain tissues. A functional study on calbrain reveals its negative effect on $Ca^{2+}$/Calmodulin-dependent CaMKII activity by competitively interacts with the CaM-binding domain of CaMKII (Yamagushi et al., J. Biol. Chem. 274 (1999), 3610-3616). One would expect similar roles in $Ca^{2+}$ signaling for other CABP1 alternative products. Participation of CABP1 gene in $Ca^{2+}$-dependent signaling pathways would make it obvious to one skilled in the art to select this gene as a candidate for bipolar affective disorder. However, all CABP1 exons were analyzed for the presence of mutations, and surprisingly only two mutations were detected in noncoding regions.

The PIN gene (Protein inhibitor of NOS (Nitric oxide synthase)) is another obvious candidate responsible for bipolar affective disorder. Nitric oxide (NO) in the brain, may be involved in apoptosis, synaptogenesis, and neuronal development. Because NO cannot be stored in vesicles like other neurotransmitters, its release is regulated by the activity of NOS (Nitric oxide synthase). PIN is a direct inhibitor of NOS by binding and destabilizing the active homodimer complex of NOS (Jaffrey et al., Science 274 (1996), 774-777). PIN is highly conserved throughout the evolution and is expressed in many cell types. A recent clinical study evaluating plasma nitrate levels in depressive states suggests that NO production is increased in depression (Suzuki et al., J. Affect. Disord. 63 (2001), 221-224) and may result from a deficiency in NOS inhibition. Moreover in a mouse model, NO synthase antagonists have been linked to antidepressant properties (Harkin et al., 1999; Karolewicz et al., Eur. J. Pharmacol. 372 (1999), 215-220). Thus, PIN would be an obvious However, due to the pleitrophic action of NO, a deficiency in PIN function would generate many unrelated disorders throughout the body. Thus, without the information presented in the disclosure herein, a person of ordinary skills in the art would have predicted PIN and not P2X7R as the gene associated with affective disorders.

The human phospholipase A2 group IB (PLA2G1B) catalyses the release of fatty acids from glycero-3-phosphocholines. Phospholipase A2 genes (PLA2) are expressed in many tissues. Some studies have demonstrated associations between excessive PLA2 activity in brain and affective disorders (Chang et al., Neurochem. Res. 23 (1998), 887-892; Hibbeln et al., Biol. Psychiatry 25 (1989), 945-961). Moreover, other genetic studies have found associations between PLA2G1B gene and bipolar affective disorder (Dawson et al., Psychiatr. Genet. 5 (1995), 177-180). Thus, PLAG1B represent a likely candidate for affective disorders. However in the present example, only a single silent mutation was found within exon 3 of the PLAG1B gene.

The human citron kinase gene, Rho-associated protein (CIT) is a 183 kDa protein which associates to the GTPase Rho. CIT shares strong similarity with ROCK and ROK proteins which are other Rho-associated kinases (Madaule et al., Nature 394 (1998), 491-494). Rho GTPases are involved in many processes such as cytoskeletal organization, membrane trafficking, cell growth, and transcriptional activation (Van Aelst and D'Souza-Schorey, Genes Dev. 11 (1997), 2295-2322). Studies on brain variants of Citron-K (without the kinase domain) reveal the association with postsynaptic density proteins (PSD-95), suggesting a role in either synapse organization or function (Zhang et al., J. Neurosci. 19 (1999), 96-108; Furuyashiki et al., J. Neurosci. 19 (1999), 109-118).

The human paxillin (PXN) gene encodes for a 68 kDa protein found in focal adhesions. It is within focal adhesions where adhesion molecules dynamically interact with the cytoskeleton (Salgia et al., J. Biol. Chem. 270 (1995), 5039-5047). The signaling pathways that regulate these dynamic interactions begin to be elucidated. Many observations suggest that paxillin is involved in transducing signals from growth factor receptors to focal adhesions. The paxillin is expressed in many tissues including brain.

However as set forth below, the gene causative for affective diseases is identified as being the P2X7 receptor (P2X7R).

Mutations were searched in coding sequences and exon-intron boundaries of the above mentioned genes since such mutations are more likely to give a functionally significant Single Nucleotide Polymorphisms (SNP). The starting sample was composed of 16 unrelated affected individuals from the Saguenay/Lac St-Jean region, which gives an 80% power to detect polymorphisms with a frequency of 0.05. To identify polymorphisms, targeted sequences were first amplified by PCR. Then, PCR products are purified on Whatman GF/C membranes (VWR, Montreal, Canada), and quantified using the PicoGreen dsDNA quantitation assay (Molecular probes, Oregon, USA). 4 ng of purified PCR products are sequenced using the DYEnamic ET terminator cycle sequencing kit (Amersham Biosciences, Baie D'Urfé, Canada). The sequencing products are resolved on an ABI PRISM 3730XL DNA analyzer, and an ABI PRISM 3700 DNA analyzer. The PCR products are sequenced in both directions. The SNPs identified in studied genes are listed in Table 10.

TABLE 10

Mutation analysis between markers D12S1666 and NBG9

| Genes | Positions | Variations | Alleles | Modifications |
|---|---|---|---|---|
| Rab35 | Exon06 | RABE06A | 486G-A | Silent Asn162 |
| Rab35 | Intron04 | RABI04A | 51C-T | unknown |
| Rab35 | Intron03 | RABI03A | 33G-A | unknown |
| Rab35 | Intron02 | RABI02B | 85G-A | unknown |
| Rab35 | Intron02 | RABI02A | 76C-G | unknown |
| PXN | Exon11 | PXNE11A | 1527C-T | Silent Thr509 |
| PXN | Exon06 | PXNE06A | 750C-T | Silent Ser250 |
| PXN | Exon02 | PXNE02A | 217G-A | Gly73Ser |
| PLA2G1B | Exon03 | PLA2G1BE03A | 294C-T | Silent Ser98 |
| PIN | 5'UTR01 | PINUTR01A | -49T-G | unknown |
| PIN | 5'UTR01 | PINUTR01B | -80T-C | unknown |
| PIN | Intron02 | PINI02A | 26C-T | unknown |
| PIN | Intron02 | PINI02B | 50C-T | unknown |
| CaBP | Intron04 | CaBPI04A | 35C-T | unknown |
| CaBP | exon01 | CaBPE01A | -23A-G | unknown |
| OASL | Exon02 | OASLE02A | 213G-T | Silent Gly72 |
| OASL | Exon02 | OASLE02B | 408C-T | Silent Leu136 |
| OASL | Exon05 | OASLE05A | 1042G-A | Val348Met |
| OASL | Exon06 | OASLE06A | 1509G-A | Silent Ser503 |

TABLE 10-continued

Mutation analysis between markers D12S1666 and NBG9

| Genes | Positions | Variations | Alleles | Modifications |
|---|---|---|---|---|
| P2X7R | 5'UTR | P2XR7UTR5L | 362T-C | unknown |
| P2X7R | 5'UTR | P2XR7UTR5M | 532T-G | unknown |
| P2X7R | 5'UTR | P2XR7UTR5K | 1100A-G | unknown |
| P2X7R | 5'UTR | P2XR7UTR5J | 1122A-G | unknown |
| P2X7R | 5'UTR | P2XR7UTR5I | 1171C-G | unknown |
| P2X7R | 5'UTR | P2XR7UTR5F | 1351T-C | unknown |
| P2X7R | 5'UTR | P2XR7UTR5N | 1702G-A | unknown |
| P2X7R | 5'UTR | P2XR7UTR5G | 1731T-G | unknown |
| P2X7R | 5'UTR | P2XR7UTR5H | 1860C-T | unknown |
| P2X7R | 5'UTR | P2XR7UTR5A | 2162C-A | unknown |
| P2X7R | 5'UTR | P2XR7UTR5B | 2238C-T | unknown |
| P2X7R | 5'UTR | P2XR7UTR5D | 2373A-G | unknown |
| P2X7R | 5'UTR | P2XR7UTR5E | 2569G-A | unknown |
| P2X7R | 5'UTR | P2XR7UTR5C | 2702G-A | unknown |
| P2X7R | Intron01 | P2XR7I01C | 3166G-C | unknown |
| P2X7R | Intron01 | P2XR7I01A | 24778C-T | unknown |
| P2X7R | Intron01 | P2XR7I01B | 24830C-T | unknown |
| P2X7R | Exon02 | P2XR7v02A | 24942T-C | Val76Ala |
| P2X7R | Exon03 | P2XR7E03A | 26188C-T | Arg117Trp |
| P2X7R | Intron03 | P2XR7I03A | 26308A-G | unknown |
| P2X7R | Intron03 | P2XR7I03B | 26422G-A | unknown |
| P2X7R | Intron04 | P2XR7I04A | 32394G-A | unknown |
| P2X7R | Intron04 | P2XR7v05B | 32434T-C | unknown |
| P2X7R | Exon05 | P2XR7E05D | 32493G-A | Gly150Arg |
| P2X7R | Exon05 | P2XR7v05A | 32507C-T | Tyr155His |
| P2X7R | Exon05 | P2XR7E05C | 32783C-T | Silent Cys168 |
| P2X7R | Intron05 | P2XR7I05C | 32783A-C | unknown |
| P2X7R | Intron05 | P2XR7I05D | 35309T-C | unknown |
| P2X7R | Intron05 | P2XR7I05B | 35374C-T | unknown |
| P2X7R | Intron05 | P2XR7I05A | 35378A-C | unknown |
| P2X7R | Exon06 | P2XR7E06A | 35438G-A | Glu186Lys |
| P2X7R | Exon06 | P2XR7E06B | 35454T-C | Leu191Pro |
| P2X7R | Intron06 | P2XR7I06C | 35549T-C | unknown |
| P2X7R | Intron06 | P2XR7I06G | 35641G-C | unknown |
| P2X7R | Intron06 | P2XR7I06D | 35725A-C | unknown |
| P2X7R | Intron06 | P2XR7I06F | 36001T-G | unknown |
| P2X7R | Intron06 | P2XR7I06E | 36064A-T | unknown |
| P2X7R | Intron06 | P2XR7I06A | 36091DelGTTT | unknown |
| P2X7R | Intron06 | P2XR7I06B | 36108C-G | unknown |
| P2X7R | Intron07 | P2XR7I07A | 36374C-T | unknown |
| P2X7R | Intron07 | P2XR7I07B | 36378G-A | unknown |
| P2X7R | Intron07 | P2XR7I07C | 36387T-A | unknown |
| P2X7R | Intron07 | P2XR7I07D | 36398G-C | unknown |
| P2X7R | Intron07 | P2XR7I07E | 37439C-T | unknown |
| P2X7R | Intron07 | P2XR7I07F | 37513T-C | unknown |
| P2X7R | Exon08 | P2XR7E08C | 37604C-T | Arg270Cys |
| P2X7R | Exon08 | P2XR7v08A | 37605G-A | Arg270His |
| P2X7R | Exon08 | P2XR7v08B | 37623G-A | Arg276His |
| P2X7R | Exon08 | P2XR7E08D | 37633C-T | Silent Asp279 |
| P2X7R | Intron09 | P2XR7I11A | 47214C-T | unknown |
| P2X7R | Exon11 | P2XR7v11B | 47383G-A | Ala348Thr |
| P2X7R | Exon11 | P2XR7v11C | 47411C-G | Thr357Ser |
| P2X7R | Intron11 | P2XR7I11D | 47563T-C | unknown |
| P2X7R | Intron12 | P2XR7I12A | 54307C-T | unknown |
| P2X7R | Intron12 | P2XR7I12B | 54308G-A | unknown |
| P2X7R | Exon13 | P2XR7v13F | 54399C-T | Ala433Val |
| P2X7R | Exon13 | P2XR7v13A | 54480A-G | Gln460Arg |
| P2X7R | Exon13 | P2XR7v13B | 54523C-T | Silent Pro474 |
| P2X7R | Exon13 | P2XR7v13G | 54562DelCCCTGAGAG CCACAGGTGCCT | Del of 7aa 488 to 494 PESHRCL |
| P2X7R | Exon13 | P2XR7v13C | 54588A-C | Glu496Ala |
| P2X7R | Exon13 | P2XR7v13H | 54664C-G | Silent His521 |
| P2X7R | Exon13 | P2XR7E13D | 54703G-T | Silent Leu534 |
| P2X7R | Exon13 | P2XR7E13J | 54804A-T | Ile568Asn |
| P2X7R | Exon13 | P2XR7v13I | 54834G-A | Arg578Gln |
| P2X7R | Exon13 | P2XR7v13E | 54847G-A | Silent Pro582 |
| P2X7R | 3'UTR | P2XR7UTR3A | 55169C-A | unknown |
| P2X7R | 3'UTR | P2XR7UTR3B | 55170A-C | unknown |
| P2X7R | 3'UTR | P2XR7UTR3C | 55171A-C | unknown |
| P2X7R | 3'UTR | P2XR7UTR3D | 55917C-T | unknown |
| P2X7R | 3'UTR | P2XR7UTR3E | 54925G-A | unknown |

TABLE 10-continued

Mutation analysis between markers D12S1666 and NBG9

| Genes | Positions | Variations | Alleles | Modifications |
|---|---|---|---|---|
| P2X4R | 5'UTR | P2XR4UTR5I | -1956G-A | unknown |
| P2X4R | 5'UTR | P2XR4UTR5H | -1649G-A | unknown |
| P2X4R | 5'UTR | P2XR4UTR5G | -800G-A | unknown |
| P2X4R | 5'UTR | P2XR4UTR5A | -648C-A | unknown |
| P2X4R | 5'UTR | P2XR4UTR5B | -537A-G | unknown |
| P2X4R | 5'UTR | P2XR4UTR5C | -437A-G | unknown |
| P2X4R | 5'UTR | P2XR4UTR5J | -206VNRG | unknown |
| P2X4R | 5'UTR | P2XR4UTR5D | -211C-G | unknown |
| P2X4R | 5'UTR | P2XR4UTR5F | -150VNRGGGCCCC | unknown |
| P2X4R | 5'UTR | P2XR4UTR5E | -98G-T | unknown |
| P2X4R | Intron01 | P2XR4I01A | 31G-T | unknown |
| P2X4R | Exon02 | P2XR4E02A | 262G-A | Silent mutation Ala87 |
| P2X4R | Intron02 | P2XR4I02A | 4600C-T | unknown |
| P2X4R | Intron03 | P2XR4I03A | 15G-A | unknown |
| P2X4R | Intron03 | P2XR4I03B | 72G-A | unknown |
| P2X4R | Exon04 | P2XR4E04A | 355G-A | Ile119Val |
| P2X4R | Exon04 | P2XR4E04A | 375G-A | Silent Val125 |
| P2X4R | Intron04 | P2XR4I04B | 17T-C | unknown |
| P2X4R | Intron04 | P2XR4I04A | 32G-A | unknown |
| P2X4R | Exon05 | P2XR4E05A | 465T-C | Silent Ser155 |
| P2X4R | Exon07 | P2XR4E07A | 724A-G | Ser242Gly |
| P2X4R | Intron08 | P2XR4I08A | DelT | unknown |
| P2X4R | Exon09 | P2XR4E09A | 944A-G | Tyr315Cys |
| P2X4R | Intron10 | P2XR4I10A | 11G-T | unknown |
| P2X4R | Intron10 | P2XR4I10B | G-C | unknown |
| P2X4R | Intron10 | P2XR4I10C | A-G | unknown |
| P2X4R | Intron11 | P2XR4I11B | C-G | unknown |
| P2X4R | Intron11 | P2XR4I11C | T-A | unknown |
| P2X4R | Intron11 | P2XR4I11A | 374C-T | unknown |
| CaMKK2 | 3'UTR | CaMKK2UTR3bA | 733C-T | unknown |
| CaMKK2 | 3'UTR | CaMKK2UTR3aB | 390G-A | unknown |
| CaMKK2 | 3'UTR | CaMKK2UTR3aA | 239G-A | unknown |
| CaMKK2 | Intron15 | CaMKK2I15B | 325T-C | unknown |
| CaMKK2 | Intron15 | CaMKK2I15A | 169G-A | unknown |
| CaMKK2 | Intron14 | CaMKK2I14A | 224A-G | unknown |
| CaMKK2 | Intron10 | CaMKK2I10A | 156DelGTGATCCGCCTG | unknown |
| CaMKK2 | intron09 | CaMKK2I09B | 528A-G | unknown |
| CaMKK2 | intron09 | CaMKK2I09A | 521A-G | unknown |
| CaMKK2 | Exon09 | SNP6f18v5 | 1095C-A | Silent Ile365 |
| CaMKK2 | Exon09 | SNP6f18v4 | 1087C-T | Arg363Cys |
| CaMKK2 | Exon05 | CaMKKE05A | 687C-T | Silent Pro229 |
| CaMKK2 | Intron03 | CaMKK2I03A | 10C-T | unknown |
| CaMKK2 | Intron02 | CaMKK2I02A | 39C-T | unknown |
| CaMKK2 | Intron01 | CaMKK2I01B | 2911G-C | unknown |
| CaMKK2 | Intron01 | CaMKK2I01A | 89C-A | unknown |
| CaMKK2 | Exon01 | SNP6f18v2 | 253A-T | Thr85Ser |
| CaMKK2 | Exon01 | SNP6f18v1 | 29G-A | Ser10Asn |
| CaMKK2 | 5'UTR01 | CaMKK2UTR01B | 253T-C | unknown |
| CaMKK2 | 5'UTR01 | CaMKK2UTR01A | 63C-A | unknown |
| APC5 | Intron01 | APC5I01A | 10G-T | unknown |
| APC5 | Intron01 | APC5I01B | 50A-T | unknown |
| APC5 | Intron05 | APC5I05A | 73T-C | unknown |
| APC5 | Intron06 | APC5I06A | 73T-G | unknown |
| APC5 | Exon11 | APC5E11A | 1416C-T | Silent His472 |

Each SNP in genes Rab35, PXN, PLA2G1B, PIN, CaBP, OASL, P2X4R, CaMKK2 and APC5 was designated according to the gene where it was found, and its location in that gene (intronic or exonic regions). Each SNP in the P2X7R gene was designated according to their position on SEQ ID NO: 1. The allele describes the position and the variation observed. In coding regions, the position is relative to the start codon, whereas the intronic SNPs are positioned relative to the beginning of the corresponding intron (when known). Primers used for identifying the SNPs in the P2X7R and the location of each SNPs included in tables 2 and 12 are defined in table 1a and SEQ ID NOs 52 to 111.

Association studies using missense SNPs were performed. Missense SNPs or SNPs that could be close to the splice sites were used, because it is more likely that diseases would be associated to an improper function in proteins. Case group was composed by bipolar I individuals, schizoaffective bipolar type (182 subjects) and bipolar II diagnosed persons (31 subjects). Many controls from the Saguenay/Lac-St-Jean region, were sampled from Steinert, Glaucoma and Paget DNA banks. The control individuals were not diagnosed for affective disorders. According to the lifetime risks of bipolar disorders (1%), there is no need to screen controls for psychiatric disorders.

Direct sequencing of PCR products is by far the most accurate method of analysis and is the method of choice in view of our sequencing platform capacity. PCR products were analyzed by direct sequencing as described above. After sequencing analysis, individuals are automatically typed for the corresponding SNP using a home-developed program, GENO.pl. The results of SNP genotyping are compiled in a 4D database.

The association hypothesis was tested with CLUMP (Sham & Curtis 1995, Ann. Hum. Genet. 59:97-105). One thousand simulations were used to estimate p-values. Results are illustrated in table 11. The T1 statistic, which is the usual chi-squared statistic on the raw contingency table, was used to test for allelic association. Moreover, the largest chi-squared statistic got by comparing one column of the original table against the total of the other columns, called T3 statistic, was added to the previous one to test for potential genotype association since T1 statistic results may be biased when the contingency table contains cells with low values.

TABLE 11

Association hypothesis using CLUMP

| | | Effective | | Allele Analysis | Genotype Analysis | |
|---|---|---|---|---|---|---|
| | | | | | p-value | p-value |
| gene | SNPs | Cases | Controls | p-value (T1) | (T2) | (T3) |
| P2X7R | P2XR7v11B | 208 | 211 | 0.795 | 0.036 | 0.028 |
| | P2XR7v13A | 212 | 214 | 0.344 | 0.250 | 0.186 |
| | P2XR7v13E | 212 | 211 | 0.780 | 0.017 | 0.017 |
| CAMKK2 | SNP6f18v5 | 206 | 135 | 1.00 | 1.00 | 1.00 |
| | SNP6f18v4 | 206 | 135 | 0.816 | 0.962 | 0.841 |
| | SNP6f18v2 | 205 | 135 | 0.057 | 0.110 | 0.095 |
| | SNP6f18v1 | 206 | 135 | 0.512 | 0.532 | 0.385 |

The association studies using SNPs in P2X7, P2X4, and CaMKK2 reveal associations significant at level of about 5% or less. Three genotype associations in P2X7 were observed. However, SNPs P2XR7v11B and P2XR7v13E are closely linked together based on a contingency table. There is also an allele association at level of 5.7% for SNP6f18v2 in CaMKK2. The information associated to each relevant SNP can be found in Tables 10 and 12.

Further association studies using CLUMP were performed on samples that contain more case and control individuals. One thousand simulations were used to estimate p-values.

TABLE 11a

Empirical p-values and odds ratio (OR) with 95% confidence interval observed with CLUMP for alleles and genotypes analysis of SNPs

| | | | | | Alleles | | | Genotypes | |
|---|---|---|---|---|---|---|---|---|---|
| | Marker | Allele | Effective | | T1 p- | OR | OR 95% | T1 p- | T3 p- |
| Gene | (marker rank) | Frequencies | case | controls | value | OR | CI | value | value |
| P2XR7 | P2XR7UTR5F (1) | C (0.18); T (0.82) | 212 | 208 | 0.280 | 1.21 | 0.86-1.71 | 0.067 | 0.069 |
| | P2XR7UTR5G (2) | G (0.09); T (0.91) | 211 | 204 | 0.481 | 1.19 | 0.76-1.87 | 0.261 | 0.231 |
| | P2XR7UTR5H (3) | C (0.95); T (0.05) | 210 | 202 | 0.549 | 1.19 | 0.67-2.13 | 0.768 | 0.582 |
| | P2XR7UTR5A (4) | A (0.05); C (0.95) | 210 | 207 | 0.526 | 1.26 | 0.68-2.34 | 0.754 | 0.517 |
| | P2XR7UTR5B (5) | C (0.78); T (0.22) | 211 | 207 | 0.629 | 1.09 | 0.79-1.50 | 0.104 | 0.128 |
| | P2XR7UTR5D (6) | A (0.96); G (0.04) | 211 | 205 | 0.268 | 1.43 | 0.77-2.65 | 0.598 | 0.240 |
| | P2XR7UTR5E (7) | A (0.04); G (0.96) | 211 | 210 | 0.658 | 1.23 | 0.65-2.33 | 0.139 | 0.234 |
| | P2XR7UTR5C (8) | A (0.22); G (0.78) | 208 | 210 | 0.889 | 1.04 | 0.75-1.44 | 0.168 | 0.293 |
| | P2XR7I01B (9) | C (0.98); T (0.02) | 210 | 207 | 0.352 | 1.71 | 0.67-4.39 | 0.348 | 0.348 |
| | P2XR7v02A (10) | C (0.05); T (0.95) | 211 | 208 | 0.189 | 1.49 | 0.84-2.64 | 0.397 | 0.167 |
| | P2XR7I04A (11) | A (0.01); G (0.99) | 211 | 211 | 0.344 | 0.25 | 0.03-2.23 | 0.356 | 0.356 |

TABLE 11a-continued

Empirical p-values and odds ratio (OR) with 95% confidence interval observed with CLUMP for alleles and genotypes analysis of SNPs

| Gene | Marker (marker rank) | Allele Frequencies | Effective case | controls | Alleles T1 p-value | OR | OR 95% CI | Genotypes T1 p-value | T3 p-value |
|---|---|---|---|---|---|---|---|---|---|
| | P2XR7v05B (12) | C (0.75); T (0.25) | 212 | 211 | 0.854 | 1.03 | 0.76-1.41 | 0.234 | 0.335 |
| | P2XR7E05D (13) | A (0.01); G (0.99) | 211 | 211 | 0.726 | 1.51 | 0.42-5.38 | 0.735 | 0.735 |
| | P2XR7v05A (14) | C (0.48); T (0.52) | 211 | 209 | 0.638 | 1.07 | 0.82-1.40 | 0.895 | 0.895 |
| | P2XR7E05C (15) | C (0.97); T (0.03) | 210 | 211 | 0.195 | 0.45 | 0.16-1.31 | 0.349 | 0.276 |
| | P2XR7I07E (16) | C (0.64); T (0.36) | 208 | 214 | 0.394 | 0.87 | 0.66-1.16 | 0.057 | 0.064 |
| | P2XR7v08A (17) | A (0.24); G (0.76) | 210 | 212 | 0.221 | 1.22 | 0.90-1.67 | 0.433 | 0.496 |
| | P2XR7v08B (18) | A (0.05); G (0.95) | 210 | 213 | 0.386 | 0.71 | 0.36-1.41 | 0.520 | 0.662 |
| | P2XR7V11A (19) | C (0.88); T (0.12) | 213 | 149 | 0.394 | 0.80 | 0.50-1.29 | 0.387 | 0.463 |
| | P2XR7v11B (20) | A (0.36); G (0.64) | 208 | 211 | 0.795 | 1.04 | 0.79-1.38 | 0.036 | 0.028 |
| | P2XR7v11C (21) | C (0.89); G (0.11) | 211 | 212 | 0.409 | 0.82 | 0.52-1.28 | 0.303 | 0.661 |
| | P2XR7v13F (22) | C (0.99); T (0.01) | 196 | 207 | 0.030 | 3.24 | 1.04-10.12 | 0.039 | 0.039 |
| | P2XR7v13A (23) | A (0.84); G (0.16) | 212 | 214 | 0.344 | 1.21 | 0.85-1.72 | 0.250 | 0.186 |
| | P2XR7v13B (24) | C (0.89); T (0.11) | 207 | 212 | 0.494 | 0.83 | 0.53-1.31 | 0.315 | 0.699 |
| | P2XR7v13C (25) | A (0.77); C (0.23) | 211 | 213 | 0.731 | 0.95 | 0.68-1.31 | 0.557 | 0.616 |
| | P2XR7V13H (26) | C (0.98); G (0.02) | 211 | 213 | 0.238 | 1.75 | 0.68-4.49 | 0.236 | 0.236 |
| | P2XR7E13D (27) | G (0.89); T (0.11) | 211 | 213 | 0.435 | 0.82 | 0.53-1.28 | 0.268 | 0.680 |
| | P2XR7E13J (28) | A (0.03); T (0.97) | 204 | 199 | 0.179 | 0.48 | 0.16-1.42 | 0.329 | 0.329 |
| | P2XR7v13E (29) | A (0.36); G (0.64) | 212 | 213 | 0.841 | 1.04 | 0.79-1.37 | 0.026 | 0.025 |
| | P2XR7UTR3E (30) | A (0.04); G (0.96) | 205 | 197 | 1.000 | 0.96 | 045-2.04 | 1.000 | 1.000 |
| | P2XR7UTR3A (31) | A (0.47); C (0.53) | 208 | 209 | 0.932 | 0.99 | 0.75-1.30 | 0.264 | 0.239 |
| | P2XR7UTR3B (32) | A (0.92); C (0.08) | 208 | 210 | 0.174 | 0.65 | 0.38-1.14 | 0.151 | 0.303 |
| | P2XR7UTR3C (33) | A (0.95); C (0.05) | 208 | 210 | 0.395 | 0.71 | 0.36-1.40 | 0.508 | 0.667 |
| P2XR4 | UTR5A | A (0.18); C (0.82) | 212 | 210 | 0.285 | 0.82 | 0.57-1.18 | 0.514 | 0.484 |
| | UTR5B | A (0.69); G (0.31) | 212 | 210 | 0.670 | 0.93 | 0.70-1.25 | 0.833 | 0.833 |
| | I06A | C (0.84); T (0.16) | 207 | 192 | 0.212 | 0.78 | 0.53-1.16 | 0.398 | 0.217 |
| | E07A | A (0.84); G (0.16) | 212 | 208 | 0.294 | 0.81 | 0.55-1.19 | 0.536 | 0.479 |
| | UTR3A | C (0.74); G (0.26) | 211 | 203 | 0.015 | 1.50 | 1.11-2.02 | 0.021 | 0.014 |
| | UTR3B | A (0.97); T (0.03) | 211 | 209 | 0.653 | 0.81 | 0.33-1.97 | 0.649 | 0.649 |
| | UTR3C | C (0.03); G (0.97) | 211 | 209 | 0.653 | 0.81 | 0.33-1.97 | 0.672 | 0.672 |
| CAMKK2 | E09B | A (0.03); C (0.97) | 208 | 214 | 0.830 | 0.85 | 0.36-2.00 | 0.829 | 0.829 |
| | E09A | C (0.83); T (0.17) | 208 | 214 | 0.202 | 0.78 | 0.54-1.14 | 0.446 | 0.473 |
| | E01B | A (0.35); T (0.65) | 207 | 214 | 0.048 | 1.33 | 1.01-1.76 | 0.126 | 0.218 |
| | E01A | C (0.93); T (0.07) | 208 | 214 | 0.189 | 1.44 | 0.86-2.39 | 0.439 | 0.237 |

Thirty-three SNPs in P2X7R, seven SNPs in P2X4R, and four SNPs in CAMKK2, with minor allele frequency higher or equal to 1% were genotyped (Table 11a). The genotype distributions of these SNPs did not deviate significantly from HWE. At the 5% level, statistically significant increases of minor allele frequency were observed in the bipolar affective disorder group at p2XR7v13F (p-value=0.030, OR=3.24, 95% CI=1.04-10.12), P2XR4UTR3A (p-value=0.015, OR=1.50, 95% CI=1.11-2.02) and CAMKK2E01B (p-value=0.048, OR=1.33, 95% CI=1.01-1.76). The distribution of genotypes at SNPs P2XR7v13F and P2XR4UTR3A also differed significantly at this level for T1 and T3 statistics, with an increase of heterozygotes in the case sample. One SNP from exon 11 of P2X7R, P2XR7v11B, and another from exon 13, P2XR7v13E, displayed difference in genotype distributions with minimum p-value of 0.028 and 0.025 observed both with T3 statistic. Again, increase in heterozygote frequency of 12% and 13% were respectively observed in the bipolar sample at these polymorphisms.

Significant haplotypic association tests led to p-values less than 0.5% for different SNP groups overlapping the P2X7R gene (Table 11b). Considering the SNPs collection ranging from SNP32507 to SNP54847 (table 11c) as an example for haplotype distribution, we observed the largest difference of frequencies between cases and controls with the haplotype no 1 (table 11d). The haplotype no 2 is another example of haplotype that is more frequently observed in cases group. On the other hand, the frequency for haplotype no 3 is slightly increased in control sample (difference of frequencies=0.091). Table 11e presents the peptidic products derived from the nucleotidic haplotypes shown in table 11d.

TABLE 11c

Position and Allele for haplotype-forming SNPs.
Haplotypes are described in table 11d.

| SEQ ID NO | Polymorphism | Position |
|---|---|---|
| 1 | C-T | 32507 |
| 1 | C-T | 32548 |
| 1 | C-T | 37439 |
| 1 | G-A | 37605 |
| 1 | G-A | 37623 |
| 1 | C-T | 47214 |
| 1 | G-A | 47383 |
| 1 | C-G | 47411 |
| 1 | C-T | 54399 |
| 1 | A-G | 54480 |
| 1 | C-T | 54523 |
| 1 | A-C | 54588 |
| 1 | C-T | 54664 |
| 1 | G-T | 54703 |
| 1 | T-A | 54804 |
| 1 | G-A | 54847 |

TABLE 11b

Haplotypes showing allelic association significant at the 0.5% level for T1 or T3 statistics.

| Haplotype (marker ranks[1]) | #SNPs | Distance[2] (bp) | Haplotype effective case | Haplotype effective control | T1 statistic (p-value) | T3 statistic (p-value) | #haplotype[3] |
|---|---|---|---|---|---|---|---|
| P2XR7I01B-P2XR7v13A (9-23) | 15 | 29618 | 361 | 257 | 0.0003 | 0.0252 | 20 |
| P2XR7v02A-P2XR7v13B (10-24) | 15 | 29550 | 361 | 260 | 0.00008 | 0.0294 | 20 |
| P2XR7I04A-P2XR7v13C (11-25) | 15 | 22164 | 360 | 264 | 0.0003 | 0.0323 | 19 |
| P2XR7v05B-P2XR7v13H (12-26) | 15 | 22200 | 361 | 265 | 0.0004 | 0.0065 | 18 |
| P2XR7E05D-P2XR7E13D (13-27) | 15 | 22180 | 365 | 268 | 0.0035 | 0.0287 | 16 |
| P2XR7v05A-P2XR7E13J (14-28) | 15 | 22267 | 352 | 246 | 0.0007 | 0.0163 | 15 |
| P2XR7E05C-P2XR7v13E (15-29) | 15 | 22269 | 353 | 250 | 0.0012 | 0.0200 | 10 |
| P2XR7I07E-P2XR7UTR3E (16-30) | 15 | 17452 | 355 | 247 | 0.0020 | 0.0192 | 11 |

[1]The marker ranks of SNPs in the haplotype indicated in table 11b refer to those genotyped in table 11a
[2]Distance between the two most distal SNPs of the haplotype
[3]Number of haplotypes with frequencies >1% in case or control groups.

TABLE 11d haplotypes with significant difference of frequencies between affected and control individuals.

| Haplotype | 32507 | 32548 | 37439 | 37605 | 37623 | 47214 | 47383 | 47411 | 54399 | 54480 |
|---|---|---|---|---|---|---|---|---|---|---|
| No 1 | C | C | C | A | G | C | G | C | C | A |
| No 2 | C | C | C | G | G | C | G | C | C | A |
| No 3 | C | C | T | G | G | C | A | C | C | A |

| Haplotype | 54523 | 54588 | 54664 | 54703 | 54804 | 54847 | $F_{affected}$ | $F_{controls}$ |
|---|---|---|---|---|---|---|---|---|
| No 1 | C | A | C | G | T | G | 0.20 | 0.13 |
| No 2 | C | C | C | G | T | G | 0.05 | 0.01 |
| No 3 | C | A | C | G | T | A | 0.11 | 0.20 |

TABLE 11e

Corresponding amino acids for cSNPs described in table 11c. They are positioned according to SEQ ID NO3.

| | Position in SEQ ID NO3 | | | | | | |
|---|---|---|---|---|---|---|---|
| | 155 | 168 | 270 | 276 | 348 | 357 | 433 |
| Haplotype 1 | Y | C | H | R | A | T | A |
| Haplotype 2 | Y | C | R | R | A | T | A |
| Haplotype 3 | Y | C | R | R | T | T | A |

| | Position in SEQ ID NO3 | | | | | | |
|---|---|---|---|---|---|---|---|
| | 460 | 474 | 496 | 521 | 534 | 568 | 582 |
| Haplotype 1 | Q | P | E | H | L | I | P |
| Haplotype 2 | Q | P | A | H | L | I | P |
| Haplotype 3 | Q | P | E | H | L | I | P |

EXAMPLE 3

Polymorphisms Found in the P2X7R in Individuals Suffering from Depression

Association studies using SNPs in the P2X7R gene was performed in a case/control sample (535 individuals) from a German population. The case group was composed of 36 individuals diagnosed with bipolar type I or type II, and 279 individuals diagnosed with unipolar disorders (i.e. depression) representing 133 affected males and 182 affected females. Among controls, we count The remaining 220 control individuals were normal (i.e. diagnosed as non depressive), and comprising 81 males, 182 females and 14 of unknown gender. The same sexual distribution was noted in both groups.

SNPs were identified in this sample by using a subgroup of 24 affected individuals. SNPs in the P2X7R gene detected in the German population were similar if not identical to the SNPs seen in the Saguenay/Lac-St-Jean population (see table 12). Other rare missense SNPs were also noted in the German population, such as Arg117Trp (P2XR7E03A), Glu186Lys (P2XR7E06A), Leu191Pro (P2XR7E06B), Ile568Asn (P2XR7E13J). These amino acids are quite conserved between ortholog P2X7 genes. It is possible that the Ile568Asn (P2XR7E13J) mutation may be involved in the surface expression of P2X7.

TABLE 12

Comparison Between Polymorphisms in the Saguenay/Lac-St-Jean Population and the German Population in the Human P2XR7 Gene

| Associated exons or introns | Variation (SNP or others) | Allele | Position* | Modification | Frequency (Canda) | Frequency (Germany) |
|---|---|---|---|---|---|---|
| 5'UTR | P2XR7UTR5L | T-C | 362 | unknown | 0,13 | 0,08 |
| 5'UTR | P2XR7UTR5M | T-G | 532 | unknown | 0,16 | 0,1 |
| 5'UTR | P2XR7UTR5K | A-G | 1100 | unknown | 0,13 | 0,13 |
| 5'UTR | P2XR7UTR5J | A-G | 1122 | unknown | 0,13 | 0,13 |
| 5'UTR | P2XR7UTR5I | C-G | 1171 | unknown | 0,06 | 0,02 |
| 5'UTR | P2XR7UTR5F | T-C | 1351 | unknown | 0,3 | 0,12 |
| 5'UTR | P2XR7UTR5N | G-A | 1702 | unknown | — | 0,02 |
| 5'UTR | P2XR7UTR5G | T-G | 1731 | unknown | 0,17 | 0,15 |

TABLE 12-continued

Comparison Between Polymorphisms in the Saguenay/Lac-St-Jean Population and the German Population in the Human P2X7R Gene

| Associated exons or introns | Variation (SNP or others) | Allele | Position* | Modification | Frequency (Canda) | Frequency (Germany) |
|---|---|---|---|---|---|---|
| 5'UTR | P2XR7UTR5H | C-T | 1860 | unknown | 0,07 | 0,15 |
| 5'UTR | P2XR7UTR5A | C-A | 2162 | unknown | 0,07 | 0,12 |
| 5'UTR | P2XR7UTR5B | C-T | 2238 | unknown | 0,3 | 0,27 |
| 5'UTR | P2XR7UTR5D | A-G | 2373 | unknown | 0,07 | 0,12 |
| 5'UTR | P2XR7UTR5E | G-A | 2569 | unknown | 0,1 | 0,02 |
| 5'UTR | P2XR7UTR5C | G-A | 2702 | unknown | 0,31 | 0,27 |
| Intron01 | P2XR7I01C | G-C | 3166 | unknown | 0,03 | — |
| Intron01 | P2XR7I01A | C-T | 24778 | unknown | 0,03 | — |
| Intron01 | P2XR7I01B | C-T | 24830 | unknown | 0,03 | RARE |
| Exon02 | P2XR7v02A | T-C | 24942 | Val76Ala | 0,06 | 0,08 |
| Exon03 | P2XR7E03A | C-T | 26188 | Arg117Trp | — | RARE |
| Intron03 | P2XR7I03A | A-G | 26308 | unknown | 0,7 | 0,44 |
| Intron03 | P2XR7I03B | G-A | 26422 | unknown | 0,18 | 0,12 |
| Intron04 | P2XR7I04A | G-A | 32394 | unknown | 0,03 | 0,01 |
| Intron04 | P2XR7v05B | T-C | 32434 | unknown | 0,33 | 0,29 |
| Exon05 | P2XR7E05D | G-A | 32493 | Gly150Arg | RARE | 0,02 |
| Exon05 | P2XR7E05E | G-A | 32506 | Silent Val154 | — | RARE |
| Exon05 | P2XR7v05A | C-T | 32507 | Tyr155His | 0,33 | 0,44 |
| Exon05 | P2XR7E05C | C-T | 32548 | Silent Cys168 | RARE | 0,02 |
| Intron05 | P2XR7I05C | A-C | 32783 | unknown | 0,25 | — |
| Intron05 | P2XR7I05D | T-C | 35309 | unknown | ND | 0,35 |
| Intron05 | P2XR7I05B | C-T | 35374 | unknown | 0,7 | 0,67 |
| Intron05 | P2XR7I05A | A-C | 35378 | unknown | 0,7 | 0,65 |
| Exon06 | P2XR7E06A | G-A | 35438 | Glu186Lys | — | 0,02 |
| Exon06 | P2XR7E06B | T-C | 35454 | Leu191Pro | — | 0,02 |
| Intron06 | P2XR7I06C | T-C | 35549 | unknown | 0,04 | 0,08 |
| Intron06 | P2XR7I06G | G-C | 35641 | unknown | — | 0,02 |
| Intron06 | P2XR7I06D | A-C | 35725 | unknown | 0,21 | 0,27 |
| Intron06 | P2XR7I06F | T-G | 36001 | unknown | 0,17 | 0,3 |
| Intron06 | P2XR7I06E | A-T | 36064 | unknown | 0,11 | 0,1 |
| Intron06 | P2XR7I06A | DelGTTT | 36091-36094 | unknown | 0,14 | 0,3 |
| Intron06 | P2XR7I06B | C-G | 36108 | unknown | 0,14 | 0,29 |
| Intron07 | P2XR7I07A | C-T | 36374 | unknown | 0,07 | — |
| Intron07 | P2XR7I07B | G-A | 36378 | unknown | 0,21 | 0,28 |

TABLE 12-continued

Comparison Between Polymorphisms in
the Saguenay/Lac-St-Jean Population and the German Population in the Human P2X7R Gene

| Associated exons or introns | Variation (SNP or others) | Allele | Position* | Modification | Frequency (Canda) | Frequency (Germany) |
|---|---|---|---|---|---|---|
| Intron07 | P2XR7I07C | T-A | 36387 | unknown | 0,21 | 0,28 |
| Intron07 | P2XR7I07D | G-C | 36398 | unknown | 0,42 | 0,4 |
| Intron07 | P2XR7I07E | C-T | 37439 | unknown | 0,41 | — |
| Intron07 | P2XR7I07F | T-C | 37513 | unknown | — | RARE |
| Exon08 | P2XR7E08C | C-T | 37604 | Arg270Cys | RARE | — |
| Exon08 | P2XR7v08A | G-A | 37605 | Arg270His | 0,46 | 0,24 |
| Exon08 | P2XR7v08B | G-A | 37623 | Arg276His | 0,03 | 0,02 |
| Exon08 | P2XR7E08D | C-T | 37633 | Silent Asp279 | RARE | — |
| Intron09 | P2XR7v11A | C-T | 47214 | unknown | 0,08 | 0,03 |
| Exon11 | P2XR7v11B | G-A | 47383 | Ala348Thr | 0,5 | 0,44 |
| Exon11 | P2XR7v11C | C-G | 47411 | Thr357Ser | 0,08 | 0,07 |
| Intron11 | P2XR7I11D | T-C | 47563 | unknown | 0,43 | 0,44 |
| Intron12 | P2XR7I12A | C-T | 54307 | unknown | 0,32 | — |
| Intron12 | P2XR7I12B | G-A | 54308 | unknown | 0,03 | — |
| Exon13 | P2XR7v13F | C-T | 54399 | Ala433Val | 0,13 | — |
| Exon13 | P2XR7v13A | A-G | 54480 | Gln460Arg | 0,13 | 0,17 |
| Exon13 | P2XR7v13B | C-T | 54523 | Silent Pro474 | 0,1 | 0,07 |
| Exon13 | P2XR7v13G | DelCCCTGAGAGCCACAGGTGCCT | 54562-54582 | Del of 7aa 488 to 494 (PESHRCL) | RARE | — |
| Exon13 | P2XR7v13C | A-C | 54588 | Glu496Ala | 0,13 | 0,06 |
| Exon13 | P2XR7v13H | C-G | 54664 | His521Gln | 0,03 | — |
| Exon13 | P2XR7E13D | G-T | 54703 | Silent Leu534 | 0,1 | 0,02 |
| Exon13 | P2XR7E13J | A-T | 54804 | Ile568Asn | — | 0,01 |
| Exon13 | P2XR7v13I | G-A | 54834 | Arg578Gln | — | RARE |
| Exon13 | P2XR7v13E | G-A | 54847 | Silent Pro582 | 0,4 | 0,45 |
| 3'UTR | P2XR7UTR3A | C-A | 55169 | unknown | 0,48 | 0,37 |
| 3'UTR | P2XR7UTR3B | A-C | 55170 | unknown | 0,09 | 0,1 |
| 3'UTR | P2XR7UTR3C | A-C | 55171 | unknown | 0,05 | 0,06 |
| 3'UTR | P2XR7UTR3D | C-T | 55917 | unknown | 0,001 | — |
| 3'UTR | P2XR7UTR3E | G-A | 54925 | unknown | — | 0,01 |

The position and numbering of the polymorphism corresponds to the human P2X7R gene as defined in SEQ ID NO: 1. To identify the genomic organization of the P2X7R gene, BAC clones were firstly organized using known polymorphic markers, sequence tag sites (STSs), BAC-end sequences and expressed sequence tags (ESTs). Unorientated and unordered DNA regions were reassembled into a sequences using Phrap and reordered the pieces using P2X7R exons as scaffolds. No complete gene organization for P2X7R has been done. There is only a partial gene structure from exon6 to 13, NT_037809. Therefore, this genomic sequence encompassing the P2X7R gene as depicted in SEQ ID NO: 1 could contain some sequence errors, specifically in intronic regions. Primers used for SNP amplification and sequencing are shown in Table 1a and depicted in SEQ ID NOs: 52 to 111.

Statistical analysis was performed according to the CLUMP method (Sham & Curtis 1995, Ann. Hum. Genet. 59:97-105). Table 13 resumes the allelic and genotypic association studies for SNPs in P2X7 gene.

of a as q, then p plus q represent the sum total of alleles at this locus, that is p+q=1. The HWP is useful to evaluate some population problems like marital assortment, Inbreeding, population stratification, admixture, decreased viability of a particular genotype. The SNP P2XR7v13A did not respect the Hardy-Weinberg equilibrium.

The association hypothesis was also tested using an allele positivity table known to be suitable for the detection of susceptibility alleles showing a dominant mode of inheritance (Ohashi and Tokunaga, J. Hum. Genet. 44 (1999), 246-248; Ohashi et al., Ann. Hum. Genet. 65 (2001), 197-206). Similar results were obtained using this method as those obtained using the allele frequency tables, with the exception of P2XR7v05A where the p-values were 0.253. Thus, P2XR7v05A presented a less significant association in this analysis. This difference can be attributed to the mode of inheritance.

The proportion of unipolar individuals in analysis of the German population is quite important since the American

TABLE 13

Allelic and genotypic association studies using CLUMP

| Locus | Allele Frequencies* | Effective Cases | Effective Controls | Allele Analysis p-value (T1) | Genotype Analysis p-value (T1) | Genotype Analysis p-value (T3) |
|---|---|---|---|---|---|---|
| P2XR7UTR5F | 2(0.23); 4(0.77) | 311 | 217 | 0.109 | 0.319 | 0.339 |
| P2XR7UTR5N | 1(0.001); 3(0.999)** | 314 | 218 | 0.038 | 0.048 | 0.048 |
| P2XR7UTR5G | 2(0.001); 3(0.105); 4(0.894) | 314 | 218 | 0.993 | 0.714 | 0.761 |
| P2XR7UTR5H | 2(0.92); 4(0.08) | 312 | 215 | 0.743 | 0.884 | 0.754 |
| P2XR7UTR5A | 1(0.08); 2(0.92) | 312 | 219 | 0.557 | 0.786 | 0.678 |
| P2XR7UTR5B | 2(0.73); 4(0.27) | 310 | 218 | 0.485 | 0.761 | 0.814 |
| P2XR7UTR5D | 1(0.92); 3(0.08) | 311 | 217 | 0.555 | 0.787 | 0.691 |
| P2XR7v02A | 2(0.09); 4(0.91) | 313 | 218 | 0.501 | 0.729 | 0.591 |
| P2XR7I04A | 1(0.04); 3(0.96) | 314 | 220 | 0.604 | 0.433 | 0.348 |
| P2XR7v05B | 2(0.69); 4(0.31) | 314 | 220 | 0.133 | 0.270 | 0.325 |
| P2XR7E05D | 1(0.03); 3(0.97) | 314 | 220 | 0.842 | 0.827 | 0.827 |
| P2XR7E05E | 1(0.006); 3(0.994)** | 314 | 220 | 0.048 | 0.045 | 0.045 |
| P2XR7v05A | 2(0.60); 4(0.40) | 314 | 220 | 0.038 | 0.144 | 0.219 |
| P2XR7E05C | 2(0.98); 4(0.02) | 314 | 220 | 1.000 | 1.000 | 1.000 |
| P2XR7I07F | 2(0.002); 4(0.98) | 315 | 219 | 1.000 | 1.000 | 1.000 |
| P2XR7v08A | 1(0.23); 3(0.77) | 315 | 219 | 0.454 | 0.673 | 0.634 |
| P2XR7v08B | 1(0.02); 3(0.98) | 315 | 219 | 0.636 | 0.638 | 0.638 |
| P2XR7v11A | 2(0.95); 4(0.05) | 311 | 218 | 0.348 | 0.391 | 0.436 |
| P2XR7v11B | 1(0.45); 3(0.55) | 312 | 218 | 0.605 | 0.803 | 0.790 |
| P2XR7v11C | 2(0.93); 3(0.07) | 312 | 218 | 0.793 | 0.256 | 0.924 |
| P2XR7I11D | 2(0.45); 4(0.55) | 312 | 219 | 0.665 | 0.735 | 0.740 |
| P2XR7v13A | 1(0.87); 3(0.13) | 305 | 215 | 0.017 | <0.001 | <0.001 |
| P2XR7v13B | 2(0.93); 4(0.07) | 305 | 216 | 1.000 | 0.228 | 0.677 |
| P2XR7V13C | 1(0.91); 2(0.09) | 305 | 216 | 0.151 | 0.006 | 0.008 |
| P2XR7E13D | 3(0.94); 4(0.06) | 315 | 219 | 0.402 | 0.429 | 0.474 |
| P2XR7E13J | 1(0.01); 4(0.99) | 315 | 219 | 0.618 | 0.603 | 0.603 |
| P2XR7E13I | 1(0.004); 3(0.996) | 315 | 219 | 0.999 | 1.000 | 1.000 |
| P2XR7v13E | 1(0.46); 3(0.54) | 314 | 219 | 0.699 | 0.866 | 0.845 |
| P2XR7UTR3A | 1(0.518); 2(0.482) | 314 | 219 | 0.617 | 0.850 | 0.875 |
| P2XR7UTR3B | 1(0.966); 2(0.034) | 313 | 219 | 0.522 | 0.850 | 0.643 |
| P2XR7UTR3C | 1(0.979); 2(0.021) | 313 | 219 | 0.636 | 0.505 | 0.382 |
| P2XR7UTR3E | 1(0.02); 3(0.98) | 315 | 219 | 0.147 | 0.161 | 0.161 |

*The column Allele Frequencies presents the allele for each SNP (A = 1, C = 2, G = 3, T = 4) and their respective frequency.
**For this SNP we observed a zero cell in both (allele and genotype) 2 × 2 contingency tables. p-value < 0.045 was observed exact Fisher test.

For the SNP analysis, the Hardy-Weinberg (HW) equilibrium was controlled in the control samples. The Hardy-Weinberg principle (HWP) may be stated as follow: In a large, randomly mating population, in which there is no migration, or selection against a particular genotype and the mutation rate remains constant, the proportions of the various genotypes will remain unchanged from one generation to another. Take a two allele system with alleles A and a. If the proportion of A in the population is represented as p and the proportion Psychiatric Association (Diagnostic and Statistical Manual of Mental Disorders—4th Edition Text Revision (DMS-IV-TR), American_Psychiatric Press, 2000) has reported an increase in susceptibility for unipolar disorders in female groups. To determine whether the sexual variable could influence the association analysis, additional association studies were performed by controlling the sexual parameter. Normal individuals in the German population without gender information were omitted from the study. Then, a logistic regression model was derived by including the sex as factor. In order to obtain a model that is as stable as possible, the regression model was minimised by using the difference between log-likelihood's for models with or without interaction (Hosmer, and Lemeshow, "Applied logistic regression", John Wiley and Sons, 1989). The strategy used for handling the zero cells from contingency tables was to eliminate associated category completely. Calculations were done with SAS v8.0 SAS is a statistical software package that allows the user to manipulate and analyze data in many different ways. Because of its capabilities, this software package is used in many disciplines, including medical sciences, biological sciences, and social sciences.

The introduction of a sexual parameter did not perturb the association already observed in previous analysis. Moreover, this analysis model revealed additional results: a potential allele association with P2XR7v05B (p=0.064), and a genotypic association for P2XR7v08A (p=0.042) was observed.

Association studies using pooled samples was performed by merging individuals from the samples of the Saguenay/Lac St-Jean with those of the German population. Results are illustrated in table 14. The aim of this analysis is to highlight common features between both populations. However, according to differences between both samples (mainly the phenotype of affected individuals i.e. bipolar disorder in the Saguenay/Lac St-Jean samples, versus mostly unipolar disorder in the German population) some parameters were controlled, including sex and ethnicity. The modelling strategy for logistic regressions was described above.

An allelic and genotypic association was observed for the P2XR7v13A locus (p=0.0047) which was stronger than in the separate analyses. A significant allelic association was also noted for the P2XR7v08A locus (p=0.0452). In addition, the present analysis also demonstrate the potential relationship between SNP P2XR7v05A and the origin with a p-value=0.0515 (not shown in the table) which is in agreement with previous association analysis done in both samples separately (see Table 13).

The haplotype analysis was performed using the German population. The PHASE program (Stephens et al., Am. J. Hum. Genet. 68 (2001), 978-989) was used to estimate SNPs haplotypes within exons of the P2X7R gene. Haplotypes were created for each exon having more than one associated SNP (see Table 15 for exon-associated SNPs). Case groups varied from 218-220 individuals, whereas control groups varied between 312-316 individuals. Association hypothesis was tested with the CLUMP method since many haplotypes were created for each exon. T1 and T3 statistic tests performed as described above. T2 and T4 statistics were also calculated owing to the presence of small effective cells in the contingency tables. T2 statistic is the usual chi-squared statistic applied on the contingency table obtained after collapsing columns with small expected values. T4 statistic is the largest chi-squared statistic obtained by comparing one column of the original table against the total of the other columns. One thousand simulations were used to estimate p-values. The resulting data was analyzed with the logistic regression model (describe above) using SAS V8.0 in order to consider the sexual parameter (for these tests the sample was reduced by 14 normal individuals). However, this analysis method is limited by the reliability of reconstructed haplotypes.

TABLE 14

Association studies using pooled samples from both populations

| | Allele analysis | | Genotype analysis | |
|---|---|---|---|---|
| Locus | p-value for SNP | p-value for sex | p-value for SNP | p-value for sex |
| P2XR7v02A | 0.8254 | 0.0085 | 0.8650 | 0.4531 |
| P2XR7v05B | 0.1751 | 0.3714 | 0.2034 | 0.5110 |
| P2XR7v05A | 0.3808 | 0.0266 | 0.0885 | 0.1392 |
| P2XR7v08A | 0.0452 | 0.0041 | 0.1021 | 0.3452 |
| P2XR7v08B | 0.3471 | 0.0040 | 0.3413 | 0.3617 |
| P2XR7v11A | 0.3559 | 0.0136 | 0.5888 | 0.4404 |
| P2XR7v11B | 0.5902 | 0.0093 | 0.3897 | 0.4302 |
| P2XR7v11C | 0.3731 | 0.0094 | 0.7648 | 0.4615 |
| P2XR7v13A | 0.0047 | 0.0209 | <0.0001 | 0.4814 |
| P2XR7v13B | 0.5129 | 0.2352 | 0.9584 | 0.4092 |
| P2XR7v13C | 0.2466 | 0.0284 | 0.2225 | 0.4228 |
| P2XR7v13E | 0.8168 | 0.0159 | 0.3713 | 0.4990 |

TABLE 15

Exon-associated SNPs

| Exons | Associated SNPs |
|---|---|
| 5 | P2XR7E05D |
| | P2XR7E05E |
| | P2XR7v05A |
| | P2XR7E05C |
| 8 | P2XR7v08A |
| | P2XR7v08B |
| 11 | P2XRv11B |
| | P2XRv11C |
| 13 | P2XR7v13A |
| | P2XR7v13B |
| | P2XR7v13C |
| | P2XR7E13D |
| | P2XR7E13J |
| | P2XR7v13I |
| | P2XR7v13E |

TABLE 16

Genotypic association with haplotypes in exon 13 of P2X7R

| Exon (haplotype) | Allele analysis | | | Genotype analysis | | |
|---|---|---|---|---|---|---|
| | Clump* | p-value(sex) | p-value(haplo) | Clump | p-value(sex) | p-value(haplo) |
| 5(5) | T1: 0.032 | 0.3133 | 0.1947 | T1: 0.193 | 0.460 | 0.5355 |
| | T2: 0.068 | | | T2: 0.159 | | |
| | T3: 0.054 | | | T3: 0.099 | | |
| | T4: 0.059 | | | T4: 0.304 | | |

TABLE 16-continued

Genotypic association with haplotypes in exon 13 of P2X7R

| Exon (haplotype) | Allele analysis | | | Genotype analysis | | |
|---|---|---|---|---|---|---|
| | Clump* | p-value(sex) | p-value(haplo) | Clump | p-value(sex) | p-value(haplo) |
| 8(3) | T1: 0.551<br>T2: 0.585<br>T3: 0.646<br>T4: 0.646 | 0.3813 | 0.3064 | T1: 0.812<br>T2: 0.689<br>T3: 0.644<br>T4: 0.756 | 0.5428 | 0.6652 |
| 11(3) | T1: 0.750<br>T2: 0.786<br>T3: 0.726<br>T4: 0.726 | 0.0886 | 0.7396 | T1: 0.625<br>T2: 0.919<br>T3: 0.929<br>T4: 0.921 | 0.2305 | 0.9494 |
| 13(15**) | T1: 0.088<br>T2: 0.079<br>T3: 0.147<br>T4: 0.072 | 0.1871 | 0.1264 | T1: 0.001<br>T2: 0.002<br>T3: 0.057<br>T4: <0.001 | 0.4610 | 0.019 |

*T1 test should not be considered because of contingency tables with zero cells.
**Among these 15 haplotypes, we observed 8 haplotypes where case cells have less than 3 individuals.

Table 16 illustrates a genotypic association with haplotypes in exon 13 of the P2X7R genes. Interestingly, many haplotypes for the exon 13 were observed. The differences between statistics in exon 13 (T3 less significant) can be explained by the involvement of more than one genotype of haplotypes in the disease. A potential allelic association was also noted with haplotypes in exon 5 of the P2X7R gene.

The following are clinical results illustrating the functional consequences of polymorphisms in P2X7R.

The development and course of depression is causally linked to impairments in the central regulation of the hypothalamic-pituitary-adrenocortical (HPA) axis. Abnormalities in the HPA axis can be measured using the dexamethasone-suppression test (DST) or the combined dexamethasone/corticotropin-releasing hormone (Dex/CRH) test. Changes in cortisol and/or adrenocorticotropic hormone (ACTH) measurements during the DST or Dex/CHR test are indicative of HPA dysfunction in depressed patients (Heuser et al, J. Psychiat. Res. 28 (1994) 341-356; Rybakowski and Twardowska, J. Psychiat. Res. 33 (1999) 363-370; Zobel et al, J. Psychiat. Res. 35 (2001) 83-94; Künzel et al, Neuropsychopharmacology 28 (2003) 2169-2178). In order to demonstrate that P2X7R SNPs associated with affective disorders also correlate with changes in the HPA axis, cortisol and ATCH levels in response to the DST and Dex/CRH text were measured for the P2XR7v13A and P2XR7v13C SNPs. P2XR7v13A consist of an A to G nucleotide change resulting in a Gln460Arg modification in the P2X7R protein. The P2XR7v13C SNP corresponds to an A to C nucleotide change resulting in a Glu496Ala modification that has been shown to drastically reduce protein activity (Wiley et al, Drug Dev. Res. 53 (2001) 72-76).

Methods and conditions for performing the DST and Dex/CRH test are well known in the art, see for example Heuser et al, J. Psychiat. Res. 28 (1994) 341-356; Künzel et al, Neuropsychopharmacology 28 (2003) 2169-2178. Briefly, individuals were pre-treated at 23:00 with an oral administration of 1.5 mg dexamethasone. For the DST test, a blood sample was drawn at 8:00 prior to dexamethasone administration (i.e. pre-dexamethasone) and at 8:00 the morning following dexamethasone administration (i.e. post-dexamethasone). For the Dex/CRH test, a venous catheter was inserted at 14:30 the day following dexamethasone administration and blood was collected at 15:00, 15:30, 15:45, 16:00, and 16:15 into tubes containing EDTA and trasylol (Bayer Inc., Germany). At 15:02, 100 mg of human CRH (Ferring Inc., Germany) was administered intravenously. Measurement of plasma cortisol concentrations was done using a commercial radioimmunoassay kit (ICN Biomedicals, USA) while plasma ACTH concentrations was measured using a commercial immunometric assay (Nichols Institute, USA). Both assays were performed according to the manufacturer specifications.

For the P2XR7v13A SNP, a decrease in basal cortisol levels was seen at admission in individuals with an AG or GG allele when compared to individuals with the AA allele (FIG. 1f). During the Dex/CRH test, a reduction in cortisol and ATCH response was measured in individuals with the GG allele when compared to individuals with an AA or AG allele (FIGS. 1g and 1h). Furthermore, response to antidepressant treatment was delayed in GG individuals (FIG. 1i).

For the P2XR7v13C SNP, an increase in basal cortisol levels was measured post-dexamethasone administration (FIG. 1j). During the Dex/CRH test, individuals with the CC allele displayed elevated cortisol response (FIG. 1k), but reduced ATCH response (FIG. 1l) when compared to AA and AC individuals. These results are indicative of mysregulation of the HPA axis.

Thus, SNPs in P2X7R correlate with dysfunction in the HPA axis and demonstrate the functional and clinical consequences of polymorphisms in P2X7R.

EXAMPLE 4

P2X7R Gene Structure and mRNA Expression and Transcript Sequence

A 1700 bp nucleotide sequence corresponding to the human P2X7R promoter was analyzed by using Matinspector V2.2 and Transfac 4.0 algorithms. This analysis showed that the P2X7R gene does not contain a standard TATA box, but has SP1 sites that can make up for transcriptional initiation. Besides the SP1 sequences, there are binding sites for the transcription factors GATA, Oct and Ikarus. These sites are thought to provide tissue specificity. Interestingly, the P2X7R promoter has binding sites that suggest responsiveness to different cytokines such as AP-1, NFAT and CEBPB.

P2X7R possesses 13 exons and 12 introns (Buell et al., Receptors Channels 5 (1998), 347), providing a basis for alternative splicing that would yield in theory different transcripts and produce different isoforms with possible different functions. No alternatively spliced variant was clearly identified. However, experiments of EST clustering allowed the description of three splicing variants. One is defined by the lack of the exon 5. This P2X7v02 variant corresponds to the clone IMAGE: 3628076 isolated from brain-derived cell lines. The P2X7v02 lacking the exon 5 produces a frame shift, thus generating a shorter polypeptide. The second splicing variant, P2X7v03, is characterized by the presence of the short intron 10 into the mRNA. This variant is supported by two high quality sequences, the cDNA clone BRAMY2008977 (AC number: AK090866) from human amygdala and the EST clone dbEST: 7339877 derived from an unknown human tumor. The last variant, P2X7v04, is defined by the lack of the first exon that suggests an alternative promoter usage closed to the exon 2. A high quality EST clone dbEST: 4782844 derived form a head and neck tumor supports this variant. These variants are shown in FIGS. 16a to 16e.

```
P2X7 variants.
P2X7v01    MPACCSCSDVFQYETNKVTRIQSMNYGTIKWFFHVIIFSYVCFALVSDKLYQRKEPVISS
P2X7v04    MPPVD-----------------------APPCLPFS---FALVSDKLYQRKEPVISS
P2X7v02    MPACCSCSDVFQYETNKVTRIQSMNYGTIKWFFHVIIFSYVCFALVSDKLYQRKEPVISS
P2X7v03    MPACCSCSDVFQYETNKVTRIQSMNYGTIKWFFHVIIFSYVCFALVSDKLYQRKEPVISS
                  1........10........20........30........40........50

P2X7v01    VHTKVKGIAEVKEEIVENGVKKLVHSVFDTADYTFPLQGNSFFVMTNFLKTEGQEQRLCP
P2X7v04    VHTKVKGIAEVKEEIVENGVKKLVHSVFDTADYTFPLQGNSFFVMTNFLKTEGQEQRLCP
P2X7v02    VHTKVKGIAEVKEEIVENGVKKLVHSVFDTADYTFPLQGNSFFVMTNFLKTEGQEQRLCP
P2X7v03    VHTKVKGIAEVKEEIVENGVKKLVHSVFDTADYTFPLQGNSFFVMTNFLKTEGQEQRLCP
                 61.......70........80........90........100.......110

P2X7v01    EYPTRRTLCSSDRGCKKGWMDPQSKGIQTGRCVVHEGNQKTCEVSAWCPIEAVEEAPRPA
P2X7v04    EYPTRRTLCSSDRGCKKGWMDPQSKGIQTGRCVVHEGNQKTCEVSAWCPIEAVEEAPRPA
P2X7v02    EYPTRRTLCSSDRGCKKGWMDPQSKGLLS-------------------------------
P2X7v03    EYPTRRTLCSSDRGCKKGWMDPQSKGIQTGRCVVHEGNQKTCEVSAWCPIEAVEEAPRPA
                121......130.......140.......150.......160.......170

P2X7v01    LLNSAENFTVLIKNNIDFPGHNYTTRNILPGLNITCTFHKTQNPQCPIFRLGDIFRETGD
P2X7v04    LLNSAENFTVLIKNNIDFPGHNYTTRNILPGLNITCTFHKTQNPQCPIFRLGDIFRETGD
P2X7v02    ------------------------------------------------------------
P2X7v03    LLNSAENFTVLIKNNIDFPGHNYTTRNILPGLNITCTFHKTQNPQCPIFRLGDIFRETGD
                181......190.......200.......210.......220.......230

P2X7v01    NFSDVAIQGGIMGIEIYWDCNLDRWFHHCHPKYSFRRLDDKTTNVSLYPGYNFRYAKYYK
P2X7v04    NFSDVAIQGGIMGIEIYWDCNLDRWFHHCHPKYSFRRLDDKTTNVSLYPGYNFRYAKYYK
P2X7v02    ------------------------------------------------------------
P2X7v03    NFSDVAIQGGIMGIEIYWDCNLDRWFHHCHPKYSFRRLDDKTTNVSLYPGYNFRYAKYYK
                241......250.......260.......270.......280.......290

P2X7v01    ENNVEKRTLIKVFGIRFDILVFGTGGKFDIIQLVVYIGSTLSYFGLAAVFIDFLIDTYSS
P2X7v04    ENNVEKRTLIKVFGIRFDILVFGTGGKFDIIQLVVYTGSTLSYFGLAAVFIDFLIDTYSS
P2X7v02    ------------------------------------------------------------
P2X7v03    ENNVEKRTLIKVFGIRFDILVFGTGGKFDIIQLVVYIGSTLSYFGLVRDSLFHALGKWFG
                301......310.......320.......330.......340.......350

P2X7v01    NCCRSHIYPWCKCCQPCVVNEYYYRKKCESIVEPKPTLKYVSFVDESHIRMVNQQLLGRS
P2X7v04    NCCRSHIYPWCKCCQPCVVNEYYYRKKCESIVEPKPTLKYVSFVDESHIRMVNQQLLGRS
P2X7v02    ------------------------------------------------------------
P2X7v03    EGSD--------------------------------------------------------
                361......370.......380.......390.......400.......410

P2X7v01    LQDVKGQEVPRPAMDFTDLSRLPLALHDTPPIPGQPEEIQLLRKEATPRSRDSPVWCQCG
P2X7v04    LQDVKGQEVPRPAMDFTDLSRLPLALHDTPPIPGQPEEIQLLRKEATPRSRDSPVWCQCG
P2X7v02    ------------------------------------------------------------
P2X7v03    ------------------------------------------------------------
                421......430.......440.......450.......460.......470

P2X7v01    SCLPSQLPESHRCLEELCCRKKPGACITTSELFRKLVLSRHVLQFLLLYQEPLLALDVDS
P2X7v04    SCLPSQLPESHRCLEELCCRKKPGACITTSELFRKLVLSRHVLQFLLLYQEPLLALDVDS
P2X7v02    ------------------------------------------------------------
P2X7v03    ------------------------------------------------------------
                481......490.......500.......510.......520.......530

P2X7v01    TNSRLRHCAYRCYATWRFGSQDMADFAILPSCCRWRIRKEFPKSEGQYSGFKSPY
P2X7v04    TNSRLRHCAYRCYATWRFGSQDMADFAILPSCCRWRIRKEFPKSEGQYSGFKSPY
P2X7v02    -------------------------------------------------------
P2X7v03    -------------------------------------------------------
                541......550.......560.......570.......580........590
```

Therefore the transcriptional and translational start sequences of the human P2X7R were analyzed using Blast, Genescan and HMMgene computer software. This analysis indicated that P2X7R possesses with high probability only one translation start site. Most P2X7R expression sequence tags (ESTs; Unique cluster Hs. 193470) having a reliable 5' end showed identical transcriptional start site. None of the ESTs showed any indication of alternative splicing. Therefore, in silico analysis suggests that there is a low probability to find different transcripts produced by alternative splicing or alternative promoter usage.

The above mentioned in silico data were confirmed by RT-PCR analysis spanning the whole predicted human P2X7R coding sequence using 14 and 19 bases (5'-ATGC-CGGCTTGCTG-3'; 5'-GTAGGGATACTTGAAGCCA-3') oligonucleotides corresponding to the beginning and end of the coding sequence, respectively. Total RNA from whole brain, different dissected brain areas, thymus, spleen and kidney were isolated and analyzed for P2X7R expression. RT-PCR reactions were performed using the C. Therm One Step polymerase system (Roche Applied Science) and a protocol for touch down PCR with hot start. Briefly, Reverse Transcription was performed at 52° C. according to the manufacturer's conditions. PCR reactions were executed with an annealing temperatures of 64° C. for the first five cycles and of 54° C. for the next 30 cycles.

A single specific band of the size of 1785 bp corresponding to the complete coding sequence of P2X7R was detected. P2X7R mRNA was detected in the whole brain, hippocampus, cerebellum, leukocytes and thymus but not in cerebral cortex, hypothalamus, spleen and kidney (FIG. 2). All PCR products were cloned using the pGEM-T-Easy plasmid (Promega), selected in Top-10 bacteria (Invitrogen) by blue-white selection and tested by EcoRI digestion. Clones having fragments of the expected size were amplified and purified for sequencing. The sequence confirmed the identity of the 1785 bp clones as the complete coding sequence of wild-type P2X7R. Therefore, in all the tissues tested, wild-type P2X7R is expressed as a single transcript which includes the complete coding sequence. The presence of tissue specific isoforms is unlikely. These studies provide useful information about the P2X7R mRNA expression and transcript processing. This information can be used to synthesize riboprobes for in situ hybridization, Northern and Southern blot as well as engineering cells for the overexpression of P2X7R.

EXAMPLE 5

P2X7R Expression in the Mouse Brain

The expression of P2X7R was further studied by immunohistochemistry of serial sections of complete mouse brains using a polyclonal antibody directed against an internal peptide of P2X7R (Santa Cruz Biotechnology). The brains from stress-free mice were shock frozen, cut into 16 μm slices and fixed with paraformaldehyde for 5 minutes. The sections were blocked for 30 minutes at room temperature with 1:10 horse serum. All antibodies were diluted in TBST buffer (Tris-buffered saline with 0.05% Tween-20). The first antibody was used in a dilution 1:200 and incubated overnight. All washes were performed with TBST buffer. As a secondary antibody, an anti-goat IgG biotinylated (Vector Laboratories) was used and detection was performed using the streptavidin-biotin-horse-radish peroxidase complex system (Vector Laboratories) in combination with diaminobencidine. Slides were counterstained with toluidine blue using standard procedures. The same procedure in the absence of the primary antibody was performed as a negative control. As a positive control to test the Preservation of the tissue was verified with an antibody specific for the protein Patched1 (Santa Cruz Biotechnology). Patched1 was used as positive control since it stains all relevant brain structures and is not affected by stress or antidepressants. Very specific staining pattern was detected, consistent with the specific subcellular localization of P2X7R in brain cells. Negative controls were completely devoid of signal. Positive control with Patched1 showed identical signal intensity and distribution in all samples, indicating that all tissues were equally well preserved and processed.

Figure 3:
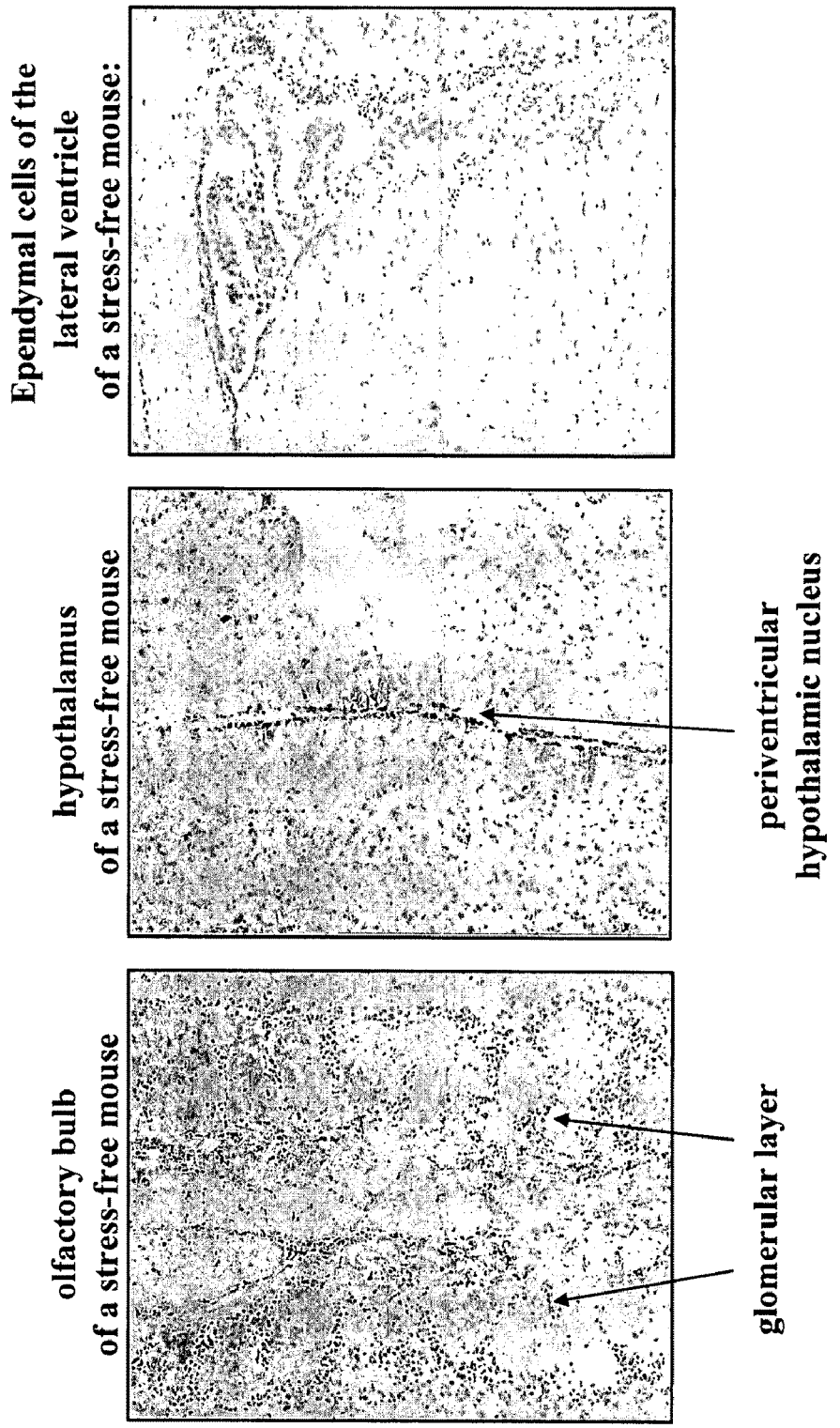

Proceeding from frontal to caudal, P2X7R protein was observed in the glomerular layer of the olfactory bulb at low levels (FIG. 3). P2X7R was also present at very low levels in a restricted area of the periventricular hypothalamic nucleus (FIG. 3). Ependymal cells surrounding the lateral ventricles also showed a fainted staining (FIG. 3). A stronger signal was detected in restricted areas of the hippocampus, where the signal was present in single cells of the polymorph layer, the lacunosum moleculare and the oriens layer (FIG. 4). In more posterior areas of the hippocampus, the signal was present in the molecular layer, stratum radiatum and near the CA3. In a further caudal position, P2X7R was expressed in the subcomisural organ (FIG. 4). Therefore, the basal P2X7R expression in the brain of stress-free mice is restricted to areas that had been previously associated with depression, stress, learning and memory.

EXAMPLE 6

P2X7R is Modulated in Mice Treated with an Antidepressant

Further validation of role of P2X7R in affective disorders was performed by examining its expression pattern in response to stress and treatment with antidepressant drugs. A treatment schedule which has been proven to produce antidepressant effects on the behavioural level was administered to mice which were characterized as antidepressant-responsive by using a variety of behavioural paradigms suitable to detect anxiolytic and antidepressant effects of classical antidepressants like the selective serotonin reuptake inhibitor paroxetine. Paroxetine was delivered by gavage to naive male mice over a time period of 28 days at a dosage of 10 mg/kg body-weight twice per day. In parallel, a control group of mice was given vehicle solution (i.e. without paroxetine) using the same treatment regiment while a second control group of mice was left undisturbed and stress-free (i.e. untreated) during the same period of the experiments. At the end of the long-term treatment, part of the mice of each experimental group were tested in the dark/light box (test of anxiety behaviour) and in the Porsolt's forced swim test (test of depressive-like behaviour) to confirm the effectiveness of the treatment (FIG. 5). Passive stress coping behaviour decreased after long-term treatment with the antidepressant paroxetine. The other part of the experimental groups (i.e. mice without test experience) were decapitated, brains rapidly removed and frozen at −80° C. until usage.

The expression of P2X7R in the brains of mice under stress-free conditions, and mice under mild stress produced by the vehicle application, and mice under paroxetine treatment was evaluated using three different brains from each group. Serial slides from each group of animals were analyzed in parallel by immunohistochemistry using the same materials in order to produce completely comparable results. No significant change in P2X7R expression in the olfactory bulb was seen in response to stress or to paroxetine treatment (FIG. 6). However, in the periventricular nucleus of the hypothalamus, paroxetine produced a slight inhibition of P2X7R expression (FIG. 7). No significant change was observed in the ependymal cells from different brain areas (FIG. 8). The most dramatic changes were observed in the hippocampus, where P2X7R was strongly inhibited by stressful handling whereas paroxetine treatment produced a marked stimulation above basal levels (FIGS. 9, 10 and 11). This effect was observed all along the hippocampus but was more evident in the polymorph layer near the dentate gyrus. In the subcommissural organ, P2X7R expression remained unchanged by the different treatments. Therefore, P2X7R expression is strongly regulated in two specific brain areas involved in depression and stress. Other brain areas, which showed low levels of P2X7R and are not directly involved in depression, did not show changes.

In the samples from mice treated with paroxetine and showing a strong P2X7R expression, it was possible to analyze the distribution of P2X7R in more detail (FIGS. 10 and 11). The P2X7R protein was not only present in cell bodies but also was clearly detected in projections innervating the granular layer of the dentate gyrus (FIG. 12). This subcellular localization of P2X7R is consistent with a role in neurotransmitter release and long term potentiation.

Since some reports (Muria et al., Biochem. J. 288 (1992), 897-901; Ferrari et al., FEBS Lett. 447 (1999), 71-75) suggest that chronic and high dose stimulation of P2X7R may cause apoptosis in some cell types, the hippocampus of the above described animals were analyzed for the co-localization of apoptotic cells and P2X7R expressing cells, in consecutive sections, using TUNNEL staining and immunohistochemistry. In correlative sections, only few apoptotic cells were detected and they were present along the granular layers of the hippocampus where no P2X7R expression was observed (FIG. 13). No significant differences in the numbers of apoptotic cells were observed between the different treatment conditions. Therefore, the location and number of apoptotic cells did not correlate with the location and number of cells expressing P2X7R and rules out an involvement of P2X7R in the induction of apoptosis in the hippocampus.

Thus, P2X7R expression is considerably restricted to specific brain areas involved in depression. Moreover, P2X7R expression is inhibited by stress and strongly stimulated by antidepressant treatment in these specific areas. Therefore, P2X7R fulfils all criteria required for the actions of antidepressants according to the highest standards in the field of depression research. In addition, these results suggest that modulation of function of P2X7R is associated with chronic stress, which serves as a model for several aspects of affective disorders.

EXAMPLE 7

The Behavioural Effect of P2X7R Inhibition in Mice

To demonstrate that P2X7R inhibition acts as a causative agent for affective disorders, P2X7R function was specifically inhibited in distinct regions of the brain without affecting any other brain function. This was achieved by delivering double stranded small interference RNA molecules (siRNA) into restricted areas of the brain.

According to the observed expression pattern of P2X7R in the hippocampus (FIGS. 9, 10, and 11) and the known involvement of the hippocampus in depression, the dentate gyrus (hippocampus) was selected as target region for siRNA application. Male, naive mice were bilaterally implanted with a guide cannulae (23 gauge, length 8 mm) by means of a stereotactic instrument. The coordinates, in relation to bregma, were −2.0 mm posterior, ±1.0 mm lateral, and −1.0 mm ventral. Following a recovery period of 5 days, the mice were divided into three experimental groups: vehicle (veh), control double stranded RNA (control), and P2X7R specific double stranded siRNA (siRNA). Sequences used for P2X7R siRNA are 5'-GUGGGUCUUGCACAUGAUCTT-3' and 5'-GAUCAUGUGCAAGACCCACTT-3'. Both sequences and were annealed and injected together as a double stranded RNA. On day 6 after surgery, mice were slightly anaesthetized with Isofluran and injections of siRNA were carried out. The concentration of the control and siRNA was 0.1 nmol/µl, and a volume of 1 µl per side was infused using specifically adapted injection systems (30 gauge, length 9 mm). The anaesthesia for the infusion was of short duration and the mice were awake immediately or few seconds after the manipulation.

Once delivered into the brain the siRNA molecules specific for P2X7R were taken up by brain cells and specifically induce the degradation of the complementary P2X7R mRNA with high efficiency. As a result, P2X7R function was specifically inhibited for a short period without affecting any other brain function. In this regard, injection of vehicle or control siRNA did not result in any obvious changes in normal behaviour, i.e., food and water intake, or motor behaviour in the home cage.

The effects of P2X7R inhibition on depressive-like behaviour was assessed 24 hours and 48 hours after infusion of siRNA, control or vehicle according to the standard test paradigm, the Porsolt's forced swim test (Porsolt et al., Arch. Int. Pharmacodym. 229 (1977), 327-336; Porsolt, Rev. Neurosci. 11 (2000), 53-58). The parameter used to evaluate depressive-like behaviour is the time the animal is floating in the water, a behaviour which is associated with behavioural despair as the animal does not make any effort to actively cope with the stressful situation. Compared to vehicle application, no influence of control double stranded RNA (5'-CAACUUCAUCU-UCUACGCGTT-3') on floating behaviour (passive stress coping) was detected. In contrast, compared to controls, mice infused with P2X7R specific siRNA showed a significant increase in passive behaviour, which is construed as depressive-like behaviour (FIG. 14). This interpretation becomes moreover evident when the effects of antidepressants on passive stress coping behaviour in the forced swim test are visualized (FIG. 5). Passive stress coping behaviour increased after acute intrahippocampal injection (bilateral, dentate gyrus) of siRNA targeting P2X7R. The Porsolt's forced swim test is a standard test used to assess the effectiveness of antidepressants and it has been proven by many studies that the test is selectively sensitive for these effects, given that the right animal model is used. The paradigm has been widely used to test pharmaceutical compounds and to validate animal models of depression, which show an increase in passive behaviour as do the mice where P2X7R has been inhibited (siRNA).

At the end of the experiment, the mice were sacrificed and the brains were examined to confirm the location and efficiency of the siRNA injections. For this purpose the brains were cut into sections and the slides were stained by immunohistochemistry using the above mentioned protocols. Brains from mice injected with the specific double stranded siRNA, with control double stranded RNA and with vehicle were examined in parallel. Under these conditions, the specific siRNA directed against P2X7R injected near the dentate gyrus induced on average an 80% inhibition of P2X7R protein expression as compared to the samples from mice injected with vehicle or with control double stranded RNA.

Both the number of cells expressing P2X7R as well as the intensity of the expression were strongly reduced (FIG. 15). The injections with siRNA did not produce any sign of local inflammation or infiltration at the hippocampus. Thus, P2X7R expression is specifically and locally inhibited by siRNA application in vivo. This inhibition produced behavioural changes indicating a causative role for P2X7R in affective disorders. These results in combination with those mentioned above support and confirm the observation of mutations in P2X7R being associated with affective diseases in humans and that modulation of P2X7R activity has anti-depressive effects.

EXAMPLE 8

Drug Screening Assay

Methods for identifying P2X7R agonists were established using an immortalised mouse hippocampal cell line expressing the endogenous P2X7 gene. Briefly, the expression of P2X7 was confirmed by culturing the cells at 37° C./5% $CO_2$ in DMEM with 10% foetal calf serum (Gibco). Upon reaching 80% confluence, cells were collected in PBS and homogenized by repeated passage through a syringe (18 G needle). The amount of total protein was measured by the Bradford assay (Sigma; diluted 1:5, O.D. measured at 595 nm) according to the manufacturer's recommendation. Protein homogenates were then mixed with an equal volume of loading buffer (50 mM Tris-Cl pH 6.8; 25% glycerol; 7.2 mM bromophenol blue; 2% SDS; 200 nM β-mercaptoethanol) and subsequently denaturated in boiling water for 10 minutes. 20 mg of each sample were loaded onto a 10% polyacrylamide gel containing 0.4% SDS. Electrophoresis and Western blot transfer were performed according to conventional protocols described, for example, in Sambrook, Russell "Molecular Cloning, A Laboratory Manual", Cold Spring Harbor Laboratory, N.Y. (2001). Membranes were then blocked with 5% dry milk and incubated with an antibody against P2X7R (1:1000 dilution; Santa Cruz Biotech) followed by incubation with a horse anti-goat peroxidase-coupled secondary antibody (1:10000 dilution; Santa Cruz Biotech). Membranes were then incubated for 1 hour at 37° C. in Lumi-Light Western Blotting Substrate (Roche Applied Science) followed by a 10 minute exposure on a BioMax MR Film (Kodak).

A 70 kD band corresponding to the expected size of the P2X7R protein was detected in HT-22 cells demonstrating expression of the endogenous mouse P2X7 gene (FIG. 17). A second mouse hippocampal cell line (HT-39) did not express P2X7.

Since P2X7R is an ATP-gated ion channel which allows the entry of calcium and sodium ions into cells, a method for identifying P2X7R agonist was established by monitoring calcium influx into HT-22 cells. Cells were first loaded with the fluorescent dye Oregon green AM ester (Molecular Probes) for 30 minutes at room temperature, washed 2 times with DMEM/10% foetal calf serum to remove excess dye and cultured for 15 minutes in the presence of 100 μM 2- and 2'-3'-O-(4-Benzoylbenzoyl)adenosine 5'-triphosphate (BzATP: $C_{24}H_{24}N_5O_{15}P_3$)). BzATP is a known agonist of P2X7R (North and Surprenant, Annu. Rev. Pharmacol. Toxicol. 40 (2000), 563-580). Calcium movement into the cells was visualised under a fluorescent microscope with a fluorescein filter (wavelength 492/517 nm). Oregon green AM ester is a fluorescent dye that binds to intracellular calcium. Accordingly, an increase in green fluorescence was observed in cells treated with BzATP (FIG. 18) signalling an activation of P2X7R which results in an influx of calcium into the cells and an increase binding of Oregon green dye to intracellular calcium. Alternatively, Oregon green AM ester can be replaced by Fluo-3, fluo-4, fluo-5F, fluo-5N, fluo4FF, Fluo4 dextran, Fluo-3 AM, Fluo-4 AM, Fluo-5F AM, Fluo-5N AM and Fluo4FF AM (Molecular Probes). Calcium influx in HT-22 cells can also be measured in 96-well and 384-well microplate using the Calcium Plus Assay Kit (Molecular Device) or FLIPR® Calcium Assay Kit for Fluorometric Imaging Plate Reader Systems (Molecular Device). HT-22 cells can be replaced by any cells expressing P2X7R, including cells that have been genetically modified by introducing an exogenous P2X7 gene.

The specificity of the P2X7R agonist on calcium influx was confirmed by pre-treatment of HT-22 cells with 100 mM Oxidized ATP (oATP; Sigma) for 1 hour before the addition of BzATP. oATP is an irreversible inhibitor of the receptor (Chen et al., J. Biol. Chem., 268 (1993), 8199-8203). Activation of P2X7R by the agonist was inhibited by oATP (FIG. 18) as illustrated by the absence of green fluorescence in the cells.

Yet another method of measuring P2X7R activity involves the entry of ethidium bromide into P2X7R expressing cells. Activation of P2X7R by an agonist allows the entry of ethidium bromide which binds nuclear DNA and emits a fluorescence signal. Alternatively, the propidium dye YOPRO-1 can be substituted for ethidium bromide. An increase in fluorescence can be used as a measure of P2X7 receptor activation. Therefore, the assay can be used to test and quantify the effect of an agent or compound with agonist properties on P2X7R. In the present example, $10^3$ HT-22 cells were seeded per well in a 96-well flat bottom microtitre plates and incubated at 37° C./5% $CO_2$ in DMEM medium containing 10% FCS until the cells attached to the culture surface. Once attached, cells were incubated for 60 minutes in DMEM medium containing 10% FCS, $10^{-4}$M ethidium bromide and increasing concentrations of BzATP (1 μM, 10 μM, 100 μM, 500 μM, 1 mM). The number of fluorescent cells which have integrated the ethidium bromide to the DNA can then be counted using a fluorescent microscope (Zeiss, Germany). Concentrations above 100 μM BzATP increased the number of fluorescent nuclei signalling activation of P2X7R (FIG. 19a). Alternatively, ethidium bromide fluorescence can be measured using a Perkin-Elmer fluorescent plate reader (excitation 520 nm, emission 595 nm, slit widths: Ex 15 nm, Em 20 nm). From the readings obtained, a pIC50 figure can be calculated for each candidate agent or compound. Accordingly, a P2X7R agonist is defined as an agent or a compound with an EC50 equal or below 300 micromolar, whereas the term EC 50 is defined as the concentration eliciting 50% of maximal response to an agonist (North and Surprenant, Annu. Rev. Pharmacol. Toxicol. 40 (2000), 563-580). The specificity of an agonist for P2X7R can be evaluated by pre-incubation of the cells for 60 minutes with 100 μM o-ATP before adding the agonist and ethidium bromide dye. Under these conditions, activation of P2X7R by the agonist is inhibited by oATP resulting in a reduction in the number of fluorescent cells (FIG. 19b).

Yet another method for identifying P2X7R agonists was devised by generating a immortalised mouse cell line that overexpresses the human P2X7R gene under the control of the human cytomegalovirus (CMV) early promoter/enhancer region. The human P2X7R cDNA was inserted into the pcDNA3.1 vector (Invitrogen) and transfected into the mouse hippocampal cell line HT-22 using Lipofectamine (Invitrogen) according to the manufacturer's specifications. One day after transfection, culture medium containing 500 μg/ml G418 was added to the cells. Resistant clones were separately isolated and cultured 14 days after applying the selection medium.

The agonistic activity of a compound was evaluated by measuring calcium entry in the cells that overexpress the human P2X7R. Cells were cultured in 96 well plates and incubated at 37° C. with 5% $CO_2$ DMEM with 10% foetal calf serum (Gibco) until they reached confluence. Cells were then loaded for one hour with 10 µM of Fluo4 AM (Molecular Probes). Fluo-4 AM is a fluorescent dye that binds to intracellular calcium. After loading, cells were washed once with a buffer containing 0.5 mM $CaCl_2$ and 20 mM Hepes and were treated with 20 µM BzATP or 50 µM tenidap. Agonist activity was detected by measuring an increase in calcium influx which results in increased binding to Fluo4 AM and increased fluorescence. Changes in fluorescence signal are measured using a Fluostar Optima plate reader (BMG biotech). Both BzATP and tenidap produced a rapid increase in fluorescence intensity which declined slowly over time (FIG. 19c). Thus, both compound stimulated the activity of P2X7R which results in an influx of ions into the cells.

EXAMPLE 9

Activation of P2X7R with Agonists has Antidepressive Effects

To demonstrate that activation of P2X7R has therapeutic effects on affective disorders, the P2X7R agonist BzATP (2'-3'-O-(4-Benzoylbenzoyl)adenosine 5'-triphosphate ($C_{24}H_{24}N_5O_{15}P_3$)) was administered to a selected DBA/2OIa mouse strain that displays characteristics of being highly anxious, responding to antidepressants, and showing anxiolysis after subchronic antidepressant treatment (Lucki et al., Psychopharmacology 155 (2001), 315-322). BzATP is a compound with strong specificity to P2X7R (North and Surprenant, Annu. Rev. Pharmacol. Toxicol. 40 (2000), 563-580). In the present example, the P2X7R agonist was directly injected into the hippocampus of mice. However, a P2X7R agonist agent or compound could also be delivered orally, subcutaneously, intravenously, intra-arterial, intranodal, intramedullary, intrathecal, intraventricular, intranasally, intrabronchial, transdermally, intrarectally, intraperitoneally, intramuscularly, intrapulmonary, vaginally, rectally, or intraocularly.

Four months old male mice were bilaterally implanted with guide cannulae (23 gauge, length 8 mm) by means of a stereotactic instrument (David Kopf Instruments). The coordinates, in relation to bregma, were −2.0 mm posterior, ±1.0 mm lateral, and −1.0 mm ventral. After surgery, the mice were allowed to recover for 10 to 12 days. Following this recovery period, mice were injected with 1 µl vehicle solution (0.5% DMSO, Sigma) or 50 µM BzATP (Sigma, prepared in 0.5% DMSO) in each side of the brain over a period of 60 seconds. Injections were performed using a 9 mm-30 gauge needle inserted into the guide cannulae and connected via tubing to a 10 µl Hamilton syringe.

The behaviour of individual mice was assessed using the Porsolt's forced swim test 24 hours after injection of vehicle solution or BzATP. A pre-exposure of 5 minutes to the test was done 10-15 minutes after vehicle or BzATP injection. The forced swim test is a standard test that measures primary stress-induced reductions in avoidance or escape, termed behavioural despair. The test is used to determine the effectiveness of antidepressants, test new pharmaceutical compounds and validate animal models of depression (Porsolt et al., Arch. Int. Pharmacodym. 229 (1977), 327-336; Porsolt, Rev. Neurosci. 11 (2000), 53-58; Rénéric et al., Behav. Brain Res. 136 (2002), 521-532; Page et al., Psychopharmacology 165 (2003), 194-201; Kelliher et al., Psychoneuroendocrinology 28 (2003), 332-347). The test consists of placing a mouse for a period of 5 minutes into a glass cylinder containing water. Under such circumstances, the mouse cannot touch the bottom of the cylinder and is thus forced to swim. Time, latency and frequency of struggling versus floating are scored as behavioural parameters. Floating (i.e. movements made only for keeping balance and breath) is a passive behaviour associated with despair and represents a depressive-like symptom since the animal does not make any effort to actively cope with the stressful situation. Increased struggling (i.e. active attempts to escape) indicates active coping behaviour that can be interpreted as an improvement of depression-like symptoms. For example, treatment with serotonergic antidepressants reduce the total time spent floating (Borsini, Neurosci. Biobehav. Rev. 19 (1995), 377-395; Redrobe and Bourin, Psychopharmacology 138 (1998), 198-206, and in parallel increases the time of active behaviour (i.e. swimming or struggling; Lucki et al., Psychopharmacology 155 (2001), 315-322).

The P2X7R agonist BzATP was found to increase active escape attempts (i.e. increase in time and frequency of struggling, decrease in latency of struggling) while a decrease in passive behaviour (i.e. decrease in time and frequency of floating, increase in latency of floating) was measured when compared to control mice injected with vehicle solution (FIG. 20). Observed results were verified statistically using Mann-Whitney U and one-way MANOVA tests. The differences in time struggling, latency of floating and frequency of floating were found to be statistically significant. While latency and frequency of struggling and time floating results were not supported statistically, they still represented a tendency towards improvement in stress coping behaviour. These results demonstrate that a P2X7R agonist can lead to improvements in depressive-like symptoms.

Since conclusions drawn from the forced swim test can be influenced by unspecific effects of an agent or compound on animal activity (i.e. increase in struggling behaviour can be the result of hyperactivity instead of increased active coping behaviour), the potential effect of BzATP on locomotor activity was assessed by the open field test (Crawley "What's wrong with my mouse: Behavioral phenotyping of transgenic and knockout mice", Wiley-Liss (2000)). Locomotor activity in mice treated with control vehicle solution or 50 µM BzATP was assessed 24 hours after injection by placing individual animal in a dark-grey wooden box (30×30×40 cm). Locomotor activity was monitored for a period of 30 minutes using a video camera. Overall distance traveled by the animals during the testing period was then analysed by means of VideoMot2 computer software (TSE GmbH, Bad Homburg). No difference in locomotor activity was measured between mice treated with control vehicle solution and BzATP (FIG. 21). Therefore, the application of BzATP did not induce hyperactivity. These results confirm that activation of P2X7R by an agonist agent or compound leads to improvements in depressive-like symptoms and is not the result of an unspecific effect on animal activity per se.

Several reports suggest that activation of P2X7R can induce apoptosis and cell death in vitro (Di Virgilio et al., Cell Death Differ. 5 (1998), 191-199, Virginio et al., J. Physiol. 519 (1999), 335-346). To test whether P2X7R activation in the hippocampus resulted in cell death, apoptosis levels were quantified in the brain of the mice treated with BzATP. Mice were sacrificed at the end of the behavioural experiments, the brains were removed, shock frozen and sectioned into 16 µm slices. Brain sections were then studied for apoptosis using the DeadEnd fluorometric TUNEL system according to the manufacturer's recommendation (Promega Corporation). The TUNEL system measures the fragmented DNA of apoptotic cells. Positive control for the assay are made by pretreating brain sections for 10 minutes with 1 unit/ml of DNAse I.

Very few apoptotic cells (i.e. less than one cell per brain section) were observed in brains of mice treated with control vehicle or the P2X7R agonist (FIG. 22) when compared to positive control sections pre-treated with DNAse. Moreover, no significant differences in the numbers of apoptotic cells was observed between the control animals and mice treated with BzATP, indicating that activation of P2X7R did not result in cerebral cell death in vivo.

EXAMPLE 10

P2X7R Antagonists have No Antidepressive Effects

The P2X7R antagonists KN-62 (1-(N,O-bis[5-isoquinolinesulphonyl]-N-methyl-L-tyrosyl)-4-phenylpiperazine) and oxidized ATP (oATP) were administered to DBA/201a mice (Harlan Winkelmann, Germany) that exhibit the behavioural characteristic of being highly anxious. KN-62 has been shown to be a non competitive antagonist of P2X7R (Chessel et al., Brit. J. Pharmacol., 124 (1998), 1314-1320) while oATP acts as an irreversible inhibitor of P2X7R (Chen et al., J. Biol. Chem., 268 (1993), 8199-8203).

In the present example, the P2X7R antagonists were directly injected into the dentate gyrus region of the hippocampus. Briefly, three months old male mice were bilaterally implanted with guide cannulae (23 gauge, length 8 mm) by means of a stereotactic instrument (David Kopf Instruments). The coordinates, in relation to bregma, were −1.5 mm posterior, ±1.0 mm lateral, and −0.8 mm ventral. Mice were allowed to recover for 10 to 13 days after surgery. Following this recovery period, mice were injected with 1 μl vehicle solution (0.01% DMSO, Sigma), or 100 nM KN-62 (Sigma, prepared in 0.01% DMSO), or 10 μM oATP (Sigma, prepared in PBS) in each side of the brain over a period of 60 seconds. All injections were performed using a 9 mm-31 gauge needle inserted into the guide cannulae and connected via tubing to a 10 μl Hamilton syringe.

The behaviour of individual mice was assessed using the Porsolt's forced swim test 24 hours after injection of vehicle solution, KN-62, or oATP. A pre-exposure of 5 minutes to the test was performed 15-17 minutes after administration of vehicle, KN-62, or oATP. A description of the Porsolt's forced swim test is given in example 9. In the present example, no changes in active escape attempts (i.e. time, frequency, latency of struggling) or in passive behaviour (i.e. time, frequency, latency of floating) was measured between vehicle, KN-62 or oATP treated mice (FIG. 23). Observed results were verified statistically using one-way MANOVA test. The differences seen in the different parameters between vehicle, KN-62 or oATP treated mice were not supported statistically. These results demonstrate that P2X7R antagonists do not improve depressive-like symptoms and have no antidepressive action.

Figure 24:
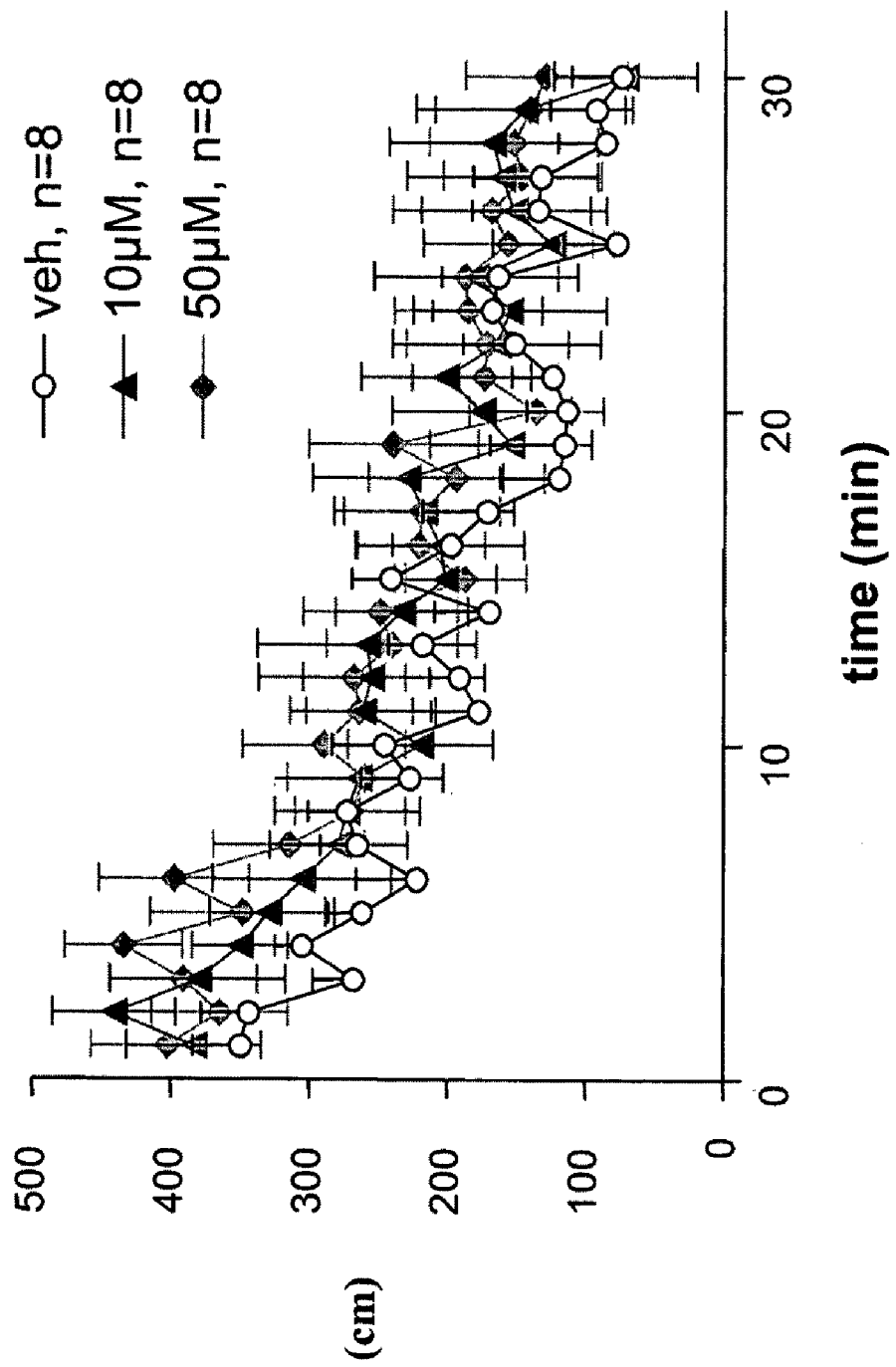

Since conclusions drawn from the forced swim test can be influenced by unspecific effects of an agent or compound on animal activity (i.e. increase in struggling behaviour can be the result of hyperactivity instead of increased active coping behaviour), the potential effect of the P2X7R antagonist oATP on locomotor activity was assessed by performing the open field test. Locomotor activity in mice treated with control vehicle solution, 10 μM oATP, or 50 μM oATP was assessed 15 minutes after injection by placing individual animal in a dark-grey wooden box (30×30×40 cm). Locomotor activity was monitored for a period of 30 minutes using a video camera. Overall distance traveled by the animals during the testing period was then analysed by means of VideoMot2 computer software (TSE GmbH, Bad Homburg). No difference in locomotor activity was measured between mice treated with control vehicle solution and oATP (FIG. 24). Therefore, the application of a P2X7R antagonist did not induce hypo- or hyperactivity in the animals.

The invention claimed is:

1. A method for diagnosing an affective disorder or a susceptibility to an affective disorder in an individual comprising the steps of (a) determining in a sample obtained from an individual whether the ATP-gated ion channel purinergic receptor P2X7 gene sequence or encoded protein thereof comprises a mutation in comparison to the wild-type ATP-gated ion channel purinergic receptor P2X7 sequence, wherein said mutation is a nucleotide replacement or deletion in exon 13, nucleotide A, at position 54480 in the nucleotide sequence of the wild-type ATP-gated ion channel P2X7R as depicted in SEQ ID NO: 1, and the presence of said mutation indicates that the individual suffers from or is susceptible to an affective disorder; and (b) detecting an affective disorder or a susceptibility to an affective disorder.

2. The method of claim 1, wherein the occurrence of the mutation in the ATP-gated ion channel purinergic receptor P2X7 gene is determined by PCR.

3. A method for diagnosing an affective disorder of an individual comprising:
   (a) isolating DNA from cells obtained from an individual;
   (b) determining all or part of the nucleotide composition of the ATP-gated ion channel purinergic receptor P2X7 gene;
   (c) analyzing said nucleotide composition of the ATP-gated ion channel purinergic receptor P2X7 for the presence of a mutation, wherein said mutation is a nucleotide replacement or deletion in exon 13, nucleotide A, at position 54480 in the nucleotide sequence of the wild-type ATP-gated ion channel P2X7R as depicted in SEQ ID NO: 1, and the presence of said mutation indicates that the individual suffers from or is susceptible to an affective disorder; and
   (d) detecting an affective disorder.

4. A method for diagnosing an affective disorder of an individual comprising:
   (a) isolating RNA from cells obtained from an individual;
   (b) converting said RNA into cDNA;
   (c) determining all or part of the nucleotide composition of the ATP-gated ion channel purinergic receptor P2X7 gene;
   (d) analyzing said nucleotide composition of the ATP-gated ion channel purinergic receptor P2X7 for the presence of a mutation, wherein said mutation is a nucleotide replacement or deletion in exon 13, nucleotide A, at position 54480 in the nucleotide sequence of the wild-type ATP-gated ion channel P2X7R as depicted in SEO ID NO: 1, and the presence of said mutation indicates that the individual suffers from or is susceptible to an affective disorder; and
   (e) detecting an affective disorder.

* * * * *